US012612392B2

(12) United States Patent
Cao et al.

(10) Patent No.: US 12,612,392 B2
(45) Date of Patent: *Apr. 28, 2026

(54) COMPOUND, PHARMACEUTICAL COMPOSITIONS CONTAINING SAME, SYNTHESIS METHOD THEREFOR AND USE THEREOF

(71) Applicant: SHENZHEN ZHONGGE BIOLOGICAL TECHNOLOGY CO., LTD., Shenzhen (CN)

(72) Inventors: Bin Cao, Shenzhen (CN); Liyu Zhao, Shenzhen (CN); Guosheng Dou, Shenzhen (CN); Sizhu Lu, Shenzhen (CN); Dewei Xie, Shenzhen (CN)

(73) Assignee: SHENZHEN ZHONGGE BIOLOGICAL TECHNOLOGY CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 19/261,393

(22) Filed: Jul. 7, 2025

(65) Prior Publication Data

US 2025/0382284 A1 Dec. 18, 2025

Related U.S. Application Data

(63) Continuation of application No. 19/116,858, filed as application No. PCT/CN2023/132911 on Nov. 21, 2023.

(30) Foreign Application Priority Data

Nov. 21, 2022 (CN) ........................ 202211455519.X
Jun. 19, 2023 (CN) ........................ 202310731972.7

(51) Int. Cl.

| | |
|---|---|
| ***C07D 413/04*** | (2006.01) |
| ***A61K 31/422*** | (2006.01) |
| ***A61P 1/16*** | (2006.01) |
| ***C07D 401/06*** | (2006.01) |

(52) U.S. Cl.

CPC .......... *C07D 413/04* (2013.01); *A61K 31/422* (2013.01); *A61P 1/16* (2018.01); *C07D 401/06* (2013.01)

(58) Field of Classification Search

CPC ... C07D 401/06; C07D 413/04; A61K 31/422
See application file for complete search history.

(56) References Cited

FOREIGN PATENT DOCUMENTS

| | | | |
|---|---|---|---|
| CN | 109641853 | A | 4/2019 |
| CN | 111094233 | A | 5/2020 |
| CN | 112204012 | A | 1/2021 |
| CN | 113993850 | A | 1/2022 |
| CN | 114008041 | A | 2/2022 |
| CN | 114206848 | A | 3/2022 |
| CN | 114980894 | A | 8/2022 |
| CN | 115190813 | A | 10/2022 |
| WO | 2022/084447 | A1 | 4/2022 |
| WO | 2022/094244 | A1 | 5/2022 |
| WO | 2022/212902 | A1 | 10/2022 |

OTHER PUBLICATIONS

International Search Report and Written Opinion for Application No. PCT/CN2023/132911, dated Feb. 23, 2024, 17 pages.

*Primary Examiner* — Theodore R. Howell
(74) *Attorney, Agent, or Firm* — McCarter & English, LLP; Wei Song

(57) ABSTRACT

The present application provides a compound as shown in formula (0), a pharmaceutical composition containing same, a synthesis method therefore and a use thereof. The compound of the present application can significantly reduce the integrated stress response (ISR) of cells and activate the activity of eIF2B, so that the protein in the cells tends to be synthesized normally, providing more possible drugs for ISR pathway-mediated diseases or condition eIF2B-related diseases, and/or diseases related to regulation of the activity or level of eIF2B activity or level, and regulation of the activity or level of the eIF2 pathway or ISR pathway.

(0)

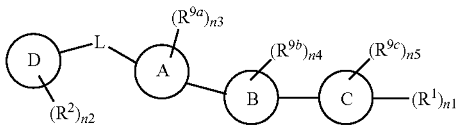

4 Claims, No Drawings

COMPOUND, PHARMACEUTICAL COMPOSITIONS CONTAINING SAME, SYNTHESIS METHOD THEREFOR AND USE THEREOF

CROSS-REFERENCE TO RELATED APPLICATIONS

This application is a continuation of U.S. patent application Ser. No. 19/116,858, filed on Mar. 28, 2025, which is a U.S. National Stage Application filed under 35 U.S.C. § 371, based on International Application No. PCT/CN2023/132911, filed on Nov. 21, 2023, which claims priority to Chinese patent application 202211455519.X filled Nov. 21, 2022 and Chinese patent application 202310731972.7 filled Jun. 19, 2023, the entire contents of which are incorporated herein by reference in their entirety.

TECHNICAL FIELD

The present invention relates to a compound, a pharmaceutical composition containing same, a synthesis method therefor and the use thereof.

BACKGROUND ART

Amyotrophic Lateral Sclerosis (ALS), also known as motor neuron disease (MND) and Lou Gehrig's disease, is an irreversible, fatal motor neuron disease. The main symptoms of amyotrophic lateral sclerosis is progressive muscle weakness and atrophy of muscles of the limbs and trunk, and gradual loss of motor function, as if being "frozen", so it is called "jian dong ren", meaning "gradually frozen men". Most ALS patients die from respiratory failure, usually within three to five years after the first appearance of symptoms. Currently, there is no cure for ALS and no effective treatment methods that can stop or reverse the progression of the disease. The core pathological finding in ALS is motor neuron death in the motor cortex and spinal cord. Degeneration of corticospinal axons leads to thinning and scarring (sclerosis) of the lateral aspects of the spinal cord.

Loss of protein-folding homeostasis is a hallmark of many of the most prevalent neurodegenerative diseases. As a mechanism to cope with folding stress in the endoplasmic reticulum (ER), the unfolded protein response (UPR) comprises a set of signaling mechanisms that initiate gene expression programs to restore protein homeostasis or, when the stress is chronic or overloaded, promote neuron death. This function of the UPR has been proposed to play a key role in ALS.

The integrated stress response (ISR) is an evolutionarily conserved intracellular signaling network that helps the cell, tissue and organism to adapt to a variable environment and maintain health. In response to various changes, the ISR restores balance by reprogramming gene expression. In the brain, long-term memory formation requires new protein synthesis, and therefore inhibition of the ISR can enhance long-term memory formation, whereas ISR activation prevents it. Furthermore, age-related cognitive disorders are commonly associated with ISR activation.

As a central regulator of protein homeostasis, the ISR is activated in a wide range of diseases of the brain. This activation is evidenced by detection of eIF2-P and phosphorylation of PKR, PERK and GCN2 in brains, including those from patient samples and animal model samples of neurodegenerative diseases, such as Alzheimer's disease, Parkinson's disease, Huntington's disease, traumatic brain injury, Down syndrome, and Charcot-Marie-Tooth disease. Notably, ISR activation causes cognitive defects in mouse models of traumatic brain injury, aging and Alzheimer's disease.

eIF2B (eukaryotic translation initiation factor 2B) is a key enzyme in the regulation of protein synthesis and is a guanine nucleotide exchange factor (GEF) specific for translation initiation factor 2. As an eIF2B activator, ISRIB can restore protein translation, revert UPR transcription to basal levels, and alleviate the integrated stress response (ISR).

In addition, the eIF2B activators ABBV-CLS-7262 (AbbVie/Calico) and DNL-343 (Denali Therapeutics) both are indicated for ALS and have entered Phase 1 clinical trials, wherein DNL-343 has demonstrated its safety and tolerability by the Phase 1 data in healthy participants which is already published.

A large number of animal experiments have confirmed that the eIF2B activator ISRIB can improve long-term memory in mouse models. After oral administration of the eIF2B activator ABBV-CLS-7262 for three days, the brain function of model animals can be restored to youthful levels. It means that ABBV-CLS-7262 may be capable of suppressing some neurodegenerative diseases in the later stages and has the potential to treat diseases such as Alzheimer's disease and Parkinson's disease.

SUMMARY OF THE INVENTION

The present application provides a compound, a pharmaceutical composition comprising same, a synthesis method therefor and the use thereof, so as to provide a compound that can significantly reduce the integrated stress response (ISR) of cells and activate the activity of eIF2B, so that the protein in the cells tends to be synthesized normally, providing more possible drugs for ISR pathway-mediated diseases or condition eIF2B-related diseases, and/or diseases related to regulation of the activity or level of eIF2B, and regulation of the activity or level of the eIF2 pathway or ISR pathway.

A first aspect of the present application provides a compound as shown in formula 0, or a stereoisomer thereof, a tautomer thereof, a geometric isomer thereof, an enantiomer thereof, a diastereomer thereof, a racemate thereof, a polymorph thereof, a solvate thereof, a hydrate thereof, an N-oxide thereof, an isotopically labeled compound thereof, a metabolite thereof, an ester thereof, a prodrug thereof or a pharmaceutically acceptable salt thereof.

formula 0

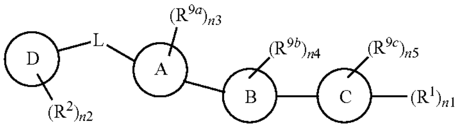

wherein ring A is selected from C3-C10 cycloalkylene or 3- to 10-membered heterocycloalkylene, and ring A is not

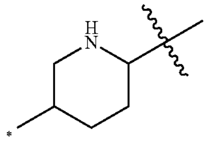
, wherein the * end is connected to L, the end is connected to ring B, and the $n_3$ is any integer from 0-5;

ring B is selected from 5- to 10-membered heteroarylene, and $n_4$ is any integer from 0-4;

ring C is selected from 3- to 10-membered heterocycloalkylene, C3-C10-membered cycloalkylene, or $\#^B$-$X^{21}$—C3-C12 cycloalkylene-$\$^{R1}$, $X^{21}$ is —$NR^3$ or —C(O)$NR^3$, $\#^B$-represents a connecting bond connected to ring B, and -$\$^{R1}$ represents a connecting bond connected to $R^1$;

each $R^3$ is independently H, halogen, C1-C6 alkyl or C1-C6 haloalkyl, and when ring C is C3-C10-membered cycloalkylene, ring A is not

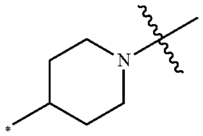 [SMILES: *N1CCC(C)CC1]

and cyclohexenylene, the * end is connected to L, the end is connected to ring B, and $n_5$ is any integer from 0-5;

ring D is selected from C6-C10 arylene, 5- to 10-membered heteroarylene, C3-C10 cycloalkylene or 3- to 10-membered heterocycloalkylene;

L is $\#^D$-$L^1$-$L^2$-$L^3$-$\$^A$ or 5- to 6-membered heteroaryl, $L^1$ is a bond, —O—, —S— or —$NR^4$—, $L^2$ is a bond, or substituted or unsubstituted C1-C10 alkylene, $L^3$ is —$C(X^{10})NR^5$-$\$^A$ or —$C(X^{10})$-$\$^A$, $X^{10}$ is O or S, $R^4$ and $R^5$ are each independently selected from H, C1-C10 alkyl, C2-C10 alkenyl, C2-C10 alkynyl, C3-C10 cycloalkyl, 3- to 10-membered heterocycloalkyl, C6-C10 aryl or 5- to 10-membered heteroaryl; as $R^4$ and $R^5$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{11}$, $L^1$ is connected to ring D, and the $L^3$ is connected to ring A; $\#^D$-represents a connecting bond connected to ring D, and -$\$^A$ represents a connecting bond connected to ring A;

$R^1$, $R^2$, $R^{9a}$, $R^{9b}$ and $R^{9c}$ are each independently substituent $R^{11}$;

each $R^{11}$ is independently selected from halogen, cyano, nitro, carbonyl, =O, —$OR^6$, —$SR^6$, $SF_5$, —$NR^6R^7$, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^6$, —C(O)$OR^6$, —OC(O)$OR^5$, OC(O)$R^6$, —C(O)$NR^6R^7$, —C(O)$ONR^6R^7$, —$NR^6$C(O)$NR^7R^8$, —$S(O)_{1-2}R^6$, —$S(O)_{1-2}NR^6$, $NR^6S(O)_{1-2}R^7$, —$NR^6S(O)_{1-2}NR^7R^8$, —$NR^6$C(O)$R^7$, —P(O)$R^5R^7$ or —$NR^5$OC(O)$OR^7$, wherein as $R^{9a}$, $R^{9b}$, $R^{9c}$ and $R^{11}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{12}$;

$R^6$, $R^7$ and $R^8$ are each independently selected from H, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^{20}$, —C(O)$OR^{20}$, —C(O)$NR^{20}R^{21}$, —$S(O)_{1-2}R^{20}$ or —$S(O)_{1-2}$ $NR^{20}$, wherein as $R^6$, $R^7$ and $R^8$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{13}$; or two of $R^6$, $R^7$ and $R^8$ together with the atom(s) to which they are shared form heterocycloalkyl, and the heterocycloalkyl may be substituted with 1-6 halogen, or substituted with C1-C10 alkyl optionally substituted with 1-6 carbonyl, halogen, hydroxyl or amino;

$R^{12}$ and $R^{13}$ are each independently H, halogen, cyano, nitro, carbonyl, =O, —$OR^{30}$, —$SR^{30}$, $SF_5$, $NR^{30}R^{31}$, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^{30}$, —C(O)$OR^{30}$, —OC(O)$OR^{30}$, OC(O)$R^{30}$, —C(O)$NR^{30}R^{31}$, —C(O)$ONR^{30}R^{31}$, —$NR^{30}$C(O)$NR^{30}R^{31}$, —$S(O)_{1-2}R^{30}$, —$S(O)_{1-2}NR^{30}$, $NR^{30}S(O)_{1-2}R^{31}$, —$NR^{30}S(O)_{1-2}NR^{30}R^{31}$, —$NR^{30}$C(O)$R^{31}$ or —$NR^{30}$C(O)$OR^{31}$, wherein as $R^{12}$ and $R^{13}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 halogen, or substituted with C1-C10 alkyl optionally substituted with 1-6 carbonyl, halogen, hydroxyl or amino;

$R^{20}$ and $R^{21}$ are each independently selected from H, or C1-C10 alkyl optionally substituted with 1-6 carbonyl, halogen, hydroxyl or amino;

$R^{20}$ and $R^{21}$ together with the atom(s) to which they are shared form heterocycloalkyl, and the heterocycloalkyl may be substituted with 1-6 halogen, or substituted with C1-C10 alkyl optionally substituted with 1-6 carbonyl, halogen, hydroxyl or amino;

$R^{30}$ and $R^{31}$ are each independently selected from H, or C1-C10 alkyl optionally substituted with 1-6 carbonyl, halogen, hydroxyl or amino;

$R^{30}$ and $R^{31}$ together with the atom(s) to which they are shared form heterocycloalkyl, and the heterocycloalkyl may be substituted with 1-6 halogen, or substituted with C1-C10 alkyl optionally substituted with 1-6 carbonyl, halogen, hydroxyl or amino;

n1 and n2 are each independently any integer from 0-4.

It should be noted that although the present application describes ring A, ring B, ring C and ring D in formula 0 as divalent groups with a main chain structure of $(R^2)_{n2}$-ring D-L-ring A-ring B-ring C—$(R^1)_{n1}$, those skilled in the art should understand that due to changes of substituents, the valence states of the ring A, ring B, ring C and ring D may also change adaptively in accordance with the rules of valence change in chemistry. Taking ring A as an example, when n3 is 0, ring A is a divalent ring; when n3 is not 0, ring A can be understood as being selected from a multivalent ring with a valence of three or more according to the valence and number of $R^{9a}$. The same applies to ring B. Taking ring D as an example, when n2 is 0, ring D can be understood as a monovalent ring; when n2 is not 0, ring D can be understood as being selected from a multivalent ring with a valence of two or more according to the valence and number of $R^2$. Taking ring C as an example, when n1 and n5 are 0, ring C can be understood as a monovalent ring; when either n1 or n5 is 0, ring C can be understood as being selected from a multivalent ring with a valence of two or more according to the valence and number of $R^{9c}$ and $R^2$; when neither n1 nor n5 is 0, ring C can be understood as being selected from a multivalent ring with a valence of three or more according to the valence and number of $R^{9c}$ and $R^2$.

The above descriptions regarding ring A, ring B, ring C and ring D are applicable throughout the document.

In some embodiments, the compound is as shown in formula 0, wherein ring A is selected from C3-C10 cycloalkylene or 3- to 10-membered heterocycloalkylene, and ring A is not

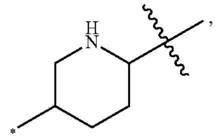 [SMILES: *C1CCC(C)CN1], wherein the * end is connected to L, the end is connected to ring B, and the n3 is any integer from 0-5;

ring B is selected from 5- to 10-membered heteroarylene, and n4 is any integer from 0-4;

ring C is selected from 3- to 10-membered heterocycloalkylene, C3-C10 cycloalkylene, or $\#^{B}$-$X^{21}$—C3-C12 cycloalkylene -$\$^{R1}$, $X^{21}$ is —$NR^3$ or —C(O)$NR^3$, $\#^{B}$-represents a connecting bond connected to ring B, and -$\$^{R1}$ represents a connecting bond connected to $R^1$; each $R^3$ is independently H, deuterium, halogen, C1-C6 alkyl or C1-C6 haloalkyl, and when ring C is C3-C10 cycloalkylene, ring A is not cyclohexenylene, and n5 is any integer from 0-5;

ring D is selected from C6-C10 arylene, 5- to 10-membered heteroarylene, C3-C10 cycloalkylene or 3- to 10-membered heterocycloalkylene;

L is $\#^{D}$-$L^1$-$L^2$-$L^3$-$\$^{A}$, 5- to 6-membered heteroaryl or $\#^{D}$—$NR^{14}$C(O)—C1-C6 alkylene-O-$\$^{A}$, $L^1$ is a bond, —O—, —S— or —$NR^4$—, $L^2$ is a bond, or substituted or unsubstituted C1-C10 alkylene, $L^3$ is —C($X^{10}$)$NR^5$-$\$^{A}$ or —C($X^{10}$)-$\$^{A}$, $X^{10}$ is O or S, $R^4$, $R^5$ and $R^{14}$ are each independently selected from H, deuterium, C1-C10 alkyl, C2-C10 alkenyl, C2-C10 alkynyl, C3-C10 cycloalkyl, 3- to 10-membered heterocycloalkyl, C6-C10 aryl or 5- to 10-membered heteroaryl; as $R^4$, $R^5$ and $R^{14}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{11}$; $\#^{D}$-represents a connecting bond connected to ring D, and -$\$^{A}$ represents a connecting bond connected to ring A;

$R^1$, $R^2$, $R^{9a}$, $R^{9b}$ and $R^{9c}$ are each independently substituent $R^{11}$;

each $R^{11}$ is independently selected from deuterium, halogen, cyano, nitro, =O, —$OR^6$, —$SR^6$, $SF_5$, —$NR^6R^7$, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^6$, —C(O)$OR^6$, —OC(O)$OR^6$, OC(O)$R^6$, —C(O)$NR^6R^7$, —C(O)$ONR^6R^7$, —$NR^6$C(O)$NR^7R^8$, —$S(O)_{1-2}R^6$, —$S(O)_{1-2}NR^6$, $NR^6S(O)_{1-2}R^7$, —$NR^6S(O)_{1-2}NR^7R^8$, —$NR^6$C(O)$R^7$, —P(O)$R^6R^7$ or —$NR^6$C(O)$OR^7$, wherein as $R^{9a}$, $R^{9b}$, $R^{9c}$ and $R^{11}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{12}$;

$R^6$, $R^7$ and $R^8$ are each independently selected from H, deuterium, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^{20}$, —C(O)$OR^{20}$, —C(O)$NR^{20}R^{21}$, —$S(O)_{1-2}R^{20}$ and —$S(O)_{1-2}NR^{20}$, wherein as $R^6$, $R^7$ and $R^8$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{13}$; or $R^6$ and $R^7$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino; or $R^7$ and $R^8$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino;

$R^{12}$ and $R^{13}$ are each independently H, deuterium, halogen, cyano, nitro, =O, —$OR^{30}$, —$SR^{30}$, $SF_5$, $NR^{30}R^{31}$, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^{30}$, —C(O)$OR^{30}$, —OC(O)$OR^{30}$, OC(O)$R^{30}$, —C(O)$NR^{30}R^{31}$, —C(O)$ONR^{30}R^{31}$, —$NR^{30}$C(O)$NR^{30}R^{31}$, —$S(O)_{1-2}R^{30}$, —$S(O)_{1-2}NR^{30}$, $NR^{30}S(O)_{1-2}R^{31}$, —$NR^{30}S(O)_{1-2}NR^{30}R^{31}$, —$NR^{30}$C(O)$R^{31}$ or —$NR^{30}$C(O)$OR^{31}$, wherein as $R^{12}$ and $R^{13}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 halogen, or substituted with C1-C10 alkyl optionally substituted with 1-6 carbonyl, halogen, hydroxyl or amino;

$R^{20}$ and $R^{21}$ are each independently selected from H, deuterium or C1-C10 alkyl optionally substituted with 1-6 halogen, hydroxyl or amino; or $R^{20}$ and $R^{21}$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino;

$R^{30}$ and $R^{31}$ are each independently selected from H, deuterium or C1-C10 alkyl optionally substituted with 1-6 halogen, hydroxyl or amino; or $R^{30}$ and $R^{31}$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino;

n1 and n2 are each independently any integer from 0-4.

In some embodiments, the compound is as shown in formula 0, wherein ring A is selected from C3-C10 cycloalkylene or 3- to 10-membered heterocycloalkylene, and ring A is not

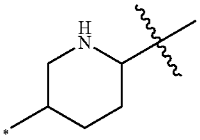, 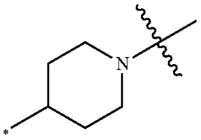 or

-continued

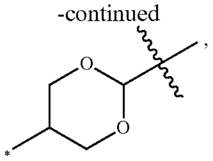

wherein the * end is connected to L, the  end is connected to ring B, and the n3 is any integer from 0-5;

ring B is selected from 5- to 10-membered heteroarylene, and n4 is any integer from 0-4;

ring C is selected from 3- to 10-membered heterocycloalkylene, C3-C10 cycloalkylene, or $\#^{B}$—$X^{21}$—C3-C12 cycloalkylene-$\$^{R1}$, $X^{21}$ is —$NR^3$ or —C(O)$NR^3$, $\#^{B}$-represents a connecting bond connected to ring B, and -$\$^{R1}$ represents a connecting bond connected to $R^1$; each $R^3$ is independently H, deuterium, halogen, C1-C6 alkyl or C1-C6 haloalkyl; when ring C is C3-C10 cycloalkylene, ring A is not cyclohexenylene; and when ring A is

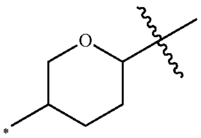

or

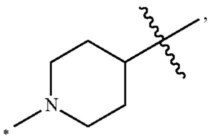

, the * end is connected to L, the  end is connected to ring B, ring C is 3- to 10-membered heterocycloalkylene, and n5 is any integer from 0-5;

ring D is selected from C6-C10 arylene, 5- to 10-membered heteroarylene, C3-C10 cycloalkylene or 3- to 10-membered heterocycloalkylene;

L is $\#^{D}$-$L^1$-$L^2$-$L^3$-$\$^{A}$, 5- to 6-membered heteroaryl or $\#^{D}$—$NR^{14}$C(O)—C1-C6 alkylene-O-$\$^{A}$, $L^1$ is a bond, —O—, —S— or —$NR^4$—, $L^2$ is a bond, or substituted or unsubstituted C1-C10 alkylene, $L^3$ is —C($X^{10}$)$NR^5$-$\$^{A}$ or —C($X^{10}$)-$\$^{A}$, $X^{10}$ is O or S, $R^4$, $R^5$ and $R^{14}$ are each independently selected from H, deuterium, C1-C10 alkyl, C2-C10 alkenyl, C2-C10 alkynyl, C3-C10 cycloalkyl, 3- to 10-membered heterocycloalkyl, C6-C10 aryl or 5- to 10-membered heteroaryl; as $R^4$, $R^5$ and $R^{14}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{11}$; $\#^{D}$-represents a connecting bond connected to ring D, and -$\$^{A}$ represents a connecting bond connected to ring A;

$R^1$, $R^2$, $R^{9a}$, $R^{9b}$ and $R^{9c}$ are each independently substituent $R^{11}$;

each $R^{11}$ is independently selected from deuterium, halogen, cyano, nitro, =O, —$OR^6$, —$SR^6$, $SF_5$, —$NR^6R^7$, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^6$, —C(O)$OR^6$, —OC(O)$OR^5$, OC(O)$R^6$, —C(O)$NR^6R^7$, —C(O)O$NR^6R^7$, —$NR^6$C(O)$NR^7R^8$, —$S(O)_{1-2}R^6$, —$S(O)_{1-2}NR^6$, $NR^6S(O)_{1-2}R^7$, —$NR^6S(O)_{1-2}NR^7R^8$, —$NR^6$C(O)$R^7$, —P(O)$R^6R^7$ or —$NR^6$C(O)$OR^7$, wherein as $R^{9a}$, $R^{9b}$, $R^{9c}$ and $R^{11}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{12}$;

$R^6$, $R^7$ and $R^8$ are each independently selected from H, deuterium, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^{20}$, —C(O)$OR^{20}$, —C(O)$NR^{20}R^{21}$, —$S(O)_{1-2}R^{20}$ and —$S(O)_{1-2}NR^{20}$, wherein as $R^6$, $R^7$ and $R^8$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 $R^{13}$; or $R^6$ and $R^7$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino; or $R^7$ and $R^8$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino;

$R^{12}$ and $R^{13}$ are each independently H, deuterium, halogen, cyano, nitro, =O, —$OR^{30}$, —$SR^{30}$, —$SF_5$, $NR^{30}R^{31}$, C1-C10 alkyl, C2-C10 alkenyl, C2-C10 alkynyl, C3-C10 cycloalkyl, 3- to 10-membered heterocycloalkyl, C6-C10 aryl, 5- to 10-membered heteroaryl, —C(O)$R^{30}$, —C(O)$OR^{30}$, —OC(O)$OR^{30}$, OC(O)$R^{30}$, —C(O)$NR^{30}R^{31}$, —C(O)O$NR^{30}R^{31}$, —$NR^{30}$C(O)$NR^{30}R^{31}$, —$S(O)_{1-2}R^{30}$, —$S(O)_{1-2}NR^{30}$, —$NR^{30}S(O)_{1-2}R^{31}$, —$NR^{30}S(O)_{1-2}NR^{30}R^{31}$, —$NR^{30}$C(O)$R^{31}$ or —$NR^{30}$C(O)$OR^{31}$, wherein as $R^{12}$ and $R^{13}$, C1-C10 alkyl, C2-C10 alkenyl, C2-C10 alkynyl, C3-C10 cycloalkyl, 3- to 10-membered heterocycloalkyl, C6-C10 aryl and 5- to 10-membered heteroaryl may each be independently substituted with 1-6 halogen, or substituted with C1-C10 alkyl optionally substituted with 1-6 carbonyl, halogen, hydroxyl or amino;

$R^{20}$ and $R^{21}$ are each independently selected from H, deuterium or C1-C10 alkyl optionally substituted with 1-6 halogen, hydroxyl or amino; or $R^{20}$ and $R^{21}$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino;

$R^{30}$ and $R^{31}$ are each independently selected from H, deuterium or C1-C10 alkyl optionally substituted with 1-6 halogen, hydroxyl or amino; or $R^{30}$ and $R^{31}$ together with the atom(s) to which they are attached form heterocycloalkyl, and the heterocycloalkyl may be substituted with 1-6 halogen, or substituted with C1-C10 alkyl optionally substituted with 1-6 carbonyl, halogen, hydroxyl or amino;

n1 and n2 are each independently any integer from 0-4.

Preferably, the compound of formula 0 is not any one of the following compounds:

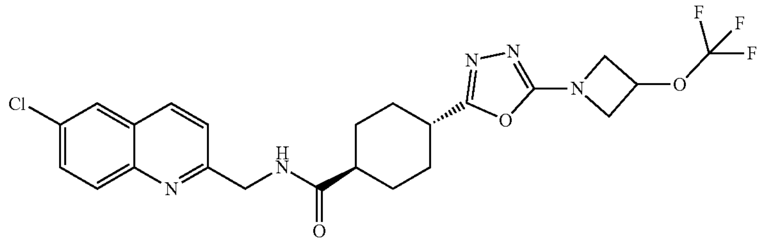

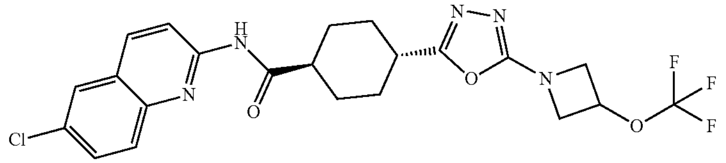

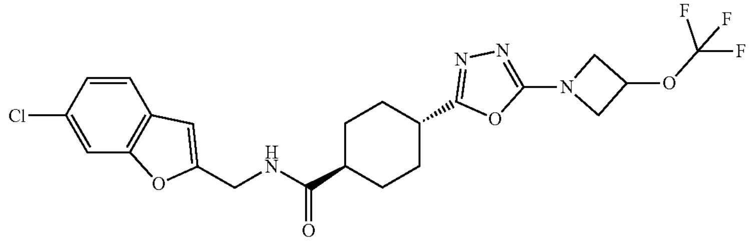

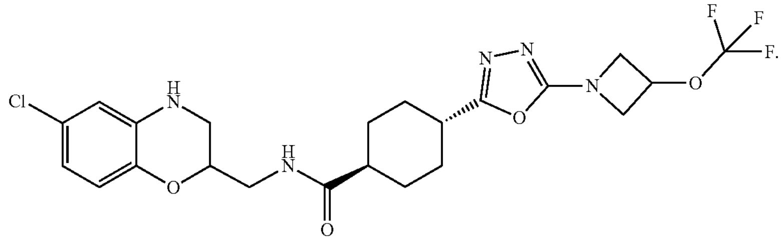

Preferably, the above-described solutions do not include any one of the following compounds, or a stereoisomer thereof, a tautomer thereof, a geometric isomer thereof, an enantiomer thereof, a diastereomer thereof, a racemate thereof, a polymorph thereof, a solvate thereof, a hydrate thereof, an N-oxide thereof, an isotopically labeled compound thereof, a metabolite thereof, an ester thereof, a prodrug thereof or a pharmaceutically acceptable salt thereof:

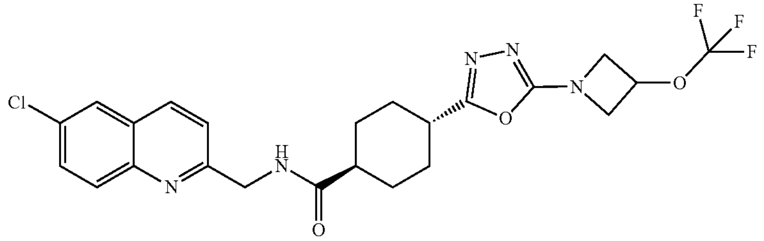

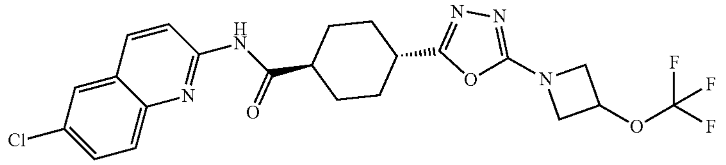

-continued

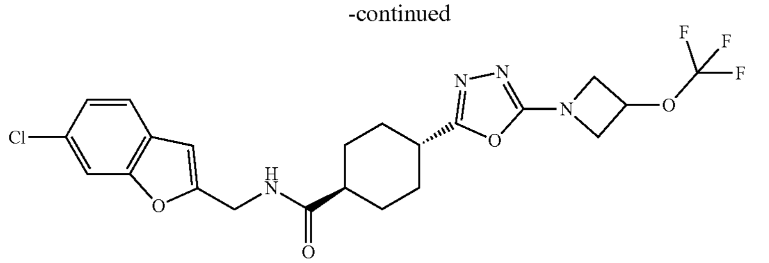

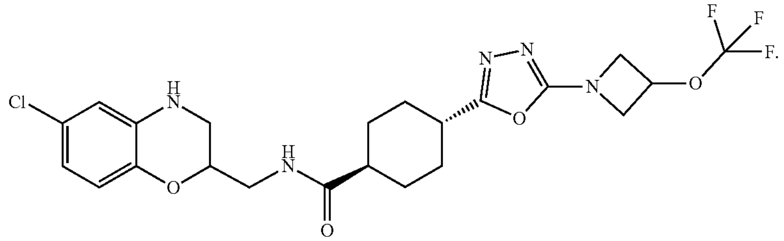

The compound of the present application can significantly weaken the integrated stress response (ISR) of cells and activate the activity of eIF2B, so that proteins in the cells tend to be synthesized normally.

In some embodiments, the n4 is 0, 1, 2 or 3;

preferably, each of the $R^{9b}$ is independently halogen, cyano, nitro, carbonyl, —OH or C1-C3 alkyl, further preferably, each of the $R^{9b}$ is independently halogen, cyano, nitro, —OH or C1-C3 alkyl;

more preferably, each of the $R^{9b}$ is independently halogen, —OH, methyl, ethyl or propyl;

further preferably, the n4 is 0.

Preferably, the ring B is selected from

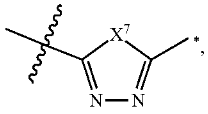, 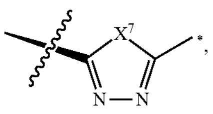, 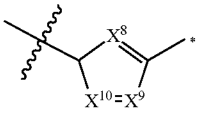 or 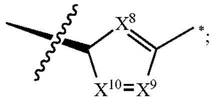;

further preferably, the ring B is selected from

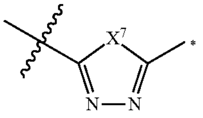 (e.g., 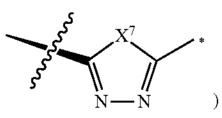) or 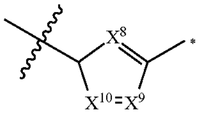 (e.g., 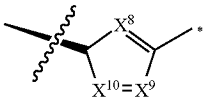), wherein $X^7$ is O or S, $X^8$, $X^9$ and $X^{10}$ are each independently CH or N, the * end is connected to ring C, and the  end is connected to ring A; more preferably, at most two of $X^8$, $X^9$ and $X^{10}$ are N;

further preferably, one of $X^8$, $X^9$ and $X^{10}$ is N.

In some embodiments, the ring B is selected from any one of the following groups:

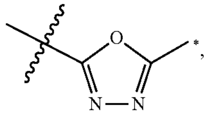, 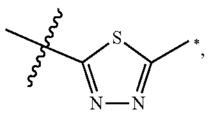, 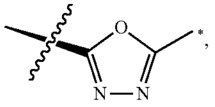, 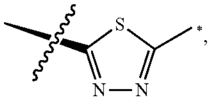, 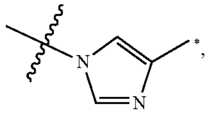, 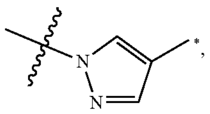, 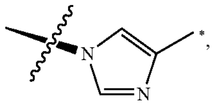, or 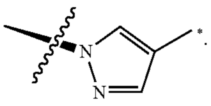.

In some embodiments, the ring B is selected from any one of the following groups:

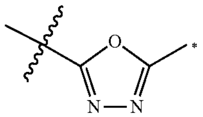 (e.g., 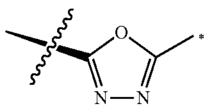), 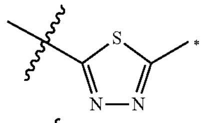 (e.g., 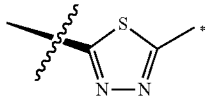), 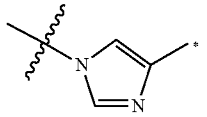 (e.g., 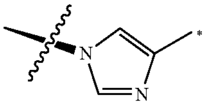) or 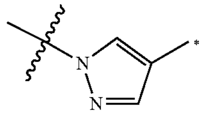 (e.g., 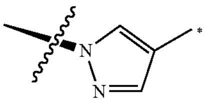).

In some embodiments, the ring B is selected from any one of the following groups:

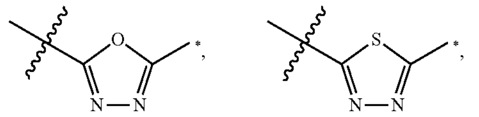

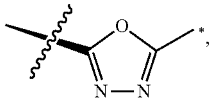, or 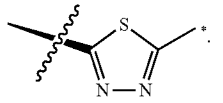.

In some embodiments, the ring B is selected from any one of the following groups:

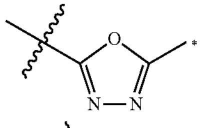 (e.g., 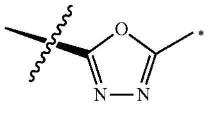) or

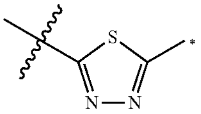 (e.g., 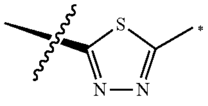).

In some embodiments, the ring B is

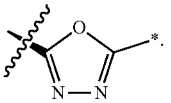

In some embodiments, the compound has a structure as shown in general formula I general formula I

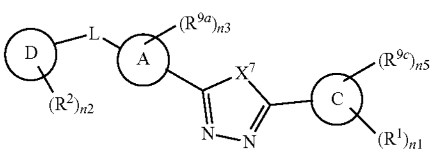

wherein ring A, ring C, ring D, L, $R^1$, $R^2$, $R^{9a}$, $R^{9c}$, n2, n2, n3 and n5 are as defined in any one of the above embodiments, and $X^7$ is O or S; or ring A, ring D, L, $R^1$, $R^2$, $R^{9a}$, $R^{9c}$, n2, n2, n3 and n5 are as defined in any one of the above embodiments, and $X^7$ is O or S.

Preferably, n1 and n2 are each independently an integer from 1-3;

further preferably, n1 is 1, and n2 is an integer from 1-3.

In some embodiments, each of the $R^{9c}$ is independently halogen, cyano, nitro, carbonyl, =O, —OH, —$NR^{30}R^{31}$, C1-C3 alkyl, —$C(O)R^{30}$ or —$C(O)OR^{30}$; preferably each of the $R^{9c}$ is independently halogen, cyano, nitro, =O, —OH, —$NR^{30}R^{31}$, C1-C3 alkyl, —$C(O)R^{30}$ or —$C(O)OR^{30}$, and $R^{30}$ and $R^{31}$ are each independently selected from H, or C1-C3 alkyl optionally substituted with 1-6 halogen, hydroxyl or amino;

preferably, the ring C may be substituted with 1 or 2 $R^{9c}$, preferably each of the $R^{9c}$ is independently halogen, cyano, nitro, carbonyl, —OH or C1-C3 alkyl, and more preferably each of the $R^{9c}$ is independently halogen, cyano, nitro, —OH or C1-C3 alkyl;

more preferably, each of the $R^{9c}$ is independently halogen, —OH, methyl, ethyl or propyl;

more preferably, each of the $R^{9c}$ is independently F or methyl.

Preferably, n5 is 0, 1 or 2;

further preferably, n5 is 0 or 1.

Preferably, as the ring C, 3- to 10-membered heterocycloalkylene is selected from

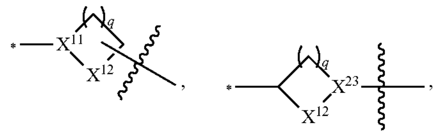

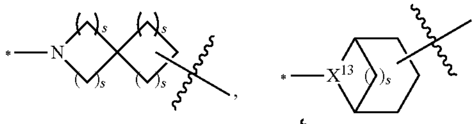 or

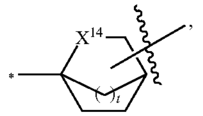

wherein $X^{11}$ and $X^{23}$ are each N or B, $X^{12}$ is $CH_2$, NH, O or S, q is an integer from 0-3, and preferably q is 1 or 2; $X^{13}$ is N or B, and s is an integer from 1-3, preferably s is 1 or 2; $X^{14}$ is O, S or NH, and t is an integer from 1-3, preferably t is 1 or 2; the * end is connected to ring B, and the  end is connected to $R^1$;

preferably, as the ring C, 3- to 10-membered heterocycloalkylene is selected from

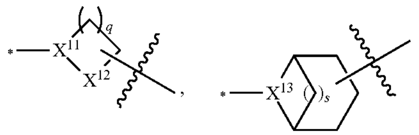 or

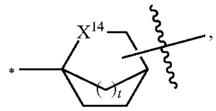

wherein $X^{11}$ is N or B, $X^{12}$ is $CH_2$, NH, O or S, q is 0-3, and preferably q is 1 or 2; $X^{13}$ is N or B, and s is an integer from 1-3, preferably s is 1 or 2; $X^{14}$ is O, S or NH, and t is an integer from 1-3, preferably t is 1 or 2;

further preferably, as the ring C, 3- to 10-membered heterocycloalkylene is selected from

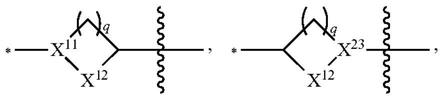

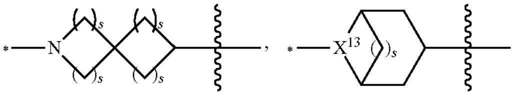 or

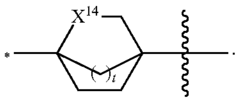

Preferably, as the ring C, $\#^{B}$—$X^{21}$—C3-C12 cycloalkylene -$\$^{R1}$ is

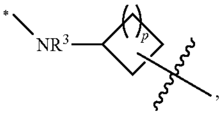

wherein $R^3$ is H, halogen, C1-C3 alkyl or C1-C3 haloalkyl, and p is an integer from 1-3, preferably 1 or 2; $\#^{B}$-represents a connecting bond connected to ring B, and -$\$^{R1}$ represents a connecting bond connected to $R^1$; the * end is connected to ring B, and the end is connected to $R^1$; Furthermore, as the ring C, $\#^{B}$—$X^{21}$—C3-C12 cycloalkylene -$\$^{R1}$ is

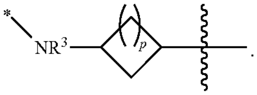

In some embodiments, the ring C is selected from

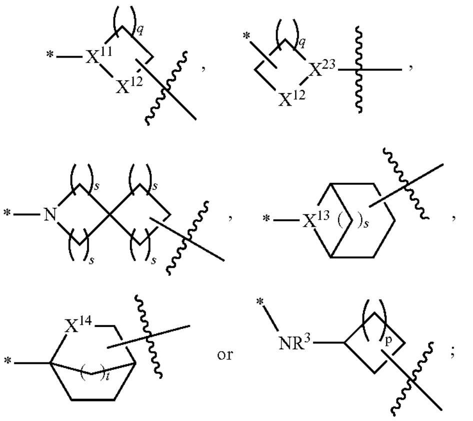

the * end is connected to ring B, and the end is connected to $R^1$.

In some embodiments, the ring C is selected from

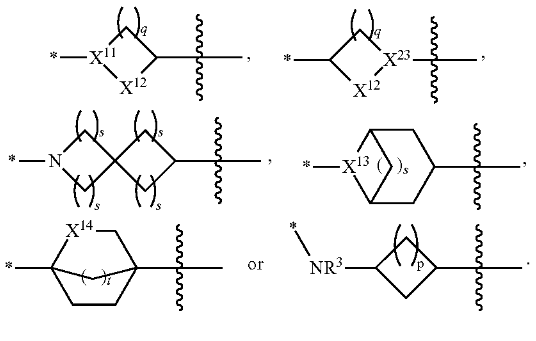

In some embodiments, the ring C is selected from

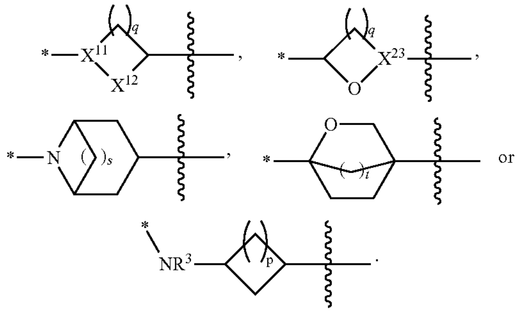

In some embodiments, the ring C is selected from

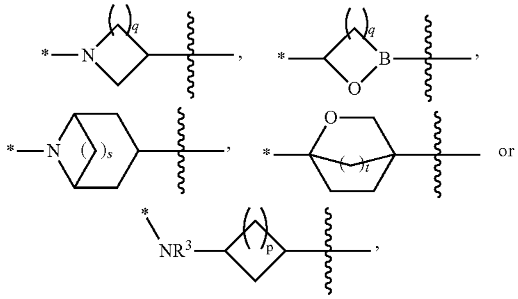

and q, p, s and t are each independently 1 or 2.

In some embodiments, the

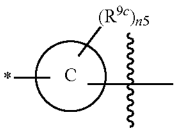

is selected from

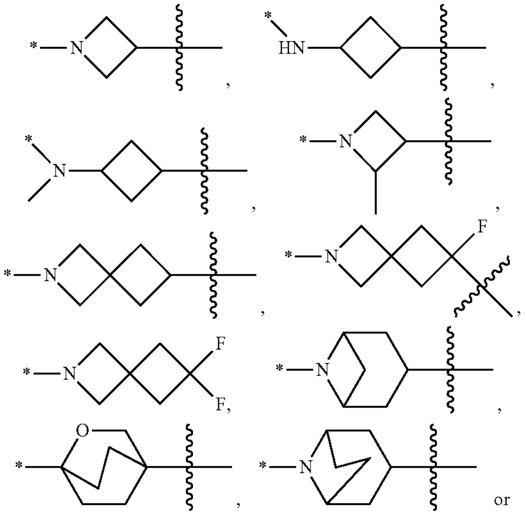

-continued

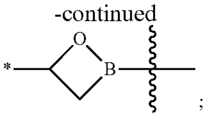

the * end is connected to ring B, and the end is connected to $R^1$.

In some embodiments, the

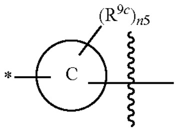

is selected from

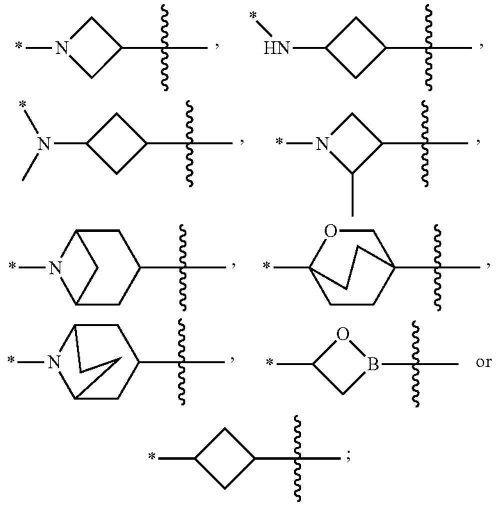

the * end is connected to ring B, and the end is connected to $R^1$.

In some embodiments, the

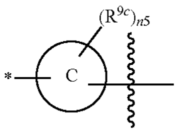

is selected from

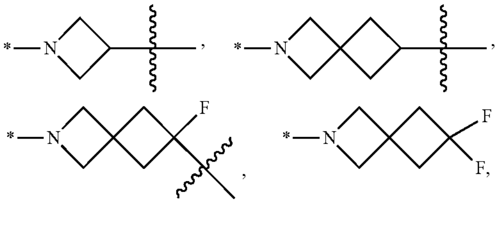

-continued

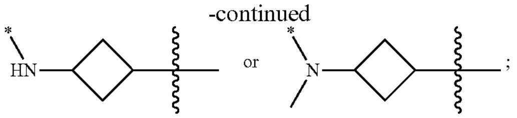

the end is connected to ring B, and the end is connected to $R^1$.

In some embodiments, the

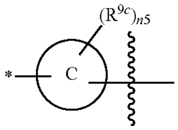

is selected from

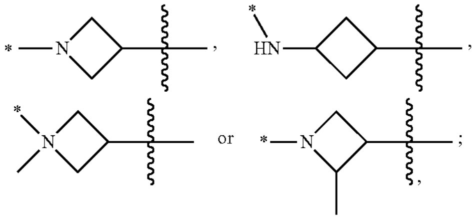

the * end is connected to ring B, and the end is connected to $R^1$.

In some embodiments, the

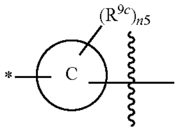

is selected from

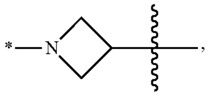 [SMILES: *C1CN(*)C1]

the * end is connected to ring B, and the end is connected to $R^1$.

In some embodiments, each $R^1$ is independently $R^{11}$, each $R^1$ is independently $R^{11}$, each $R^{11}$ is independently selected from halogen, cyano, nitro, carbonyl, ═O, —$OR^6$, —$SR^6$, —$NR^6R^7$, C1-C10 alkyl, C2-C10 alkenyl, C2-C10 alkynyl, C3-C10 cycloalkyl, 3- to 10-membered heterocycloalkyl, —$C(O)R^6$, —$C(O)OR^6$, —$OC(O)OR^6$, —$S(O)_{1-2}R^6$ or —$P(O)R^6R^7$, preferably each $R^{11}$ is independently selected from halogen, cyano, nitro, ═O, —$OR^6$, —$SR^6$, —$NR^6R^7$, C1-C10 alkyl, C2-C10 alkenyl, C2-C10 alkynyl, C3-C10 cycloalkyl, 3- to 10-membered heterocycloalkyl, —$C(O)R^6$, —$C(O)OR^6$, —$OC(O)OR^6$, —$S(O)_{1-2}R^6$ or —$P(O)R^6R^7$, wherein as $R^{11}$, C1-C10 alkyl, C2-C10 alkenyl, C2-C10 alkynyl, C3-C10 cycloalkyl and 3- to 10-membered heterocycloalkyl may each be independently substituted with 1-6 $R^{12}$, $R^6$ and $R^7$ are each independently selected from H, C1-C10 alkyl, C2-C10 alkenyl, C2-C10 alkynyl, C3-C10 cycloalkyl or 3- to 10-membered heterocycloalkyl, wherein as $R^6$ and $R^7$, C1-C10 alkyl, C2-C10 alkenyl, C2-C10 alkynyl, C3-C10 cycloalkyl and 3- to 10-membered heterocycloalkyl may each be independently substituted with 1-3 $R^{13}$;

$R^{12}$ and $R^{13}$ are each independently H, halogen, cyano, nitro, carbonyl, =O, —$OR^{30}$, C1-C10 alkyl, C2-C10 alkenyl, C2-C10 alkynyl, C3-C10 cycloalkyl or 3- to 10-membered heterocycloalkyl, preferably $R^{12}$ and $R^{13}$ are each independently H, halogen, cyano, nitro, =O, —$OR^{30}$, C1-C10 alkyl, C2-C10 alkenyl, C2-C10 alkynyl, C3-C10 cycloalkyl or 3- to 10-membered heterocycloalkyl, wherein as $R^{12}$ and $R^{13}$, C1-C10 alkyl, C2-C10 alkenyl, C2-C10 alkynyl, C3-C10 cycloalkyl and 3- to 10-membered heterocycloalkyl may each be independently substituted with 1-3 halogen, or substituted with C1-C3 alkyl optionally substituted with 1-3 carbonyl, halogen, hydroxyl or amino; preferably as $R^{12}$ and $R^{13}$, C1-C10 alkyl, C2-C10 alkenyl, C2-C10 alkynyl, C3-C10 cycloalkyl and 3- to 10-membered heterocycloalkyl may each be independently substituted with 1-3 halogen, or substituted with C1-C3 alkyl optionally substituted with 1-3 carbonyl, halogen, hydroxyl or amino, each $R^{30}$ is independently selected from H, or C1-C3 alkyl optionally substituted with 1-6 carbonyl, halogen, hydroxyl or amino, preferably each $R^{30}$ is independently selected from H, or C1-C3 alkyl optionally substituted with 1-6 halogen, hydroxyl or amino.

In some embodiments, the $R^1$ is selected from —$OR^6$, C1-C3 alkyl, halogen, C2-C4 alkenyl, —$S(O)_2R^6$ or —$P(O)R^6R^7$, preferably $R^6$ and $R^7$ are each independently selected from H or C1-C3 alkyl, wherein as $R^6$ and $R^7$, C1-C3 alkyl may be substituted with 1-3 $R^{13}$; preferably each $R^{13}$ is independently halogen, cyano or nitro.

In some embodiments, the $R^1$ is selected from —$OR^6$, C1-C3 alkyl, halogen, —$S(O)_2R^6$ or —$P(O)R^6R^7$, wherein preferably as $R^1$, C1-C3 alkyl may be substituted with 1-6 $R^{12}$, $R^{12}$ is selected from halogen or —$S(O)_2R^{30}$, $R^{30}$ is selected from C1-C3 alkyl, halo C1-C3 alkyl, C3-C6 cycloalkyl or halo C3-C6 cycloalkyl; each $R^6$ is independently selected from C1-C3 alkyl, C2-C4 alkenyl or C3-C6 cycloalkyl, wherein as $R^6$, C1-C3 alkyl, C2-C4 alkenyl or C3-C6 cycloalkyl may each be independently substituted with 1-6 $R^{13}$, and $R^{13}$ is halogen; $R^7$ is C1-C3 alkyl.

In some embodiments, the $R^1$ is —$OCH_3$, —$OCF_3$,

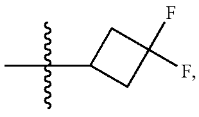, 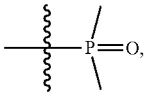,

—$CF_2CF_3$, —$CF_3$, —$CHF_2$, —$OCF_2Cl$, —$CH_2CF_3$, —$CF_3$, —F,

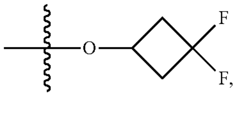, 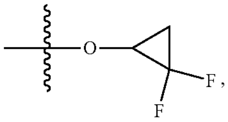,

—$OCF=CF_2$,

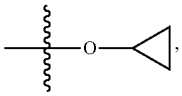, 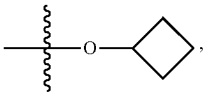,

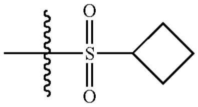, 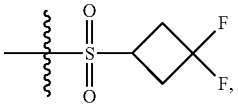,

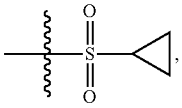, 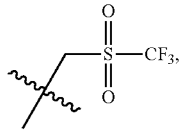, 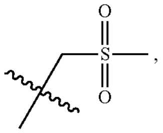,

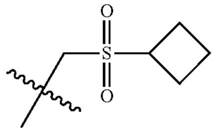 or 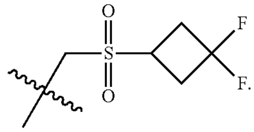.

In some embodiments, the $R^1$ is selected from —$OCH_3$, —$OCF_3$,

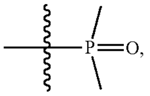 [SMILES: *P(C)(C)=O],

—$CF_2CF_3$, —$CF_3$, —$OCHF_2$, —$OCF_2CF_3$, —$OCF_2Cl$, —$CH_2CF_3$, —F,

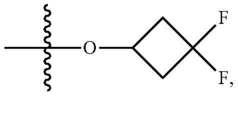, 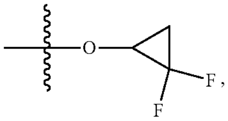,

—$OCF=CF_2$,

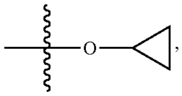, 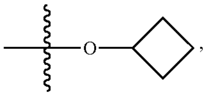,

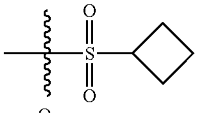, 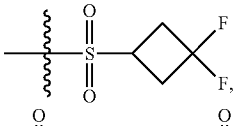,

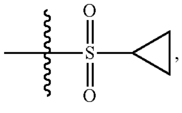, 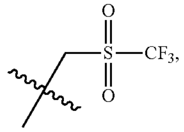, 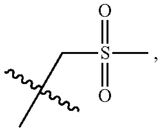,

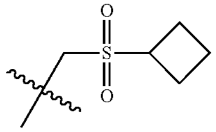 or 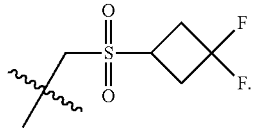.

Preferably, the $R^1$ is selected from —$OCF_3$, —$CF_2CF_3$, —$OCH_3$, —F,

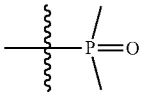 [SMILES: *P(C)(C)=O]

or $—CF_3$;

further preferably, the $R^1$ is selected from $—OCF_3$ or $—OCF_2CF_3$;

more preferably, the $R^1$ is $—OCF_3$.

In some embodiments, preferably n1 is 0 or 1.

In some embodiments, the compound has a structure as shown in general formula II general formula II

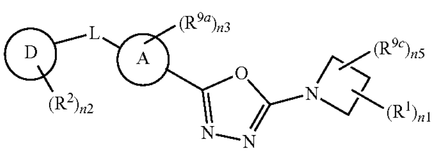

wherein ring A, ring D, L, $R^2$, $R^{9a}$, n2 and n3 are as defined in any one of the above embodiments. Preferably, the $R^1$ is $—OCH_3$, $—OCF_3$,

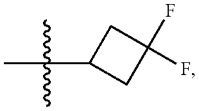 [SMILES: *C1CC(F)(F)C1] 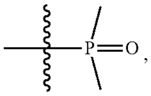

$—CF_2CF_3$, $—CF_3$, $—CHF_2$, $—OCF_2Cl$, $—CH_2CF_3$,

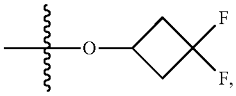 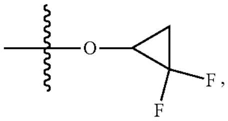

$—OCF{=}CF_2$,

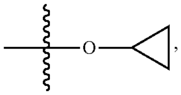, 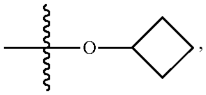,

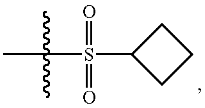, 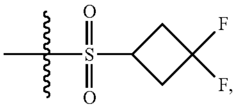

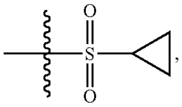, 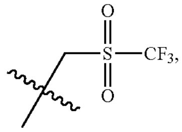 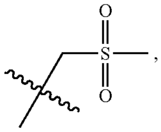

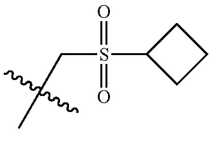 or 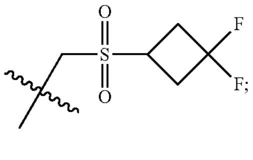

preferably, the $R^1$ is selected from $—OCH_3$, $—OCF_3$,

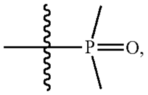

$—CF_2CF_3$, $—CF_3$, $—CHF_2$, $—OCF_2Cl$, $—CH_2CF_3$, F,

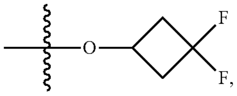 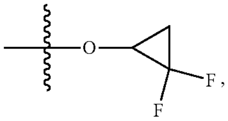

$—OCF{=}CF_2$,

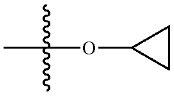 or 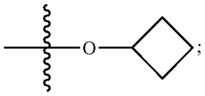;

preferably, the $R^1$ is selected from $—OCH_3$, $—OCF_3$,

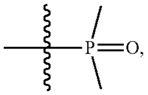 [SMILES: *P(C)(C)=O]

$—CF_2CF_3$, $—CF_3$, $—OCHF_2$, $—OCF_2CF_3$, $—OCF_2Cl$, $—CH_2CF_3$, F,

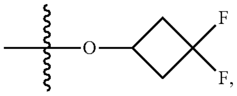 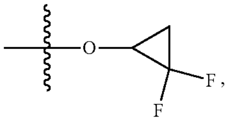

$—OCF{=}CF_2$,

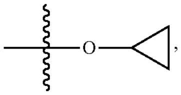, 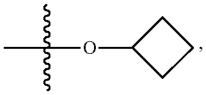,

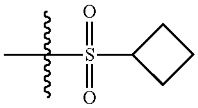, 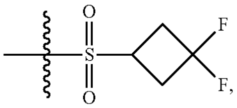

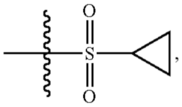, 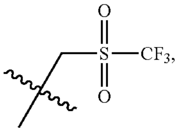 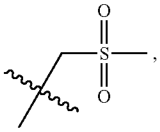

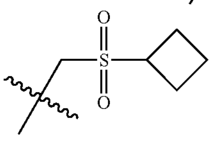 or 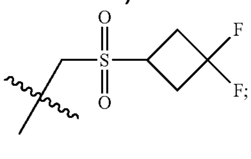

further preferably, the $R^1$ is selected from $—OCH_3$, $—OCF_3$,

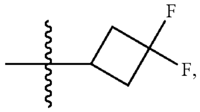 [SMILES: *C1CC(F)(F)C1]

—$CF_2CF_3$, —$CF_3$, —$CHF_2$, —$OCF_2Cl$, —$CH_2CF_3$, —$CF_3$,

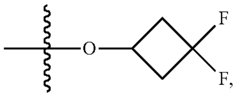 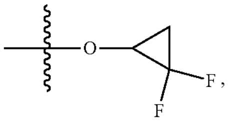,

—$OCF$=$CF_2$,

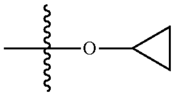 or 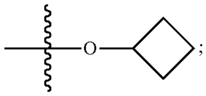;

further preferably, the $R^1$ is selected from —$OCH_3$, —$OCF_3$, —$CF_2CF_3$, —F,

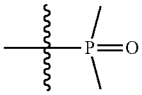

or —$CF_3$;

further preferably, the $R^1$ is —$OCF_3$ or —$OCF_2CF_3$;

more preferably, the $R^1$ is —$OCF_3$; preferably, n1 is 1;

preferably, n5 is 0, 1 or 2, each of the $R^{9c}$ is independently halogen, cyano, nitro, carbonyl, —OH or C1-C3 alkyl, preferably each of the $R^{9c}$ is independently halogen, cyano, nitro, —OH or C1-C3 alkyl;

further preferably, each of the $R^{9c}$ is independently halogen, —OH, methyl, ethyl or propyl;

more preferably, each of the $R^{9c}$ is independently F.

In some embodiments, the compound has a structure as shown in general formula II-1 general formula II-1

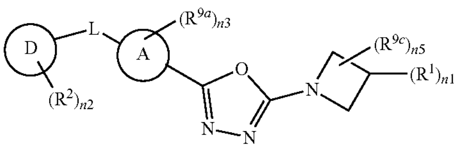

wherein ring A, ring D, L, $R^2$, $R^{9a}$, n2 and n3 are as defined in any one of the above embodiments.

Preferably, n5 is 0 or 1, preferably n5 is 1, the $R^{9c}$ is selected from halogen, cyano, nitro, carbonyl, —OH or C1-C3 alkyl; preferably the $R^{9c}$ is selected from halogen, cyano, nitro, —OH or C1-C3 alkyl;

further preferably, the $R^{9c}$ is selected from halogen, methyl or ethyl;

more preferably, the $R^{9c}$ is F.

Preferably, the

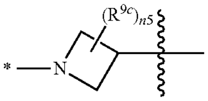

is selected from

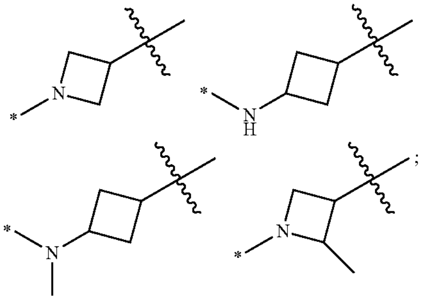

further preferably, the

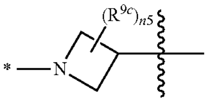

is selected from

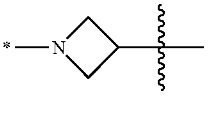 or 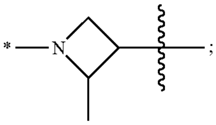;

preferably, n1 is 1, and the $R^1$ is selected from —$OCH_3$, —$OCF_3$,

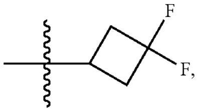 [SMILES: *C1CC(F)(F)C1]

—$CF_2CF_3$, —$CF_3$, —$CHF_2$, —$OCF_2Cl$, —$CH_2CF_3$,

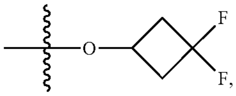 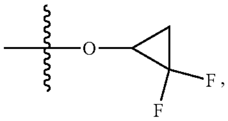,

—$OCF$=$CF_2$,

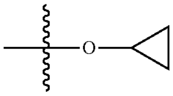 or 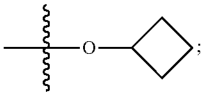;

further preferably, the $R^1$ is selected from —$OCH_3$, —$OCF_3$,

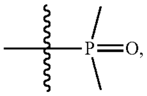 [SMILES: *P(C)(C)=O]

—$CF_2CF_3$, —$CF_3$, —$CHF_2$, —$OCF_2Cl$, —$CH_2CF_3$, —$OCF_2CF_3$,

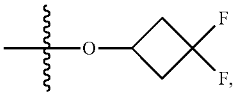 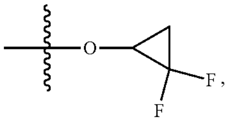

—OCF=$CF_2$,

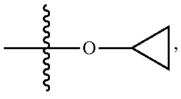, 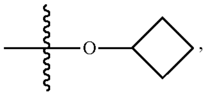,

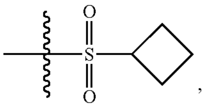, 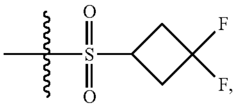

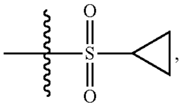, 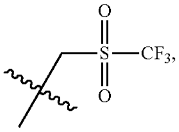, 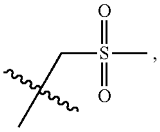,

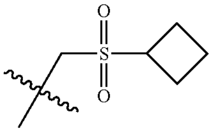 or 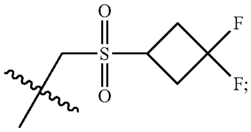

further preferably, the $R^1$ is selected from —$OCH_3$, —$OCF_3$,

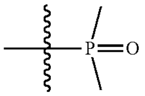

or —$OCF_2CF_3$;

further preferably, the $R^1$ is selected from —$OCF_3$ or —$OCF_2CF_3$;

more preferably, the $R^1$ is —$OCF_3$.

In some embodiments, n3 is 0, 1 or 2;

preferably, the ring A is selected from C5-C8 cycloalkylene or 5- to 8-membered heterocycloalkylene.

In some embodiments, the ring A is selected from cyclohexylene or 6-membered heterocycloalkylene.

In some embodiments, the ring A is selected from cyclohexylene or

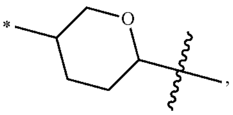

the * end is connected to L, and the  end is connected to ring B.

In some embodiments, the ring A is selected from

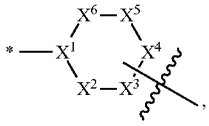

C5-C8 bridged cycloalkylene or 6- to 8-membered bridged heterocycloalkylene, wherein $X^1$ is CH or N, $X^2$, $X^3$, $X^4$, $X^5$ and $X^6$ are each independently $CH_2$, CH, NH, N or O, the * end is connected to L, and the  end is connected to ring B.

In some embodiments, the ring A is selected from

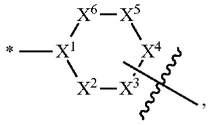

C6-C8 bridged cycloalkylene or 6- to 8-membered bridged heterocycloalkylene, wherein $X^1$ is CH or N, $X^2$, $X^3$, $X^4$, $X^5$ and $X^6$ are each independently $CH_2$, CH, NH, N or O, the * end is connected to L, and the  end is connected to ring B.

In some embodiments, in the

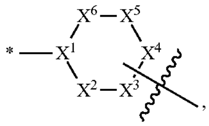

$X^5$ is $CH_2$ or O, and $X^2$, $X^3$, $X^4$ and $X^6$ are each independently $CH_2$ or CH;

preferably, the $X^2$, $X^3$ and $X^6$ are $CH_2$, and $X^4$ is CH.

In some embodiments, as the ring A,

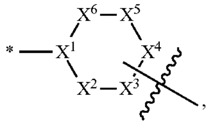

C6-C8 bridged cycloalkylene or 6- to 8-membered bridged heterocycloalkylene may each be independently substituted with 1-4 $R^{9a}$, preferably is substituted with 1 or 2 $R^{9a}$.

In some embodiments, as the ring A,

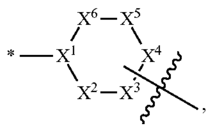

C5-C8 bridged cycloalkylene or 6- to 8-membered bridged heterocycloalkylene may each be independently substituted with 0-4 $R^{9a}$;

preferably, the ring A is substituted with 0, 1 or 2 $R^{9a}$;

more preferably, the ring A is substituted with 0 or 1 $R^{9a}$.

In some embodiments, the C6-C8 bridged cycloalkylene is

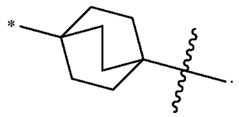

In some embodiments, the C5-C8 bridged cycloalkylene is

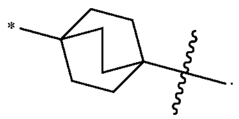

In some embodiments, the bridged heterocycloalkylene is

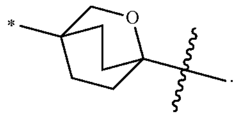

In some embodiments, the bridged heterocycloalkylene is

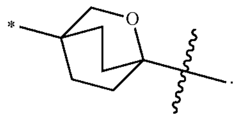

In some embodiments, each of the $R^{9a}$ is independently halogen, cyano, nitro, carbonyl, =O, —$OR^6$, —$SR^6$, $SF_5$, —$NR^6R^7$, C1-C6 alkyl, C2-C6 alkenyl, C2-C6 alkynyl, C3-C8 cycloalkyl, 3- to 8-membered heterocycloalkyl, C6-C10 aryl, 5- to 10-membered heteroaryl, —C(O)$R^6$, —C(O)$OR^6$, —OC(O)$OR^6$, OC(O)$R^6$, —C(O)$NR^6R^7$, —C(O)$ONR^6R^7$, —$NR^6$C(O)$NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6$C(O)$R^7$ or —$NR^6$C(O)$OR^7$, preferably each of the $R^{9a}$ is independently halogen, cyano, nitro, =O, —$OR^6$, —$SR^6$, —$SF_5$, —$NR^6R^7$, C1-C6 alkyl, C2-C6 alkenyl, C2-C6 alkynyl, C3-C8 cycloalkyl, 3- to 8-membered heterocycloalkyl, C6-C10 aryl, 5- to 10-membered heteroaryl, —C(O)$R^6$, —C(O)$OR^6$, —OC(O)$OR^6$, —OC(O)$R^6$, —C(O)$NR^6R^7$, —C(O)$ONR^5R^7$, —$NR^6$C(O)$NR^7R^8$, —$S(O)_{1-2}R^6$, —$S(O)_{1-2}NR^6$, —$NR^6S(O)_{1-2}R^7$, —$NR^6$ $S(O)_{1-2}NR^7R^8$, —$NR^6$C(O)$R^7$ or —$NR^6$C(O)$OR^7$, wherein as $R^{9a}$, C1-C6 alkyl, C2-C6 alkenyl, C2-C6 alkynyl, C3-C8 cycloalkyl, 3- to 8-membered heterocycloalkyl, C6-C10 aryl and 5- to 10-membered heteroaryl may each be independently substituted with 1-6 $R^{12}$;

$R^6$, $R^7$ and $R^8$ are each independently selected from H, C1-C6 alkyl, C2-C6 alkenyl, C2-C6 alkynyl, C3-C8 cycloalkyl, 3- to 8-membered heterocycloalkyl, C6-C10 aryl, 5- to 10-membered heteroaryl, —C(O)$R^{20}$, —C(O)$OR^{20}$, —C(O)$NR^{20}R^{21}$, —$S(O)_{1-2}R^{20}$ or —$S(O)_{1-2}NR^{20}$, wherein as $R^6$, $R^7$ and $R^8$, C1-C6 alkyl, C2-C6 alkenyl, C2-C6 alkynyl, C3-C8 cycloalkyl, 3- to 8-membered heterocycloalkyl, C6-C10 aryl and 5- to 10-membered heteroaryl may each be independently substituted with 1-4 $R^{13}$;

$R^{12}$ and $R^{13}$ are each independently H, halogen, cyano, nitro, carbonyl, =O, —$OR^{30}$, —$SR^{30}$, $SF_5$, —$NR^{30}R^{31}$, C1-C6 alkyl, C2-C6 alkenyl, C2-C6 alkynyl, C3-C8 cycloalkyl, 3- to 8-membered heterocycloalkyl, C6-C10 aryl, 5- to 10-membered heteroaryl, —C(O)$R^{30}$, —C(O)$OR^{30}$, —OC(O)$OR^{30}$, —OC(O)$R^{30}$, —C(O)$NR^{30}R^{31}$, —C(O)$ONR^{30}R^{31}$, —$NR^{30}$C(O)$NR^{30}R^{31}$, —$S(O)_{1-2}R^{30}$, —$S(O)_{1-2}NR^{30}$, $NR^{30}S(O)_{1-2}R^{31}$, —$NR^{30}S(O)_{1-2}NR^{30}R^{31}$, —$NR^{30}$C(O)$R^{31}$ or —$NR^{30}$C(O)$OR^{31}$, preferably $R^{12}$ and $R^{13}$ are each independently H, halogen, cyano, nitro, =O, —$OR^{30}$, —$SR^{30}$, $SF_5$, —$NR^{30}R^{31}$, C1-C6 alkyl, C2-C6 alkenyl, C2-C6 alkynyl, C3-C8 cycloalkyl, 3- to 8-membered heterocycloalkyl, C6-C10 aryl, 5- to 10-membered heteroaryl, —C(O)$R^{30}$, —C(O)$OR^{30}$, —OC(O)$OR^{30}$, —OC(O)$R^{30}$, —C(O)$NR^{30}R^{31}$, —C(O)$ONR^{30}R^{31}$, —$NR^{30}$C(O)$NR^{30}R^{31}$, —$S(O)_{1-2}R^{30}$, —$S(O)_{1-2}NR^{30}$, —$NR^{30}S(O)_{1-2}R^{31}$, —$NR^{30}S(O)_{1-2}NR^{30}R^{31}$, —$NR^{30}$C(O)$R^{31}$ or —$NR^{30}$C(O)$OR^{31}$, wherein as $R^{12}$ and $R^{13}$, C1-C6 alkyl, C2-C6 alkenyl, C2-C6 alkynyl, C3-C8 cycloalkyl, 3- to 8-membered heterocycloalkyl, C6-C10 aryl and 5- to 10-membered heteroaryl may each be independently substituted with 1-6 halogen, or substituted with C1-C6 alkyl optionally substituted with 1-6 carbonyl, halogen, hydroxyl or amino, preferably as $R^{12}$ and $R^{13}$, C1-C6 alkyl, C2-C6 alkenyl, C2-C6 alkynyl, C3-C8 cycloalkyl, 3- to 8-membered heterocycloalkyl, C6-C10 aryl and 5- to 10-membered heteroaryl may each be independently substituted with 1-6 halogen, or substituted with C1-C6 alkyl optionally substituted with 1-6 carbonyl, halogen, hydroxyl or amino, $R^{20}$ and $R^{21}$ are each independently selected from H, or C1-C6 alkyl optionally substituted with 1-6 carbonyl, halogen, hydroxyl or amino, preferably $R^{20}$ and $R^{21}$ are each independently selected from H, or C1-C6 alkyl optionally substituted with 1-6 halogen, hydroxyl or amino;

$R^{30}$ and $R^{31}$ are each independently selected from H, or C1-C6 alkyl optionally substituted with 1-6 carbonyl, halogen, hydroxyl or amino, preferably $R^{30}$ and $R^{31}$ are each independently selected from H, or C1-C6 alkyl optionally substituted with 1-6 halogen, hydroxyl or amino.

In some embodiments, each of the $R^{9a}$ is independently halogen, cyano, nitro, carbonyl, =O, —OH, —$NR^{30}R^{31}$, C1-C3 alkyl, C1-C3 haloalkyl, —C(O)$R^{30}$ or —C(O)$OR^{30}$, and $R^{30}$ and $R^{31}$ are each independently selected from H, or C1-C3 alkyl optionally substituted with 1-6 halogen, hydroxyl or amino; preferably each of the $R^{9a}$ is independently halogen, cyano, nitro, =O, —OH, —$NR^{30}R^{31}$, C1-C3 alkyl, C1-C3 haloalkyl, —C(O)$R^{30}$ or —C(O)$OR^{30}$, and $R^{30}$ and $R^{31}$ are each independently selected from H, or C1-C3 alkyl optionally substituted with 1-6 halogen, hydroxyl or amino.

In some embodiments, each of the $R^{9a}$ is independently halogen, cyano, nitro, carbonyl, =O, —OH, methyl, ethyl, fluoromethyl or fluoroethyl; preferably each of the $R^{9a}$ is independently halogen, cyano, nitro, =O, —OH, methyl, ethyl, fluoromethyl or fluoroethyl.

In some embodiments, each of the $R^{9a}$ is independently —OH or =O.

In some embodiments, each of the $R^{9a}$ is independently —OH.

In some embodiments, the

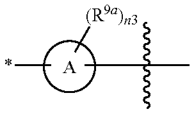

is selected from

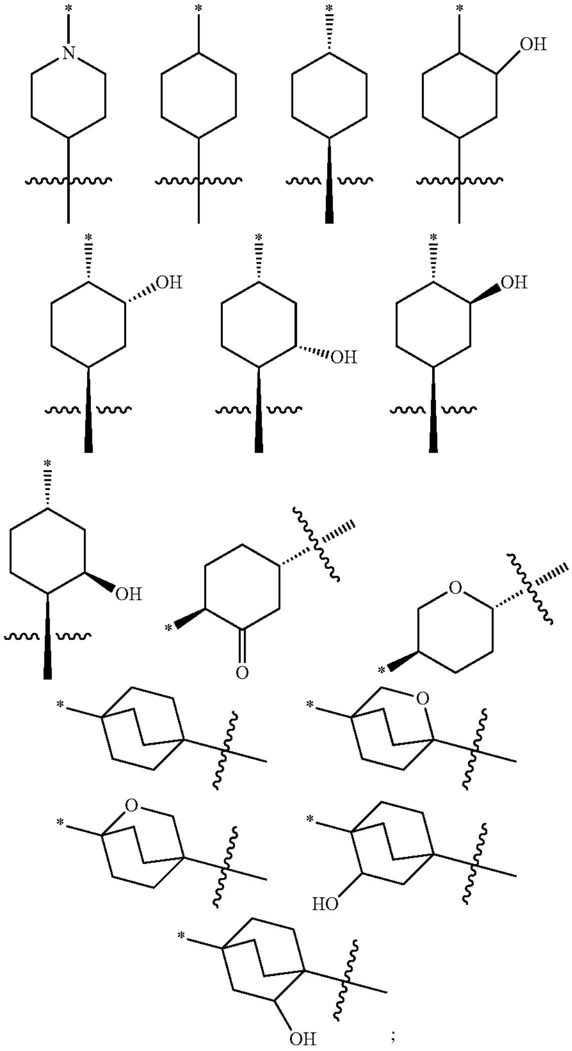

;

the * end is connected to L, and the end is connected to ring B.

In some embodiments, the

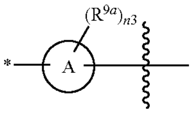

is selected from

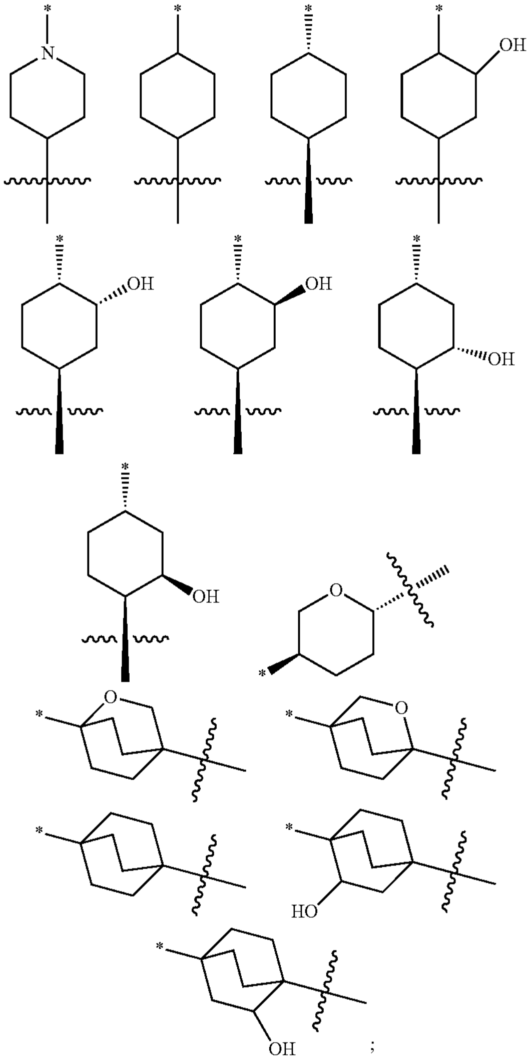

;

the * end is connected to L, and the end is connected to ring B.

In some embodiments, the

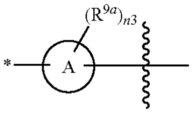

is selected from
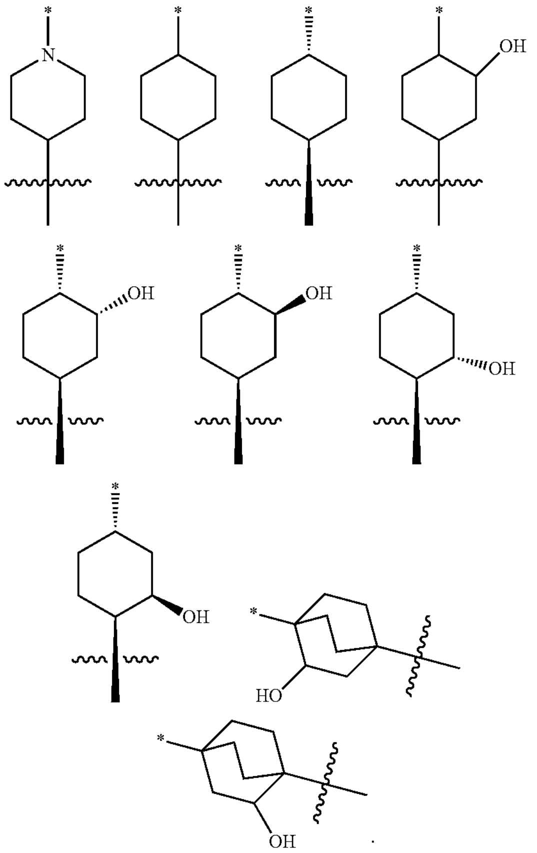
In some embodiments, the
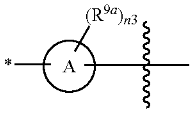
is selected from
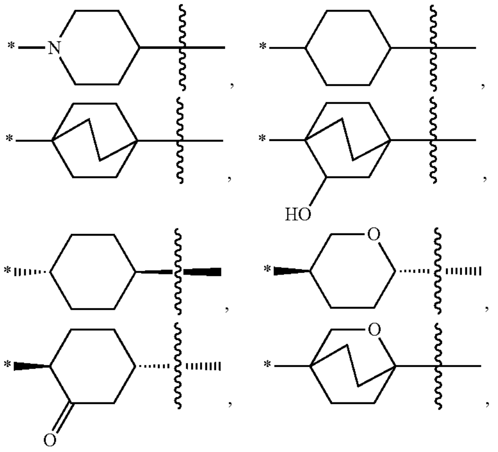
-continued
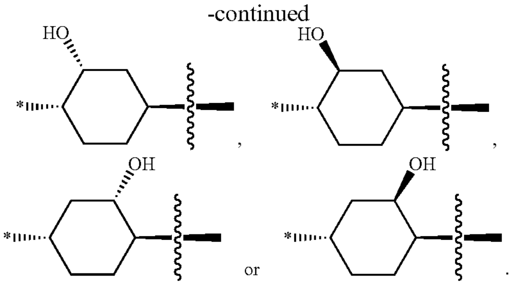
or
In some embodiments, the
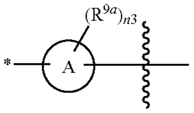
is selected from
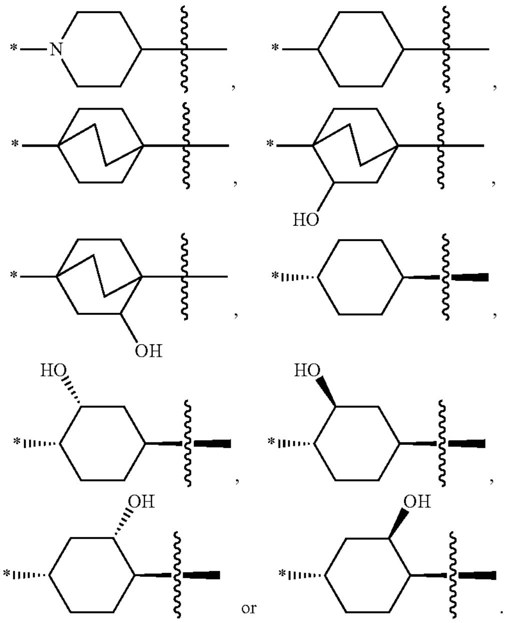
or
In some embodiments, the
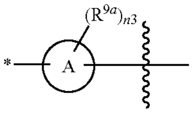
is selected from
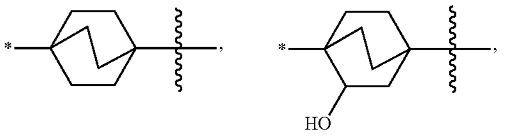

-continued

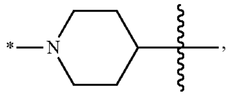,

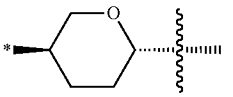 or

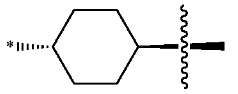.

In some embodiments, the

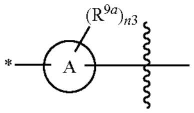

is selected from

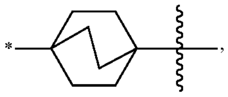,

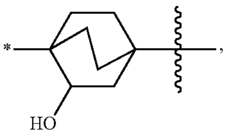,

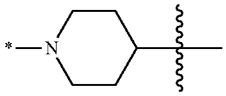 or

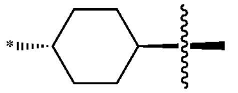.

In some embodiments, the compound has a structure as shown in general formula III general formula III

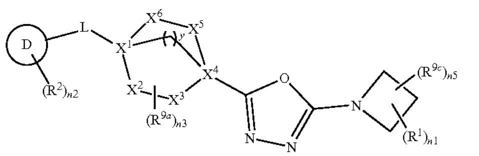

wherein $X^1$ is CH or N, $X^2$, $X^3$, $X^4$, $X^5$ and $X^6$ are each independently $CH_2$, CH, NH, N or O;

preferably $X^1$ and $X^4$ are each independently CH or N, $X^2$, $X^3$, $X^5$ and $X^6$ are each independently $CH_2$, CH, NH, N or C, and v is an integer from 0-2; ring D, L, $R^1$, $R^2$, $R^{9a}$, $R^{9c}$, n1, n2, n3 and n5 are as defined in any one of the above embodiments.

Preferably, each of the $R^{9a}$ is independently halogen, =O, —OH or C1-C3 alkyl, more preferably —OH.

ring D, L, $R^1$, $R^2$, $R^{9a}$, $R^{9c}$, $n_1$, $n_2$, $n_3$ and $n_5$ are as defined in any one of the above embodiments.

In some embodiments, the compound has a structure as shown in any one of general formulas III-1 to III-6 general formula III-1

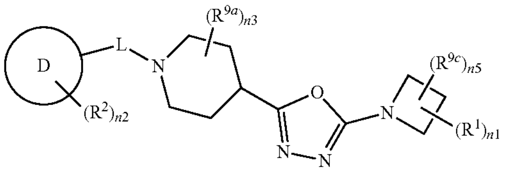

general formula III-2

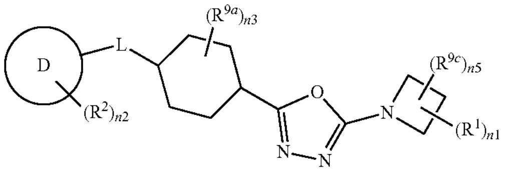

general formula III-3

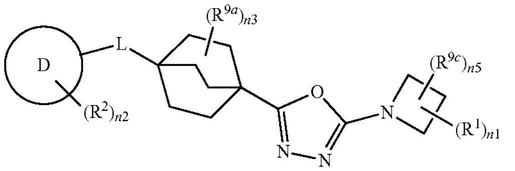

general formula III-4

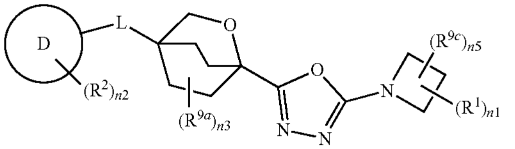

general formula III-5

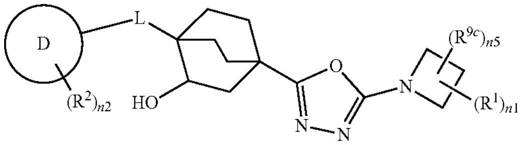

general formula III-6

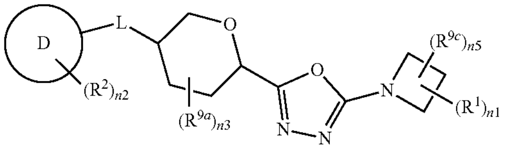

wherein ring D, L, $R^1$, $R^2$, $R^{9a}$, $R^{9c}$, n1, n2, n3 and n5 are defined in any one of the above embodiments.

Preferably, $R^{9a}$ is hydroxyl or halogen;

more preferably, $R^{9a}$ is hydroxyl;

preferably, n3 is an integer from 0-3, more preferably 0, 1 or 2.

In some embodiments, the compound has a structure as shown in any one of the following general formulas:

general formula III-1-1

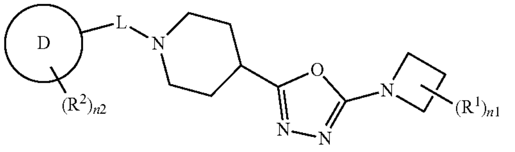

-continued general formula III-2-1

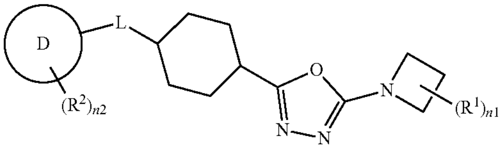

general formula III-2-2

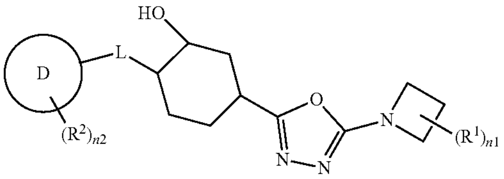

general formula III-2-3

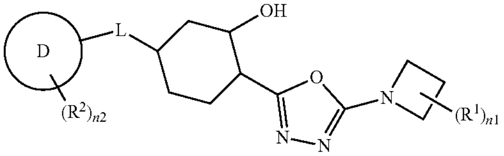

general formula III-3-1

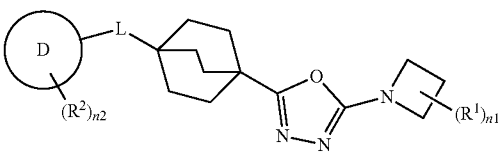

general formula III-4-1

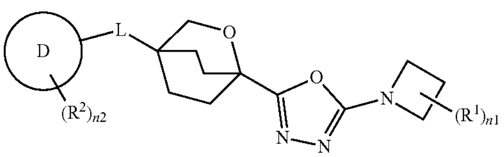

general formula III-4-2

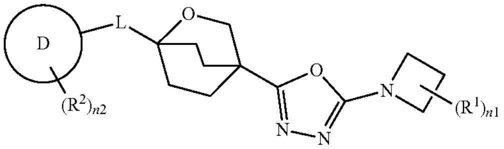

general formula III-5-1

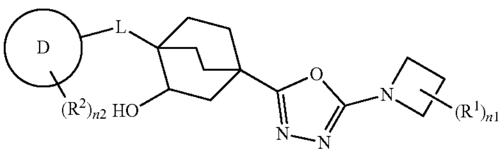

general formula III-5-2

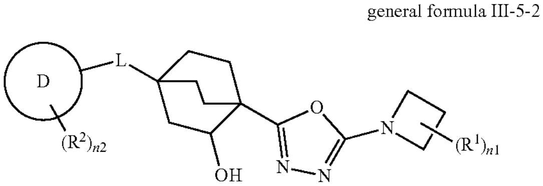

-continued general formula III-6-1

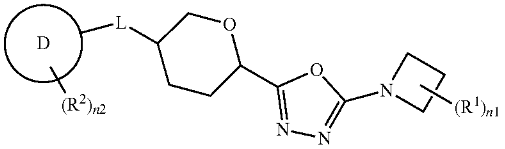

wherein the ring D, L, $R^1$, $R^2$, n1 and n2 are as defined in any one of the above embodiments.

In some embodiments, the L is $\#^D$-$L^1$-$L^2$-$L^3$-$\$^A$ or

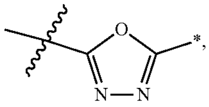

$L^1$ is a bond, —O—, —S— or —$NR^4$—, preferably $L^1$ is —O—, —S— or —$NR^4$—, $L^2$ is a bond, or substituted or unsubstituted C1-C3 alkylene, preferably $L^2$ is substituted or unsubstituted C1-C3 alkylene, $L^3$ is —$C(X^{10})NR^5$-$\$^A$ or —$C(X^{10})$-$\$^A$, $X^{10}$ is O or S, $R^4$ and $R^5$ are each independently selected from H, C1-C3 alkyl, C2-C4 alkenyl, C2-C4 alkynyl, C3-C6 cycloalkyl, or 3- to 6-membered heterocycloalkyl; as $R^4$ and $R^5$, C1-C3 alkyl, C2-C4 alkenyl, C2-C4 alkynyl, C3-C6 cycloalkyl and 3- to 6-membered heterocycloalkyl may each be independently substituted with 1-3 $R^{11}$; each $R^{11}$ is independently selected from halogen, cyano, nitro, carbonyl, ═O, —OH, —SH or —$NH_2$, preferably each $R^{11}$ is independently selected from halogen, cyano, nitro, ═O, —OH, —SH or —$NH_2$, and preferably each $R^{11}$ is independently selected from halogen, cyano, nitro, —OH, —SH or —$NH_2$; $\#^D$-represents a connecting bond connected to ring D, and -$\$^A$ represents a connecting bond connected to ring A; the * end is connected to ring A, and the  end is connected to ring D.

In some embodiments, the L is $\#^D$-$L^1$-$L^2$-$L^3$-$\$^A$,

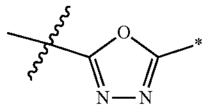 [SMILES: *c1nnc(*)o1]

or $\#^D$—$NR^{14}C(O)$—C1-C6 alkylene-O-$\$^A$, $L^1$ is a bond, —O—, —S— or —$NR^4$—, $L^2$ is a bond, or substituted or unsubstituted C1-C3 alkylene, $L^3$ is —$C(X^{10})NR^5$-$\$^A$ or —$C(X^{10})$-$\$^A$, $X^{10}$ is O or S, $R^4$, $R^5$ and $R^{14}$ are each independently selected from H, C1-C3 alkyl, C2-C4 alkenyl, C2-C4 alkynyl, C3-C6 cycloalkyl or 3- to 6-membered heterocycloalkyl; as $R^4$, $R^5$ and $R^{14}$, C1-C3 alkyl, C2-C4 alkenyl, C2-C4 alkynyl, C3-C6 cycloalkyl and 3- to 6-membered heterocycloalkyl may each be independently substituted with 1-3 $R^{11}$; each $R^{11}$ is independently selected from halogen, cyano, nitro, ═O, —OH, —SH or —$NH_2$, and preferably each $R^{11}$ is independently selected from halogen, cyano, nitro, —OH, —SH or —$NH_2$; $\#^D$-represents a connecting bond connected to ring D, -$\$^A$ represents a connecting bond connected to ring A, the * end is connected to ring A, and the  end is connected to ring D.

In some embodiments, the L is selected from

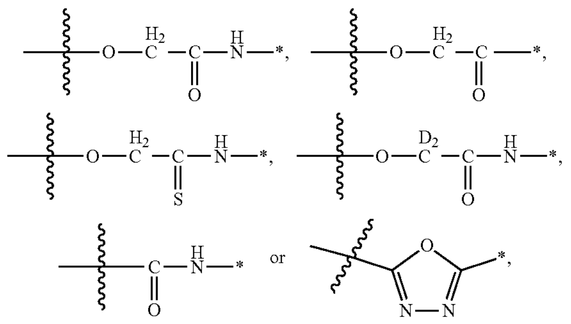

the * end is connected to ring A, and the end is connected to ring D.

In some embodiments, the L is selected from

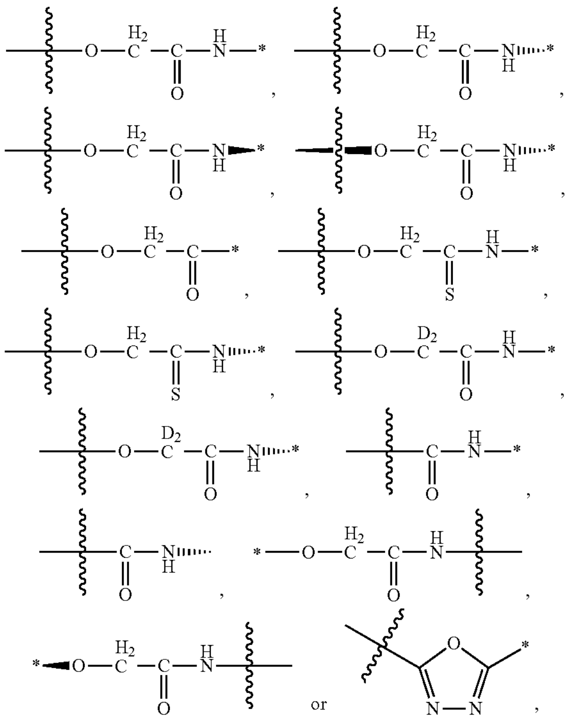

the * end is connected to ring A, and the end is connected to ring D.

In some embodiments, the L is selected from

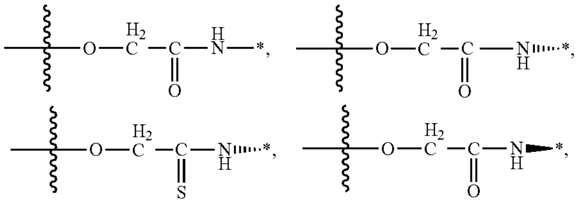

-continued

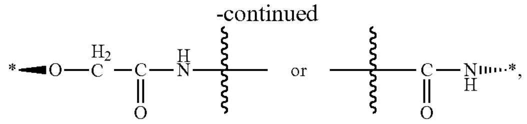

the * end is connected to ring A, and the end is connected to ring D.

In some embodiments, the L is selected from

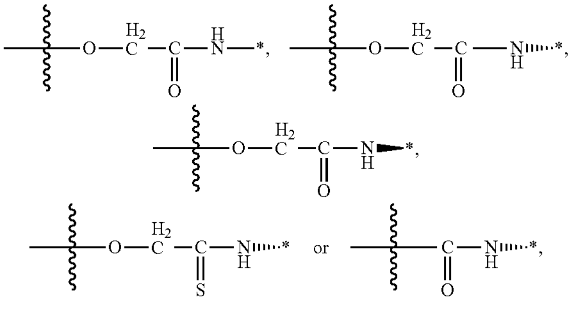

the * end is connected to ring A, and the end is connected to ring D.

In some embodiments, the L is selected from

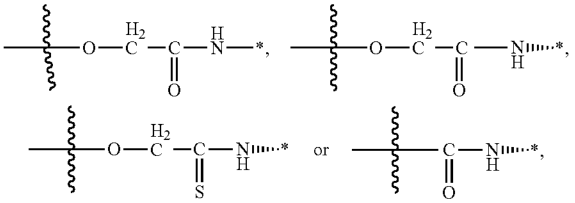

the * end is connected to ring A, and the end is connected to ring D.

In some embodiments, the L is selected from

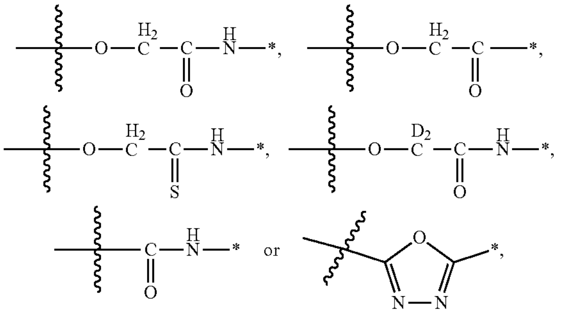

the * end is connected to ring A, and the end is connected to ring D.

In some embodiments, the compound has a structure as shown in general formula IV-1 or IV-2 general formula IV-1

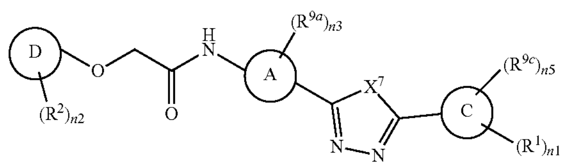

general formula IV-2

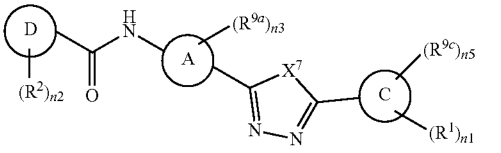

wherein ring D, $R^1$, $R^2$, $R^{9a}$, $R^{9c}$, n1, n2, n3 and n5 are defined in any one of the above embodiments, preferably ring A, ring C, ring D, $R^1$, $R^2$, $R^{9a}$, $R^{9c}$, n1, n2, n3 and n5 are as defined in any one of the above embodiments, and $X^7$ is O or S.

In some embodiments, the compound has a structure as shown in general formula V-1 or V-2 general formula V-1

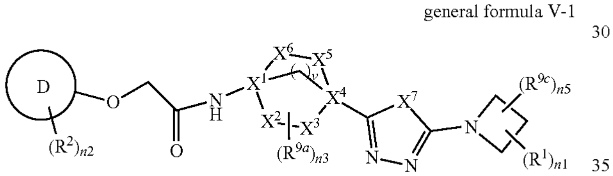

general formula V-2

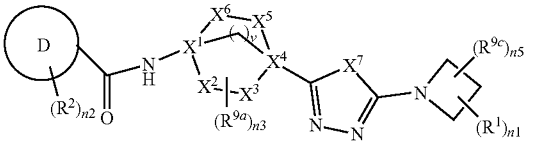

wherein v is an integer from 0-2, ring D, $R^1$, $R^2$, $R^{9a}$, $R^{9c}$, n1, n2, n3 and n5 are as defined in any one of the above embodiments, and $X^7$ is O or S.

In some embodiments, the

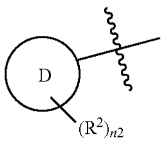

is selected from

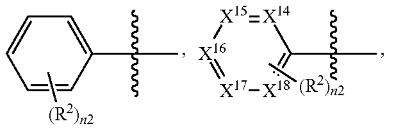

-continued

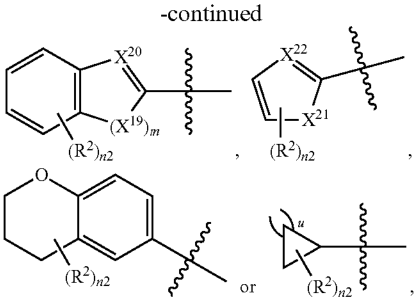

wherein $X^{14}$, $X^{15}$, $X^{16}$, $X^{17}$ and $X^{18}$ are each independently selected from CH or N, with at least one being N, preferably at most three being N, and more preferably at most two being N; $X^{19}$ and $X^{20}$ are each independently selected from CH, N, NH, O or S, and are not S or O simultaneously, and m is 1 or 2; $X^{21}$ and $X^{22}$ are each independently selected from CH, N, NH, O or S, and are not S or O simultaneously, and m is 1 or 2; u is 1, 2 or 3.

In some embodiments, the

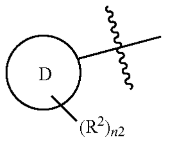

is selected from

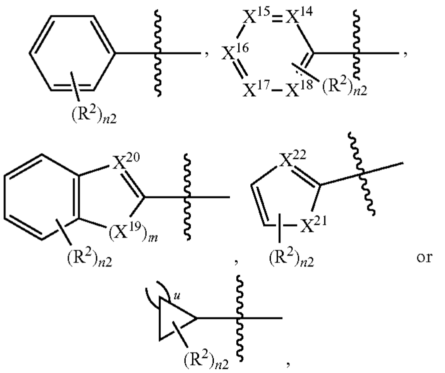

wherein $X^{14}$, $X^{15}$, $X^{16}$, $X^{17}$ and $X^{18}$ are each independently selected from CH or N, with at least one being N, preferably at most three being N, and more preferably at most two being N; $X^{19}$ and $X^{20}$ are each independently selected from CH, N, NH, O or S, and are not S or O simultaneously, and m is 1 or 2; $X^{21}$ and $X^{22}$ are each independently selected from CH, N, NH, O or S, and are not S or O simultaneously, and m is 1 or 2; u is 1, 2 or 3.

In some embodiments, the

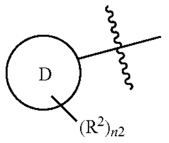

is selected from
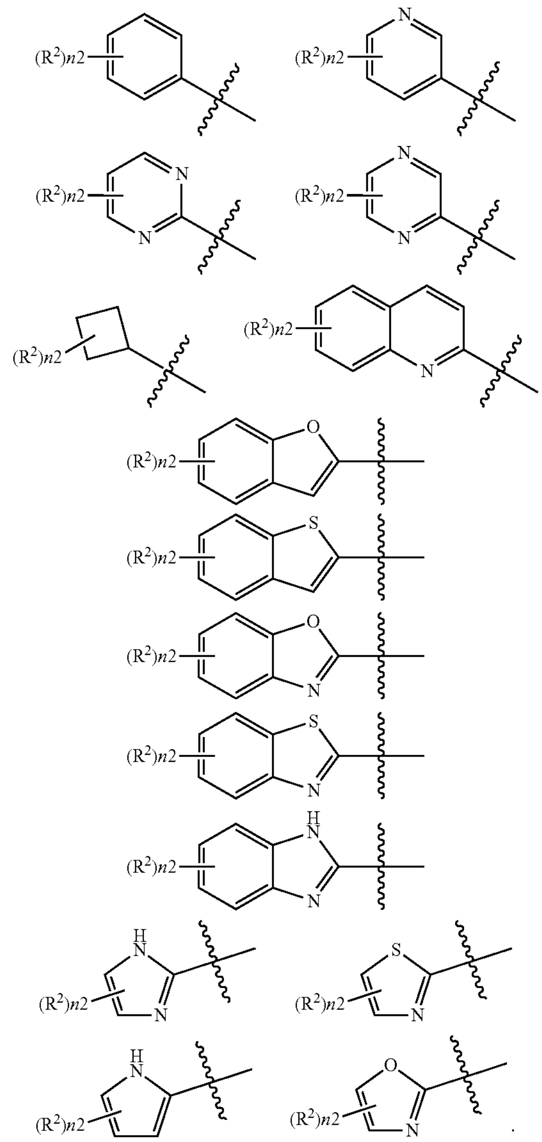
In some embodiments, the
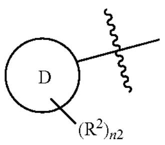
is selected from
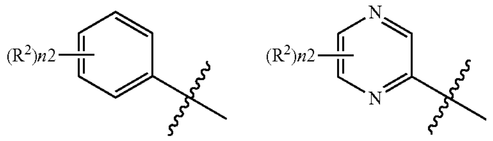
-continued
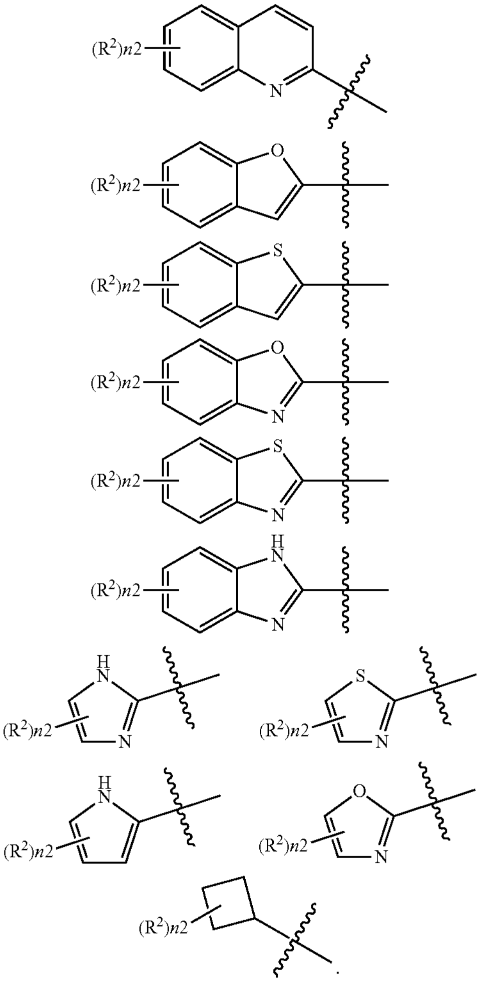
In some embodiments, the
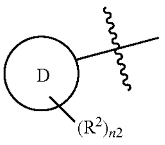
is selected from
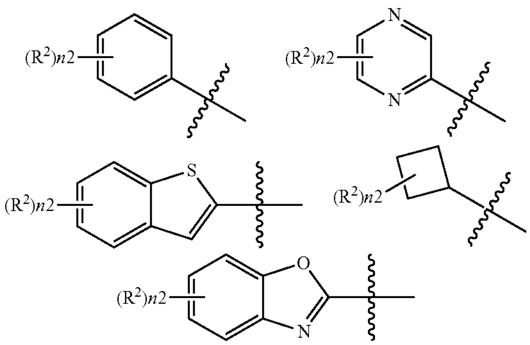

-continued
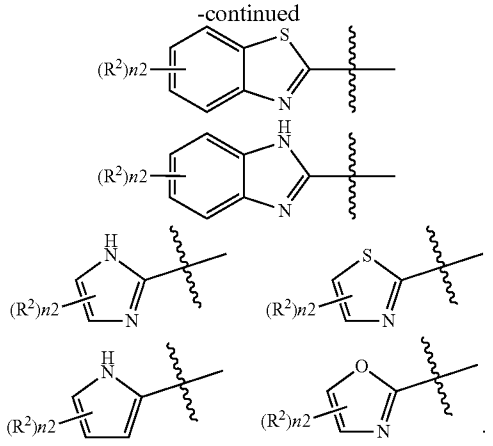
In some embodiments, the
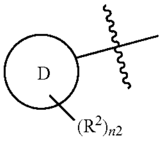
is selected from
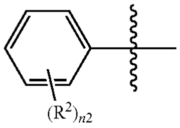 , 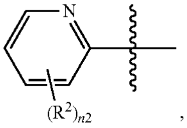 ,
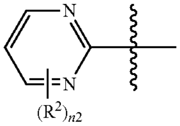 , 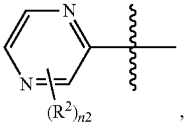 ,
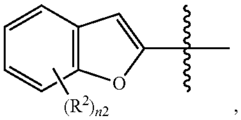 , 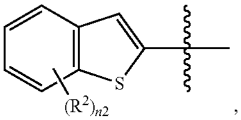 ,
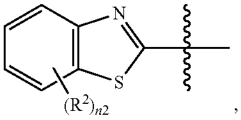 , 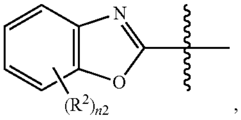 ,
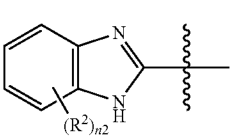 , 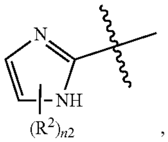 ,
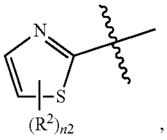 , 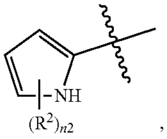 ,
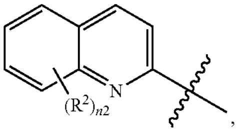 , 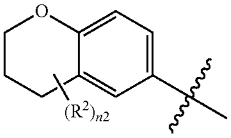 or
-continued
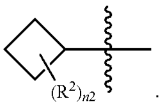 .
In some embodiments, the
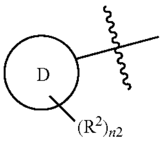
is selected from
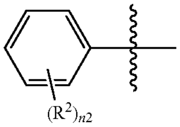 , 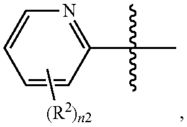 ,
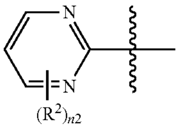 , 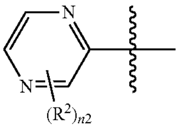 ,
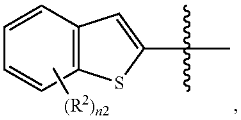 , 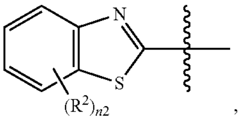 ,
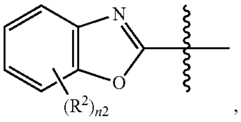 , 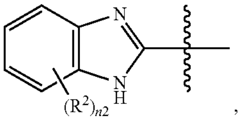 ,
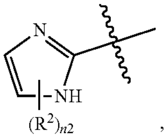 , 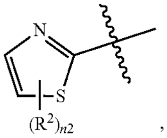 , 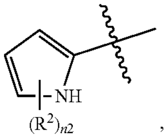 ,
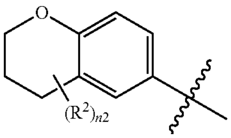 or 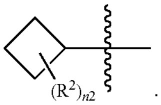 .
In some embodiments, the
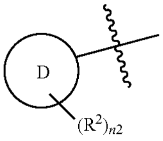

is selected from

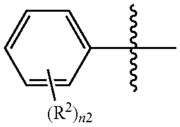
,
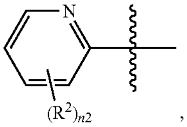
,
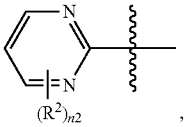
,
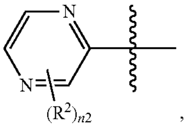
,
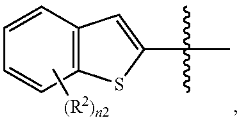
,
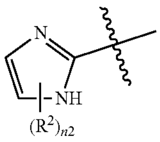
,
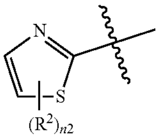
,
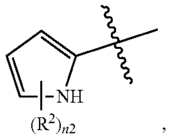
,
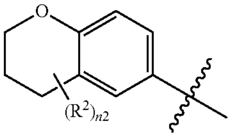
or
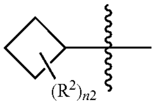
.

In some embodiments, the

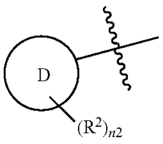

is selected from

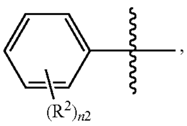
,
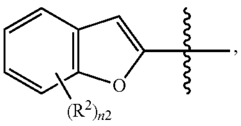
,
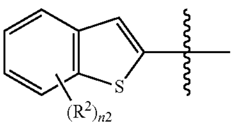
or
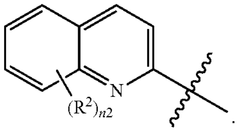
.

In some embodiments,

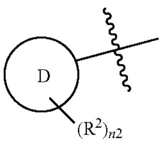

the is selected from

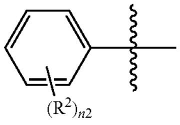
or
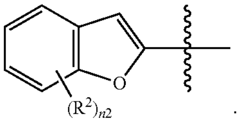
.

In some embodiments, $R^2$ is $R^{11}$, each $R^{11}$ is independently selected from halogen, cyano, nitro, carbonyl, ═O, —$OR^6$, —$SR^6$, —$NR^6R^7$, C1-C6 alkyl, C3-C6 cycloalkyl, 3- to 8-membered heterocycloalkyl, —C(O)$R^6$, —C(O)$OR^6$, —OC(O)$OR^6$, OC(O)$R^6$, —C(O)$NR^6R^7$ or —C(O)$ONR^6R^7$, preferably each $R^{11}$ is independently selected from halogen, cyano, nitro, ═O, —$OR^6$, —$SR^6$, —$NR^6R^7$, C1-C6 alkyl, C3-C6 cycloalkyl, 3- to 8-membered heterocycloalkyl, —C(O)$R^6$, —C(O)$OR^6$, —OC(O)$OR^6$, OC(O)$R^6$, —C(O)$NR^6R^7$ or —C(O)$ONR^6R^7$, wherein as $R^{11}$, C1-C6 alkyl, C2-C6 alkenyl, C3-C8 cycloalkyl and 3- to 8-membered heterocycloalkyl may each be independently substituted with 1-6 $R^{12}$, $R^6$, $R^7$ and $R^8$ are each independently selected from H, C1-C6 alkyl, C3-C8 cycloalkyl, 3- to 8-membered heterocycloalkyl, —C(O)$R^{20}$, —C(O)$OR^{20}$ or —C(O)$NR^{20}R^{21}$, wherein as $R^6$, $R^7$ and $R^8$, C1-C6 alkyl, C3-C8 cycloalkyl and 3- to 8-membered heterocycloalkyl may each be independently substituted with 1-3 $R^{13}$, $R^{12}$ and $R^{13}$ are each independently H, halogen, cyano, nitro, carbonyl, ═O, —$OR^{30}$, $NR^{30}R^{31}$, C1-C6 alkyl, C3-C8 cycloalkyl, 3- to 8-membered heterocycloalkyl, —C(O)$R^{30}$, —C(O)$OR^{30}$, —OC(O)$OR^{30}$ or OC(O)$R^{30}$, preferably $R^{12}$ and $R^{13}$ are each independently H, halogen, cyano, nitro, ═O, —$OR^{30}$, $NR^{30}R^{31}$, C1-C6 alkyl, C3-C8 cycloalkyl, 3- to 8-membered heterocycloalkyl, —C(O)$R^{30}$, —C(O)$OR^{30}$, —OC(O)$OR^{30}$ or OC(O)$R^{30}$, wherein as $R^{12}$ and $R^{13}$, C1-C6 alkyl, C3-C8 cycloalkyl and 3- to 8-membered heterocycloalkyl may each be independently substituted with 1-3 halogen, or substituted with C1-C3 alkyl optionally substituted with 1-3 carbonyl, halogen, hydroxyl or amino; preferably as $R^{12}$ and $R^{13}$, C1-C6 alkyl, C3-C8 cycloalkyl and 3- to 8-membered heterocycloalkyl may each be independently substituted with 1-3 halogen, or substituted with C1-C3 alkyl optionally substituted with 1-3 carbonyl, halogen, hydroxyl or amino, $R^{20}$ and $R^{21}$ are each independently selected from H, or C1-C3 alkyl optionally substituted with 1-6 halogen, hydroxyl or amino;

$R^{30}$ and $R^{31}$ are each independently selected from H, or C1-C3 alkyl optionally substituted with 1-6 halogen, hydroxyl or amino;

n2 is 1, 2 or 3.

In some embodiments, each $R^2$ is independently selected from halogen, cyano, C1-C3 haloalkyl, C1-C3 alkyl, —OC1-C3 alkyl, —OC1-C3 haloalkyl, —$NR^6R^7$, C3-C6 cycloalkyl or 3- to 6-membered heterocycloalkyl, $R^6$ and $R^7$ are each independently selected from H, C1-C3 alkyl, C1-C3 haloalkyl, C3-C6 cycloalkyl or C3-C6 halocycloalkyl, preferably, when the $R^2$ is C3-C6 cycloalkyl or 3- to 6-membered heterocycloalkyl, n is 1, and the $R^2$ and the ring D share two carbon atoms to form a fused ring.

In some embodiments, each $R^2$ is independently selected from halogen, C1-C3 haloalkyl, C1-C3 alkyl, —OC1-C3 alkyl, —OC1-C3 haloalkyl, —$NH_2$ or

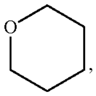
, wherein preferably when $R^2$ is

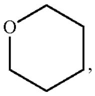,
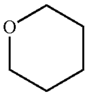

and the ring D share two carbon atoms to form a fused ring.

In some embodiments, each $R^2$ is independently selected from F, Cl, Br, $—CF_3$, $—CH_3$, $—CFH_2$, $—CF_2H$, $—OCH_3$, $O—CF_3$ or $—NH_2$, and n2 is 1 or 2.

In some embodiments, each $R^2$ is independently selected from F, Cl, Br, $—CF_3$, $—CH_3$, $—CF_2H$, $—OCF_3$ or $—NH_2$, and n2 is 1, 2 or 3.

In some embodiments, the

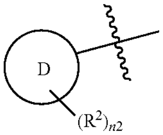

is selected from

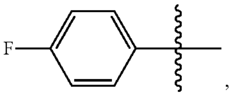,
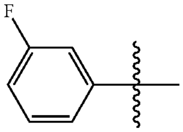,
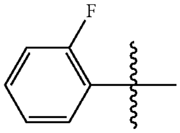,
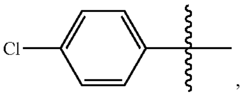,
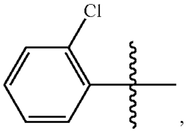,
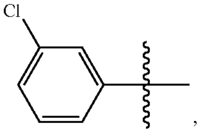,
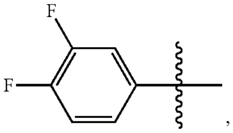,
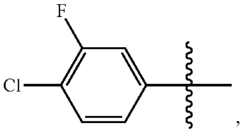,
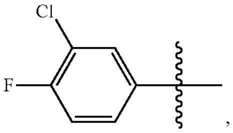,
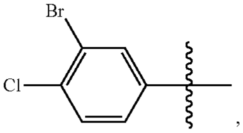,
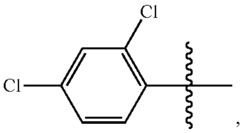,
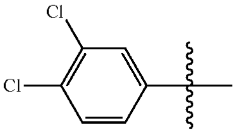,
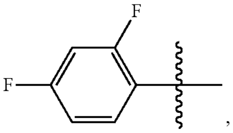,
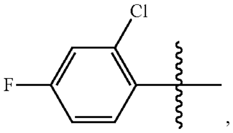, -continued

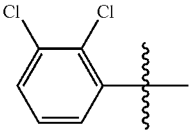,
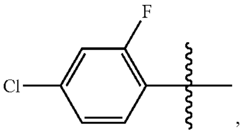,
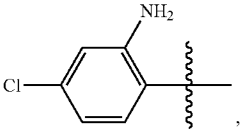,
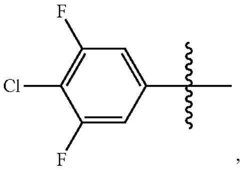,
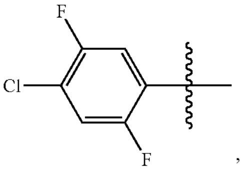,
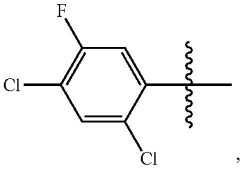,
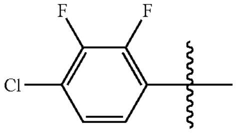,
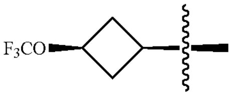,
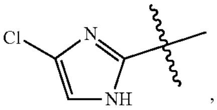,
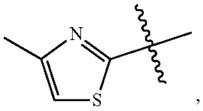,
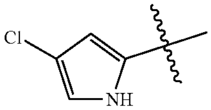,
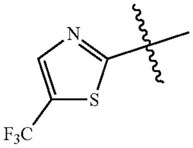,
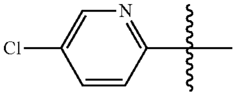,
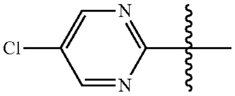,
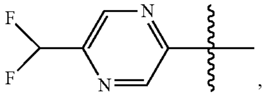,
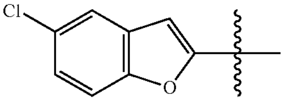,
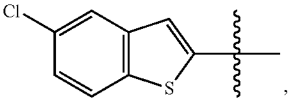,
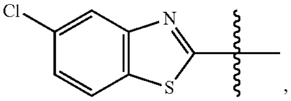,
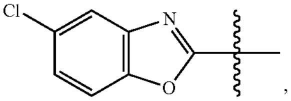,
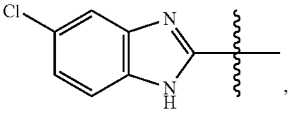,
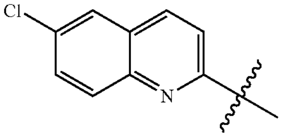
or
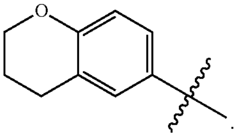.

In some embodiments, the
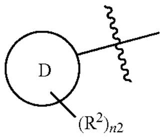
is selected from
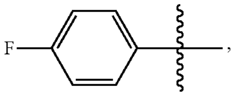,
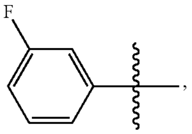,
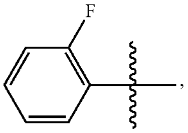,
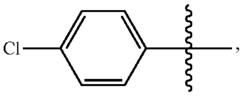,
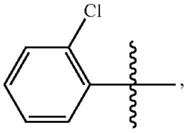,
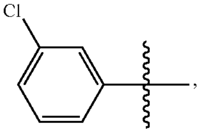,
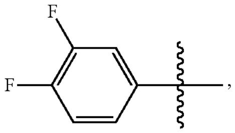,
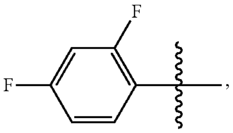,
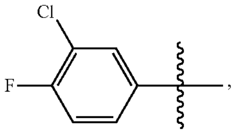,
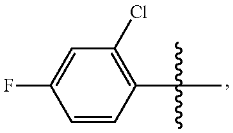,
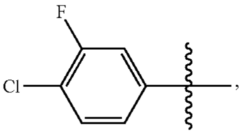,
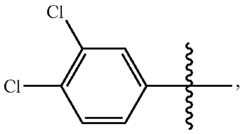,
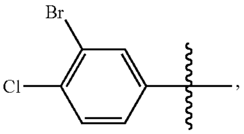,
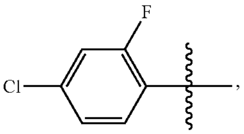,
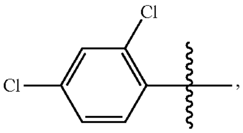,
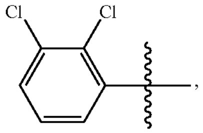,
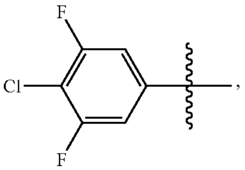,
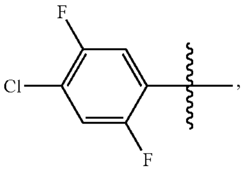,
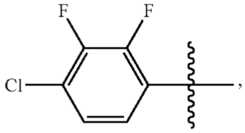,
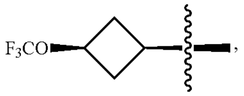,
-continued
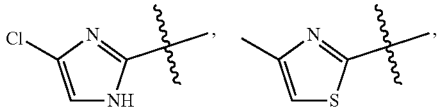, ,
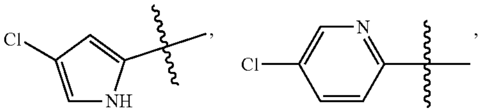, ,
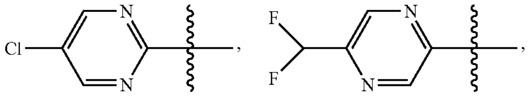, ,
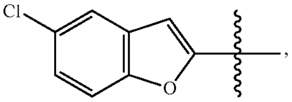,
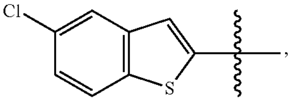,
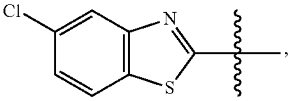,
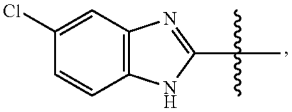,
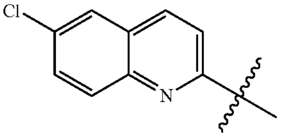
or
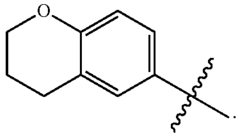.
In some embodiments, the
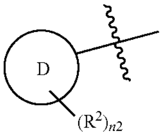
is selected from
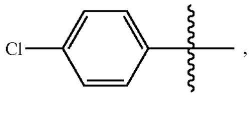,
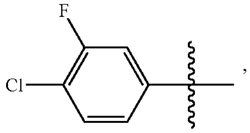,
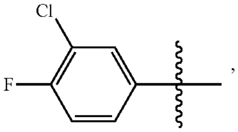,
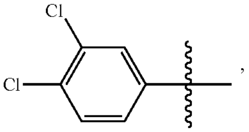,
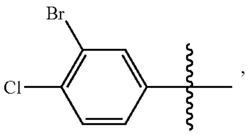,
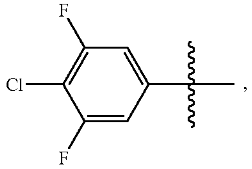, -continued

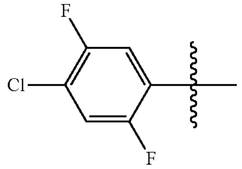,
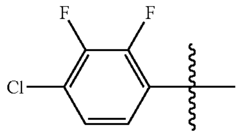,
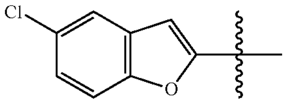,
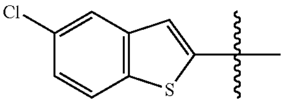
or
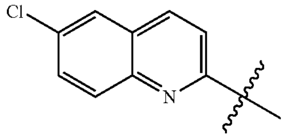.

In some embodiments, the

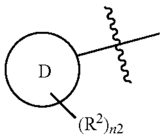

is selected from

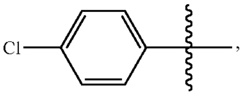,
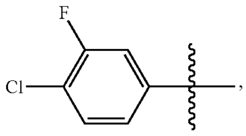,
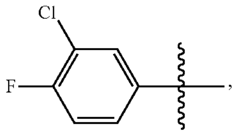,
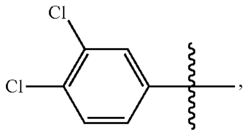,
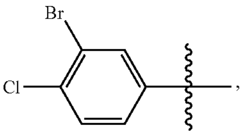,
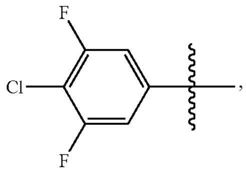,
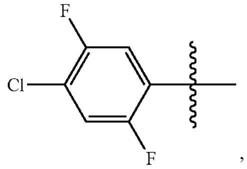,
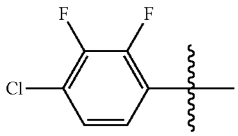
or
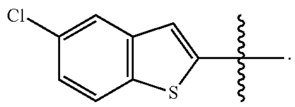.

In some embodiments, the

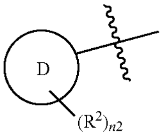

is selected from

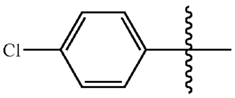,
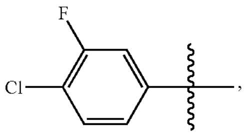,
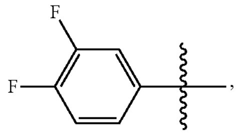,
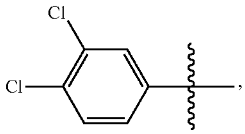,
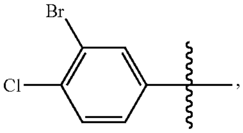,
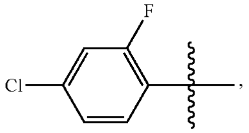,
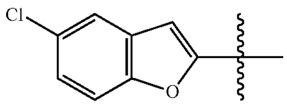
or
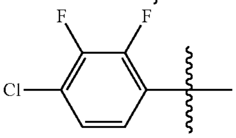.

In some embodiments, preferably the compound has a structure as shown in general formula VI

VI

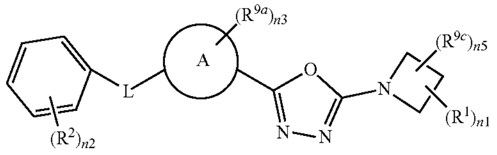

wherein the ring A is selected from cyclohexylene or 6-membered heterocycloalkylene; the L, $R^1$, $R^2$, $R^{9a}$, $R^{9c}$, n1, n2, n3 and n5 are as defined in any one of the above embodiments.

In some embodiments, each of the $R^2$ is independently selected from F, Cl or Br.

In some embodiments, the n2 is 1 or 2.

In some embodiments, the $R^2$ is in a para-position relationship and/or a meta-position relationship with L.

In some embodiments, the L is selected from

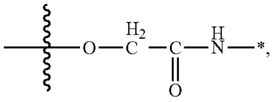,
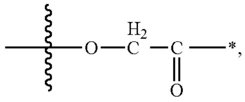,
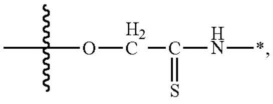,
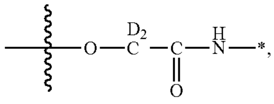,

-continued

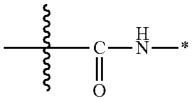 or 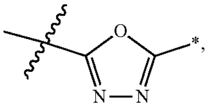

the * end is connected to ring A, and the  end is connected to ring D.

Preferably, the L is selected from

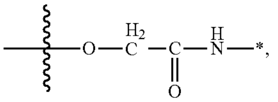 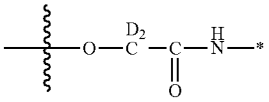 or

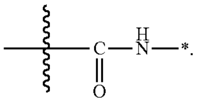

In some embodiments, the L is selected from

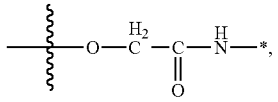 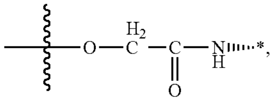

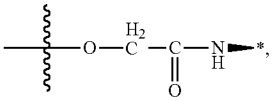 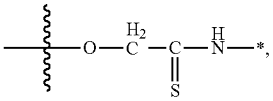

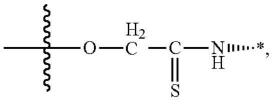 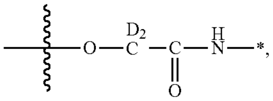

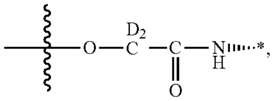 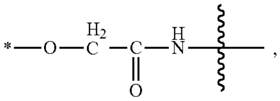

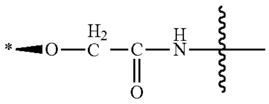 or 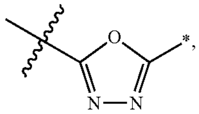

the * end is connected to ring A, and the  end is connected to ring D.

In some embodiments, the L is selected from

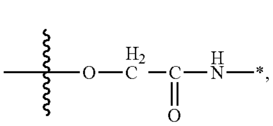 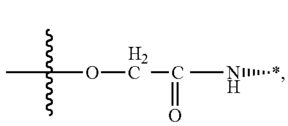

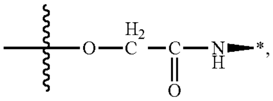 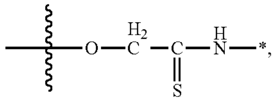

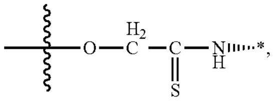 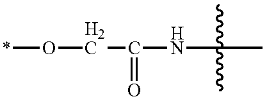 or

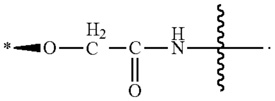

In some embodiments, the L is selected from

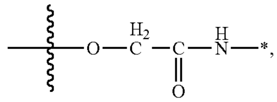 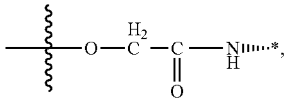

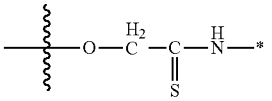 or 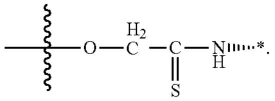

In some embodiments, the L is selected from

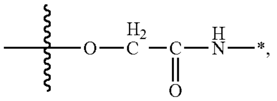 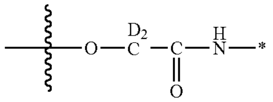 or

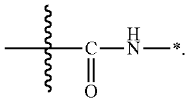

In some embodiments, the n1 and n5 are not 0 simultaneously.

In some embodiments, the $R^1$ is in a para-position relationship with the N on the C ring where the $R^1$ is located.

In some embodiments, the $R^1$ is selected from —$OR^6$, C1-C3 alkyl, halogen, C2-C4 alkenyl, —$S(O)_2R^6$ or —$P(O)R^6R^7$, preferably $R^6$ and $R^7$ are each independently selected from H or C1-C3 alkyl, wherein as $R^6$ and $R^7$, C1-C3 alkyl may be substituted with 1-3 $R^{13}$; preferably each $R^{13}$ is independently halogen, cyano or nitro;

preferably, the $R^1$ is —$OCH_3$, —$OCF_3$,

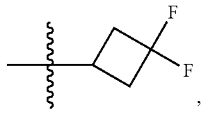, 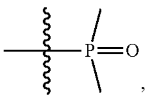,

—$CF_2CF_3$, —$CF_3$, —$CHF_2$, —$OCF_2Cl$, —$CH_2CF_3$, —$CF_3$, —F,

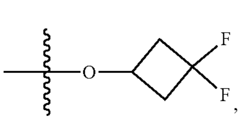 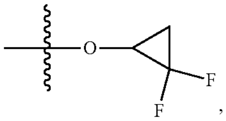,

—$OCF{=}CF_2$,

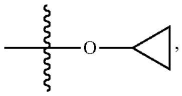 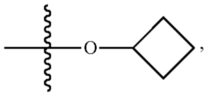

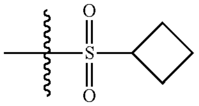, 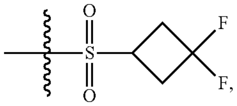

-continued

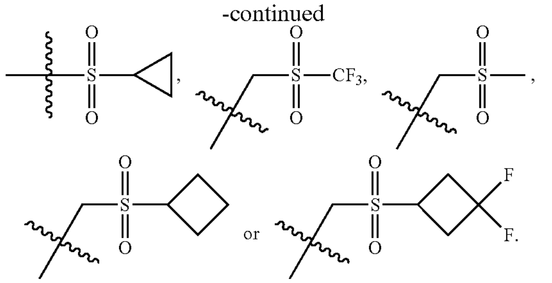

In some embodiments, the $R^1$ is selected from $—OR^6$, C1-C3 alkyl, halogen, $—S(O)_2R^6$ or $—P(O)R^6R^7$, wherein as $R^1$, C1-C3 alkyl may be substituted with 1-6 $R^{12}$, $R^{12}$ is selected from halogen or $—S(O)_2R^{30}$, and $R^{30}$ is selected from C1-C3 alkyl, halo C1-C3 alkyl, C3-C6 cycloalkyl or halo C3-C6 cycloalkyl; each $R^6$ is independently selected from C1-C3 alkyl, C2-C4 alkenyl or C3-C6 cycloalkyl, wherein as $R^6$, C1-C3 alkyl, C2-C4 alkenyl or C3-C6 cycloalkyl may each be independently substituted with 1-6 $R^{13}$, and $R^{13}$ is halogen; $R^7$ is C1-C3 alkyl.

In some embodiments, the $R^1$ is $—OCH_3$, $—OCF_3$

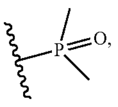 [SMILES: *P(C)(C)=O]

$—CF_2CF_3$, $—CF_3$, $—OCHF_2$, $—OCF_2CF_3$, $—OCF_2Cl$, $—CH_2CF_3$, —F,

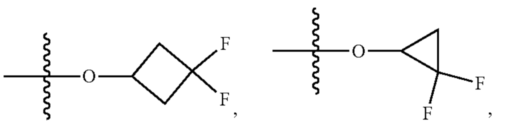 [SMILES: *OC1CC(F)(F)C1 ; *OC1CC1(F)F]

$—OCF{=}CF_2$

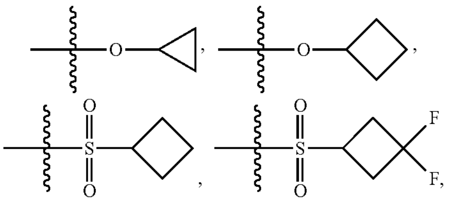

-continued

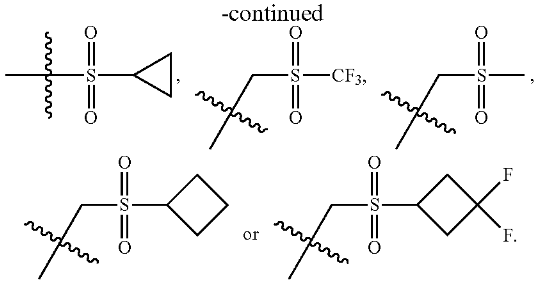

In some embodiments, the $R^1$ is $—OCF_3$, $—CF_2CF_3$, $—OCH_3$, —F,

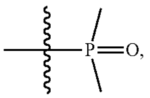 [SMILES: *P(C)(C)=O]

or $—CF_3$.

In some embodiments, the $R^1$ is $—OCF_3$ or $—OCF_2CF_3$.

In some embodiments, the $R^1$ is $—OCF_3$.

In each embodiment, $R^1$, $R^2$, $R^{9a}$, $R^{9b}$ and $R^{9c}$ are each independently substituent $R^{11}$; when n1, n2, n3, n4 and n5 are 0, $R^1$, $R^2$, $R^{9a}$, $R^{9b}$ and $R^{9c}$ are absent, and the free bonds of C forming the ring D, ring A, ring B and ring C are connected to H.

In some embodiments, the compound has a structure as shown in general formula VII general formula VII

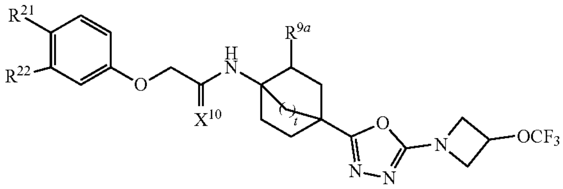

wherein $R^{9a}$ and $X^{10}$ are as defined in any one of the above embodiments, $R^{21}$ is halogen, $R^{22}$ is selected from H or halogen, and t is selected from an integer from 0-2;

preferably, $R^{21}$ is Cl;

preferably, $R^{22}$ is selected from H, F, Cl or Br;

preferably, $R^{9a}$ is selected from H or hydroxyl;

preferably, t is 0 or 2.

In some embodiments, the compound is selected from:

1

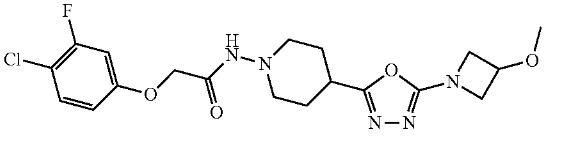

2

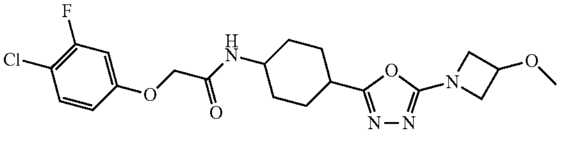

3

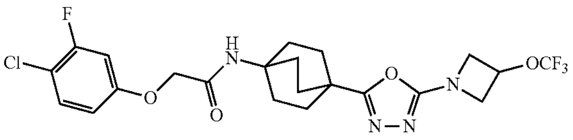

4

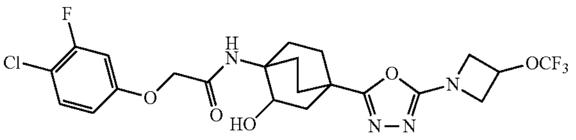

-continued
5
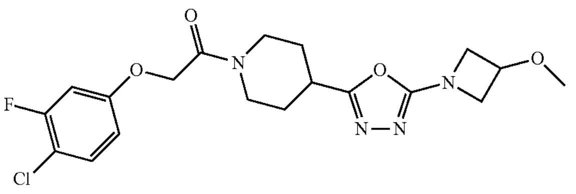
6
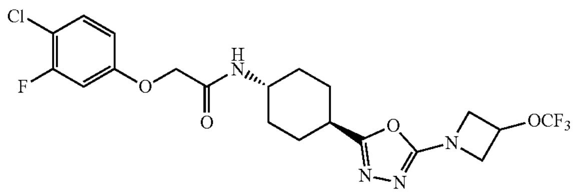
7
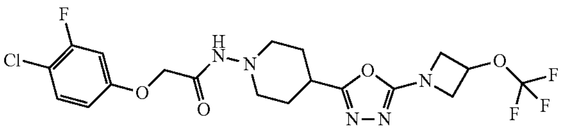
8
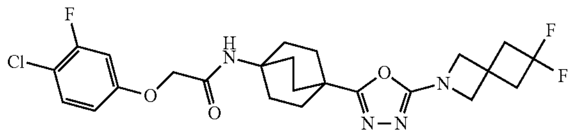
9
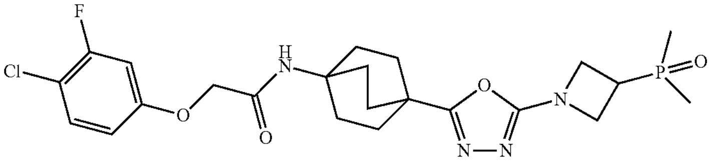
10
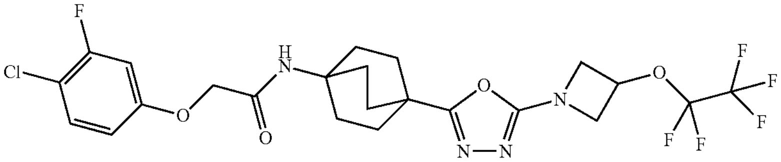
11
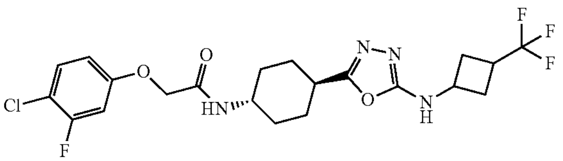
12
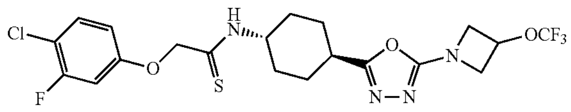
13
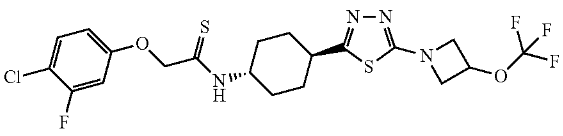
14
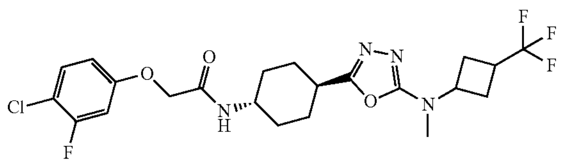
15
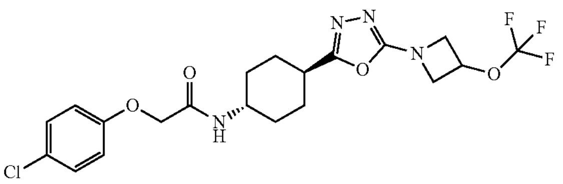
16
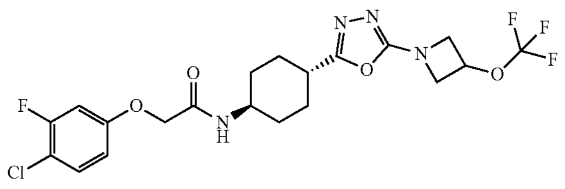
17
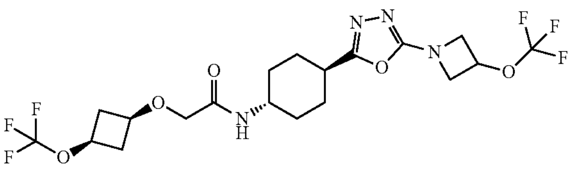
18
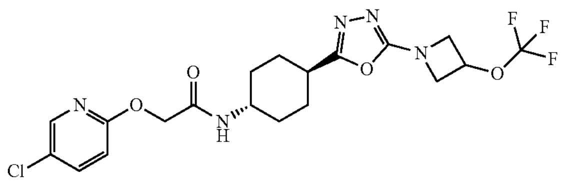

-continued
19
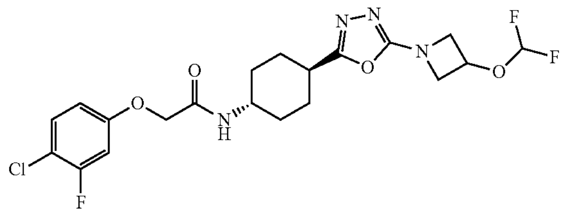
20
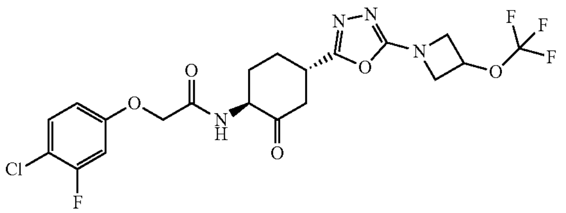
21
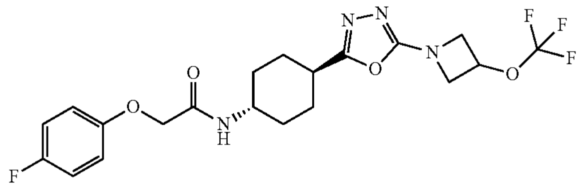
22
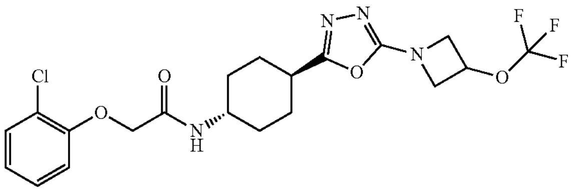
23
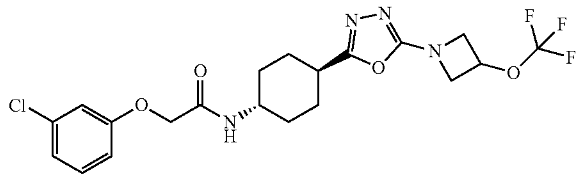
24
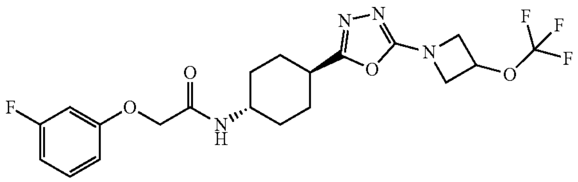
25
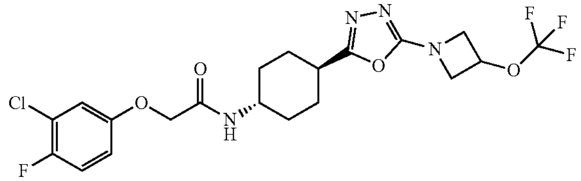
26
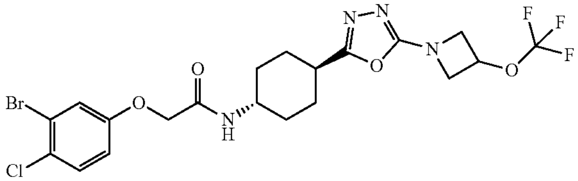
27
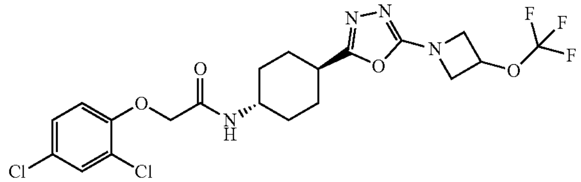
28
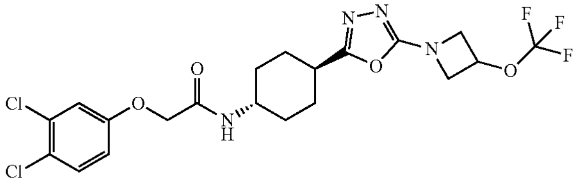
29
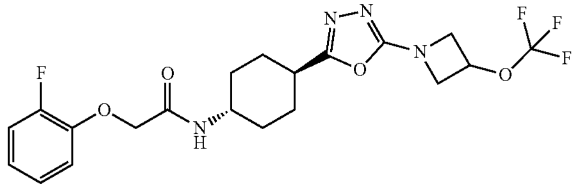
30
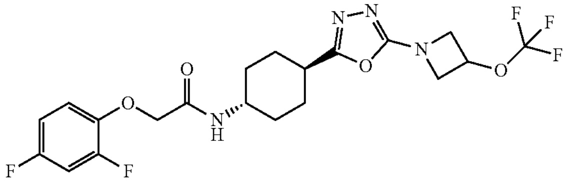
31
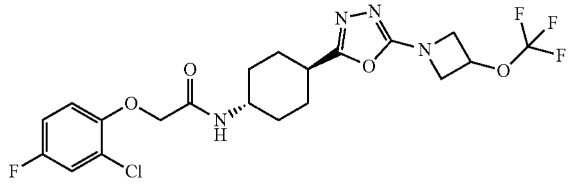
32
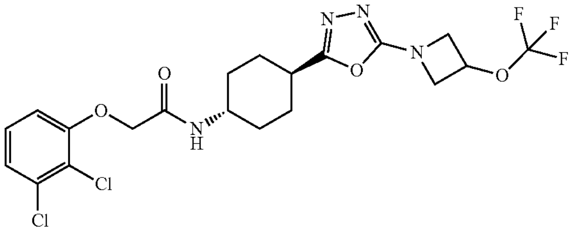

-continued
33
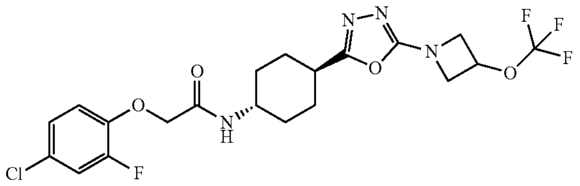
34
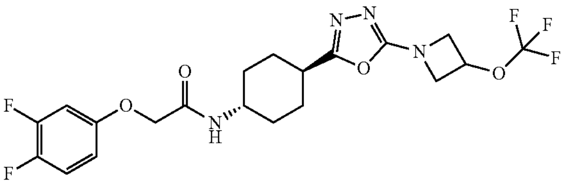
35
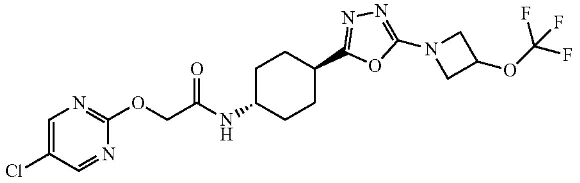
36
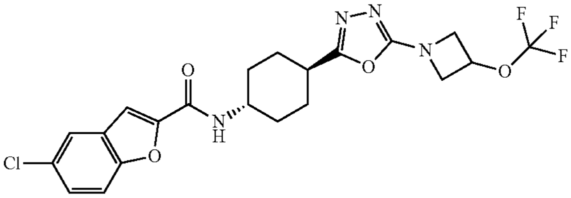
37
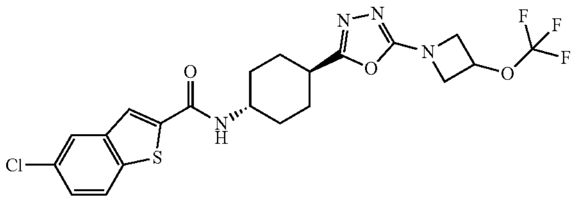
38
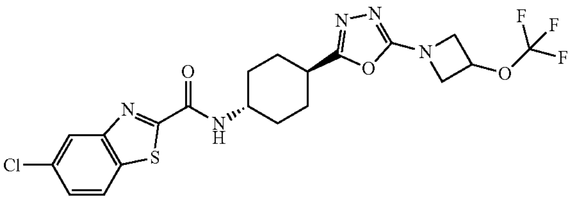
39
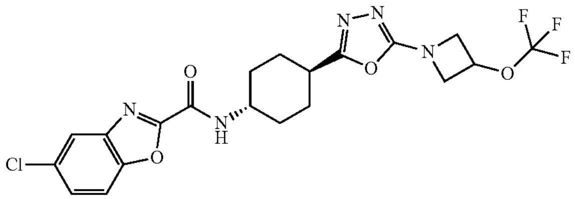
40
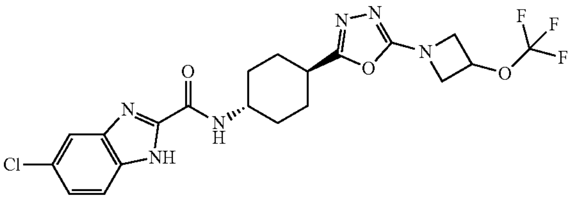
41
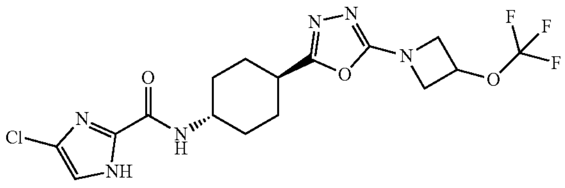
42
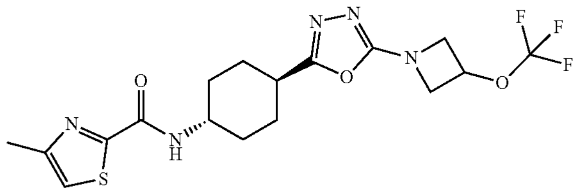
43
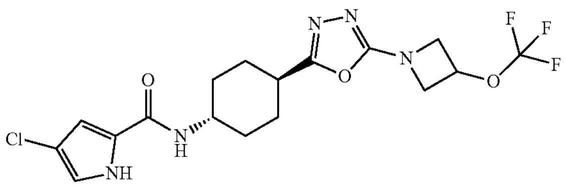
44
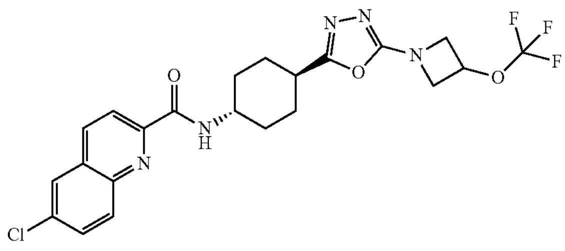

-continued
45
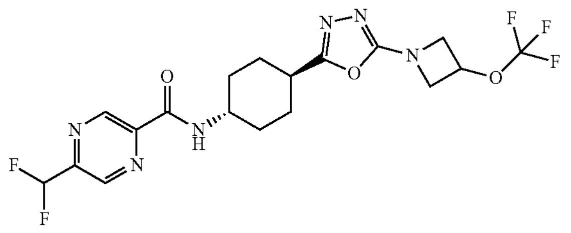
46
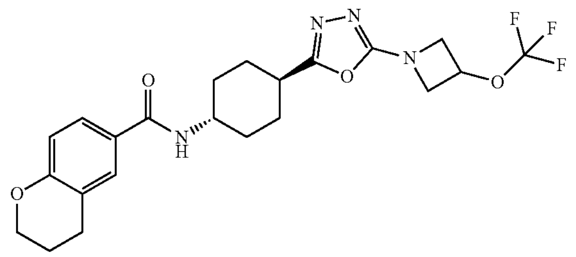
47
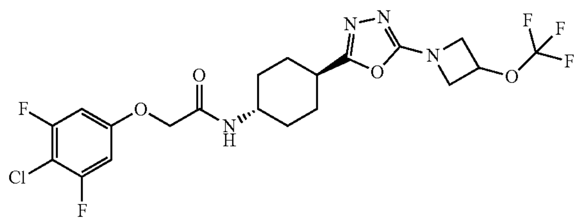
48
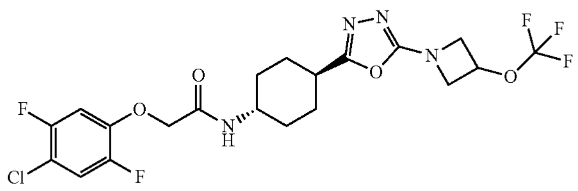
49
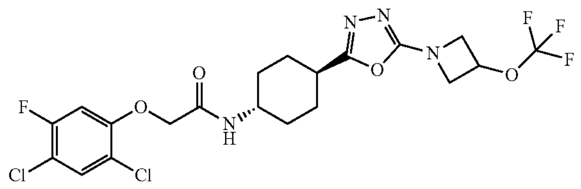
50
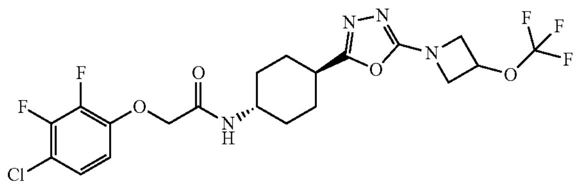
51
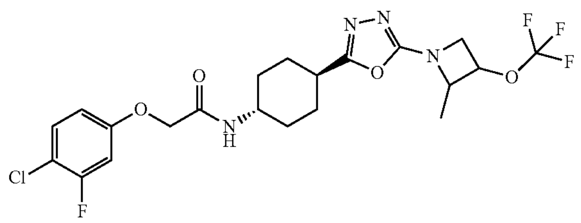
52
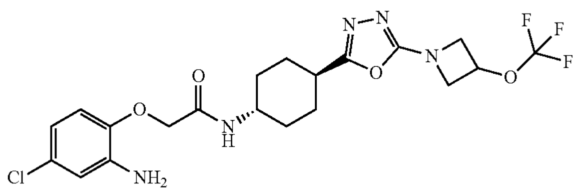
53
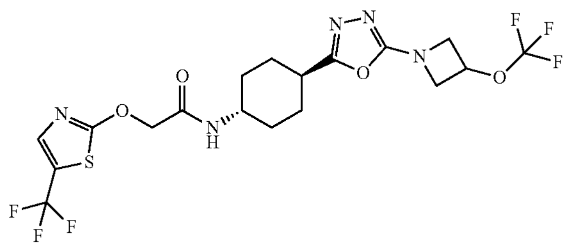
54
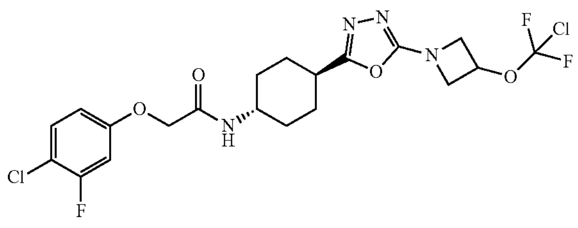
55
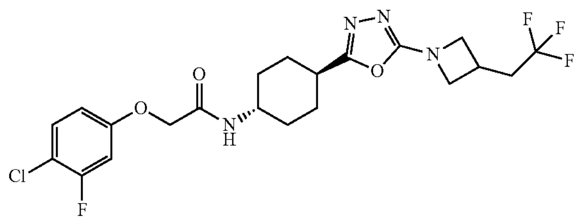
56
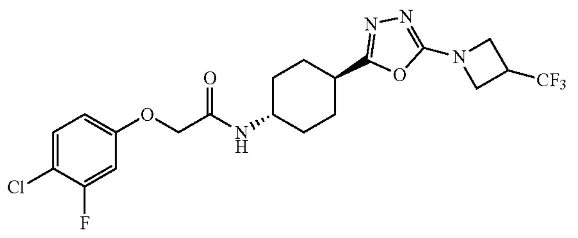

-continued
57
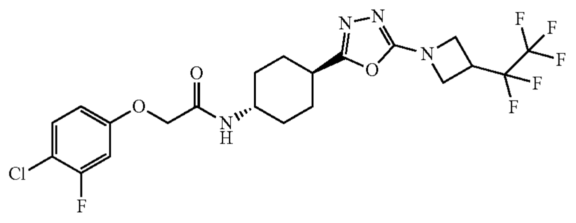
58
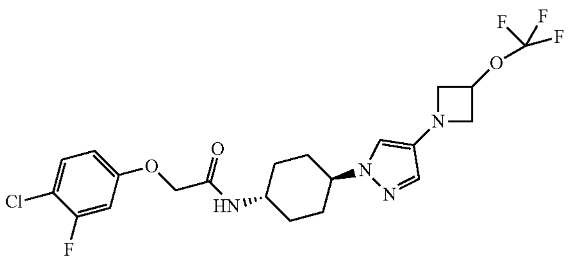
59
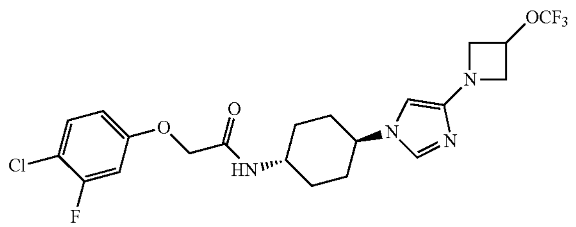
60
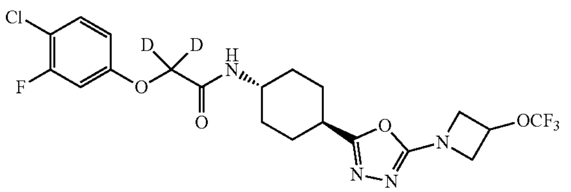
61
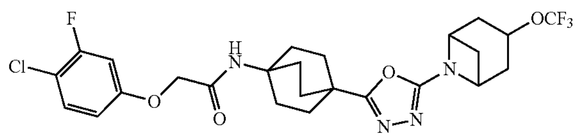
62
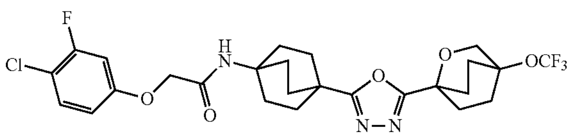
63
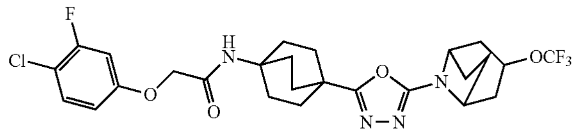
64
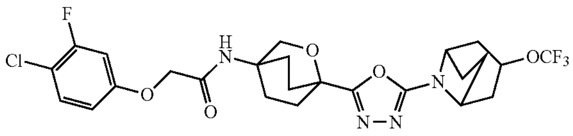
65
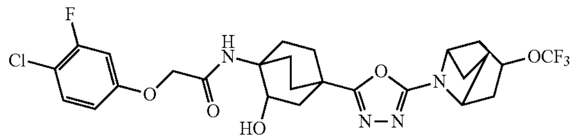
66
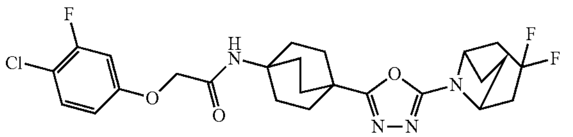
67
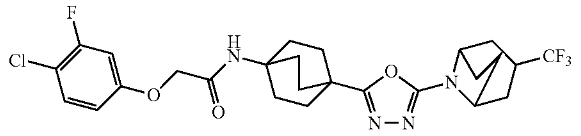
68
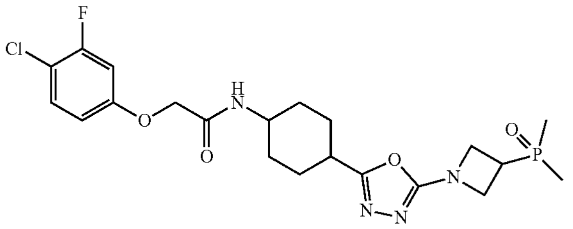
69
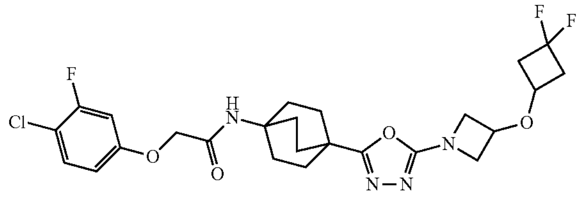
70
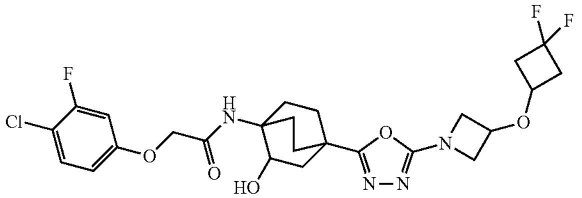

-continued
71
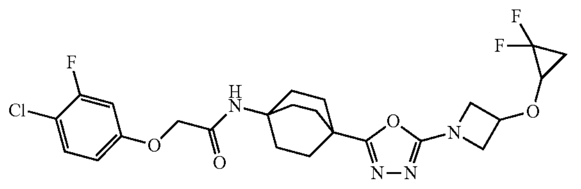
72
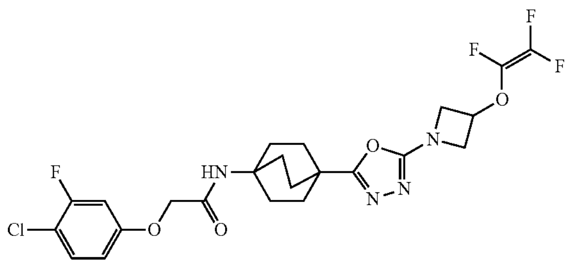
73
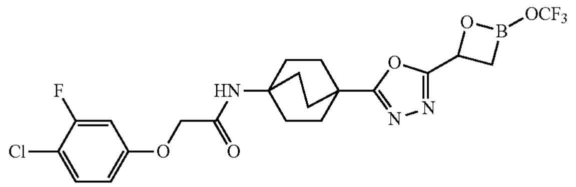
74
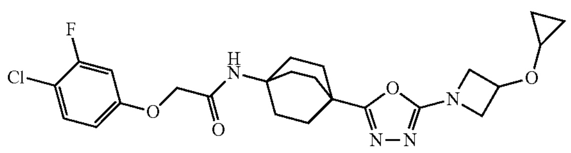
75
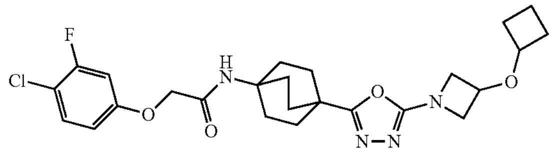
76
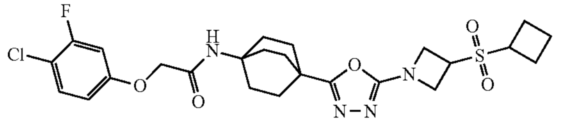
77
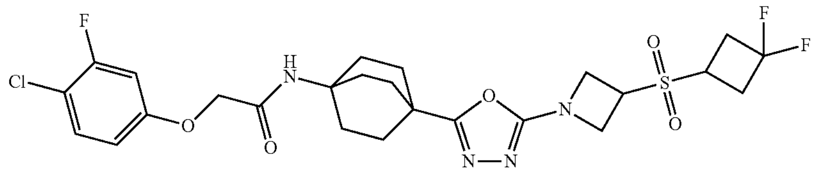
78
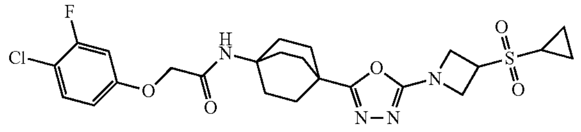
79
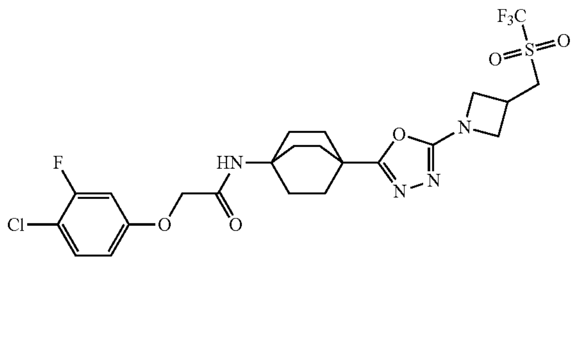
80
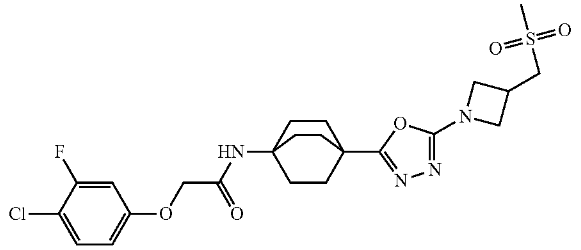
81
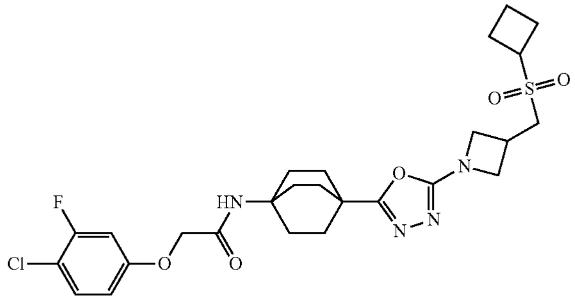

-continued
82
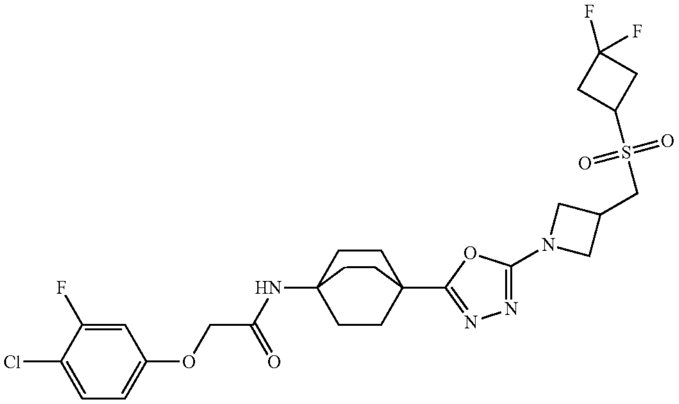
83
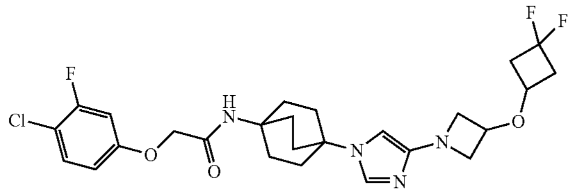
84
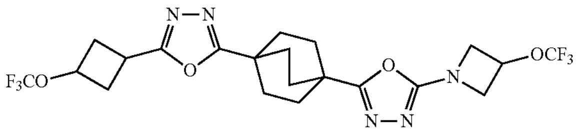
85
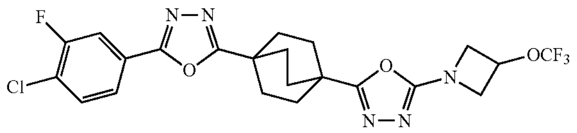
86
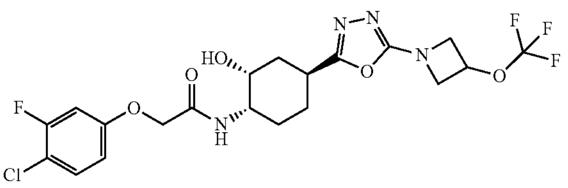
-continued
87
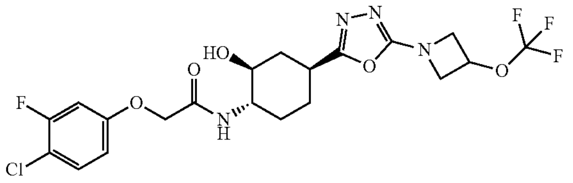
88
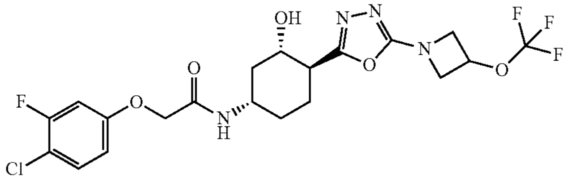
89
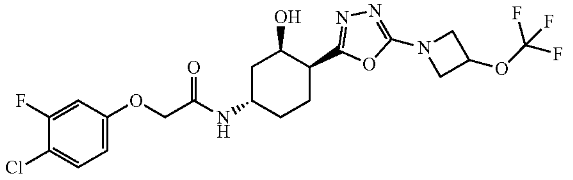
90
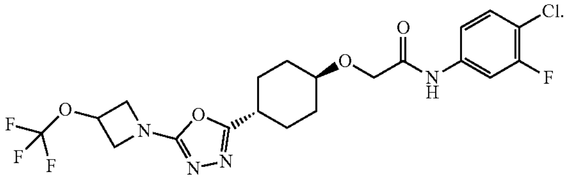
In some embodiments, the compound is specifically selected from
The results are shown in Table 1.

3
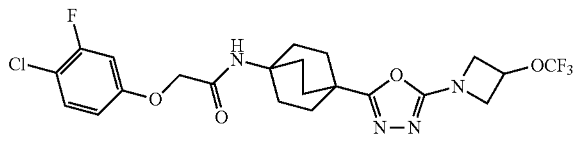
4
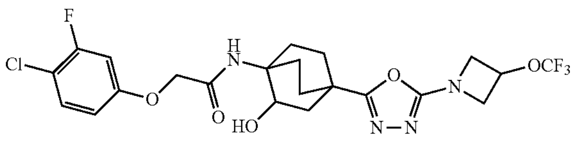
6
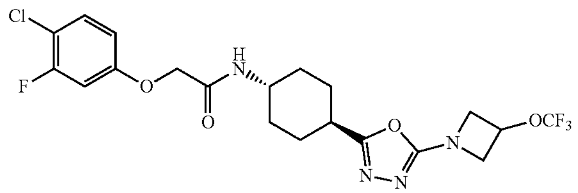
7
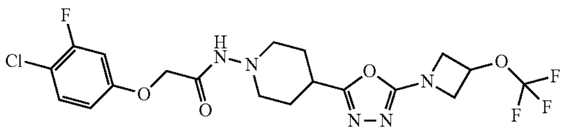
10
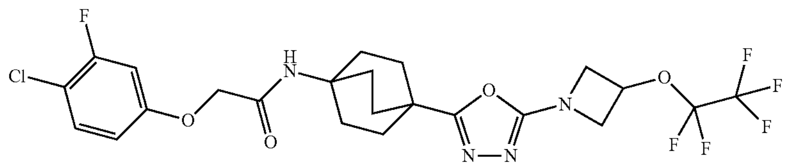
12
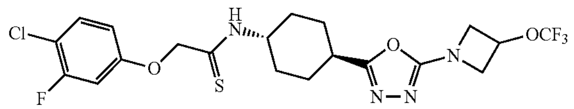
15
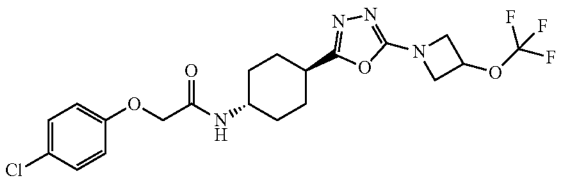
16
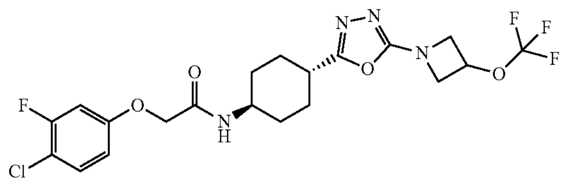
25
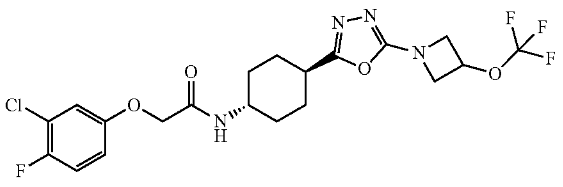
26
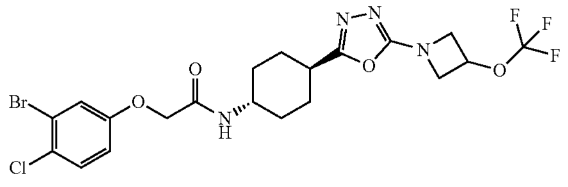
28
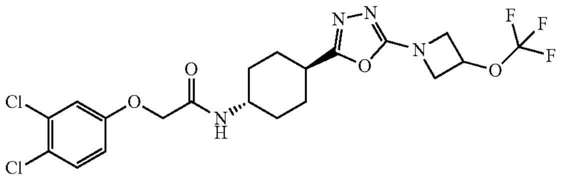
33
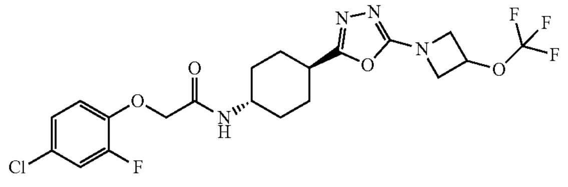
34
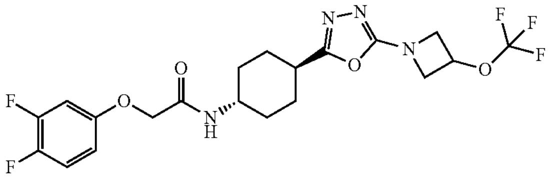
36
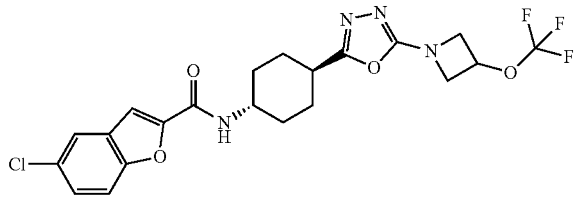
37
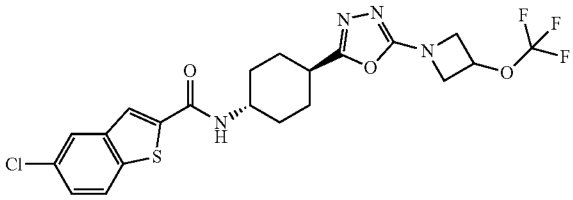

-continued
44
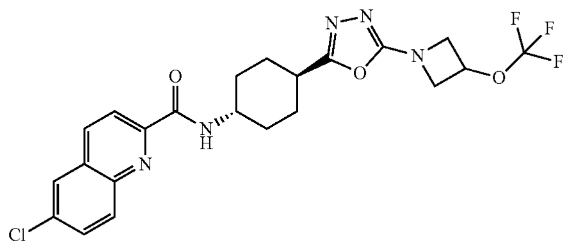
47
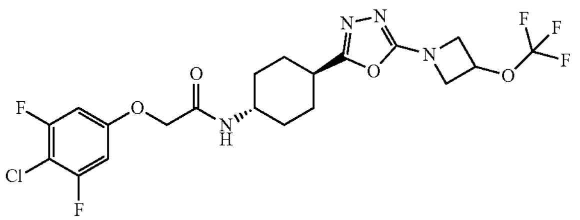
48
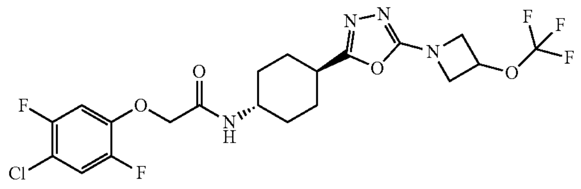
50
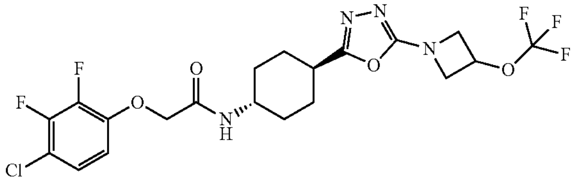
90
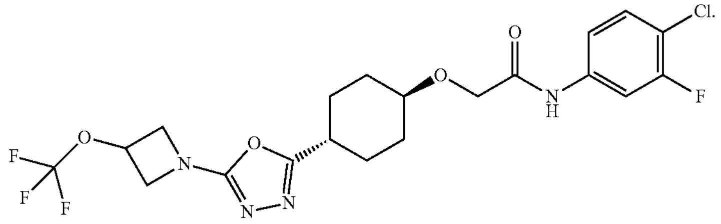
In some embodiments, the compound is specifically selected from
3
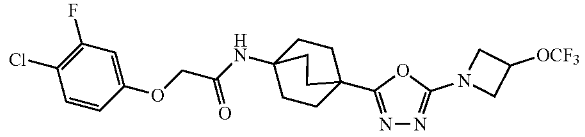
4
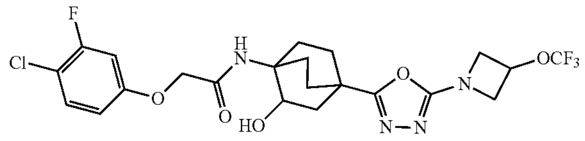
6
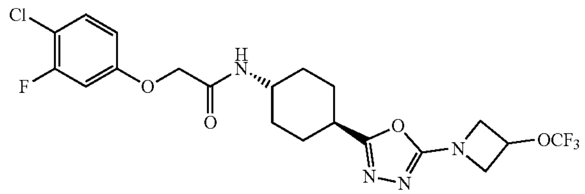
7
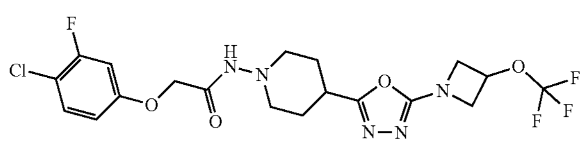
-continued
12
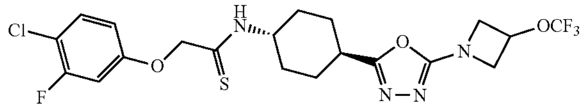
15
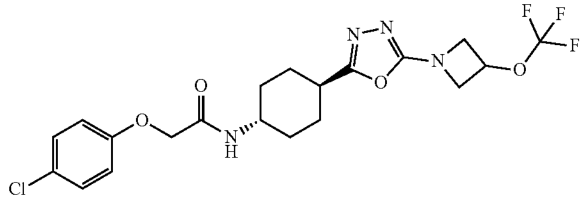
26
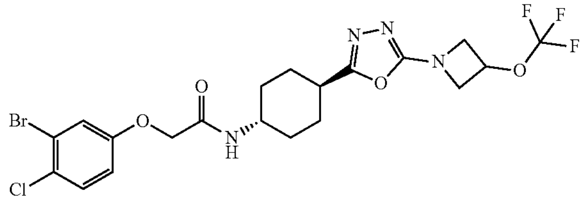
28
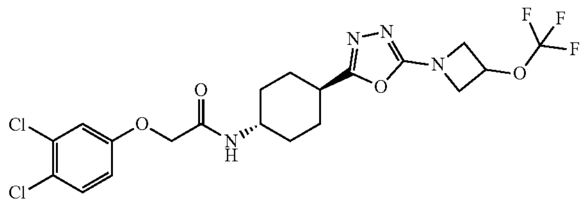

-continued

36

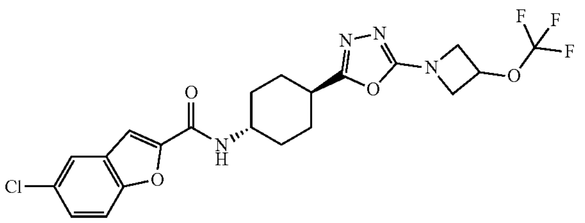

50

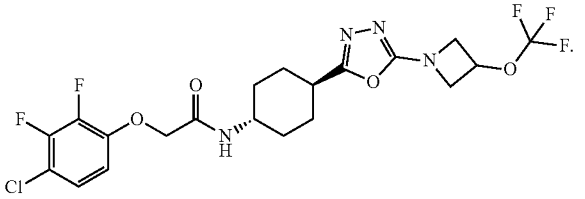

Another aspect of the present application provides a method for synthesizing the compound having a structure as shown in general formula IV-1 or IV-2 described above, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof, wherein the synthesis method is selected from any one of synthesis routes 1 to 6;

Synthesis Route 1

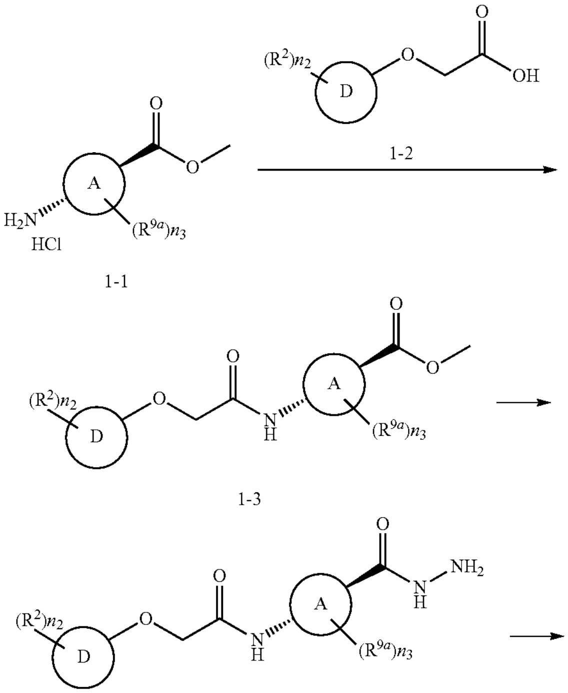

1-1

1-3

1-4

-continued

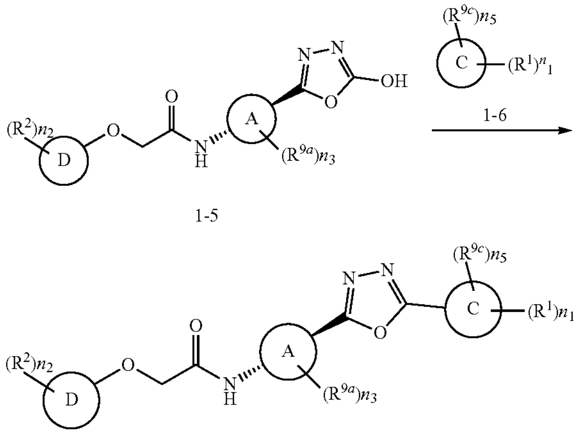

1-5

IV-1-1 wherein compound 1-1 is subjected to an amide condensation reaction with compound 1-2 to obtain compound 1-3; the compound 1-3 is reacted with hydrazine hydrate and subjected to a functional group conversion to obtain compound 1-4; the compound 1-4 is subjected to a cyclization with N,N'-carbonyldiimidazole to obtain compound 1-5; the compound 1-5 is subjected to a condensation reaction with compound 1-6 to obtain compound IV-1-1; and $R^1$, $R^2$, $R^{9a}$, $R^{9c}$, n1 and n2 are as defined in the above embodiments;

Synthesis Route 2

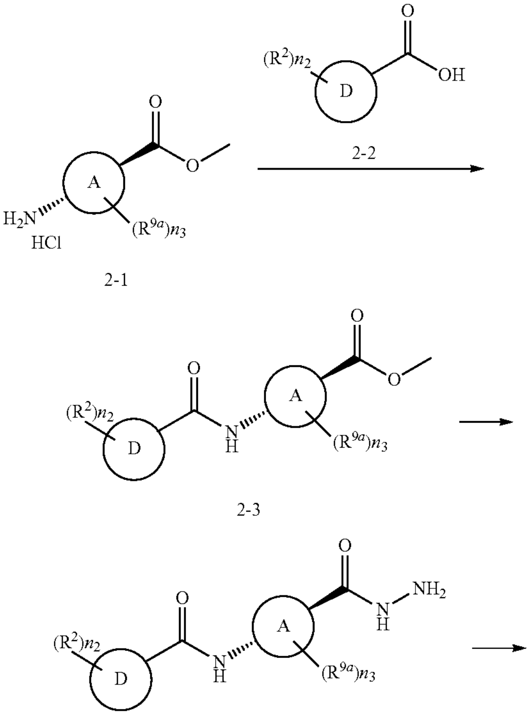

2-1

2-3

2-4

-continued

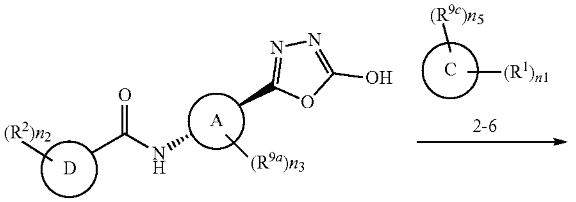

2-5

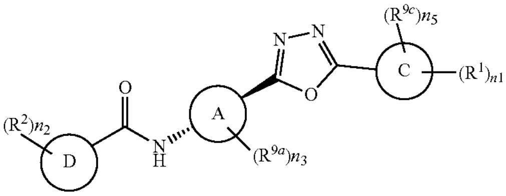

IV-2-1 wherein compound 2-1 is subjected to an amide condensation reaction with compound 2-2 to obtain compound 2-3; the compound 2-3 is reacted with hydrazine hydrate and subjected to a functional group conversion to obtain compound 2-4; the compound 2-4 is subjected to a cyclization with N,N'-carbonyldiimidazole to obtain compound 2-5; the compound 2-5 is subjected to a condensation reaction with compound 2-6 to obtain compound IV-2-1; $R^1$, $R^2$, $R^{9a}$, $R^{9c}$, n1 and n2 are as defined in the above embodiments;

Synthesis Route 3

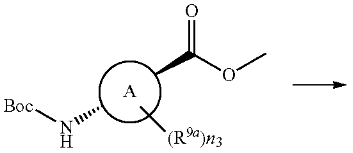

3-1

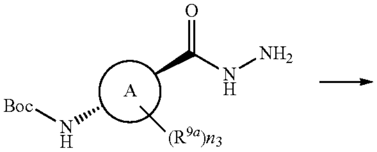

3-2

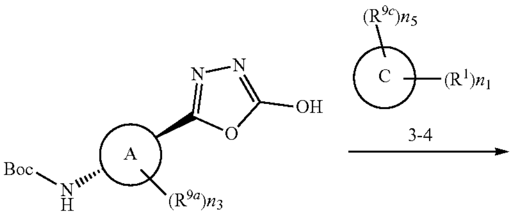

3-3

-continued

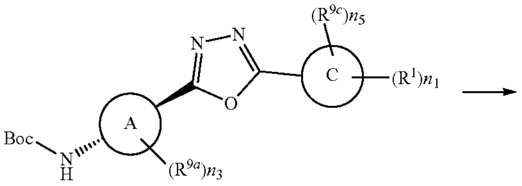

3-5

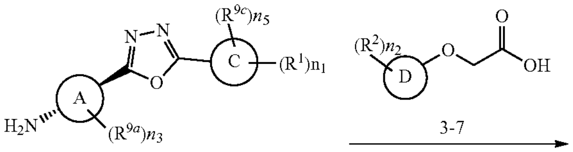

3-6

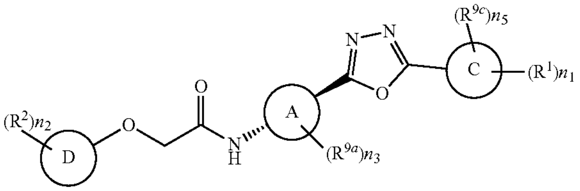

IV-1-1 wherein compound 3-1 is reacted with hydrazine hydrate and subjected to a functional group conversion to obtain compound 3-2; the compound 3-2 is subjected to a cyclization with N,N'-carbonyldiimidazole to obtain compound 3-3; the compound 3-3 is subjected to a condensation reaction with compound 3-4 to obtain compound 3-5; the compound 3-5 is subjected to protecting group removal under an acidic condition to obtain compound 3-6; the compound 3-6 is subjected to an amide condensation reaction with compound 3-7 to obtain compound IV-1-1; and $R^1$, $R^2$, $R^{9a}$, $R^{9c}$, n1 and n2 are as defined in the above embodiments;

Synthesis Route 4

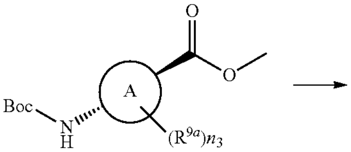

4-1

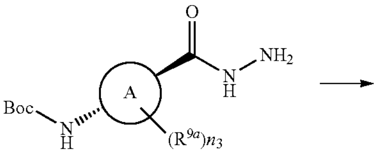

4-2

-continued

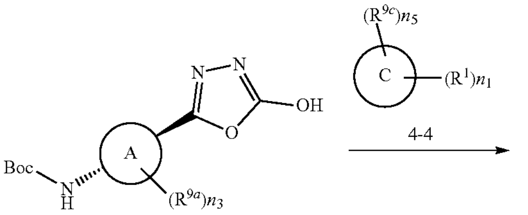

4-3

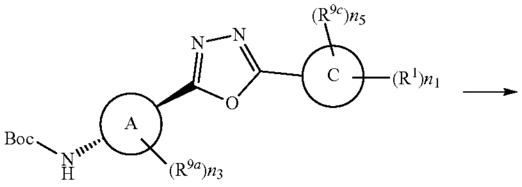

4-5

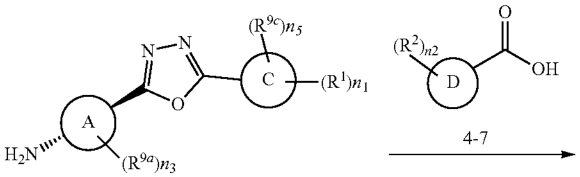

4-6

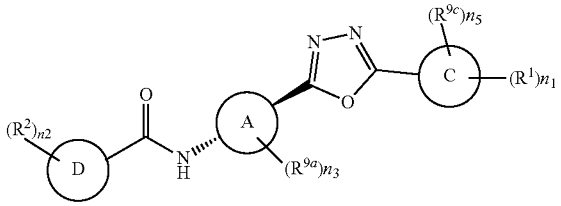

IV-2-1 wherein compound 4-1 is reacted with hydrazine hydrate and subjected to a functional group conversion to obtain compound 4-2; the compound 4-2 is subjected to a cyclization with N,N'-carbonyldiimidazole to obtain compound 4-3; the compound 4-3 is subjected to a condensation reaction with compound 4-4 to obtain compound 4-5; the compound 4-5 is subjected to protecting group removal under an acidic condition to obtain compound 4-6; the compound 4-6 is subjected to an amide condensation reaction with compound 4-7 to obtain compound IV-2-1; and $R^1$, $R^2$, $R^{9a}$, $R^{9c}$, n1 and n2 are as defined in the above embodiments;

Synthesis Route 5

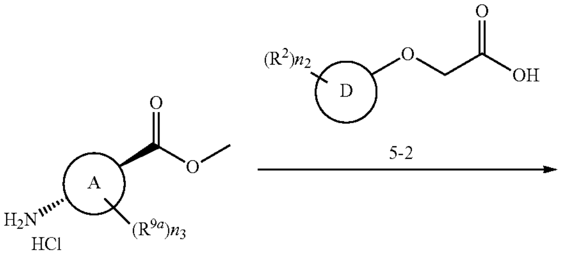

5-1

-continued

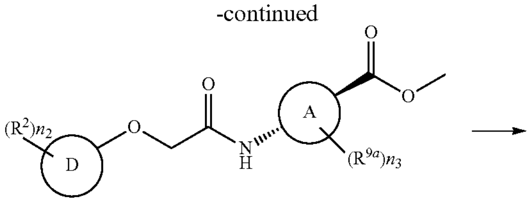

5-3

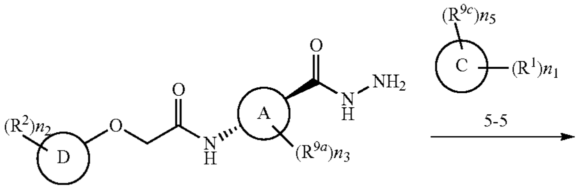

5-4

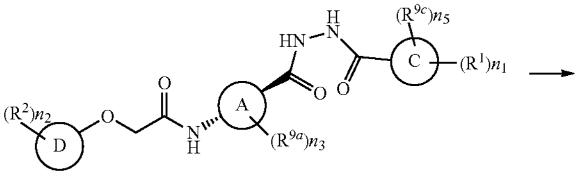

5-6

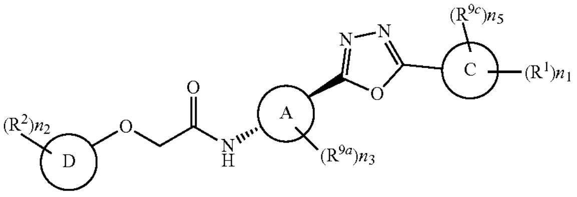

IV-1-1 wherein compound 5-1 is subjected to an amide condensation reaction with compound 5-2 to obtain compound 5-3; the compound 5-3 is reacted with hydrazine hydrate and subjected to a functional group conversion to obtain compound 5-4; the compound 5-4 is subjected to a condensation reaction with compound 5-5 to obtain compound 5-6; the compound 5-6 is subjected to a ring-closing reaction to obtain compound IV-1-1; and $R^1$, $R^2$, $R^{9a}$, $R^{9c}$, n1 and n2 are as defined in the above embodiments;

Synthesis Route 6

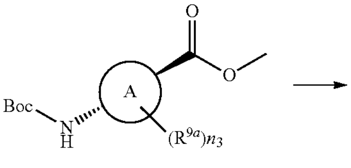

6-1

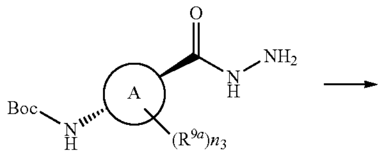

6-2

-continued

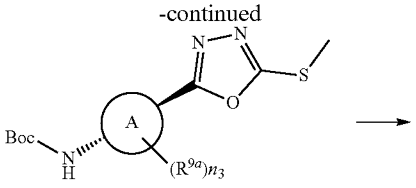

6-3

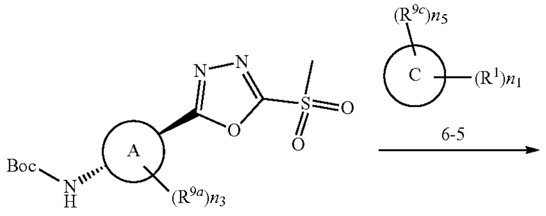

6-4

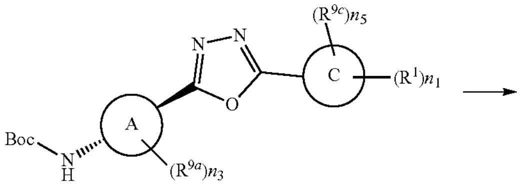

6-6

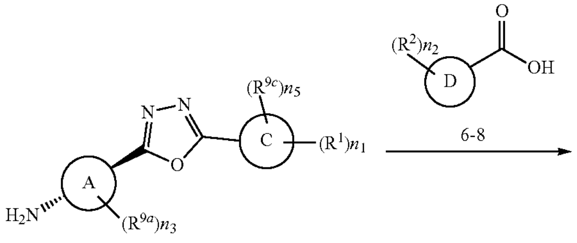

6-7

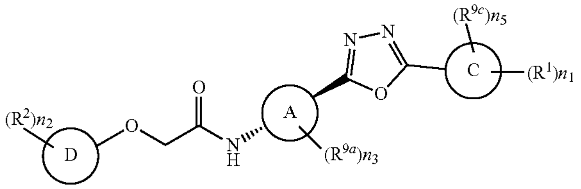

IV-1-1 wherein compound 6-1 is reacted with hydrazine hydrate and subjected to a functional group conversion to obtain compound 6-2; the compound 6-2 is subjected to a ring-closing reaction to obtain compound 6-3; the compound 6-3 is subjected to an oxidation reaction to obtain compound 6-4; the compound 6-4 is reacted with compound 6-5 to obtain compound 6-6; the compound 6-6 is subjected to protecting group removal under an acidic condition to obtain compound 6-7; the compound 6-7 is subjected to a condensation with compound 6-8 to obtain compound IV-1-1; and $R^1$, $R^2$, $R^{9a}$, $R^{9c}$, n1 and n2 are as defined in the above embodiments.

Yet another aspect of the present application provides a pharmaceutical composition comprising a preparation prepared from the compound, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof as descried in any of the above, or comprising a compound obtained by the synthesis method as descried in any of the above.

In some embodiments, the above pharmaceutical composition further comprises a pharmaceutically acceptable carrier, excipient and vehicle.

In some embodiments, provided is the use of the compound, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof as described in any of the above, or the pharmaceutical composition as described in any of the above in the preparation of a drug for preventing and/or treating neurodegenerative diseases (such as leukodystrophy, leukoencephalopathy, dysmyelination or demyelinating disease, intellectual disability syndrome, cognitive dysfunction, glial cell dysfunction, or brain injury (such as traumatic brain injury or toxin-induced brain injury)), cancer, inflammatory diseases, autoimmune diseases, viral infections, skin diseases, fibrotic diseases, hemoglobin diseases, kidney diseases, hearing loss diseases, eye diseases, diseases with mutations causing the induction of unfolded protein response (UPR), malaria infections, musculoskeletal diseases, metabolic diseases or mitochondrial diseases.

In some embodiments, provided is the use of the compound, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof as described in any of the above, or the pharmaceutical composition as described in any of the above in the preparation of a drug for preventing and/or treating a disease or condition mediated by an integrated stress response (ISR) pathway.

In some embodiments, provided is a method for treating a disease or condition mediated by an integrated stress response (ISR) pathway in an individual in need thereof, wherein the method comprises administering a therapeutically effective amount of the compound, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof as descried in any of the above, or a therapeutically effective amount of the pharmaceutical composition as descried in any of the above to the individual.

In some embodiments, provided is a method for treating a disease related to regulation of the activity or level of eIF2B, and regulation of the activity or level of the eIF2 pathway or ISR pathway, wherein the method comprises administering a therapeutically effective amount of the compound, or the stereoisomer thereof, the pharmaceutically acceptable salt thereof, the tautomer thereof, the polymorph thereof, the solvate thereof, the hydrate thereof, the N-oxide thereof, the isotopically labeled compound thereof, the metabolite thereof, the ester thereof or the prodrug thereof as described in any of the above, or a therapeutically effective amount of the pharmaceutical composition as described in any of the above to a subject.

In some embodiments, provided is a method for preventing and/or treating the above diseases, wherein the method comprises administering an effective amount of the compound, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof as described in any of the above, or the pharmaceutical composition as described in any of the above to a subject in need thereof.

In some embodiments, provided is a method for preventing and/or treating cancer, wherein the method comprises administering an effective amount of the compound, or the stereoisomer thereof, the tautomer thereof, the geometric isomer thereof, the enantiomer thereof, the diastereomer thereof, the racemate thereof, the polymorph thereof, the solvate thereof, the hydrate thereof, the N-oxide thereof, the isotopically labeled compound thereof, the metabolite thereof, the ester thereof, the prodrug thereof or the pharmaceutically acceptable salt thereof as described in any of the above, or the pharmaceutical composition as described in any of the above to a subject in need thereof.

In some embodiments, the neurodegenerative diseases include, but are not limited to: leukodystrophy, leukoencephalopathy, dysmyelination or demyelinating disease, intellectual disability syndrome, cognitive dysfunction, glial cell dysfunction, or brain injury (such as traumatic brain injury or toxin-induced brain injury), Alexander's disease, Alper's disease, Alzheimer's disease, amyotrophic lateral sclerosis (ALS), ataxia microvascular dilatation, Batten disease (also known as Spielmeyer-Vogt-Sjogren-Batten disease), bovine spongiform encephalopathy (BSE), Canavan disease, Cockayne syndrome, corticobasal degeneration, Creutzfeldt-Jakob disease, dystonia, frontotemporal dementia (FTD), Gerstmann-Straussler-Scheinker syndrome, Huntington's disease, HIV-related dementia, Kennedy's disease, Krabbe disease, kuru, lewy body dementia, Machado-Joseph disease (spinocerebellar ataxia type 3), multiple system atrophy, multisystem proteinopathy, narcolepsy, neuroborreliosis, Parkinson's disease, Pelizaeus-Merzbacher disease, Pick's disease, primary lateral sclerosis, Prion disease, Refsum's disease, Sandhoff disease, Schilder's disease, Subacute combined degeneration of spinal cord secondary to pernicious anemia, schizophrenia, spinocerebellar ataxia (multiple types with different features, such as spinocerebellar ataxia type 2 or spinocerebellar ataxia type 8), spinal muscular atrophy, Steele-Richardson-Olszewski disease, progressive supranuclear palsy, corticobasal degeneration, adrenoleukodystrophy, X-linked adrenoleukodystrophy, cerebral adrenoleukodystrophy, Pelizaeus-Merzbacher disease, Krabbe disease, leukodystrophy caused by mutations in the DARS2 gene (sometimes called leukoencephalopathy with brainstem and spinal cord involvement and lactate elevation (LBSL), DARS2-related spectrum disorder, or Tabes *dorsalis*).

The above-mentioned cancers include but are not limited to: human cancer and carcinoma, sarcoma, adenocarcinoma, lymphoma, leukemia and melanoma, including solid cancer and lymphoid cancer, renal cancer, breast cancer, lung cancer, bladder cancer, colon cancer, ovarian cancer, prostate cancer, pancreatic cancer, stomach cancer, brain cancer, head and neck cancer, skin cancer, uterine cancer, testicular cancer, glioma, esophageal cancer, liver cancer (including hepatocarcinoma), lymphoma (including B-acute lymphoblastic lymphoma, non-Hodgkin's lymphoma (such as Burkitt's lymphoma), small cell lymphoma and large cell lymphoma), Hodgkin's lymphoma, leukemia (including AML, ALL and CML) and/or multiple myeloma. In some other instances, the "cancer" refers to lung cancer, breast cancer, ovarian cancer, leukemia, lymphoma, melanoma, pancreatic cancer, sarcoma, bladder cancer, bone cancer, brain cancer, cervical cancer, colon cancer, esophageal cancer, stomach cancer, liver cancer, head and neck cancer, renal cancer, myeloma, thyroid cancer, prostate cancer, metastatic cancer or carcinoma.

The above-mentioned leukemias include but are not limited to: acute non-lymphocytic leukemia, chronic lymphocytic leukemia, acute granulocytic leukemia, chronic granulocytic leukemia, acute promyelocytic leukemia, adult T-cell leukemia, non-leukemic leukemia, aleucemic leucemia, basophilic leukemia, blastic leukemia, bovine leukemia, chronic myelogenous leukemia, leukemia cutis, stem-cell leukemia, eosinophilic leukemia, Gross' leukemia, hairy cell leukemia, hematoblast leukemia, hemoblastic leukemia, histiocytic leukemia, stem cell leukemia, acute monocytic leukemia, leukopenic leukemia, lymphatic leukemia, lymphoblastic leukemia, lymphocytic leukemia, lymphogenic leukemia, lymphoid leukemia, lymphosarcoma cell leukemia, mast cell leukemia, megakaryocytic leukemia, small myeloblast leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia or undifferentiated cell leukemia.

The above-mentioned inflammatory diseases include but are not limited to: postoperative cognitive dysfunction, arthritis (such as rheumatoid arthritis, psoriatic arthritis and juvenile idiopathic arthritis), systemic lupus erythematosus (SLE), myasthenia gravis, juvenile-onset diabetes, type 1 diabetes, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves' ophthalmopathy, inflammatory bowel disease, Addison's disease, vitiligo, asthma (such as allergic asthma), acne vulgaris, celiac disease, chronic prostatitis, inflammatory bowel disease, pelvic inflammatory disease, reperfusion injury, sarcoidosis, transplant rejection, interstitial cystitis, atherosclerosis and atopic dermatitis.

The above-mentioned musculoskeletal diseases include but are not limited to: muscular dystrophy (such as Duchenne muscular dystrophy, Becker muscular dystrophy, distal muscular dystrophy, congenital muscular dystrophy, Emery-Dreifuss muscular dystrophy, facioscapulohumeral muscular dystrophy, myotonic dystrophy type 1, or myotonic dystrophy type 2), limb-girdle muscular dystrophy, multisystem proteinopathy, rhizomelic chondrodysplasia *punctata*, X-linked recessive chondrodysplasia *punctata*, Conradi-Hünermann syndrome, autosomal dominant chondrodysplasia *punctata*, stress-induced bone disorders (such as stress-induced osteoporosis), multiple sclerosis, amyotrophic lateral sclerosis (ALS), primary lateral sclerosis, progressive muscular atrophy, progressive bulbar palsy, pseudobulbar palsy, spinal muscular atrophy, progressive spinal and bulbar muscular atrophy, spasticity of spinal origin, spinal muscular atrophy, myasthenia gravis, neuralgia, fibromyalgia, Machado-Joseph disease, Paget disease of the bone, painful fasciculation syndrome, Friedreich ataxia, muscle wasting disorders (such as muscular dystrophy, sarcopenia and cachexia), inclusion body myopathy, motor neuron disease or paralysis.

The above-mentioned metabolic diseases include but are not limited to: non-alcoholic steatohepatitis (NASH), non-alcoholic fatty liver disease (NAFLD), liver fibrosis, obesity, heart disease, atherosclerosis, arthritis, cystinosis, diabetes (such as type 1 diabetes, type 2 diabetes, or gestational diabetes), phenylketonuria, proliferative retinopathy or Kearns-Sayre disease.

The above-mentioned mitochondrial diseases include but are not limited to: Barth syndrome, chronic progressive external ophthalmoplegia (cPEO), Kearns-Sayre syndrome (KSS), Leigh syndrome (such as MILS or maternally inherited Leigh syndrome), mitochondrial DNA deletion syndrome (MDDS, e.g., Alpers syndrome), mitochondrial encephalomyopathy (such as mitochondrial encephalomyopathy with lactic acidosis and stroke-like episodes (MELAS)), mitochondrial neurogastrointestinal encephalomyopathy (MNGIE), myoclonus epilepsy with ragged-red fibers (MERRF), neuropathy, ataxia, retinitis pigmentosa (NARP), Leber's hereditary optic neuropathy (LHON) and Pearson syndrome.

The above-mentioned hearing loss diseases include but are not limited to: mitochondrial non-syndromic hearing loss and deafness, hair cell death, age-related hearing loss, noise-induced hearing loss, inherited or genetic hearing loss, hearing loss due to ototoxic exposure, disease-induced hearing loss and trauma-induced hearing loss. In some embodiments, the mitochondrial non-syndromic hearing loss and deafness is MT-RNR1-related hearing loss.

The above-mentioned eye diseases include but are not limited to: cataracts, glaucoma, endoplasmic reticulum (ER) stress, autophagy defects, age-related macular degeneration (AMD) or diabetic retinopathy.

The above-mentioned kidney diseases include but are not limited to: Abderhalden-Kaufmann-Lignac syndrome (Y-type cystinosis), abdominal compartment syndrome, acetaminophen-induced nephrotoxicity, acute renal failure/acute kidney injury, acute lobar nephropathy, acute phosphate nephropathy, acute tubular necrosis, adenine phosphoribosyltransferase deficiency, adenoviral nephritis, Alagille Syndrome, Alport Syndrome, amyloidosis, ANCA vasculitis related to endocarditis and other infections, angiomyolipoma, analgesic nephropathy, anorexia nervosa nephropathy, vasoconstrictor peptide antibodies and focal segmental glomerulosclerosis, antiphospholipid syndrome, glomerulonephritis related to anti-TNF-alpha therapy, APOL1 mutations, apparent mineralocorticoid excess syndrome, aristolochic acid nephropathy, Chinese herbal nephropathy, Balkan Endemic Nephropathy, urinary arteriovenous malformations and fistulas, autosomal dominant hypocalcemia, Bardet-Biedl Syndrome, Bartter Syndrome, acute kidney injury due to bath salts, beer potomania, beeturia, β-thalassemia nephropathy, bile cast nephropathy, autologous kidney BK polyomavirus nephropathy, rupture of bladder, bladder sphincter dyssynergia, bladder tamponade, border-crossers' nephropathy, Bourbon virus-induced acute kidney injury, burnt sugarcane harvesting-associated acute renal dysfunction, Byetta renal failure, Clq nephropathy, C3 glomerulopathy, C3 glomerulopathy with monoclonal gammopathy, C4 glomerulopathy, calcineurin inhibitor nephrotoxicity, Callilepsis Laureola poisoning, acute renal failure due to cannabinoid hyperemesis, cardiorenal syndrome, carfilzomib-induced renal injury, CFHR5 nephropathy, Charcot-Marie-Tooth disease with glomerular disease, Chinese herbal nephrotoxicity, acute kidney injury due to cherry concentrate, cholesterol embolism, Churg-Strauss syndrome, chyluria, ciliopathy, nephropathy related to cocaine, cold diuresis, colistin-induced nephrotoxicity, collagenofibrotic glomerulalopathy, collapsing glomerulopathy, CMV-related collapsing glomerulopathy, combined antiretroviral therapy (cART)-related nephropathy, congenital anomalies of the kidney and urinary tract (CAKUT), congenital nephrotic syndrome, congestive renal failure, cone-shaped epiphysis nephrotic syndrome (Mainzer-Saldino syndrome or Saldino-Mainzer disease), contrast-induced nephropathy, copper sulfate poisoning, cortical necrosis, crizotinib-related acute kidney injury, crystal cryoglobulinemia, cryoglobulinemia, crystalline globulin-induced nephropathy, crystal-induced acute kidney injury, crystal-storing histiocytosis, acquired cystic kidney disease, cystinuria, dasatinib-induced nephrotic range proteinuria, dense deposit disease (type 2 MPGN), Dent disease (X-linked recessive nephrolithiasis), DHA crystal nephropathy, dialysis disequilibrium syndrome, diabetes and diabetic nephropathy, diabetes insipidus, dietary supplement-related renal failure, diffuse mesangial sclerosis, diuresis, Djenkol bean poisoning (Djenkolism), Down Syndrome-related nephropathy, drug abuse-related nephropathy, duplicated ureters, EAST syndrome, Ebola-related nephropathy, ectopic kidney, ectopic ureter, edema, swelling, Erdheim-Chester Disease, Fabry's Disease, familial hypocalciuric hypercalcemia, Fanconi Syndrome, Fraser syndrome, fibronectin glomerulopathy, fibrillary glomerulonephritis and immunotactoid glomerulopathy, Fraley syndrome, fluid overload, hypervolemia, focal segmental glomerulosclerosis, focal sclerosis, focal glomerulosclerosis, Galloway Mowat syndrome, giant cell arteritis (temporal arteritis) involving the kidney, gestational hypertension, Gitelman syndrome, glomerular disease, tubulo-glomerular backflow, glycosuria, Goodpasture syndrome, green smoothie cleanse nephropathy, HANAC syndrome, Harvoni (ledipasvir and sofosbuvir)-induced kidney injury, acute kidney injury following hair dye poisoning, Hantavirus infection podocytopathy, heat stress nephropathy, hematuria (blood in urine), hemolytic uremic syndrome (HUS), atypical hemolytic uremic syndrome (aHUS), hemophagocytic syndrome, hemorrhagic cystitis, hemorrhagic fever with renal syndrome (HFRS, hantavirus nephropathy, Korean hemorrhagic fever, epidemic hemorrhagic fever, nephropathis epidemica), hemosiderosis, hemosiderosis related to paroxysmal nocturnal hemoglobinuria and hemolytic anemia, hepatic glomerular disease, hepatic veno-occlusive disease, hepatic sinusoidal obstruction syndrome, hepatitis C-related nephropathy, hepatocyte nuclear factor 1B-related nephropathy, hepatorenal syndrome, herbal supplement-related nephropathy, high altitude renal syndrome, hypertensive nephropathy, HIV-associated immune complex kidney disease (HIVICK), HIV-associated nephropathy (HIVAN), HNF1B-associated autosomal dominant tubulointerstitial nephropathy, horseshoe kidney (renal fusion), Hunner's ulcer, hydroxychloroquine-induced nephrolipidosis, hyperaldosteronism, hypercalcemia, hyperkalemia, hypermagnesemia, hypernatremia, hyperoxaluria, hyperphosphatemia, hypocalcemia, hypocomplementary urticaria vasculitis syndrome, hypopotassaemia, hypopotassaemia-induced renal dysfunction, hypokalemic periodic paralysis, hypomagnesemia, hyponatremia, hypophosphatemia, hypophosphatemia in marijuana users, hypertension, monogenic hypertension, Iced-tea nephropathy, Ifosfamide-induced nephrotoxicity, IgA nephropathy, IgG4 nephropathy, immersion diuresis, immune checkpoint therapy-related interstitial nephritis, infliximab-related nephropathy, interstitial cystitis, bladder pain syndrome (questionnaire), interstitial nephritis, megakaryocytic interstitial nephritis, Ivemark's syndrome, JC virus nephropathy, Joubert syndrome, ketamine-related bladder dysfunction, kidney stones, nephrolithiasis, kombucha tea toxicity, lead nephropathy and lead-related nephrotoxicity, lecithin cholesterol acyltransferase deficiency (LCAT deficiency), leptospirosis nephropathy, light chain deposition disease, monoclonal immunoglobulin deposition disease, light chain proximal tubulopathy, Liddle syndrome, Lightwood-Albright syndrome, lipoprotein glomerulopathy, lithium nephrotoxicity, hereditary FSGS caused by LMX1B mutations, loin pain-hematuria syndrome, lupus, systemic lupus erythematosus, lupus nephropathy, lupus nephritis, lupus nephritis with anti-neutrophil cytoplasmic antibody seropositivity, lupus podocytopathy, Lyme disease-related glomerulonephritis, lysinuria protein intolerance, lysozyme nephropathy, malarial nephropathy, malignant disease-related nephropathy, malignant hypertension, Malakoplakia, McKittrick-Wheelock syndrome, MDMA (Molly; Ecstacy; 3,4-methylenedioxymethamphetamine)-related renal failure, meatal stenosis, medullary cystic kidney disease, uromodulin-related nephropathy, Juvenile type 1 hyperuricemic nephropathy, medullary spongy kidney, megaureter, melamine-induced nephropathy, MELAS syndrome, membranoproliferative glomerulonephritis, membranous nephropathy, membranous glomerulopathy with occult IgGk deposition, MesoAmerican nephropathy, metabolic acidosis, metabolic alkalosis, methotrexate-related renal failure, microscopic polyangitis, milk-alkali syndrome, minimal change nephrosis, monoclonal gammopathy of renal significance, dysproteinemia, mouthwash toxicity, MUC1 nephropathy, multicystic renal dysplasia, multiple myeloma, myeloproliferative neoplastic glomerulopathy, nail-patella syndrome, NARP syndrome, nephrocalcinosis, nephrogenic systemic fibrosis, nephroptosis (floating kidney, renal ptosis), nephrotic syndrome, neurogenic bladder, 9/11 and kidney disease, nodular glomerulosclerosis, nongonococcal urethritis, nutcracker syndrome, oligomeganephronia, orofacial-digital syndrome, orotic aciduria, orthostatic hypotension, orthostatic proteinuria, osmotic diuresis, osmotic nephropathy, ovarian hyperstimulation syndrome, oxalate nephropathy, Page Kidney, Papillary necrosis, Papillorenal syndrome (renal coloboma syndrome, solitary renal dysplasia), PARN-mutated nephropathy, parvovirus B19 nephropathy, peritoneo-renal syndrome, posterior urethral valve POEMS syndrome, podocyte infolding glomerulopathy, postinfectious glomerulonephritis, poststreptococcal glomerulonephritis, atypical postinfectious glomerulonephritis, postinfectious glomerulonephritis (IgA dominant), mimicking IgA nephropathy, polyarteritis nodosa, posterior urethral valve polycystic kidney disease, postobstructive diuresis, preeclampsia, propofol infusion syndrome, proliferative glomerulonephritis with monoclonal IgG deposits (Nasr Disease), propolis (bee resin)-related renal failure, proteinuria (protein in urine), pseudohyperaldosteronism, pseudohypobicarbonatemia, pseudohypoparathyroidism, pulmonary renal syndrome, pyelonephritis (kidney infection), pyonephrosis, Pyridium-induced renal failure, radiation-induced nephropathy, Ranolazine-induced nephropathy, refeeding syndrome, reflux nephropathy, rapidly progressive glomerulonephritis, renal abscess, perirenal abscess, renal hypoplasia, acute kidney injury related to renal arcuate vein microthrombosis, renal artery aneurysm, spontaneous renal artery dissection, renal artery stenosis, renal cell carcinoma, renal cyst, renal hypouricemia with exercise-induced acute renal failure, renal infarction, renal osteodystrophy, renal tubular acidosis, renin mutation and autosomal dominant tubulointerstitial nephropathy, renin-secreting tumor (juxtaglomerular cell tumor), reset osmostat, retrocaval ureter, retroperitoneal fibrosis, rhabdomyolysis, rhabdomyolysis related to bariatric surgery, nephropathy related to rheumatoid arthritis, sarcoidosis-related nephropathy, salt loss in the kidney and brain, schistosomal glomerulopathy, Schimke immunoosseous dysplasia, scleroderma renal crisis, serpentine fibula-polycystic kidney syndrome, Exner syndrome, sickle cell nephropathy, chronic kidney disease due to silica exposure, Sri lankan farmers' kidney disease, Sjogren's syndrome-related nephropathy, acute kidney injury due to synthetic cannabinoid use, post-hematopoietic cell transplant nephropathy, nephropathy related to stem cell transplantation, TAFRO syndrome, tea and toast-induced hyponatremia, tenofovir-induced nephrotoxicity, thin basement membrane disease, benign familial hematuria, ranolazine-induced nephropathy related to monoclonal gammopathy, refeeding syndrome, reflux nephropathy, rapidly progressive glomerulonephritis, renal abscess, perirenal abscess, renal hypoplasia, acute kidney injury related to renal arcuate vein microthrombosis, renal artery aneurysm, spontaneous renal artery dissection, renal artery stenosis, renal cell carcinoma, renal cyst, renal hypouricemia with exercise-induced acute renal failure, renal infarction, renal osteodystrophy, renal tubular acidosis, renin mutation and autosomal dominant tubulointerstitial nephropathy, renin-secreting tumor (juxtaglomerular cell tumor), reset osmostat, retrocaval ureter, retroperitoneal fibrosis, rhabdomyolysis, rhabdomyolysis related to bariatric surgery, nephropathy related to rheumatoid arthritis, sarcoidosis-related nephropathy, salt loss in the kidney and brain, schistosomal glomerulopathy, Schimke immunoosseous dysplasia, scleroderma renal crisis, serpentine fibula-polycystic kidney syndrome, Exner syndrome, sickle cell nephropathy, chronic kidney disease due to silica exposure, Sri lankan farmers' kidney disease, Sjogren's syndrome-related nephropathy, acute kidney injury due to synthetic cannabinoid use, post-hematopoietic cell transplant nephropathy, nephropathy related to stem cell transplantation, TAFRO syndrome, tea and toast-induced hyponatremia, tenofovir-induced nephrotoxicity, thin basement membrane disease, benign familial hematuria, monoclonal gammopathy-related thrombotic microangiopathy, trench nephritis, trigonitis, urogenital tuberculosis, tuberous sclerosis, tubular dysgenesis, immune complex tubulointerstitial nephritis due to autoantibodies to the brush border of proximal tubules, tumor lysis syndrome, uremia, uremic optic neuropathy, cystic ureteritis, ureteral hernia, urethral caruncle, urethral stricture, urinary incontinence, urinary tract infection, urinary tract obstruction, urogenital fistula, uromodulin-related nephropathy, vancomycin-related cast nephropathy, vasomotor nephropathy, vesicoenteric fistula, vesicoureteric reflux, VGEF-inhibited renal thrombotic microangiopathy, volatile anesthetic-induced acute kidney injury, Von Hippel-Lindau disease, Waldenstrom's macroglobulinemic glomerulonephritis, warfarin-related nephropathy, acute kidney injury following wasp sting, Wegener's granulomatosis, granulomatosis with polyangiitis, West Nile virus-induced chronic kidney disease, Wunderlich syndrome, Zellweger syndrome, or cerebrohepatorenal syndrome.

The above-mentioned skin diseases include but are not limited to: acne, alopecia areata, basal cell carcinoma, Bowen's disease, congenital erythropoietic *porphyria*, contact dermatitis, Darier's disease, disseminated superficial actinic po-rokeratosis, dystrophic epidermolysis bullosa, eczema (atopic eczema), extramammary Paget's disease, simplex epidermolysis bullosa, erythropoietic protoporphyria, fungal infections of the nails, Hailey-Hailey disease, herpes simplex, hidradenitis suppurativa, hirsutism, hyperhidrosis, ichthyosis, impetigo, keloid, keratosis pilaris, lichen planus, lichen sclerosus, melanoma, melanoderma, mucous membrane pemphigoid, pemphigoid, pemphigus vulgaris, *Pityriasis* lichenoid, *Pityriasis rubra* pilaris, plantar warts (warts), polymorphous light eruption, psoriasis, plaque psoriasis, pyoderma gangrenosum, rosacea, scabies, scleroderma, herpes zoster, squamous cell carcinoma, Sweet's syndrome, urticaria, angioedema and vitiligo.

The above-mentioned fibrotic diseases include but are not limited to: adhesive capsulitis, arterial stiffness, arthrofibrosis, atrial fibrosis, cardiac fibrosis, cirrhosis, congenital hepatic fibrosis, Crohn's disease, cystic fibrosis, Dupuytren's contracture, endomyocardial fibrosis, glial scar, hepatitis C, hypertrophic cardiomyopathy, hypersensitivity pneumonitis, idiopathic pulmonary fibrosis, idiopathic interstitial pneumonia, interstitial lung disease, keloid, mediastinal fibrosis, myelofibrosis, nephrogenic systemic fibrosis, non-alcoholic fatty liver disease, old myocardial infarction, Peyronie's disease, pneumoconiosis, pneumonia, progressive massive fibrosis, pulmonary fibrosis, radiation-induced lung injury, retroperitoneal fibrosis, scleroderma/systemic sclerosis, silicosis and ventricular remodeling.

The above-mentioned hemoglobin diseases include but are not limited to: "dominant" β-thalassemia, acquired (toxic) methemoglobinemia, carboxy hemoglobinemia, congenital Heinz-body hemolytic anemia, HbH disease, HbS/β-thalassemia, HbE/β-thalassemia, HbSC disease, homozygous α+-thalassemia (α0-thalassemia), hydrops fetalis with Hb Bart's, sickle cell anemia/disease, sickle cell trait, sickle cell β-thalassemia disease, α+-thalassemia, α0-thalassemia, α-thalassemia related to myelodysplastic syndrome, α-thalassemia with mental retardation syndrome (ATR), β0-thalassemia, β+-thalassemia, δ-thalassemia, γ-thalassemia, β-thalassemia major, β-thalassemia intermediate, δβ-thalassemia and εγδβ-thalassemia.

The above-mentioned autoimmune diseases include but are not limited to: achalasia, Addison's disease, adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticaria, axonal and neuronal neuropathy (AMAN), Baló disease, Behcet's disease, benign mucosal pemphigoid, bullous pemphigoid, Castleman disease (CD), celiac disease, Chagas disease, chronic inflammatory demyelinating polyneuropathy (CIDP), chronic recurrent multifocal osteomyelitis (CRMO), Chagas-Strauss syndrome (CSS) or eosinophilic granulomatosis with polyangiitis (EGPA), cicatricial pemphigoid, Cogan's syndrome, cold agglutinin disease, congenital heart block, coxsackiemyocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture Syndrome, granulomatosis with polyangiitis, Graves' disease, Guillain-Barre syndrome, Hashimoto's thyroiditis, hemolytic anemia, henochschonlein purpura (HSP), herpes gestationis or pemphigoid gestationis (PG), hidradenitis suppurativa (HS) (acne inversa), hypogammaglobulinemia, IgA nephropathy, IgG4-related sclerosing disease, immune thrombocytopenia purpura (ITP), inclusion body myositis (IBM), interstitial cystitis (IC), juvenile arthritis, juvenile diabetes (type 1 diabetes), juvenile myositis (JM), kawasaki disease, Lambert-Eaton syndrome, leukocytoclastic vasculitis, lichen planus, lichen sclerosus, ligneous conjunctivitis, linear IgA disease (LAD), lupus, chronic Lyme disease, Meniere's disease, microscopic polyangitis (MPA), mixed connective tissue disease (MCTD), Mooren's ulcer, Mucha-Habermann disease, multifocal motor neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndrome type I, polyglandular syndrome type II, polyglandular syndrome type III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, seminal and testicular autoimmune diseases, stiff-man syndrome (SPS), subacute bacterial endocarditis (SBE), Susac's syndrome, sympathetic ophthalmia (SO), Takayasu's arteritis, temporal arteritis/giant cell arteritis, Thrombotic thrombocytopeni purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or granulomatosis with polyangiitis (GPA)).

The above-mentioned viral infections include but are not limited to: influenza, human immunodeficiency virus (HIV) and herpes.

The above-mentioned malaria infections include but are not limited to: infections caused by *Plasmodium vivax, Plasmodium ovale, Plasmodium malariae* and *Plasmodium falciparum.*

The above-mentioned diseases with mutations causing the induction of unfolded protein response (UPR) include but are not limited to: Marinesco-Sjogren syndrome, neuropathic pain, diabetic neuropathic pain, noise-induced hearing loss, nonsyndromic sensorineural hearing loss, age-related hearing loss, Wolfram syndrome, Darier White disease, Usher syndrome, collagenopathy, thin basement membrane nephropathy, Alport syndrome, skeletal chondrodysplasia, metaphyseal chondrodysplasia type Schmid and pseudoachondroplasia.

The compounds and derivatives provided in the present invention can be named according to the IUPAC (International Union of Pure and Applied Chemistry) or CAS (Chemical Abstracts Service, Columbus, OH) nomenclature system.

With regard to definitions of terms used in the present invention, the initial definitions provided for groups or terms herein are applicable to those groups or terms throughout the specification unless otherwise specified. With regard to terms not specifically defined herein, their meanings should be given in accordance with the disclosed contents and the context, which should be understandable to those skilled in the art.

"Substitution" means that a hydrogen atom in a molecule is replaced by another different atom or group; or the lone pair of electrons on an atom in a molecule is replaced by another atom or group. For example, the lone pair of electrons on an S atom can be replaced by an O atom to form

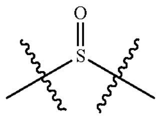 or 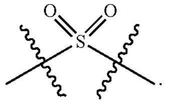

"may be substituted with . . . " and "optionally substituted with . . . " means that the "substitution" may but does not necessarily occur, encompassing both the situation where the substitution occurs and the situation where the substitution does not occur.

The minimum and maximum number of carbon atoms of a hydrocarbon group is indicated by a prefix, for example, the prefix in Ca-Cb alkyl indicates any alkyl group containing from "a" to "b" carbon atoms. Therefore, for example, C1-C6 alkyl refers to an alkyl group containing 1 to 6 carbon atoms.

"Alkyl" refers to a saturated hydrocarbon chain having a specified number of member atoms. Alkyl groups may be straight or branched. Representative branched-chain alkyl groups have one, two or three branches. For example, C1-C6 alkyl includes methyl, ethyl, propyl (n-propyl and isopropyl), butyl (n-butyl, isobutyl and tert-butyl), pentyl (n-pentyl, isopentyl and neopentyl) and hexyl.

The term "C1-C10 alkyl" refers to any straight-chain or branched-chain group containing 1 to 10 carbon atoms, such as methyl, ethyl, n-propyl, isopropyl, n-butyl, isobutyl, tert-butyl, sec-butyl, n-pentyl, tert-pentyl, n-hexyl, and the following alkyl groups that are straight or branched: C7 alkyl, C8 alkyl, C9 alkyl, C10 alkyl, etc.

Furthermore, the "C1-C10 alkyl" includes straight-chain or branched-chain groups with the number of carbon atoms in the range having any two integers between 1 and 10 as endpoints. For example, the "C1-C10 alkyl" includes C1-C10 alkyl, C1-C8 alkyl, C1-C6 alkyl, C2-C10 alkyl, C2-C8 alkyl, C2-C6 alkyl, C6-C10 alkyl, etc., which are listed merely for illustration purposes and do not serve as limitations.

The term "alkoxy" and derivatives thereof refer to groups formed by any of the above-mentioned alkyl groups (such as C1-C10 alkyl and C1-C6 alkyl) being attached to the rest of a molecule via an oxygen atom (—O—).

"Alkylene" refers to a divalent saturated aliphatic hydrocarbon group having a specified number of member atoms. Ca-Cb alkylene refers to an alkylene group having a to b carbon atoms. Alkylene groups include both branched-chain and straight-chain hydrocarbon groups. For example, the term "propylene" can be exemplified by the following structure:

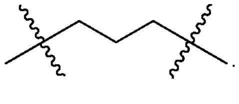 [SMILES: *CCC*]

Likewise, the term "dimethylbutylene" can be exemplified, for example, by either of the following structures:

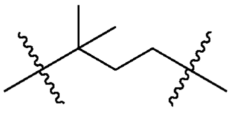 or 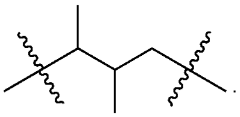

The C1-C4 alkylene of the present invention may be C1 alkylene (e.g., $—CH_2—$), C2 alkylene (e.g., $—CH_2CH_2—$), C3 alkylene or C4 alkylene.

The "cycloalkylene" in the present invention refers to a divalent saturated cyclic alkane with a single ring or multiple rings (fused rings, spiro rings or bridged rings) having multiple carbon atoms and no ring heteroatoms. Examples of monocarbocyclyl groups include, for example, divalent cyclopropyl, divalent cyclobutyl, divalent cyclohexyl, divalent cyclopentyl, divalent cyclooctyl, divalent cyclopentenyl and divalent cyclohexenyl. Examples of bridged cycloalkylene systems include bicyclo[3,1,0]hexane, bicyclo[3,1,1]hexane, bicyclo[2,2,1]hexane and bicyclo[2,2,2]hexane.

Examples of the "cycloalkylene" in the present invention include but are not limited to

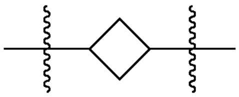, 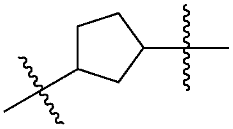, 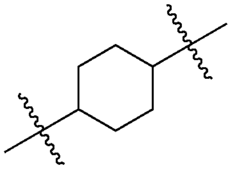, 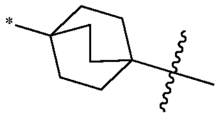 etc.

The term "C3-C10 cycloalkyl" refers to a 3- to 10-membered all-carbon monocyclic, fused and bridged ring, which may contain 0, one or more double bonds, but does not have a completely conjugated π-electron system. Examples of C3-C10 cycloalkyl include, but are not limited to, cyclopropane, cyclobutane, cyclopentane, cyclopentene, cyclohexane, cyclohexene, cyclohexadiene, etc.

The "heterocycloalkyl" in the present invention refers to a monovalent or divalent saturated ring having a single ring or multiple rings (fused rings, spiro rings and bridged rings) containing at least one heteroatom (a divalent saturated ring of heterocycloalkyl is heterocycloalkylene), wherein the heteroatoms refer to nitrogen atoms, oxygen atoms, sulfur atoms, etc. Examples of 3- to 10-membered heterocyclyl may be oxetanyl, azetidinyl, oxocyclopentyl, oxocyclohexyl, piperazinyl, piperidyl, morpholinyl, sym-trioxanyl, etc. Examples of the "heterocycloalkyl" in the present invention include but are not limited to

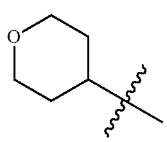, 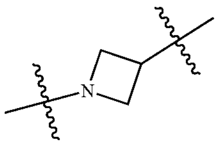,

-continued

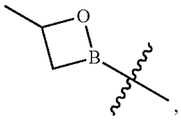
,
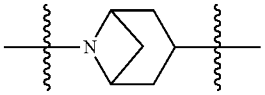
,
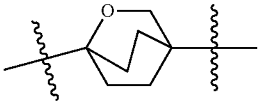
,
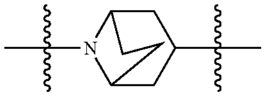
,
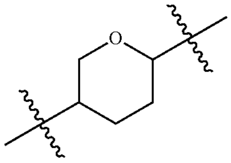
, piperidyl, etc.

The "unsaturated" in the present invention refers to the presence of carbon-carbon double bonds, carbon-carbon triple bonds, carbon-oxygen double bonds, carbon-sulfur double bonds, carbon-nitrogen triple bonds, etc. in groups or molecules.

The "aromatic ring" in the present invention refers to an aromatic hydrocarbon group having multiple carbon atoms. Aryl is typically monocyclic, bicyclic or tricyclic aryl having multiple carbon atoms. Furthermore, the term "aryl" as used herein refers to an aromatic substituent containing a single aromatic ring or multiple aromatic rings that are fused together. Non-limiting examples include phenyl, naphthyl or tetrahydronaphthyl.

The "5- to 10-membered heteroaryl" in the present invention refers to an aromatic unsaturated ring containing at least one heteroatom, wherein the heteroatoms refer to nitrogen atoms, oxygen atoms, sulfur atoms, etc., and generally comprises the aromatic monocyclic or bicyclic hydrocarbon containing a plurality of ring atoms, wherein one or more ring atoms are selected from heteroatoms of O, N, and S, and preferably containing one to three heteroatoms. For example, the 5- to 6-membered heteroaryl represents pyridyl, pyrrolyl, furyl, thienyl, pyrazolyl, imidazolyl, thiazolyl, pyranyl, thiopyranyl, piperazinyl, 1,2,3-triazolyl, 1,2,4-triazolyl, 1,2,5-triazolyl, 1,3,4-triazolyl, 1,2,3,4-tetrazolyl, 1,2,3,5-tetrazolyl, isoxazolyl, oxazolyl, 1,2,3-oxadiazolyl, 1,2,4-oxadiazolyl, 1,3,4-oxadiazolyl, furazanyl, 1,2,3,5-oxatriazolyl, 1,2,3,4-oxatriazolyl, 1,3,2-dioxazolyl, 1,2,3-dioxazolyl, 1,2,3,4-dioxadiazolyl, 1,2,3,5-dioxadiazolyl, 1,3,3,4-dioxadiazolyl, 1,3,4,5-dioxadiazolyl, 1,2,3,4-dioxadiazolyl, isothiazolyl, pyridazinyl, 1,2,3-triazinyl, 1,2,4-triazinyl, 1,3,5-triazinyl, 1,2,4,5-tetrazinyl, 1,2,4-oxazinyl, 1,2,6-oxazinyl, 1,3,2-oxazinyl, 1,3,6-oxazinyl, 1,4,2-oxazinyl, 1,2-isoxazinyl and 1,4-isoxazinyl.

The "halogen" in the present invention refers to fluorine, chlorine, bromine or iodine.

The "halogen-substituted alkyl" in the present invention refers to the alkyl having one or more hydrogen atoms substituted with halogen; for example, halogen-substituted $C_{1-4}$ alkyl refers to the alkyl containing 1 to 4 carbon atoms and having a hydrogen atom(s) substituted with one or more halogen atoms; and for example, monofluoromethyl, difluoromethyl and trifluoromethyl are included.

The "—$N(R)_2$" etc. in the present invention means that the R group is connected to the nitrogen atom via a single bond.

The "═O" in the present invention means that an oxygen atom substitutes two hydrogen atoms in a molecule via a double bond.

In the present invention, it would have been obvious to those skilled in the art that for any group with a composite name, such as "6- to 10-membered aryl-D-C1-C6 alkyl", the construction of the group is based on the part from which it is derived, such as the C1-C6 alkyl, in a left-to-right manner according to the naming convention, and it should be understood that the alkyl mentioned here is divalent alkyl.

In the present invention, the "stereoisomers" refer to compounds with the same chemical constitution but different arrangements of atoms or groups in space, including enantiomers, diastereomers, conformers (rotamers), geometric isomers (cis/trans isomers), atropisomers, etc.

In the present invention, the "tautomers" generally refer to structural isomers of different energies which are interconvertible via a low energy barrier. For example, proton tautomers (also known as prototropic tautomers) involve interconversions via proton transfer, such as keto-enol isomerizations and imine-enamine isomerizations. Valence tautomers involve the interconversion via the reorganization of some bonding electrons.

In the present invention, the "geometric isomers", also called "cis-trans isomers", are isomers caused by the inability of double bonds (including double bonds in alkenes, C═N and N═N), or single bonds of ring carbon atoms to rotate freely.

In the present invention, the "enantiomers" refer to two isomers of a compound which are non-superimposable mirror images of each other.

In the present invention, the "diastereomer" refers to stereoisomers that have two or more chiral centers and whose molecules are not mirror images of each other. Diastereomers have different physical properties, such as melting points, boiling points, spectral properties and reactivity. Diastereomeric mixtures can be separated by high-resolution analytical procedures such as electrophoresis and chromatography, for example HPLC.

In the present invention, the "racemate", "racemic substance" or "racemic mixture" refers to an equimolar mixture of two enantiomers lacking optical activity.

In the present invention, the "polymorph" refers to a crystalline form of a compound (or a salt, hydrate or solvate thereof) in a specific crystal packing arrangement. All polymorphs have the same elemental composition. Different crystal forms usually have different X-ray diffraction patterns, infrared spectra, melting points, density, hardness, crystal shapes, optical and electrical properties, stability and solubility. The recrystallization solvent, crystallization rate, storage temperature, and other factors may lead to the predominance of one crystal form.

The "solvate" in the present invention refers to a mixture produced by dissolving a compound in a solvent.

In the present invention, the "N-oxide" is also called amine oxide, which is a class of organic compounds having the general formula $R_3N+$—O— (also written as $R_3N$═O or $R_3N\rightarrow O$).

In the present invention, the "isotopically labeled compound" means that 1 or more atoms in a molecule or group are substituted with their isotope atoms; for example, hydrogen atoms are substituted with deuterium atoms, with the proportion of deuterium atoms being greater than the natural abundance of deuterium; and for example, 12C is substituted with 13C.

In the present invention, the "metabolites" refer to substances generated by chemical structural transformation of drug molecules under the action of the body after the drug molecules are absorbed by the body.

In the present invention, the "prodrug" refers to a compound obtained by chemically modifying a drug, and the "prodrug" is inactive or less active in vitro and releases active drugs via the enzymatic or non-enzymatic conversion in vivo, thereby exerting pharmacological effects.

The term "pharmaceutically acceptable" means that a carrier, vector, diluent, excipient, and/or a salt formed thereby is generally chemically or physically compatible with other ingredients constituting a pharmaceutical dosage form and is physiologically compatible with the recipient.

The term "salt" and "pharmaceutically acceptable salt" refer to acidic and/or basic salts formed by the above-mentioned compounds or the stereoisomers thereof with inorganic and/or organic acids and bases, and also include zwitterionic salts (inner salts) and quaternary ammonium salts, such as alkylammonium salts. These salts can be obtained directly during the final separation and purification of the compounds. These salts can also be obtained by appropriately (for example, in equivalent amounts) mixing the above-mentioned compounds or the stereoisomers thereof with a certain number of acids or bases. These salts may precipitate from solution and be collected by filtration, or may be recovered by evaporation of the solvent, or may be prepared by freeze-drying after reaction in an aqueous medium.

The term "preventing" includes suppressing and delaying the onset of a disease, and encompasses not only preventing a disease before its development, but also preventing the recurrence of a disease after treatment.

The term "treating" means reversing, alleviating or eliminating the disorders or conditions to which such term applies, or the progression of one or more symptoms of such disorders or conditions.

In certain embodiments, one or more compounds of the present invention may be used in combination with each other. The compounds of the present invention may also be used in combination with any other active agents to prepare drugs or pharmaceutical compositions for regulating cell functions or treating diseases. If a group of compounds are used, the compounds may be administered to a subject simultaneously, separately or sequentially.

Obviously, according to the above-mentioned contents of the present invention, in accordance with common technical knowledge and customary means in the art, and without departing from the above basic technical ideas of the present invention, other various forms of modifications, replacements or changes can be made.

The above contents of the present invention will be further described in detail in the following "Detailed Description of Embodiments" presented in the form of examples. However, this should not be construed as limiting the scope of the above-mentioned subject of the present invention to the following examples. All techniques achieved based on the above-mentioned contents of the present invention fall within the scope of the present invention.

DETAILED DESCRIPTION OF EMBODIMENTS

The embodiments of the present application will be further described in detail below with reference to the examples. The following detailed description of the examples and the accompanying drawings are used to illustrate the principle of the present application in an exemplary manner, but shall not be used to limit the scope of the present application. That is, the present application is not limited to the described examples.

The known starting materials of the present invention can be synthesized by or in accordance with methods known in the art, or can be purchased from Bidepharm, Leyan, Titan, Accela ChemBio Co., Ltd., Energy Chemical, Tansoole, PharmaBlock Sciences (Nanjing), Inc., Jiangsu Aikon Biopharmaceutical R&D Co., Ltd., Innochem (Beijing) Technology Co., Ltd., etc. Among them, tetrapropylammonium perruthenate is purchased from Tansoole, and 1-propylphosphonic anhydride is purchased from Innochem (Beijing) Technology Co., Ltd.

Unless otherwise specified in the examples, the reactions are carried out under nitrogen atmosphere. Unless otherwise specified in the examples, the solution refers to an aqueous solution. Unless otherwise specified in the examples, the reaction temperature is room temperature. The optimal reaction temperature is room temperature, which ranges from 20° C.-30° C. Unless otherwise specified in the examples, M represents mole per liter.

The structures of the compounds are determined by nuclear magnetic resonance (NMR) or mass spectrometry (MS). The NMR shift (δ) is given in the unit of $10^{-6}$ (ppm). NMR is determined by using a nuclear magnetic resonance spectrometer Bruker Avance III 400. The solvents for determination are deuterated dimethyl sulfoxide (DMSO-$d_6$), deuterated chloroform ($CDCl_3$), and deuterated methanol (Methanol-$d_4$), and the internal standard is tetramethylsilane (TMS). LC-MS is determined by using Shimadzu LC-MS 2020 (ESI). HPLC is determined by using a high-pressure liquid chromatograph Shimadzu LC-20A. MPLC (medium-pressure liquid chromatography) is performed using a reverse-phase preparative chromatograph Gilson GX-281. Yantai Huanghai HSGF254 or Qingdao GF254 silica gel plate is used as a thin layer chromatography silica plate, and the specification when a product is separated and purified by thin layer chromatography is 0.4 mm-0.5 mm. 200-300 mesh Yantai Huanghai silica gel is generally used as a carrier for the column chromatography.

Dimethylformamide is abbreviated as DMF; N,N'-diisopropylethylamine (also known as diisopropylethylamine) is abbreviated as DIEA or DIPEA; 2-(7-azobenzotriazole)-N,N,N',N'-tetramethyluronium hexafluorophosphate is abbreviated as HATU; tetrapropylammonium perruthenate is abbreviated as TPAP; 1-propylphosphonic anhydride is abbreviated as T3P; N-methylmorpholine-N-oxide is abbreviated as NMO; trifluoroacetic acid is abbreviated as TFA; tetrahydrofuran is abbreviated as THF.

Example 1: Synthesis of Compound 1

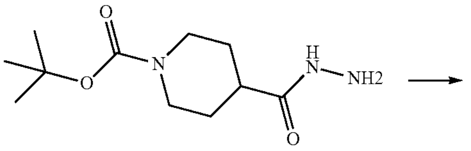

1a

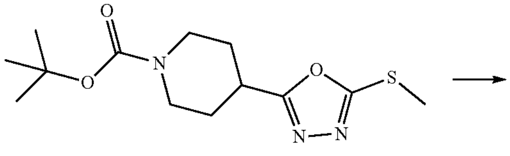

1b

-continued

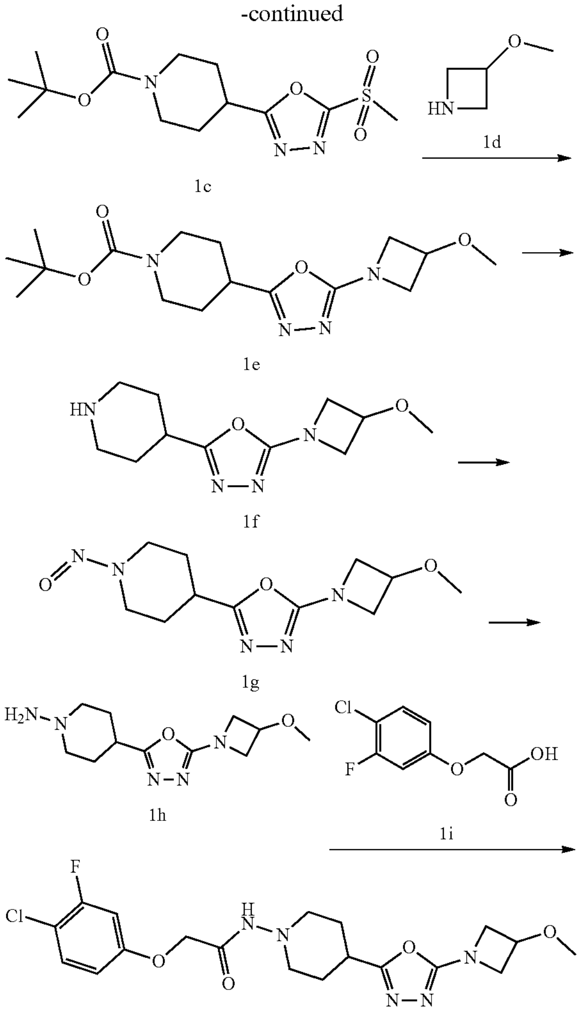

1c
1e
1f
1g
1h
1

Step 1: Synthesis of Intermediate 1b

At 25° C., to a 100 mL single-necked flask were added compound 1a (Bidepharm, Cat. No. BD57204, 4.0 g, 16.44 mmol) and dimethylformamide (20.0 mL). Under stirring, the compound N,N'-thiocarbonyldiimidazole (4.1 g, 23.02 mmol) was sequentially added. The mixture was reacted at 25° C. for 1 hour and stirred at 100° C. for 2 hours. The reaction was cooled to 0° C., and then iodomethane (2.33 g, 16.44 mmol) was added. The mixture was stirred at 25° C. for 1 hour, and then the reaction was completed. To the resulting reaction solution was added 50 ml of water, and the mixture was extracted with ethyl acetate (50 ml×3). The resulting organic phases were combined, washed with 100 mL of a saturated sodium chloride aqueous solution, dried over sodium sulfate and filtered, and then the filtrate was concentrated under reduced pressure to obtain a crude. The crude was purified by column chromatography to obtain intermediate 1b. LC-MS: m/z: 243.9 $(M+H-56)^*$.

Step 2: Synthesis of Intermediate 1c

At 25° C., to a 100 mL single-necked flask were added intermediate 1b (4.1 g, 13.71 mmol) and dichloromethane (20.0 mL). Under ice bath and stirring, the compound m-chloroperoxybenzoic acid (4.2 g, 20.58 mmol) was added. The mixture was reacted at 25° C. for 16 hours, and then the reaction was completed. The resulting reaction solution was adjusted to about pH 8 by adding a saturated sodium bicarbonate aqueous solution, extracted with ethyl acetate, dried over anhydrous sodium sulfate and filtered, and then the filtrate was concentrated under reduced pressure to obtain a crude. The crude was separated and purified by column chromatography to obtain intermediate 1c. LC-MS: m/z: 275.9 $(M+H-56)^+$.

Step 3: Synthesis of Intermediate 1e

At 25° C., to a 100 mL single-necked flask were added compound 1d (Bidepharm, Cat. No. BD25596, 197 mg, 2.26 mmol) and tetrahydrofuran (10 mL). Under stirring, the compound NaH (181 mg, 4.52 mmol) was added. At 25° C., the mixture was reacted for 0.5 hours, and then intermediate 1c (500 mg, 1.51 mmol) was added. The mixture was stirred at 25° C. for 16 hours, and then the reaction was completed. To the resulting reaction solution was added 25 ml of water, and the mixture was extracted with 25 mL of ethyl acetate. The resulting organic phase was washed with 50 ml of a saturated sodium chloride aqueous solution, dried over anhydrous sodium sulfate and filtered, and then the filtrate was concentrated under reduced pressure to obtain a crude. The crude was separated and purified by column chromatography to obtain intermediate 1e. LC-MS: m/z: 283.0 $(M+H-56)^+$.

Step 4: Synthesis of Intermediate 1f

At 25° C., to a 100 mL single-necked flask were added intermediate 1e (270 mg, 0.80 mmol) and dichloromethane (3.0 mL). Under stirring, trifluoroacetic acid (1.0 mL, 4.5 mmol) was added. The mixture was reacted at 25° C. for 2 hours, and then the reaction was completed. The reaction mixture was concentrated under reduced pressure to obtain intermediate 1f. LC-MS: m/z: 239.0 $(M+H)^+$.

Step 5: Synthesis of Intermediate 1g

Under ice bath, to a 100 mL single-necked flask were added intermediate 1f (140 mg, 0.59 mmol), glacial acetic acid (3.5 mL) and water (1.5 mL). Under stirring, sodium nitrite (121 mg, 1.75 mmol) was added, and the mixture was reacted for 1 hour. The mixture was further reacted at 25° C. for 1 hour, and then the reaction was completed. The resulting reaction solution was concentrated under reduced pressure to obtain intermediate 1g. LC-MS: m/z: 268.0 $(M+H)^+$.

Step 6: Synthesis of Intermediate 1h

Under ice bath, to a 100 mL single-necked flask were added intermediate 1g (80 mg, 0.30 mmol), glacial acetic acid (1.0 mL) and methanol (3.0 mL). Under stirring, zinc powder (97 mg, 1.48 mmol) was added. The mixture was reacted at 25° C. for 2 hours, and then the reaction was completed. The resulting reaction solution was concentrated under reduced pressure to obtain intermediate 1h. LC-MS: m/z: 254.0 $(M+H)^+$.

Step 7: Synthesis of Compound 1

Under ice bath, to a 50 mL single-necked flask were added compound 1i (Bidepharm, Cat. No. BD00901377, 71 mg, 0.35 mmol) and dimethylformamide (3.0 mL). Under stirring, 2-(7-azobenzotriazole)-N,N,N',N'-tetramethyluronium hexafluorophosphate (180 mg, 0.47 mmol) and diisopropylethylamine (123 mg, 0.95 mmol) were sequentially added. The mixture was reacted at 25° C. for half an hour, and then intermediate 1h (55 mg, 0.22 mmol) was added to the resulting reaction solution. At 25° C., the mixture was reacted overnight. To the resulting reaction solution was added 25 ml of water, and the mixture was extracted with ethyl acetate (50 ml×3). The resulting organic phases were combined, washed with 100 ml of a saturated sodium chloride aqueous solution, dried over sodium sulfate and filtered, and then the filtrate was concentrated under reduced pressure to obtain a crude. The crude was separated and purified by high performance liquid chromatography (ammonium bicarbonate/acetonitrile/water system) to obtain compound 1. $^1$H NMR (400 MHZ, $CDCl_3$) δ 7.28-7.26 (m, 1H), 6.78-6.73 (m, 1H), 6.71-6.66 (m, 1H), 4.81 (s, 1H), 4.50 (s, 2H), 4.38-4.28 (m, 3H), 4.08-4.12 (m, 2H), 3.33 (s, 3H), 3.14-3.12 (m, 2H), 2.88-2.84 (m, 1H), 2.78-2.72 (m, 2H), 2.14-2.10 (m, 4H). LC-MS: m/z: 440.0 $(M+H)^+$.

Example 2: Synthesis of Compound 2

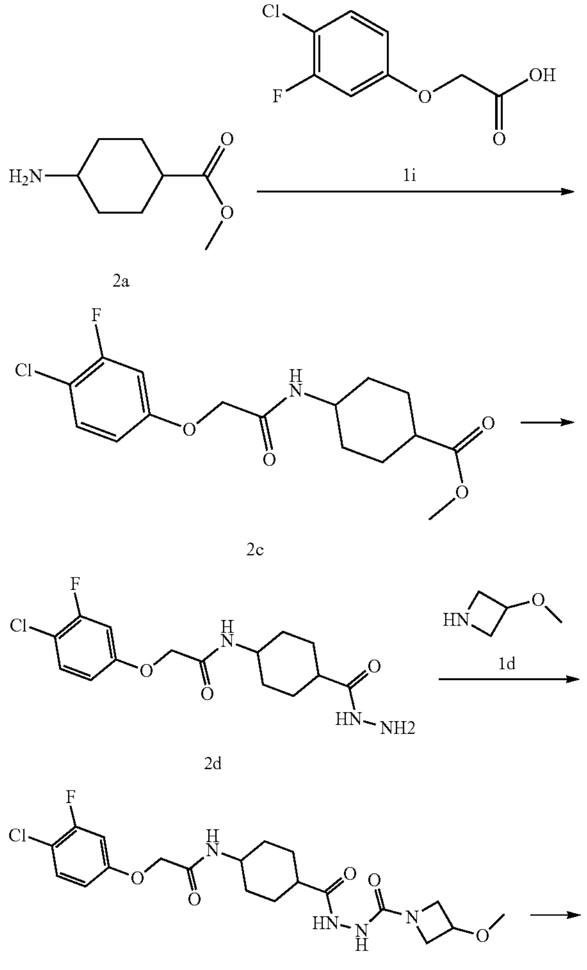

2a

2c

2d

2f

-continued

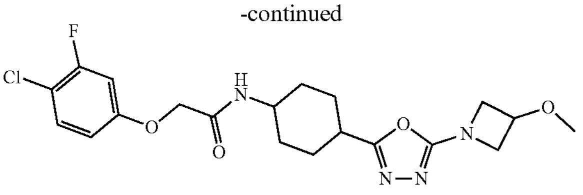

2

Step 1: Synthesis of Intermediate 2c

Under ice bath, to a 100 mL single-necked flask were added compound 1i (467 mg, 2.29 mmol) and dimethylformamide (8.0 mL). Under stirring, 2-(7-azobenzotriazole)-N,N,N',N'-tetramethyluronium hexafluorophosphate (1.08 g, 2.86 mmol) and diisopropylethylamine (986 mg, 7.64 mmol) were sequentially added. The mixture was reacted at 25° C. for half an hour, and then compound 2a (Bidepharm, Cat. No. BD283560, 300 mg, 1.91 mmol) was added to the resulting reaction solution. At 25° C., the mixture was reacted overnight. To the resulting reaction solution was added 100 ml of water, and the mixture was extracted with ethyl acetate (50 ml×2). The resulting organic phases were combined, washed with 100 ml of a saturated sodium chloride aqueous solution, dried over sodium sulfate and filtered, and then the filtrate was concentrated under reduced pressure to obtain a crude. The crude was separated and purified by column chromatography to obtain intermediate 2c. LC-MS: m/z: 344.0 $(M+H)^+$.

Step 2: Synthesis of Intermediate 2d

At 25° C., to a 100 mL single-necked flask were added intermediate 2c (360 mg, 1.05 mmol) and ethanol (3.0 mL). Under stirring, hydrazine hydrate (969 mg, 10.50 mmol) was added. The mixture was reacted overnight at 80° C., and then the reaction was completed. To the resulting reaction solution was added 25 ml of water, and the mixture was extracted with 25 ml of ethyl acetate. The resulting organic phase was washed with 25 ml of a saturated sodium chloride aqueous solution, dried over sodium sulfate and filtered, and then the filtrate was concentrated under reduced pressure to obtain a crude. The crude was separated and purified by column chromatography to obtain intermediate 2d. LC-MS: m/z: 344.0 $(M+H)^+$.

Step 3: Synthesis of Intermediate 2f

At 25° C., to a 50 mL single-necked flask were added compound 1d (17 mg, 0.2 mmol) and tetrahydrofuran (3.0 mL). Under stirring, triphosgene (181 mg, 0.61 mmol) was added. The mixture was reacted at 25° C. for 2 hours, and then intermediate 2d (70 mg, 0.2 mmol) was added. The mixture was reacted at 80° C. overnight, with a large number of solids precipitated in the reaction system. Dimethylformamide (3.0 mL) was then added, and the mixture was further reacted overnight at 80° C. To the resulting reaction solution was added 50 ml of water, and the mixture was extracted with 50 ml of ethyl acetate. The resulting organic phase was washed with 100 ml of a saturated sodium chloride aqueous solution, dried over sodium sulfate and filtered, and then the filtrate was concentrated under reduced pressure to obtain a crude. The crude was separated and purified by column chromatography to obtain intermediate 2f. LC-MS: m/z: 457.0 $(M+H)^+$.

Step 4: Synthesis of Compound 2

At 25° C., to a 50 mL single-necked flask were added intermediate 2f (26 mg, 0.06 mmol) and dimethylformamide (3.0 mL). Under stirring, cesium carbonate (55 mg, 0.17 mmol) and p-toluenesulfonyl chloride (22 mg, 0.11 mmol) were sequentially added. The mixture was reacted at 25° C. for 3 hours, and then the reaction was completed. 35 ml of water was added to the resulting reaction solution, and the mixture was extracted with 35 ml of ethyl acetate. The resulting organic phase was washed with 100 ml of a saturated sodium chloride aqueous solution, dried over sodium sulfate and filtered, and then the filtrate was concentrated under reduced pressure to obtain a crude. The crude was separated and purified by high performance liquid chromatography (ammonium bicarbonate/acetonitrile/water system) to obtain compound 2. $^1H$ NMR (400 MHZ, $CDCl_3$) δ 7.33 (t, J=8.6 Hz, 1H), 6.93-6.67 (m, 3H), 6.65-6.63 (m, 2H), 4.77-4.72 (m, 1H), 4.52-4.47 (m, 1H), 4.43 (s, 2H), 3.71-3.56 (m, 3H), 3.48-3.33 (m, 3H), 2.42-2.38 (m, 2H), 1.80-1.68 (m, 4H), 1.61-1.56 (m, 2H). LC-MS: m/z: 439.1 $(M+H)^+$.

Example 3: Synthesis of Compound 21

Step 1: Preparation of Intermediate 21a

At 25° C., to a 100 mL single-necked flask were added compound 21g (Bidepharm, Cat. No. BD212373, 5.00 g, 19.42 mmol) and ethanol (50.0 mL). Under stirring, the compound hydrazine hydrate (7.75 g, 84.00 mmol) was added. The mixture was reacted overnight at 80° C., and then the reaction was completed. The reaction solution was cooled and then concentrated under reduced pressure to obtain a crude. The crude was separated and purified by column chromatography to obtain intermediate 21a. LC-MS: m/z: 202.0 $(M+H-56)^+$.

Step 2: Preparation of Intermediate 21c

At 25° C., to a 100 mL single-necked flask were added intermediate 21a (3.8 g, 13.29 mmol) and 1,2-dichloroethane (30.0 mL). Under stirring, the compound N,N'-carbonyldiimidazole (5.0 g, 26.58 mmol) was sequentially added. The mixture was reacted at 25° C. for 18 hours, and then the reaction was completed. To the resulting reaction solution was added 25 ml of water. The organic phase was washed with 100 ml of a saturated sodium chloride aqueous solution, dried over anhydrous sodium sulfate and filtered, and then the filtrate was concentrated under reduced pressure to obtain a crude. The crude was purified by column chromatography to obtain intermediate 21c. LC-MS: m/z: 228.0 $(M+H-56)^+$.

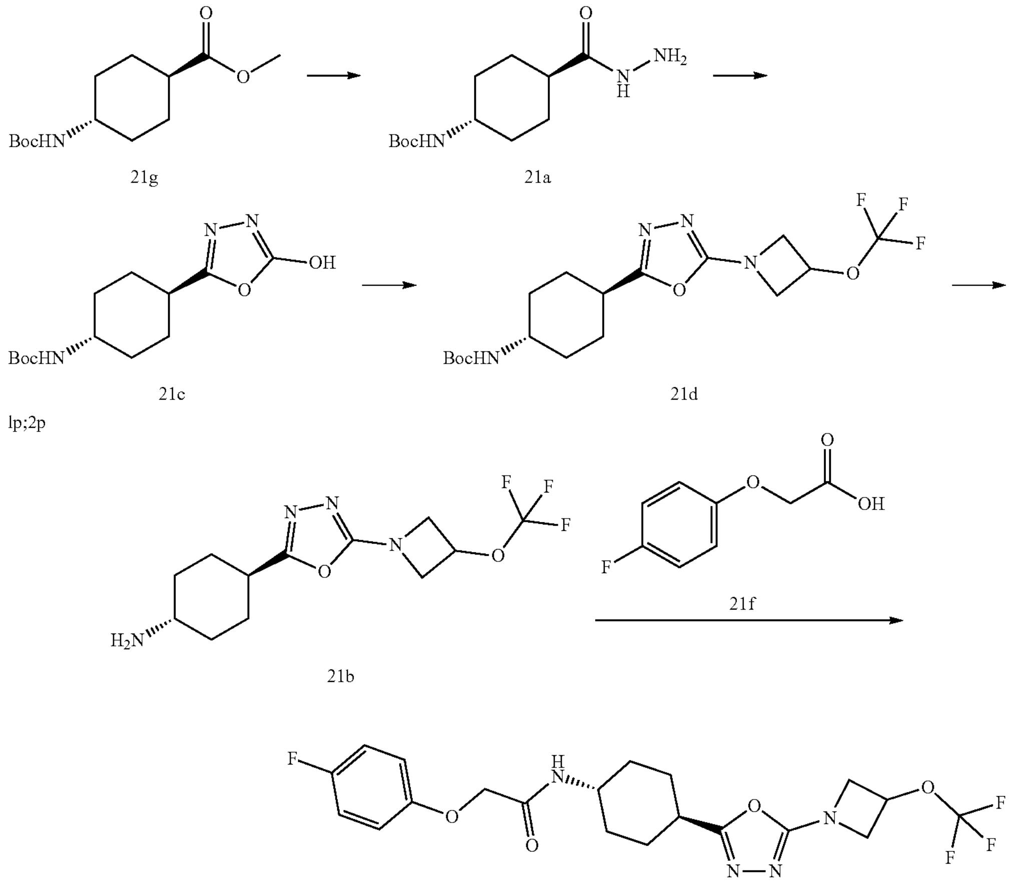

21g

21a

21c

21d lp;2p

21b

21f

21

Step 3: Preparation of Intermediate 21d

At 25° C., to a 100 mL single-necked flask were added intermediate 21c (2.9 g, 9.26 mmol) and dimethylformamide (30 mL). Under stirring, 3-(trifluoromethoxy)-azetidine (1.73 g, 12.28 mmol), diisopropylethylamine (6.65 g, 51.18 mmol) and Castro's reagent (6.45 g, 15.53 mmol) were sequentially added. The mixture was reacted at 25° C. for 16 hours, and then the reaction was completed. To the resulting reaction solution was added 100 ml of water. The organic phase was separated, washed with 100 ml of a saturated sodium chloride aqueous solution, dried over sodium sulfate and filtered, and then the filtrate was concentrated under reduced pressure to obtain a crude. The crude was separated and purified by high performance liquid chromatography (ammonium bicarbonate/acetonitrile/water system) to obtain intermediate 21d. LC-MS: m/z: 407.2 $(M+H)^+$.

Step 4: Preparation of Intermediate 21b

At 25° C., to a 100 mL single-necked flask were added intermediate 21d (140 mg, 0.34 mmol) and dichloromethane (6.0 mL). Under stirring, trifluoroacetic acid (2.0 mL, 4.5 mmol) was added. The mixture was reacted at 25° C. for 2 hours, and then the reaction was completed. The reaction mixture was concentrated under reduced pressure to obtain intermediate 21b. LC-MS: m/z: 307.2 $(M+H)^+$.

Step 5: Synthesis of Compound 21

At 25° C., in an 8 mL reaction flask, compound 21f (Bidepharm, Cat. No. BD11064, 6 mg, 0.03 mmol) and intermediate 21b (5.1 mg, 0.02 mmol) were dissolved in dimethylformamide (1.5 mL). Under stirring, triethylamine (4.048 mg, 0.04 mmol) and 2-(7-azobenzotriazole)-N,N,N',N'-tetramethyluronium hexafluorophosphate (15.21 mg, 0.03 mmol) were sequentially added. The mixture was stirred at 25° C. for 10 hours until the reaction was completed. To the reaction solution was added 20 ml of water, and the mixture was extracted with 20 ml of ethyl acetate. The resulting organic phase was washed with 20 mL of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 21. $^1H$ NMR (400 MHZ, MeOD) δ 7.15-6.89 (m, 4H), 5.37-5.20 (m, 1H), 4.60-4.51 (m, 2H), 4.49 (s, 2H), 4.33 (dd, J=9.4, 4.0 Hz, 2H), 3.84 (ddd, J=15.6, 7.9, 4.0 Hz, 1H), 2.81 (tt, J=12.1, 3.5 Hz, 1H), 2.17 (d, J=12.1 Hz, 2H), 2.03 (d, J=9.8 Hz, 2H), 1.76-1.60 (m, 2H), 1.59-1.42 (m, 2H). LC-MS: m/z: 459.1 $(M+H)^+$.

Example 4: Synthesis of Compound 22

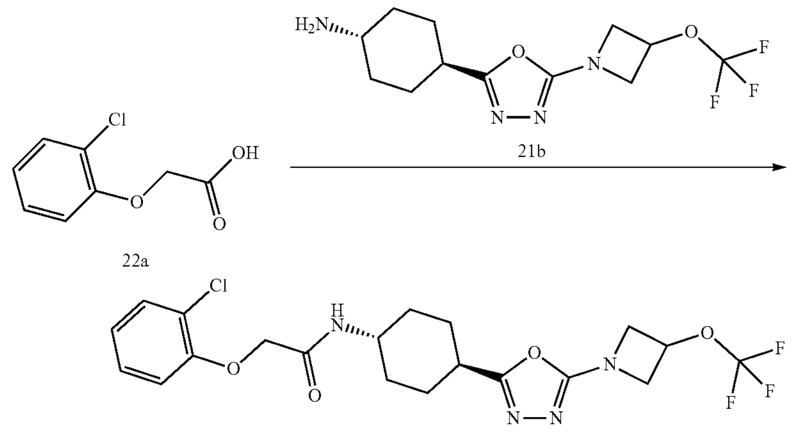

21b

22a

22

At 25° C., in an 8 mL reaction flask, compound 22a (Bidepharm, Cat. No. BD21790, 28 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the reaction solution was added 20 ml of water, and the mixture was extracted with 20 ml of ethyl acetate. The resulting organic phase was washed with 20 mL of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 22. $^1H$ NMR (400 MHZ, DMSO) δ 7.90 (d, J=7.9 Hz, 1H), 7.45 (dd, J=7.9, 1.6 Hz, 1H), 7.36-7.22 (m, 1H), 7.09-6.91 (m, 2H), 5.39-5.23 (m, 1H), 4.59 (s, 2H), 4.46 (dd, J=9.6, 6.8 Hz, 2H), 4.19 (dd, J=9.6, 4.0 Hz, 2H), 3.63 (ddd, J=11.3, 7.5, 3.8 Hz, 1H), 2.74 (ddd, J=11.8, 7.7, 3.5 Hz, 1H), 2.03 (d, J=11.3 Hz, 2H), 1.88 (dd, J=12.8, 3.1 Hz, 2H), 1.58-1.45 (m, 2H), 1.43-1.30 (m, 2H). LC-MS: m/z: 475.2 $(M+H)^+$.

Example 5: Synthesis of Compound 23

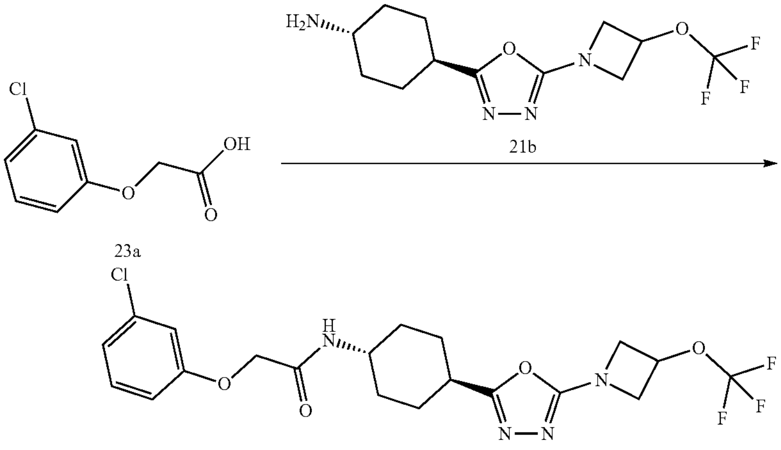

21b

23a

23

Step 1: Synthesis of Compound 23

At 25° C., in an 8 mL reaction flask, compound 23a (Bidepharm, Cat. No. BD21634, 28 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 23. $^1$H NMR (400 MHZ, DMSO) δ 8.04 (d, J=8.0 Hz, 1H), 7.32 (t, J=8.1 Hz, 1H), 7.03 (t, J=5.5 Hz, 2H), 6.93 (dd, J=8.3, 2.0 Hz, 1H), 5.37-5.26 (m, 1H), 4.50 (s, 2H), 4.46 (dd, J=9.4, 6.9 Hz, 2H), 4.19 (dd, J=9.5, 3.9 Hz, 2H), 3.74 (s, 1H), 2.78-2.67 (m, 1H), 2.03 (d, J=11.5 Hz, 2H), 1.85 (d, J=9.7 Hz, 2H), 1.51 (dd, J=25.0, 10.9 Hz, 2H), 1.44-1.31 (m, 2H). LC-MS: m/z: 475.2 $(M+H)^+$.

Example 6: Synthesis of Compound 24

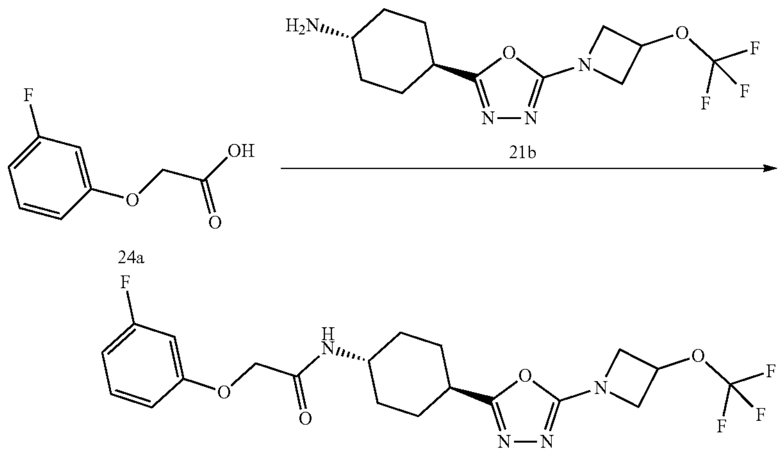

21b

24a

24

Step 1: Synthesis of Compound 24

At 25° C., in an 8 mL reaction flask, compound 24a (Bidepharm, Cat. No. BD45137, 25.5 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 24. $^1$H NMR (400 MHZ, MeOD) δ 7.37-7.26 (m, 1H), 6.92-6.70 (m, 3H), 5.32-5.28 (m, 1H), 4.58-4.53 (m, 2H), 4.53 (s, 2H), 4.31 (dd, J=9.6, 4.1 Hz, 2H), 3.84 (s, 1H), 2.81 (s, 1H), 2.17 (d, J=11.8 Hz, 2H), 2.09-1.98 (m, 2H), 1.67 (dd, J=12.6, 2.7 Hz, 2H), 1.58-1.39 (m, 2H). LC-MS: m/z: 459.2 $(M+H)^+$.

Example 7: Synthesis of Compound 25

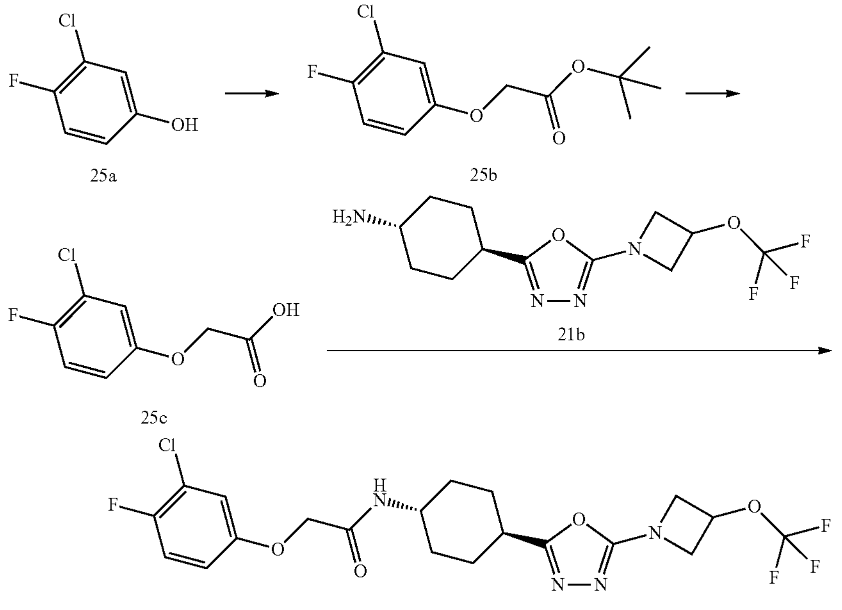

25a 25b 21b 25c 25

Step 1: Synthesis of Intermediate 25b

At 25° C., in a 50 mL reaction flask, compound 25a (Bidepharm, Cat. No. BD9830, 500 mg, 3.41 mmol), tert-butyl bromoacetate (997.68 mg, 5.11 mmol) and cesium carbonate (2.2 g, 6.82 mmol) were dissolved in acetonitrile (7 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain a crude. The crude was separated and purified by column chromatography to obtain intermediate 25b. $^1$H NMR (400 MHZ, $CDCl_3$) δ 7.07 (t, J=8.8 Hz, 1H), 6.95 (dd, J=5.9, 3.1 Hz, 1H), 6.78 (dt, J=9.1, 3.4 Hz, 1H), 4.49 (s, 2H), 1.51 (s, 9H).

Step 2: Synthesis of Intermediate 25c

At 25° C., to a 25 mL single-necked flask were added intermediate 25b (60 mg, 0.23 mmol) and dichloromethane (0.5 mL). Under stirring, trifluoroacetic acid (0.5 mL, 6.71 mmol) was added. The mixture was reacted at 25° C. for 1 hour, and then the reaction was completed. The reaction mixture was concentrated under reduced pressure to obtain intermediate 25c. LCMS: m/z: 203.0 $(M-H)^-$.

Step 3: Synthesis of Compound 25

At 25° C., in an 8 mL reaction flask, intermediate 25c (30.69 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 25. $^1$H NMR (400 MHZ, MeOD) δ 7.24-7.13 (m, 2H), 6.97 (dt, J=9.1, 3.4 Hz, 1H), 5.30 (ddd, J=10.9, 6.8, 4.3 Hz, 1H), 4.60-4.46 (m, 4H), 4.29 (dd, J=9.6, 4.1 Hz, 2H), 3.84 (tt, J=11.5, 3.9 Hz, 1H), 2.80 (tt, J=12.1, 3.5 Hz, 1H), 2.24-2.08 (m, 2H), 2.03 (dd, J=12.7, 2.8 Hz, 2H), 1.67 (qd, J=13.2, 3.0 Hz, 2H), 1.49 (ddd, J=25.5, 12.8, 3.2 Hz, 2H). LC-MS: m/z: 493.2 $(M+H)^+$.

Example 8: Synthesis of Compound 26

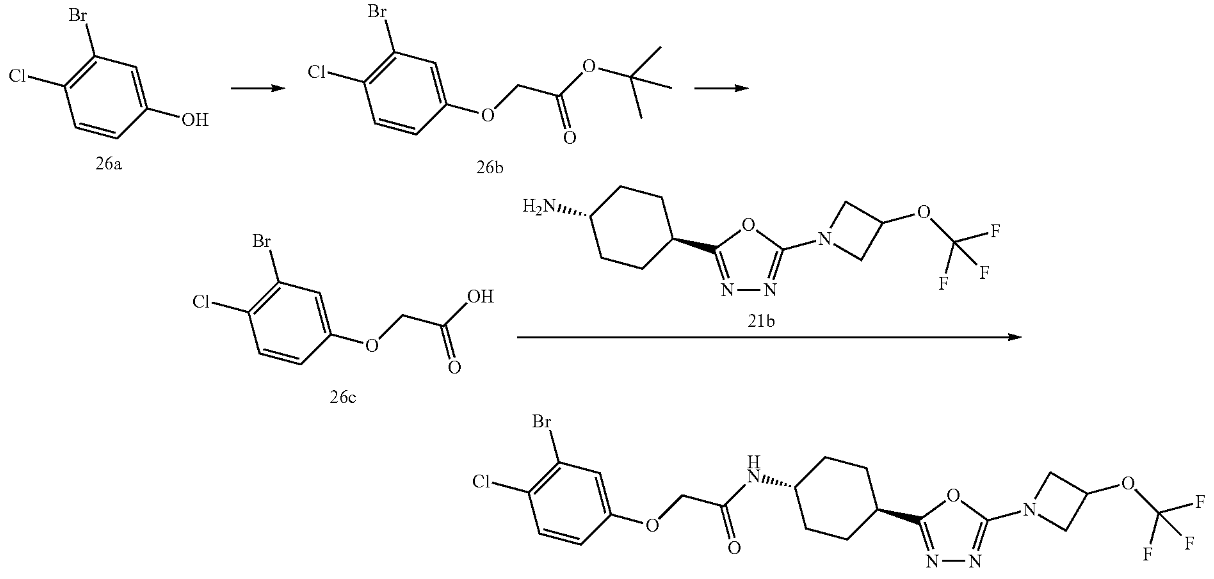

26a 26b 21b 26c 26

Step 1: Synthesis of Intermediate 26b

At 25° C., in a 50 mL reaction flask, compound 26a (Bidepharm, Cat. No. BD85025, 500 mg, 2.41 mmol), tert-butyl bromoacetate (517.08 mg, 2.65 mmol) and cesium carbonate (1.57 g, 4.82 mmol) were dissolved in acetonitrile (7 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain a crude. The crude was separated and purified by column chromatography to obtain intermediate 26b. $^{1}$H NMR (400 MHZ, $CDCl_3$) δ 7.36 (d, J=8.9 Hz, 1H), 7.17 (d, J=2.9 Hz, 1H), 6.83 (dd, J=8.9, 2.9 Hz, 1H), 4.51 (s, 2H), 1.51 (s, 9H).

Step 2: Synthesis of Intermediate 26c

At 25° C., to a 25 mL single-necked flask were added intermediate 26b (200 mg, 0.62 mmol) and dichloromethane (2 mL). Under stirring, trifluoroacetic acid (2 mL, 26.84 mmol) was added. The mixture was reacted at 25° C. for 1 hour, and then the reaction was completed. The reaction mixture was concentrated under reduced pressure to obtain intermediate 26c. LC-MS: m/z: 262.9 $(M-H)^-$.

Step 3: Synthesis of Compound 26

At 25° C., in an 8 mL reaction flask, intermediate 26c (39.82 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 26. $^{1}$H NMR (400 MHZ, MeOD) δ 7.19-6.98 (m, 2H), 6.69 (d, J=8.9 Hz, 1H), 4.97 (s, 1H), 4.28-4.11 (m, 4H), 3.95 (s, 2H), 3.51 (s, 1H), 2.48 (s, 1H), 1.76 (d, J=54.4 Hz, 4H), 1.25 (dd, J=72.6, 11.6 Hz, 4H). LC-MS: m/z: 555.2 $(M+H)^+$.

Example 9: Synthesis of Compound 27

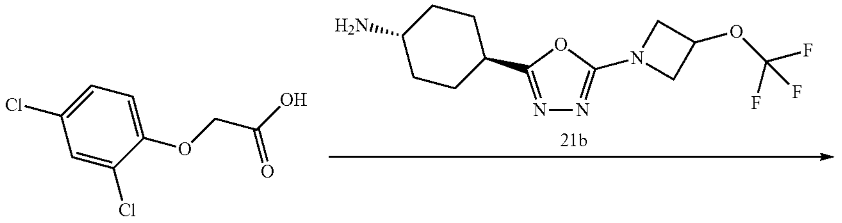

21b 27a

-continued

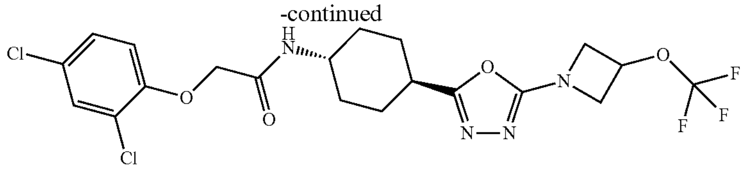

27

At 25° C., in an 8 mL reaction flask, compound 27a (Leyan, 33.16 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 27. $^{1}$H NMR (400 MHZ, DMSO) δ 7.90 (d, J=7.9 Hz, 1H), 7.45 (dd, J=7.9, 1.6 Hz, 1H), 7.36-7.22 (m, 1H), 7.09-6.91 (m, 2H), 5.39-5.23 (m, 1H), 4.59 (s, 2H), 4.46 (dd, J=9.6, 6.8 Hz, 2H), 4.19 (dd, J=9.6, 4.0 Hz, 2H), 3.63 (ddd, J=11.3, 7.5, 3.8 Hz, 1H), 2.74 (ddd, J=11.8, 7.7, 3.5 Hz, 1H), 2.03 (d, J=11.3 Hz, 2H), 1.88 (dd, J=12.8, 3.1 Hz, 2H), 1.58-1.45 (m, 2H), 1.43-1.30 (m, 2H). LC-MS: m/z: 509.2 (M+H)$^{+}$.

Example 10: Synthesis of Compound 28

At 25° C., in an 8 mL reaction flask, compound 28a (Bidepharm, Cat. No. BD81648, 33.16 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 28. $^{1}$H NMR (400 MHZ, MeOD) δ 7.46 (d, J=8.9 Hz, 1H), 7.22 (d, J=2.9 Hz, 1H), 6.97 (dd, J=8.9, 2.9 Hz, 1H), 5.36-5.22 (m, 1H), 4.61-4.44 (m, 4H), 4.28 (dd, J=9.6, 4.2 Hz, 2H), 3.84 (t, J=4.0 Hz, 1H), 2.94-2.68 (m, 1H), 2.29-2.09 (m, 2H), 2.03 (dd, J=13.1, 3.2 Hz, 2H), 1.73-1.58 (m, 2H), 1.56-1.41 (m, 2H). LC-MS: m/z: 475.2 (M+H)$^{+}$.

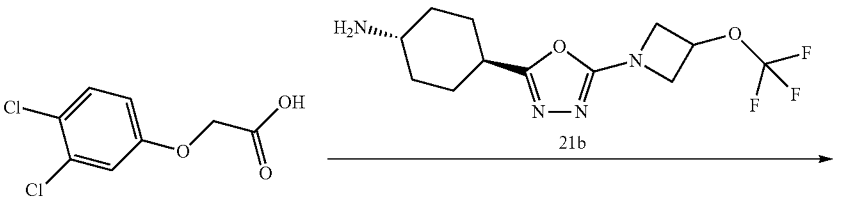

28a

21b

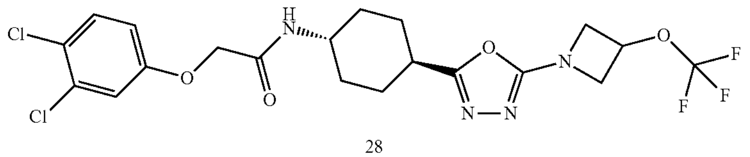

28

Example 11: Synthesis of Compound 29

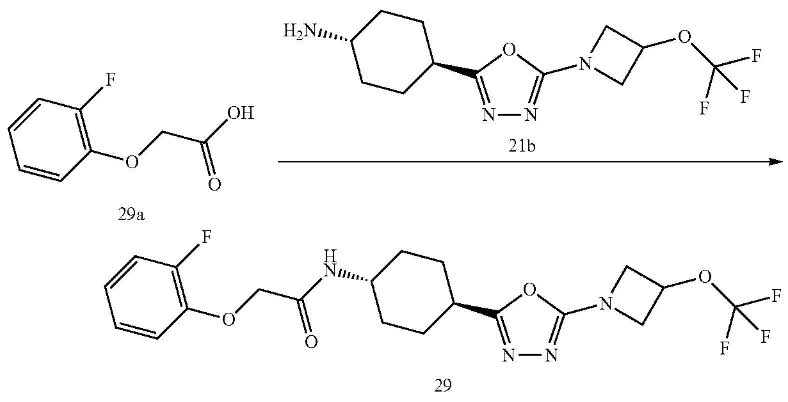

29a

21b

29

At 25° C., in an 8 mL reaction flask, compound 29a (Bidepharm, Cat. No. BD75182, 25.5 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 mL of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 29. $^1$H NMR (400 MHZ, MeOD) δ 7.22-7.06 (m, 3H), 7.06-6.97 (m, 1H), 5.29 (dd, J=9.3, 5.3 Hz, 1H), 4.58 (s, 2H), 4.54 (dd, J=9.2, 7.1 Hz, 2H), 4.29 (dd, J=9.6, 4.0 Hz, 2H), 3.90-3.79 (m, 1H), 2.87-2.75 (m, 1H), 2.16 (d, J=12.1 Hz, 2H), 2.10-1.99 (m, 2H), 1.75-1.59 (m, 2H), 1.51 (dd, J=17.3, 7.4 Hz, 2H). LC-MS: m/z: 459.2 $(M+H)^+$.

Example 12: Synthesis of Compound 30

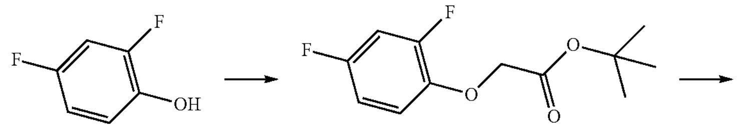

30a

30b

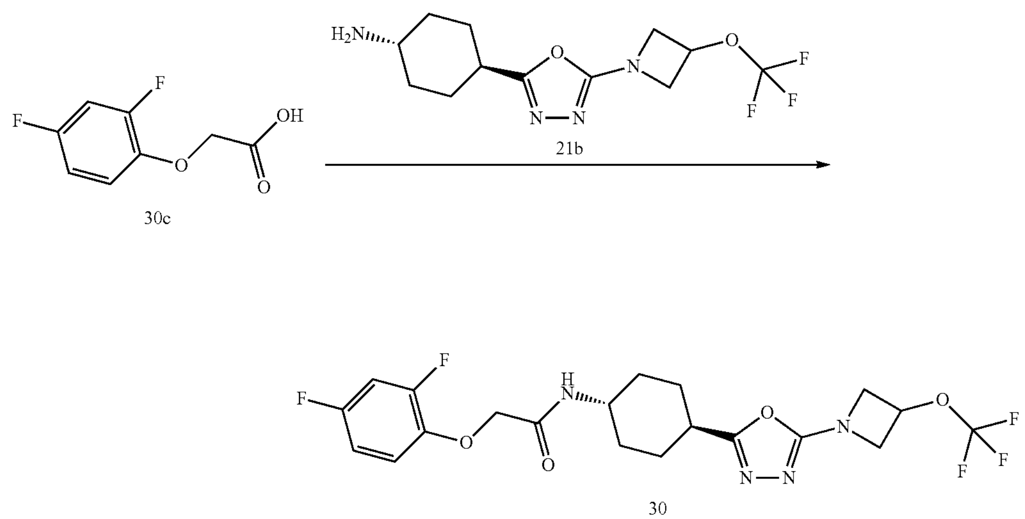

30c

21b

30

Step 1: Synthesis of Intermediate 30b

At 25° C., in a 50 mL reaction flask, compound 30a (Bidepharm, Cat. No. BD33414, 500 mg, 3.84 mmol), tert-butyl bromoacetate (1.1 mg, 5.76 mmol) and cesium carbonate (2.5 g, 7.68 mmol) were dissolved in acetonitrile (7 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain a crude. The crude was separated and purified by column chromatography to obtain intermediate 30b. $^{1}$H NMR (400 MHZ, $CDCl_3$) δ 6.88-6.75 (m, 2H), 6.71 (dd, J=11.4, 5.3 Hz, 1H), 4.48 (s, 2H), 1.41 (s, 9H).

Step 2: Synthesis of Intermediate 30c

At 25° C., to a 25 mL single-necked flask were added intermediate 30b (200 mg, 0.82 mmol) and dichloromethane (2 mL). Under stirring, trifluoroacetic acid (2 mL, 26.84 mmol) was added. The mixture was reacted at 25° C. for 1 hour, and then the reaction was completed. The reaction mixture was concentrated under reduced pressure to obtain intermediate 30c. LC-MS: m/z: 187.0 (M−H)$^-$.

Step 3: Synthesis of Compound 30

At 25° C., in an 8 mL reaction flask, intermediate 30c (28.22 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 30. $^{1}$H NMR (400 MHZ, MeOD) δ 7.05 (d, J=84.8 Hz, 3H), 5.33 (s, 2H), 4.58 (s, 4H), 4.32 (s, 2H), 3.87 (s, 1H), 2.84 (s, 1H), 2.13 (d, J=47.5 Hz, 4H), 1.61 (d, J=65.3 Hz, 4H). LC-MS: m/z: 477.2 (M+H)$^+$.

Example 13: Synthesis of Compound 31

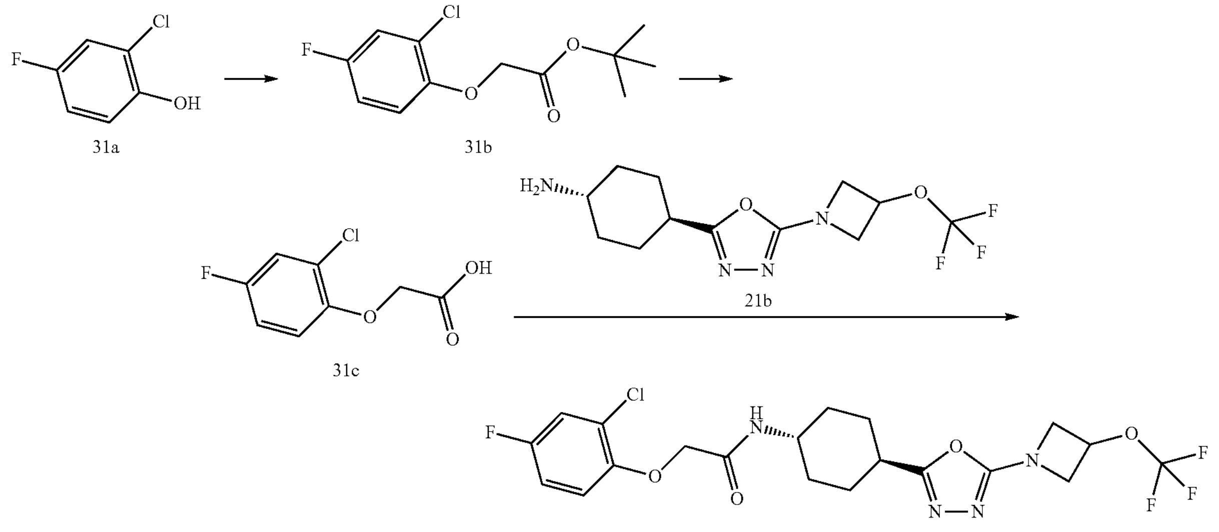

31a 31b 31c 21b 31

Step 1: Synthesis of Intermediate 31b

At 25° C., in a 50 mL reaction flask, compound 31a (Bidepharm, Cat. No. BD19192, 500 mg, 3.41 mmol), tert-butyl bromoacetate (731.63 mg, 3.75 mmol) and cesium carbonate (2.2 g, 6.82 mmol) were dissolved in acetonitrile (7 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain a crude. The crude was separated and purified by column chromatography to obtain intermediate 31b. $^{1}$H NMR (400 MHZ, $CDCl_3$) δ 7.17 (dd, J=8.0, 3.0 Hz, 1H), 6.93 (ddd, J=9.1, 7.8, 3.0 Hz, 1H), 6.83 (dd, J=9.1, 4.8 Hz, 1H), 4.58 (s, 2H), 1.50 (s, 9H).

Step 2: Synthesis of Intermediate 31c

At 25° C., to a 25 mL single-necked flask were added intermediate 31b (200 mg, 0.77 mmol) and dichloromethane (2 mL). Under stirring, trifluoroacetic acid (2 mL, 26.84 mmol) was added. The mixture was reacted at 25° C. for 1 hour, and then the reaction was completed. The reaction mixture was concentrated under reduced pressure to obtain intermediate 31c. LC-MS: m/z: 202.9 (M−H)$^-$.

Step 3: Synthesis of Compound 31

At 25° C., in an 8 mL reaction flask, intermediate 31c (30.69 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 31. $^{1}$H NMR (400 MHZ, MeOD) δ 7.29 (dd, J=8.2, 2.7 Hz, 1H), 7.09 (dt, J=8.3, 3.3 Hz, 2H), 5.36-5.24 (m, 1H), 4.60-4.48 (m, 4H), 4.29 (dd, J=9.6, 4.2 Hz, 2H), 3.89-3.73 (m, 1H), 2.83 (tt, J=12.0, 3.4 Hz, 1H), 2.25-2.02 (m, 4H), 1.77-1.40 (m, 4H). LC-MS: m/z: 493.2 $(M+H)^+$.

Example 14: Synthesis of Compound 32

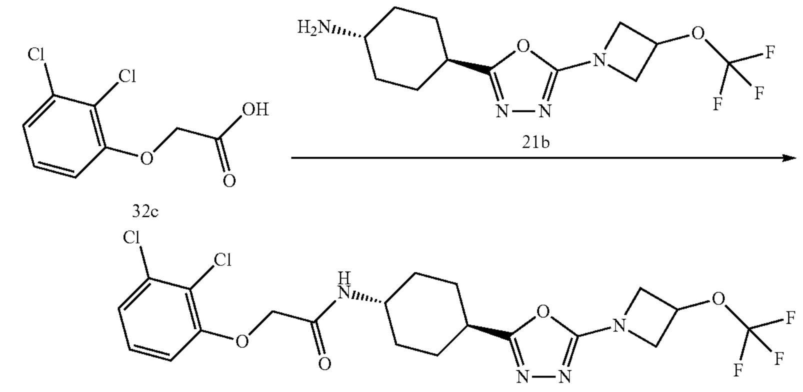

32c

21b

32

At 25° C., in an 8 mL reaction flask, compound 32a (Bidepharm, Cat. No. BD65476, 33.16 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 32. $^{1}$H NMR (400 MHZ, DMSO) δ 7.96 (d, J=7.8 Hz, 1H), 7.32 (t, J=8.2 Hz, 1H), 7.28-7.20 (m, 1H), 7.08-6.92 (m, 1H), 5.36-5.28 (m, 1H), 4.64 (s, 2H), 4.46 (dd, J=9.4, 6.9 Hz, 2H), 4.19 (dd, J=9.6, 3.9 Hz, 2H), 3.69-3.56 (m, 1H), 2.82-2.68 (m, 1H), 2.03 (d, J=11.4 Hz, 2H), 1.95-1.80 (m, 2H), 1.60-1.44 (m, 2H), 1.36 (dt, J=24.1, 6.2 Hz, 2H). LC-MS: m/z: 509.2 $(M+H)^+$.

Example 15: Synthesis of Compound 33

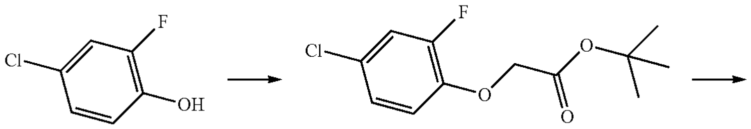

33a

33b

-continued

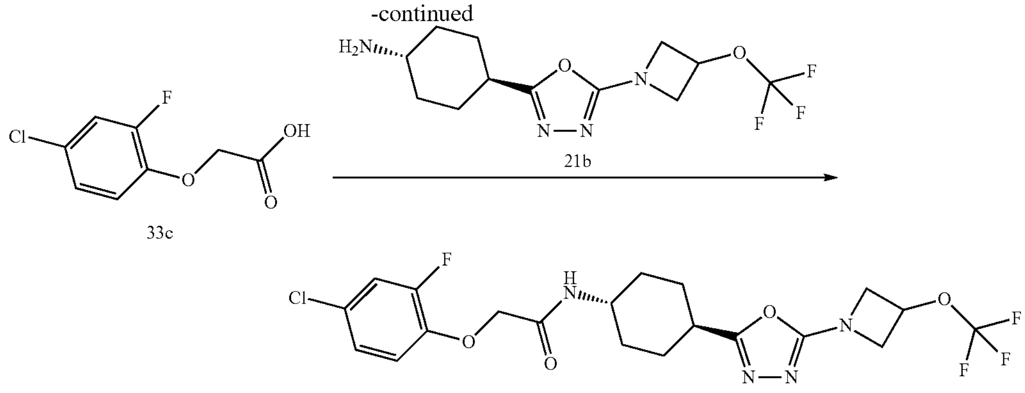

33c 21b 33

Step 1: Synthesis of Intermediate 33b

At 25° C., in a 10 mL reaction flask, compound 33a (Bidepharm, Cat. No. BD9831, 250 mg, 1.71 mmol), tert-butyl bromoacetate (498.84 mg, 2.55 mmol) and cesium carbonate (1.1 g, 3.41 mmol) were dissolved in acetonitrile (3 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain a crude. The crude was separated and purified by column chromatography to obtain intermediate 33b. LC-MS: m/z: 261.1 $(M+H)^+$.

Step 2: Synthesis of Intermediate 33c

At 25° C., to a 10 mL single-necked flask were added intermediate 33b (160 mg, 0.61 mmol) and dichloromethane (1.5 mL). Under stirring, trifluoroacetic acid (0.5 mL, 6.71 mmol) was added. The mixture was reacted at 25° C. for 1 hour, and then the reaction was completed. The reaction mixture was concentrated under reduced pressure to obtain intermediate 33c. LC-MS: m/z: 203.0 $(M-H)^-$.

Step 3: Synthesis of Compound 33

At 25° C., in an 8 mL reaction flask, intermediate 33c (30.69 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 33. $^1H$ NMR (400 MHZ, MeOD) δ 7.26 (dd, J=11.0, 2.4 Hz, 1H), 7.18-7.13 (m, 1H), 7.09 (t, J=8.7 Hz, 1H), 5.33-5.25 (m, 1H), 4.59 (s, 2H), 4.53 (dd, J=9.6, 6.8 Hz, 2H), 4.29 (dd, J=9.6, 4.2 Hz, 2H), 3.90-3.75 (m, 1H), 2.85-2.75 (m, 1H), 2.25-2.10 (m, 2H), 2.09-1.95 (m, 2H), 1.67 (qd, J=13.2, 3.1 Hz, 2H), 1.48 (qd, J=12.8, 3.3 Hz, 2H). LC-MS: m/z: 493.2 $(M+H)^+$.

Example 16: Synthesis of Compound 34

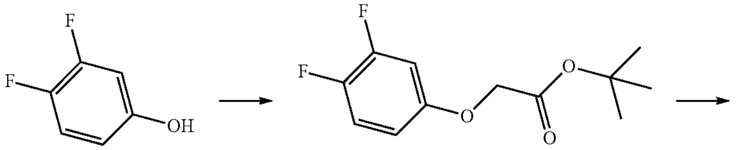

34a 34b

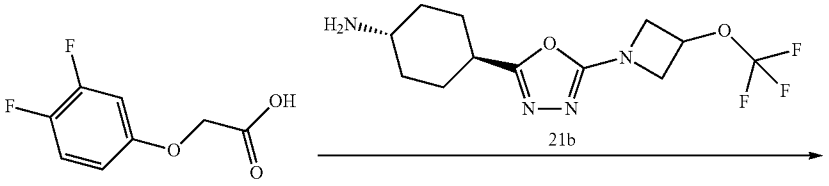

21b

34c

-continued

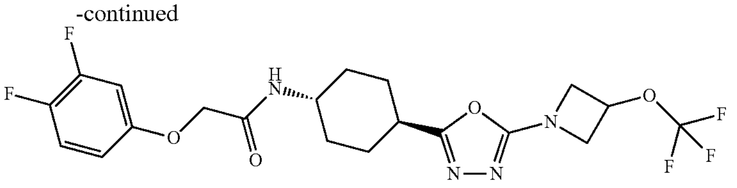

34

Step 1: Synthesis of Intermediate 34b

At 25° C., in a 10 mL reaction flask, compound 34a (Bidepharm, Cat. No. BD9841, 250 mg, 1.92 mmol), tert-butyl bromoacetate (412.50 mg, 2.11 mmol) and cesium carbonate (1.87 g, 5.76 mmol) were dissolved in acetonitrile (4 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain intermediate 34b. LC-MS: m/z: 245.1 $(M+H)^+$.

Step 2: Synthesis of Intermediate 34c

At 25° C., to a 10 mL single-necked flask were added intermediate 34b (170 mg, 0.69 mmol) and dichloromethane (1.5 mL). Under stirring, trifluoroacetic acid (0.5 mL, 6.71 mmol) was added. The mixture was reacted at 25° C. for 1 hour, and then the reaction was completed. The reaction mixture was concentrated under reduced pressure to obtain intermediate 34c. LC-MS: m/z: 189.0 $(M-H)^-$.

Step 3: Synthesis of Compound 34

At 25° C., in an 8 mL reaction flask, intermediate 34c (28.22 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 mL of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 34. $^1H$ NMR (400 MHZ, MeOD) δ 7.22 (dd, J=19.5, 9.2 Hz, 1H), 6.98 (ddd, J=12.2, 6.6, 3.0 Hz, 1H), 6.84-6.77 (m, 1H), 5.34-5.23 (m, 1H), 4.53 (dd, J=9.9, 7.0 Hz, 2H), 4.51 (s, 2H), 4.29 (dd, J=9.7, 4.2 Hz, 2H), 3.84 (tt, J=11.6, 3.9 Hz, 1H), 2.81 (tt, J=12.1, 3.5 Hz, 1H), 2.25-2.11 (m, 2H), 2.07-1.98 (m, 2H), 1.67 (qd, J=13.2, 3.2 Hz, 2H), 1.49 (qd, J=12.8, 3.3 Hz, 2H). LC-MS: m/z: 477.1 $(M+H)^+$.

Example 17: Synthesis of Compound 35

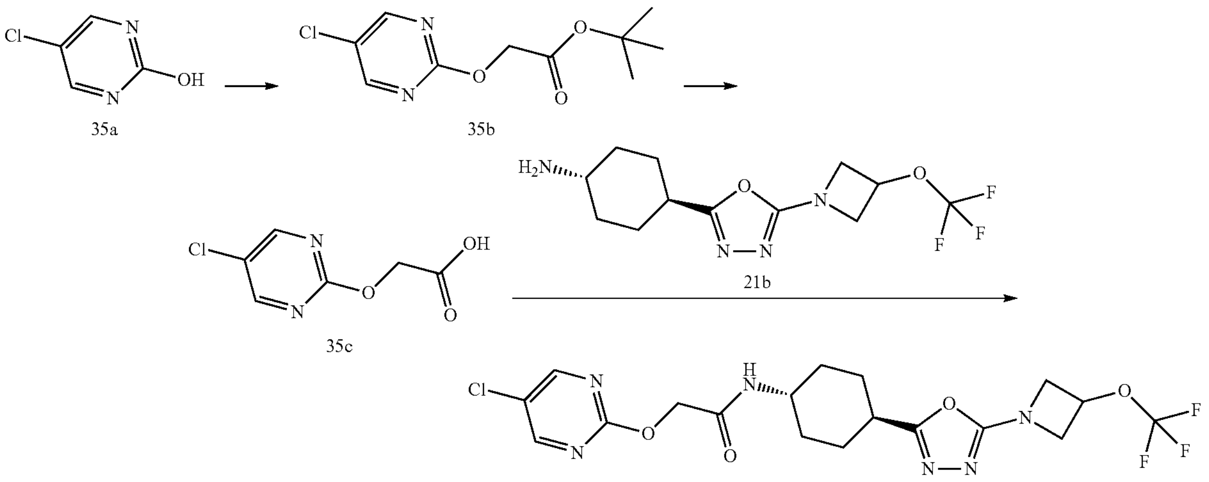

35a 35b 21b 35c 35

Step 1: Synthesis of Intermediate 35b

At 25° C., in a 25 mL reaction flask, compound 35a (Bidepharm, Cat. No. BD9390, 750 mg, 4.54 mmol), tert-butyl bromoacetate (970.01 mg, 5.00 mmol) and cesium carbonate (2.98 g, 9.09 mmol) were dissolved in acetonitrile (10 mL). The mixture was reacted at 25° C. for 2 hours, and then the reaction was completed. To the resulting reaction solution was added 15 ml of dichloromethane. The mixture was filtered, and then the filtrate was concentrated under reduced pressure to obtain a crude. The crude was separated and purified by column chromatography to obtain intermediate 35b. LC-MS: m/z: 189.0 $(M-56+H)^+$.

Step 2: Synthesis of Intermediate 35c

At 25° C., to a 10 mL single-necked flask were added intermediate 35b (50 mg, 0.20 mmol) and dichloromethane (1.5 mL). Under stirring, trifluoroacetic acid (0.5 mL, 6.71 mmol) was added. The mixture was reacted at 25° C. for 1 hour, and then the reaction was completed. The reaction mixture was concentrated under reduced pressure to obtain intermediate 35c. LC-MS: m/z: 189.0 $(M+H)^+$.

Step 3: Synthesis of Compound 35

At 25° C., in an 8 mL reaction flask, intermediate 35c (28.29 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 35. $^1H$ NMR (400 MHZ, MeOD) δ 8.63 (s, 1H), 5.35-5.24 (m, 1H), 4.85 (s, 1H), 4.52 (dd, J=9.7, 6.8 Hz, 1H), 4.28 (dd, J=9.7, 4.2 Hz, 1H), 3.90-3.68 (m, 1H), 2.91-2.73 (m, 1H), 2.16 (d, J=12.0 Hz, 1H), 2.03 (dd, J=13.4, 3.4 Hz, 1H), 1.66 (qd, J=13.3, 3.1 Hz, 1H), 1.44 (qd, J=12.9, 3.4 Hz, 1H). LC-MS: m/z: 477.1 $(M+H)^+$.

Example 18: Synthesis of Compound 36

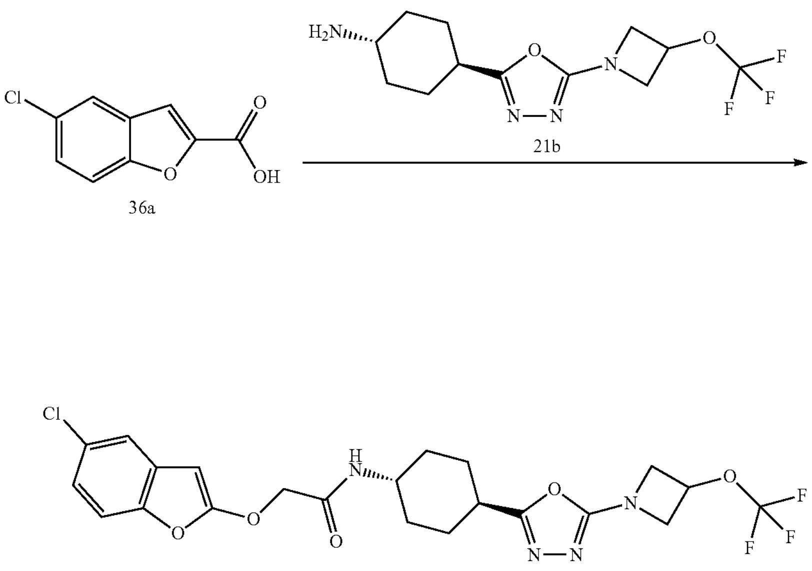

36a

21b

36

At 25° C., in an 8 mL reaction flask, compound 36a (Bidepharm, Cat. No. BD11470, 29.5 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 36. $^1H$ NMR (400 MHZ, MeOD) δ 7.77 (d, J=2.0 Hz, 1H), 7.61 (d, J=8.9 Hz, 1H), 7.48 (d, J=0.9 Hz, 1H), 7.47-7.44 (m, 1H), 5.40-5.20 (m, 1H), 4.54 (dd, J=9.7, 6.8 Hz, 2H), 4.30 (dd, J=9.7, 4.2 Hz, 2H), 4.05-3.90 (m, 1H), 2.90-2.77 (m, 1H), 2.21 (d, J=12.3 Hz, 2H), 2.17-2.06 (m, 2H), 1.78-1.66 (m, 2H), 1.66-1.53 (m, 2H). LC-MS: m/z: 485.2 $(M+H)^+$.

Example 19: Synthesis of Compound 37

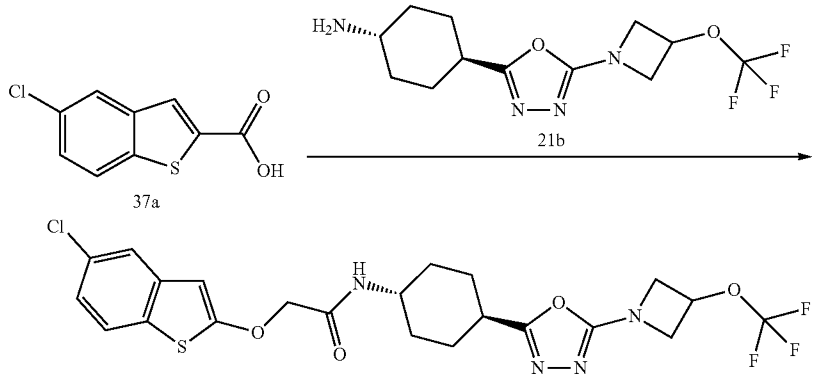

37a 21b

37

At 25° C., in an 8 mL reaction flask, compound 37a (Bidepharm, Cat. No. BD182201, 31.9 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 37. $^1$H NMR (400 MHZ, MeOD) δ 7.92 (dd, J=5.2, 3.1 Hz, 3H), 7.45 (dd, J=8.7, 2.0 Hz, 1H), 5.39-5.21 (m, 1H), 4.54 (dd, J=9.7, 6.8 Hz, 2H), 4.30 (dd, J=9.7, 4.2 Hz, 2H), 4.03-3.82 (m, 1H), 2.91-2.77 (m, 1H), 2.30-2.08 (m, 4H), 1.79-1.65 (m, 2H), 1.58 (dt, J=13.0, 9.8 Hz, 2H). LC-MS: m/z: 501.2 $(M+H)^+$.

Example 20: Synthesis of Compound 38

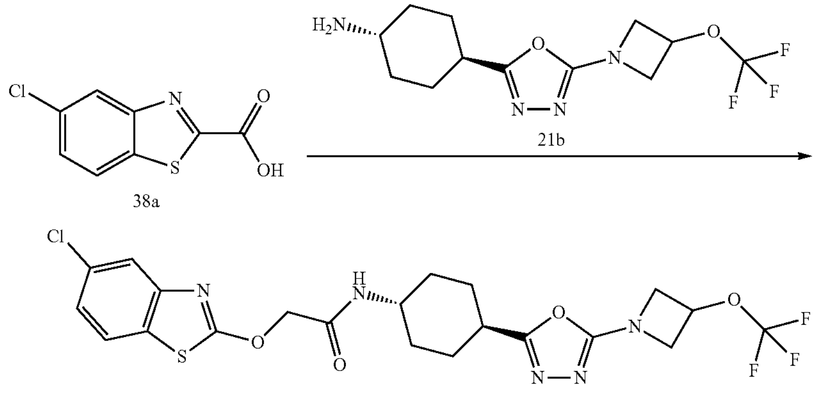

38a 21b

38

At 25° C., in an 8 mL reaction flask, compound 38a (Bidepharm, Cat. No. BD38284, 32.05 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 38. $^1$H NMR (400 MHZ, MeOD) δ 8.17 (d, J=2.0 Hz, 1H), 8.10 (d, J=8.7 Hz, 1H), 7.57 (dd, J=8.7, 2.0 Hz, 1H), 5.39-5.20 (m, 1H), 4.54 (dd, J=9.6, 6.8 Hz, 2H), 4.30 (dd, J=9.6, 4.2 Hz, 2H), 3.97 (t, J=7.5 Hz, 1H), 2.86 (ddd, J=11.7, 7.7, 3.5 Hz, 1H), 2.23 (d, J=12.2 Hz, 2H), 2.15 (d, J=11.1 Hz, 2H), 1.73 (dd, J=25.4, 11.2 Hz, 2H), 1.63 (dd, J=18.6, 8.5 Hz, 2H). LC-MS: m/z: 502.2 $(M+H)^+$.

Example 21: Synthesis of Compound 40

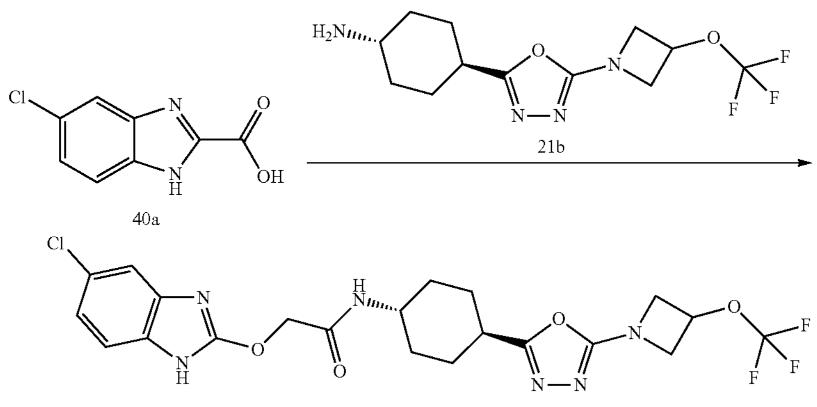

21b

40a

40

At 25° C., in an 8 mL reaction flask, 40a (Bidepharm, Cat. No. BD28605, 29.49 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 40. $^{1}$H NMR (400 MHZ, MeOD) δ 7.67 (dd, J=14.0, 5.3 Hz, 2H), 7.35 (dd, J=8.7, 2.0 Hz, 1H), 5.34-5.28 (m, 1H), 4.55 (dd, J=9.6, 6.8 Hz, 2H), 4.31 (dd, J=9.7, 4.2 Hz, 2H), 4.03-3.89 (m, 1H), 2.88 (ddd, J=12.1, 7.8, 3.4 Hz, 1H), 2.20 (t, J=14.9 Hz, 4H), 1.81-1.53 (m, 4H). LC-MS: m/z: 485.1 $(M+H)^+$.

Example 22: Synthesis of Compound 41

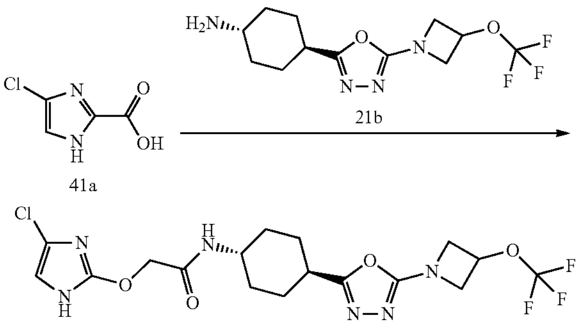

21b

41a

41

At 25° C., in an 8 mL reaction flask, compound 41a (Bidepharm, Cat. No. BD260228, 21.98 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 mL of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 41. $^{1}$H NMR (400 MHZ, MeOD) δ 7.21 (s, 1H), 5.29 (td, J=6.8, 3.6 Hz, 1H), 4.53 (dd, J=9.7, 6.8 Hz, 2H), 4.29 (dd, J=9.7, 4.2 Hz, 2H), 3.95-3.81 (m, 1H), 2.84 (ddd, J=11.8, 7.7, 3.5 Hz, 1H), 2.20 (d, J=11.6 Hz, 2H), 2.11 (d, J=9.8 Hz, 2H), 1.77-1.63 (m, 2H), 1.55 (dt, J=12.8, 6.1 Hz, 2H). LC-MS: m/z: 435.1 $(M+H)^+$.

Example 23: Synthesis of Compound 42

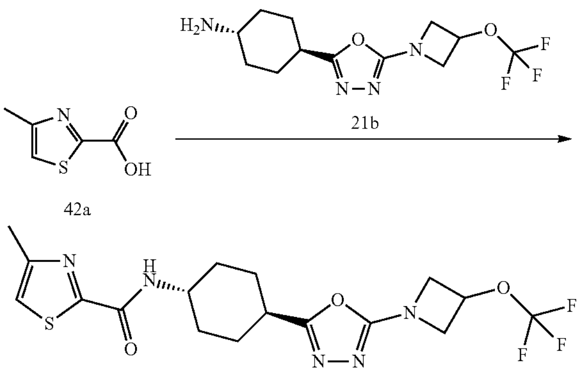

21b

42a

42

At 25° C., in an 8 mL reaction flask, compound 42a (21.47 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 mL of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 42. $^1$H NMR (400 MHZ, MeOD) δ 7.41 (d, J=0.7 Hz, 1H), 5.34-5.25 (m, 1H), 4.58-4.48 (m, 2H), 4.30 (dd, J=9.6, 4.1 Hz, 2H), 3.91 (ddt, J=11.1, 7.6, 3.9 Hz, 1H), 2.85 (tt, J=11.9, 3.4 Hz, 1H), 2.50 (d, J=0.6 Hz, 3H), 2.20 (d, J=11.9 Hz, 2H), 2.12 (dd, J=12.8, 2.8 Hz, 2H), 1.76-1.52 (m, 4H). LC-MS: m/z: 432.1 (M+H)$^+$.

Example 24: Synthesis of Compound 43

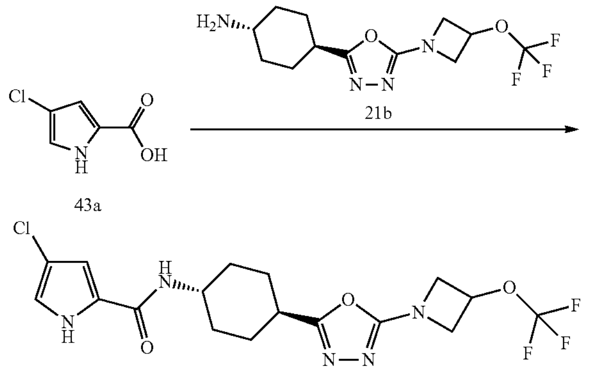

21b

43a

43

At 25° C., in an 8 mL reaction flask, compound 43a (Bidepharm, Cat. No. BD95552, 21.83 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (ammonium bicarbonate/acetonitrile/water system) to obtain compound 43. $^1$H NMR (400 MHZ, MeOD) δ 6.88 (d, J=1.6 Hz, 1H), 6.77 (d, J=1.6 Hz, 1H), 5.34-5.25 (m, 1H), 4.53 (dd, J=9.6, 6.9 Hz, 2H), 4.29 (dd, J=9.6, 4.2 Hz, 2H), 3.87 (ddd, J=11.5, 7.7, 4.0 Hz, 1H), 2.82 (ddd, J=12.1, 8.7, 3.5 Hz, 1H), 2.23-2.04 (m, 4H), 1.80-1.40 (m, 4H). LC-MS: m/z: 434.2 (M+H)$^+$.

Example 25: Synthesis of Compound 44

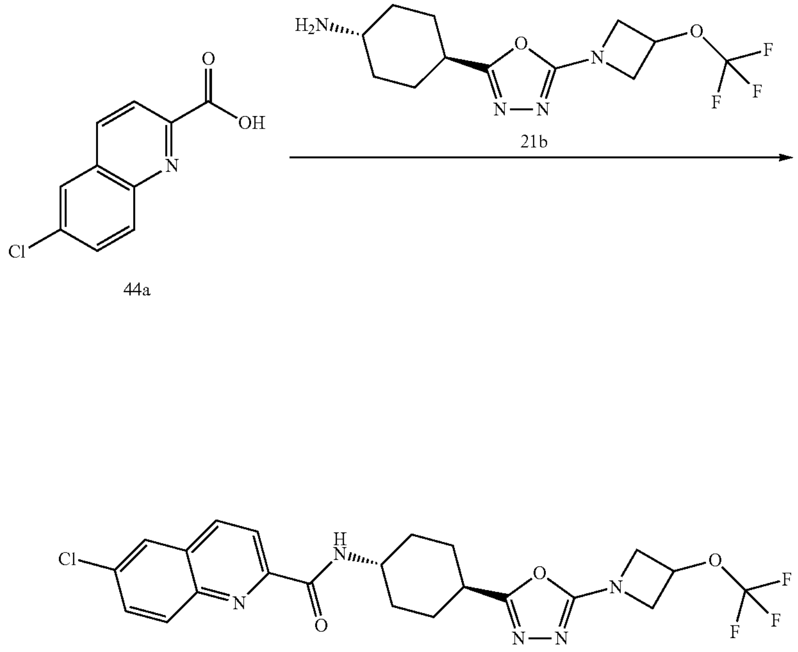

21b

44a

44

At 25° C., in an 8 mL reaction flask, compound 44a (Bidepharm, Cat. No. BD334736, 31.14 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 44. $^1H$ NMR (400 MHZ, MeOD) δ 8.46 (d, J=8.5 Hz, 1H), 8.22 (dd, J=21.6, 8.8 Hz, 2H), 8.08 (d, J=2.3 Hz, 1H), 7.83 (dd, J=9.1, 2.4 Hz, 1H), 5.31 (s, 1H), 4.60-4.48 (m, 2H), 4.30 (dd, J=9.8, 4.2 Hz, 2H), 4.02 (s, 1H), 2.90 (t, J=11.4 Hz, 1H), 2.21 (dd, J=20.6, 14.6 Hz, 4H), 1.85-1.59 (m, 4H). LC-MS: m/z: 496.1 $(M+H)^+$.

Example 26: Synthesis of Compound 45

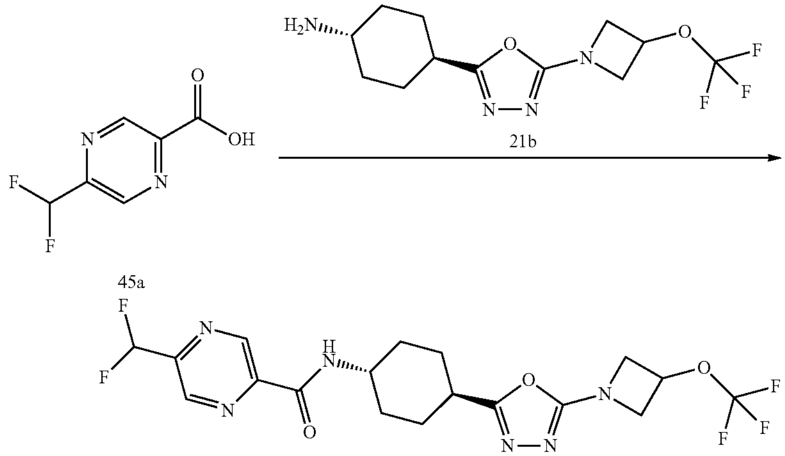

45a

21b

45

At 25° C., in an 8 mL reaction flask, compound 45a (Bidepharm, Cat. No. BD232348, 26.12 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 mL of water, and the mixture was extracted with 20 mL of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 45. $^1H$ NMR (400 MHZ, MeOD) δ 9.32 (s, 1H), 8.98 (s, 1H), 6.94 (t, J=54.3 Hz, 1H), 5.34-5.26 (m, 1H), 4.54 (dd, J=9.7, 6.8 Hz, 2H), 4.30 (dd, J=9.6, 4.2 Hz, 2H), 4.02 (qd, J=11.6, 3.6 Hz, 1H), 2.87 (tt, J=11.9, 3.5 Hz, 1H), 2.22 (d, J=12.2 Hz, 2H), 2.18-2.07 (m, 2H), 1.81-1.53 (m, 4H). LC-MS: m/z: 463.1 $(M+H)^+$.

Example 27: Synthesis of Compound 46

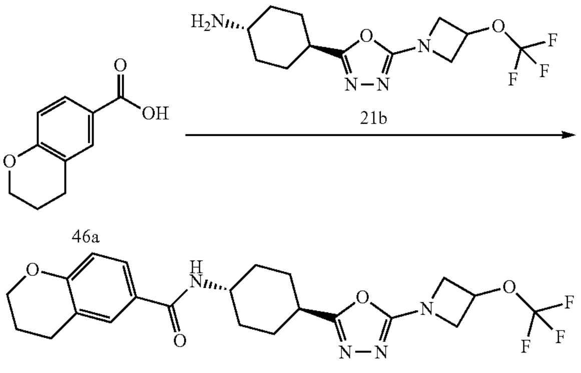

46a

21b

46

At 25° C., in an 8 mL reaction flask, compound 46a (Bidepharm, Cat. No. BD160922, 26.73 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 46. $^1H$ NMR (400 MHZ, MeOD) δ 7.62-7.49 (m, 2H), 6.79 (dd, J=8.6, 4.0 Hz, 1H), 5.34-5.27 (m, 1H), 4.53 (dd, J=9.7, 6.8 Hz, 2H), 4.29 (dd, J=9.6, 4.2

Hz, 2H), 4.25-4.17 (m, 2H), 3.91 (ddd, J=15.4, 7.7, 3.9 Hz, 1H), 2.83 (dt, J=8.7, 5.7 Hz, 3H), 2.19 (d, J=12.1 Hz, 2H), 2.15-2.07 (m, 2H), 2.07-1.99 (m, 2H), 1.70 (qd, J=13.2, 3.0 Hz, 2H), 1.53 (qd, J=12.8, 3.2 Hz, 2H). LC-MS: m/z: 467.1 $(M+H)^+$.

Example 28: Synthesis of Compound 47

Step 3: Synthesis of Intermediate 47d

At 25° C., to a 10 mL single-necked flask were added intermediate 47c (80 mg, 0.28 mmol) and dichloromethane (1.0 mL). Under stirring, trifluoroacetic acid (0.3 mL, 4.03 mmol) was added. The mixture was reacted at 25° C. for 1 hour, and then the reaction was completed. The reaction mixture was concentrated under reduced pressure to obtain intermediate 47d. LC-MS: m/z: 220.9 $(M-H)^-$.

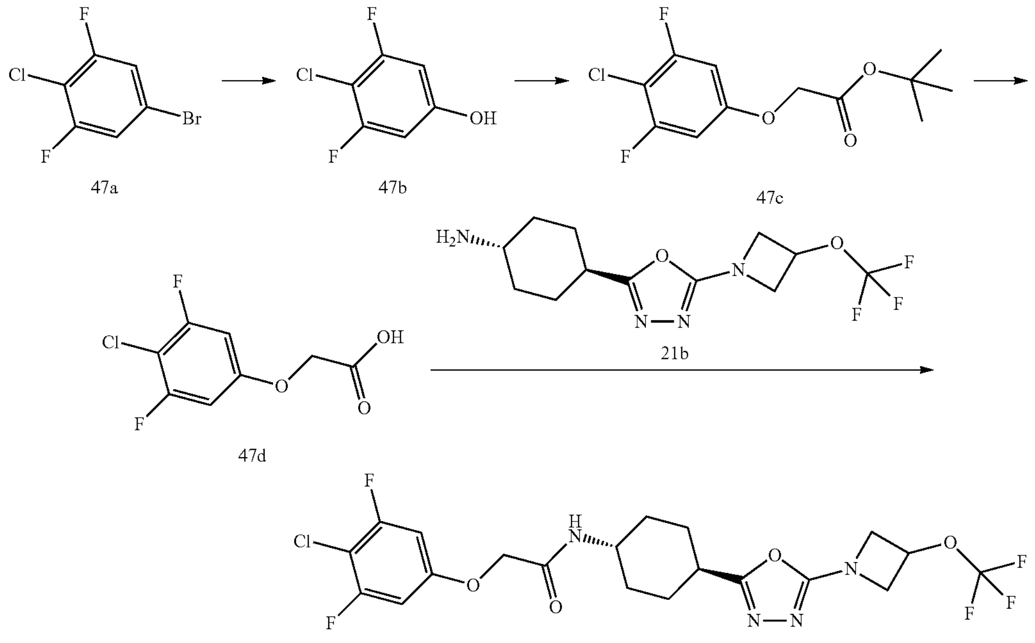

47a 47b 47c 21b 47d 47

Step 1: Synthesis of Intermediate 47b

At 25° C., to a 50 mL three-necked flask were added compound 47a (Bidepharm, Cat. No. BD9715, 0.4 g, 1.76 mmol), Rockphos-pd-$G_3$ (22.15 mg, 0.02 mmol) and cesium carbonate (1.7 g, 5.27 mmol) and then dimethylformamide (4.0 mL) and water (0.15 mL) were added. Under nitrogen protection, the mixture was reacted at 85° C. for 5 hours. The crude reaction solution (containing intermediate 47b) was directly used in the next step without purification. LC-MS: m/z: 163.0 $(M-H)^-$.

Step 2: Synthesis of Intermediate 47c

At 25° C., to the reaction solution (containing intermediate 47b) obtained in the previous step was added tert-butyl bromoacetate (889 mg, 4.56 mmol). The mixture was reacted at 25° C. for 2 hours, and then the reaction was completed. To the resulting reaction solution were added 5 ml of water and 15 ml of ethyl acetate. The resulting organic phase was washed with a saturated sodium chloride aqueous solution (40 mL×3), dried over sodium sulfate and filtered, and then the filtrate was concentrated under reduced pressure to obtain a crude. The crude was separated and purified by column chromatography to obtain intermediate 47c (80 mg, 0.28 mmol). LC-MS: m/z: 277.0 (M-H).

Step 4: Synthesis of Compound 47

At 25° C., in an 8 mL reaction flask, intermediate 47d (33 mg, 0.1 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 47. $^1H$ NMR (400 MHZ, MeOD) δ 6.94-6.70 (m, 2H), 5.41-5.13 (m, 1H), 4.55 (s, 2H), 4.54-4.37 (m, 2H), 4.28 (dd, J=9.6, 4.2 Hz, 2H), 4.11-3.68 (m, 1H), 2.81 (ddd, J=12.1, 8.6, 3.7 Hz, 1H), 2.22-2.10 (m, 2H), 2.10-1.91 (m, 2H), 1.74-1.58 (m, 2H), 1.54-1.38 (m, 2H). LC-MS: m/z: 511.1 $(M+H)^+$.

Example 29: Synthesis of Compound 48

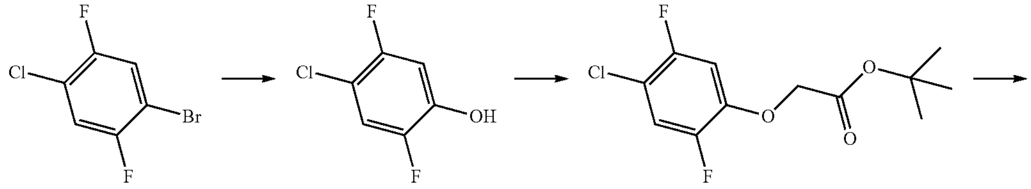

48a 48b 48c

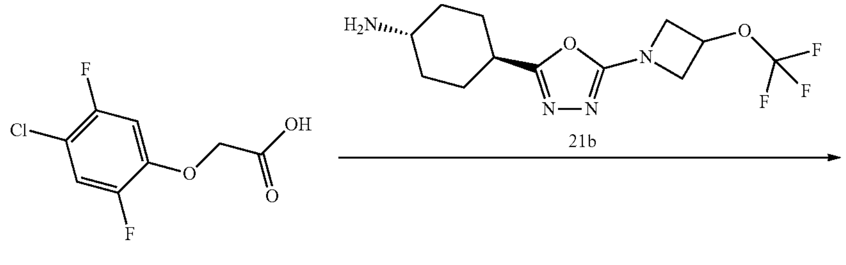

48d

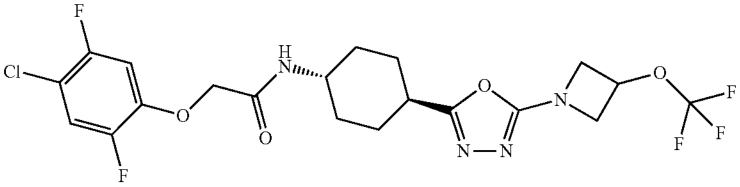

48

Step 1: Synthesis of Intermediate 48b

At 25° C., to a 50 mL three-necked flask were added compound 48a (Bidepharm, Cat. No. BD297147, 0.8 g, 3.52 mmol), Rockphos-pd-$G_3$ (44.29 mg, 0.05 mmol) and cesium carbonate (3.4 g, 10.55 mmol) and then dimethylformamide (8.0 mL) and water (0.3 mL) were added. Under nitrogen protection, the mixture was reacted at 85° C. for 5 hours, and then the reaction was completed. The resulting reaction solution (containing intermediate 48b) was directly used in the next step without purification. LC-MS: m/z: 163.0 $(M-H)^-$.

Step 2: Synthesis of Intermediate 48c

At 25° C., to the reaction solution (containing intermediate 48b) obtained in the previous step was added to the test-butyl bromoacetate (889 mg, 4.56 mmol). The mixture was reacted at 25° C. for 2 hours, and then the reaction was completed. To the resulting reaction solution were added 5 ml of water and 15 ml of ethyl acetate. The resulting organic phase was washed with 40 mL of a saturated sodium chloride aqueous solution, dried over sodium sulfate and filtered, and then the filtrate was concentrated under reduced pressure to obtain a crude. The crude was separated and purified by column chromatography to obtain intermediate 48c. $^1$H NMR (400 MHZ, $CDCl_3$): δ 7.09 (dd, J=10.4, 6.9 Hz, 1H), 6.67 (dd, J=9.8, 7.3 Hz, 1H), 4.49 (s, 1H), 1.42 (s, 9H).

Step 3: Synthesis of Intermediate 48d

At 25° C., to a 25 mL single-necked flask were added intermediate 48c (200 mg, 0.72 mmol) and dichloromethane (2.0 mL). Under stirring, trifluoroacetic acid (2.0 mL, 26.84 mmol) was added. The mixture was reacted at 25° C. for 1 hour, and then the reaction was completed. The reaction mixture was concentrated under reduced pressure to obtain intermediate 48d. LC-MS: m/z: 220.9 $(M-H)^-$.

Step 4: Synthesis of Compound 48

At 25° C., in an 8 mL reaction flask, intermediate 48d (22.26 mg, 0.1 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 48. $^1$H NMR (400 MHZ, MeOD) δ 7.38 (dd, J=10.6, 7.0 Hz, 1H), 7.11 (dd, J=10.3, 7.4 Hz, 1H), 5.34-5.24 (m, 1H), 4.62 (s, 2H), 4.53 (dd, J=9.7, 6.8 Hz, 2H), 4.29 (dd, J=9.6, 4.2 Hz, 2H), 3.89-3.75 (m, 1H), 2.87-2.75 (m, 1H), 2.21-2.12 (m, 2H), 2.05 (dd, J=13.1, 3.4 Hz, 2H), 1.67 (qd, J=13.2, 3.1 Hz, 2H), 1.48 (qd, J=12.8, 3.3 Hz, 2H). LC-MS: m/z: 511.2 $(M+H)^+$.

Example 30: Synthesis of Compound 49

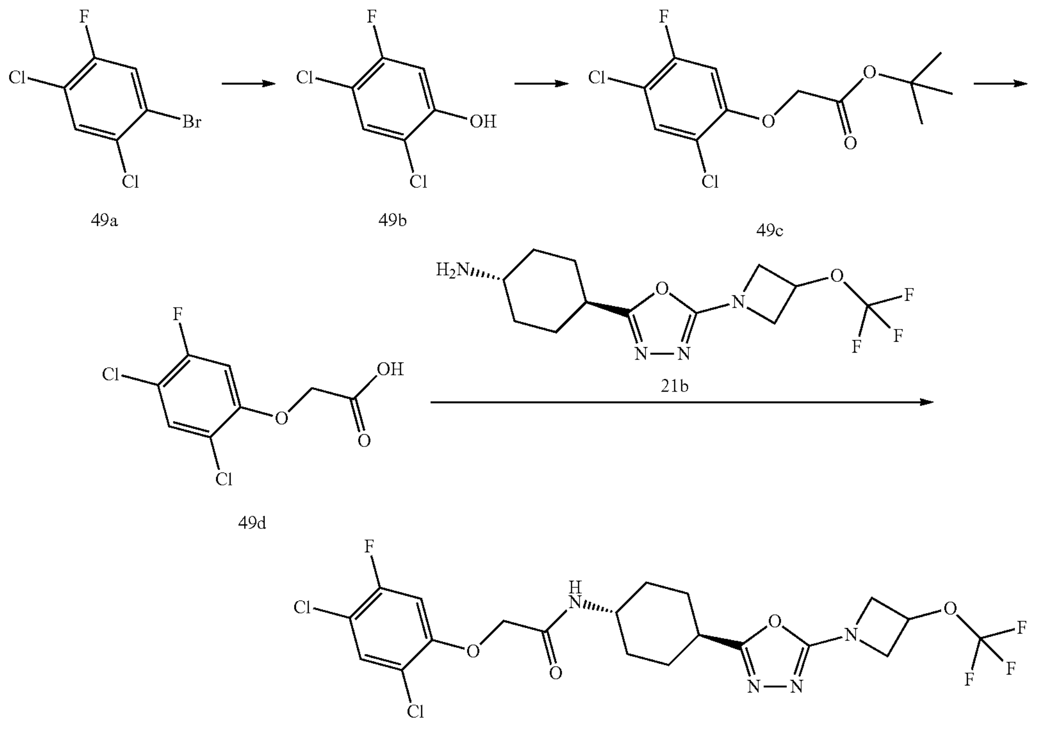

49a 49b 49c 21b 49d 49

Step 1: Synthesis of Intermediate 49b

At 25° C., to a 50 mL three-necked flask were added compound 49a (Bidepharm, Cat. No. BD66669, 0.8 g, 3.28 mmol), Rockphos-pd-G3 (41.3 mg, 0.05 mmol) and cesium carbonate (3.2 g, 9.84 mmol) and then dimethylformamide (8.0 mL) and water (0.3 mL) were added. Under nitrogen protection, the mixture was reacted at 85° C. for 5 hours, and then the reaction was completed. The resulting reaction solution (containing intermediate 49b) was directly used in the next step without purification. LC-MS: m/z: 179.0 $(M-H)^-$.

Step 2: Synthesis of Intermediate 49c

At 25° C., to the reaction solution (containing intermediate 49b) obtained in the previous step was added to the test-butyl bromoacetate (727.47 mg, 3.73 mmol). The mixture was reacted at 25° C. for 2 hours, and then the reaction was completed. To the resulting reaction solution were added 5 mL of water and 15 mL of ethyl acetate. The resulting organic phase was washed with 40 ml of a saturated sodium chloride aqueous solution, dried over sodium sulfate and filtered, and then the filtrate was concentrated under reduced pressure to obtain a crude. The crude was separated and purified by column chromatography to obtain intermediate 49c. $^1H$ NMR (400 MHZ, $CDCl_3$) δ 7.35 (d, J=7.6 Hz, 1H), 6.58 (d, J=10.2 Hz, 1H), 4.50 (s, 2H), 1.42 (d, J=2.1 Hz, 9H).

Step 3: Synthesis of Intermediate 49d

At 25° C., to a 25 mL single-necked flask were added intermediate 49c (200 mg, 0.68 mmol) and dichloromethane (2.0 mL). Under stirring, trifluoroacetic acid (2.0 mL, 26.84 mmol) was added. The mixture was reacted at 25° C. for 1 hour, and then the reaction was completed. The reaction mixture was concentrated under reduced pressure to obtain intermediate 49d. LC-MS: m/z: 236.9 $(M-H)^-$.

Step 4: Synthesis of Compound 49

At 25° C., in an 8 mL reaction flask, intermediate 49d (23.9 mg, 0.1 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 49. $^1H$ NMR (400 MHZ, DMSO) δ 7.96 (d, J=7.8 Hz, 1H), 7.80 (d, J=7.8 Hz, 1H), 7.22 (d, J=11.2 Hz, 1H), 5.32 (dd, J=8.9, 5.4 Hz, 1H), 4.66 (s, 2H), 4.51-4.37 (m, 2H), 4.19 (dd, J=9.6, 3.8 Hz, 2H), 3.63-3.60 (m, 1H), 2.83-2.69 (m, 1H), 2.03 (d, J=11.7 Hz, 2H), 1.89 (d, J=10.0 Hz, 2H), 1.51 (q, J=10.6 Hz, 2H), 1.35 (dd, J=24.1, 9.9 Hz, 2H). LC-MS: m/z: 527.2 $(M+H)^+$.

Example 31: Synthesis of Compound 50

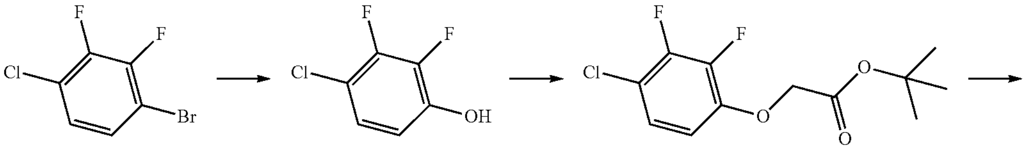

50a

50b

50c

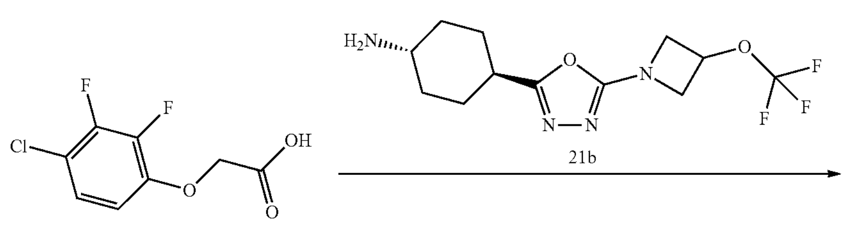

21b

50d

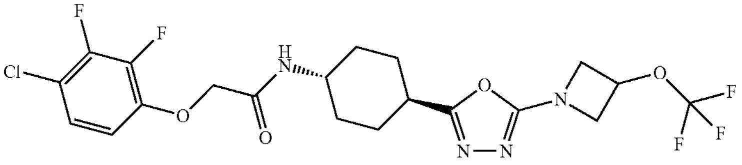

50

Step 1: Synthesis of Intermediate 50b

At 25° C., to a 50 mL three-necked flask were added compound 50a (Bidepharm, Cat. No. BD322259, 0.4 g, 1.76 mmol), Rockphos-pd-G3 (22.15 mg, 0.02 mmol) and cesium carbonate (1.7 g, 5.27 mmol) and then dimethylformamide (4.0 mL) and water (0.15 mL) were added. Under nitrogen protection, the mixture was reacted at 85° C. for 5 hours, and then the reaction was completed. The resulting reaction solution (containing intermediate 50b) was directly used in the next step without purification. LC-MS: m/z: 163.0 $(M-H)^-$.

Step 2: Synthesis of Intermediate 50c

At 25° C., to the reaction solution (containing intermediate 50b) obtained in the previous step was added tert-butyl bromoacetate (889 mg, 4.56 mmol). The mixture was reacted at 25° C. for 2 hours, and then the reaction was completed. To the resulting reaction solution were added 5 ml of water and 15 mL of ethyl acetate. The resulting organic phase was washed with 40 ml of a saturated sodium chloride aqueous solution, dried over sodium sulfate and filtered, and then the filtrate was concentrated under reduced pressure to obtain a crude. The crude was separated and purified by column chromatography to obtain intermediate 50c. LC-MS: m/z: 279.2 $(M+H)^+$.

Step 3: Synthesis of Intermediate 50d

At 25° C., to a 25 mL single-necked flask were added intermediate 50c (220 mg, 0.79 mmol) and dichloromethane (2.0 mL). Under stirring, trifluoroacetic acid (2.0 mL, 26.84 mmol) was added. The mixture was reacted at 25° C. for 1 hour, and then the reaction was completed. The reaction mixture was concentrated under reduced pressure to obtain intermediate 50d. LC-MS: m/z: 223.0 $(M+H)^+$.

Step 4: Synthesis of Compound 50

At 25° C., in an 8 mL reaction flask, intermediate 50d (33.15 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 15 ml of water, and the mixture was extracted with 15 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 50. $^1H$ NMR (400 MHZ, MeOD) δ 7.32-7.16 (m, 1H), 6.99-6.83 (m, 1H), 5.39-5.23 (m, 1H), 4.64 (s, 2H), 4.53 (dd, J=9.6, 6.9 Hz, 2H), 4.28 (dd, J=9.6, 4.2 Hz, 2H), 3.83 (dd, J=13.6, 9.6 Hz, 1H), 2.80 (tt, J=12.0, 3.4 Hz, 1H), 2.18 (t, J=12.7 Hz, 2H), 2.10-1.95 (m, 2H), 1.66 (qd, J=13.2, 3.1 Hz, 2H), 1.47 (qd, J=12.8, 3.2 Hz, 2H). LC-MS: m/z: 511.1 $(M+H)^+$.

Example 32: Synthesis of Compound 52

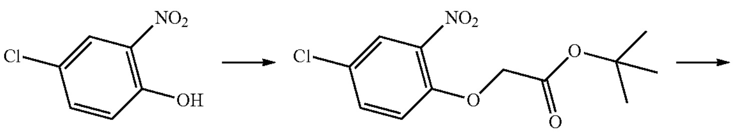

52a 52b

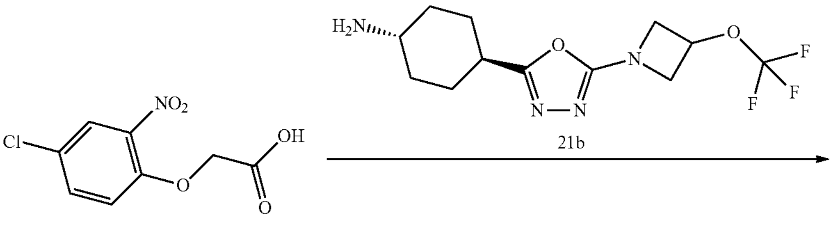

21b

52c

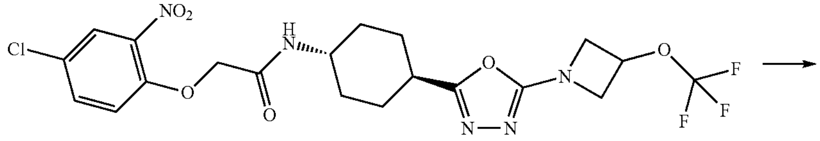

52d

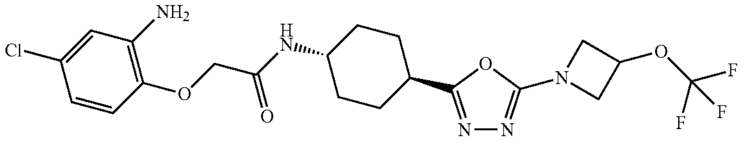

52

Step 1: Synthesis of Intermediate 52b

At 25° C., to an 8 mL reaction tube were added compound 52a (Titan, 0.2 g, 1.15 mmol), tert-butyl bromoacetate (0.25 g, 1.27 mmol) and potassium carbonate (0.317 g, 9.84 mmol), and then acetonitrile (2.0 mL) was added. The mixture was reacted at room temperature for 3 hours. The reaction solution was spun to dryness, and the crude was purified by column chromatography to obtain intermediate 52b. LC-MS: m/z: 288.0 $(M+H)^+$.

Step 2: Synthesis of Intermediate 52c

At 25° C., to intermediate 52b (240 mg, 0.83 mmol) were added trifluoroacetic acid (1 mL) and dichloromethane (1 mL). The mixture was reacted at 25° C. for 2 hours, and then the reaction was completed. The resulting reaction solution was concentrated under reduced pressure to obtain a crude. The crude was separated and purified by column chromatography to obtain intermediate 52c. LC-MS: m/z: 232.0 $(M+H)^+$.

Step 3: Synthesis of Intermediate 52d

At 25° C., to a 25 mL single-necked flask were added intermediate 52c (177 mg, 0.76 mmol) and N,N-dimethylformamide (2.0 mL). Under stirring, intermediate 21b (60 mg, 0.196 mmol) was added. The mixture was reacted at 25° C. for 4 hours, and then the reaction was completed. The resulting reaction solution was separated and purified by high performance liquid chromatography (trifluoroacetic acid/acetonitrile/water system) to obtain intermediate 52d. LC-MS: m/z: 520.1 (M+H).

Step 4: Synthesis of Compound 52

At 25° C., in a 25 mL reaction flask, intermediate 52d (20 mg, 0.038 mmol) was dissolved in methanol (1.5 mL) and water (0.5 mL). Under stirring, iron powder (11 mg, 0.19 mmol) and ammonium chloride (10.29 mg, 0.19 mmol) were sequentially added. The mixture was stirred at 70° C. for 1 hour until the reaction was completed. The resulting reaction solution was filtered while hot, and the filtrate was spun to dryness to obtain a crude. The crude was separated and purified by high performance liquid chromatography (trifluoroacetic acid/acetonitrile/water system) to obtain compound 52. $^1H$ NMR (400 MHZ, DMSO) δ 8.00 (d, J=8.2 Hz, 1H), 6.76 (d, J=8.6 Hz, 1H), 6.66 (d, J=2.5 Hz, 1H), 6.49 (d, J=8.5 Hz, 1H), 5.32 (td, J=6.5, 3.4 Hz, 1H), 4.46 (dd, J=9.7, 6.8 Hz, 3H), 4.40 (s, 2H), 4.20 (dd, J=9.7, 4.1 Hz, 3H), 3.89 (s, 1H), 2.71 (d, J=11.7 Hz, 1H), 2.05 (d, J=11.7 Hz, 2H), 1.85 (d, J=10.2 Hz, 2H), 1.60-1.38 (m, 4H). LC-MS: m/z 490.2 $(M+H)^+$.

Example 33: Synthesis of Compound 53

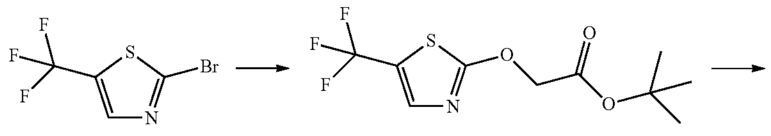

53a 53b

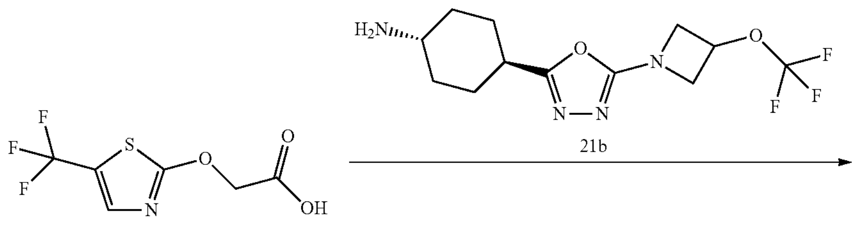

21b

53c

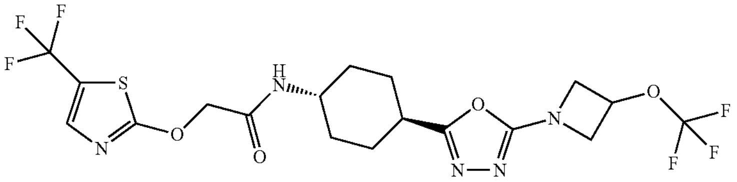

53

Step 1: Synthesis of Intermediate 53b

At 25° C., in a 25 mL reaction flask, compound 53a (Bidepharm, Cat. No. BD222433, 100 mg, 0.45 mmol), tert-butyl bromoacetate (85.45 mg, 0.65 mmol), cesium carbonate (421.3 mg, 1.3 mmol) and methanesulfonato(2-(di-t-butylphosphino)-3-methoxy-6-methyl,2,4,6-triisopropyl-1,1-biphenyl) (2-amino-1,1-biphenyl-2-yl)palladium (II) (7 mg, 0.009 mmol) were dissolved in 1,4-dioxane (5 mL). The mixture was reacted overnight at 95° C., and then the reaction was completed. To the resulting reaction solution was added 15 mL of dichloromethane. The mixture was filtered, and then the filtrate was concentrated under reduced pressure to obtain a crude. The crude was separated and purified by column chromatography to obtain intermediate 53b. $^1$H NMR (400 MHZ, $CDCl_3$) δ 7.37 (s, 1H), 4.81 (s, 2H), 1.41 (s, 9H).

Step 2: Synthesis of Intermediate 53c

At 25° C., to a 25 mL single-necked flask were added intermediate 53b (90 mg, 0.32 mmol) and dichloromethane (1 mL). Under stirring, trifluoroacetic acid (1 mL, 13.42 mmol) was added. The mixture was reacted at 25° C. for 1 hour, and then the reaction was completed. The reaction mixture was concentrated under reduced pressure to obtain intermediate 53c. LC-MS: m/z: 225.9 $(M-H)^-$.

Step 3: Synthesis of Compound 53

At 25° C., in an 8 mL reaction flask, intermediate 53c (34.07 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 15 mL of water, and the mixture was extracted with 15 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 53. $^1$H NMR (400 MHZ, MeOD) δ 8.16 (d, J=8.1 Hz, 1H), 7.52 (d, J=1.4 Hz, 1H), 5.17 (ddd, J=10.9, 6.8, 4.3 Hz, 1H), 4.85 (s, 2H), 4.40 (dd, J=9.7, 6.8 Hz, 2H), 4.16 (dd, J=9.6, 4.2 Hz, 2H), 3.68 (td, J=11.6, 5.9 Hz, 1H), 2.68 (ddd, J=12.1, 8.6, 3.5 Hz, 1H), 2.12-1.99 (m, 2H), 1.97-1.86 (m, 2H), 1.54 (ddd, J=25.6, 13.2, 3.1 Hz, 2H), 1.33 (ddd, J=25.4, 13.1, 3.5 Hz, 2H). LC-MS: m/z 516.2 $(M+H)^+$.

Examples 34 and 35: Synthesis of Compounds 6 and 12
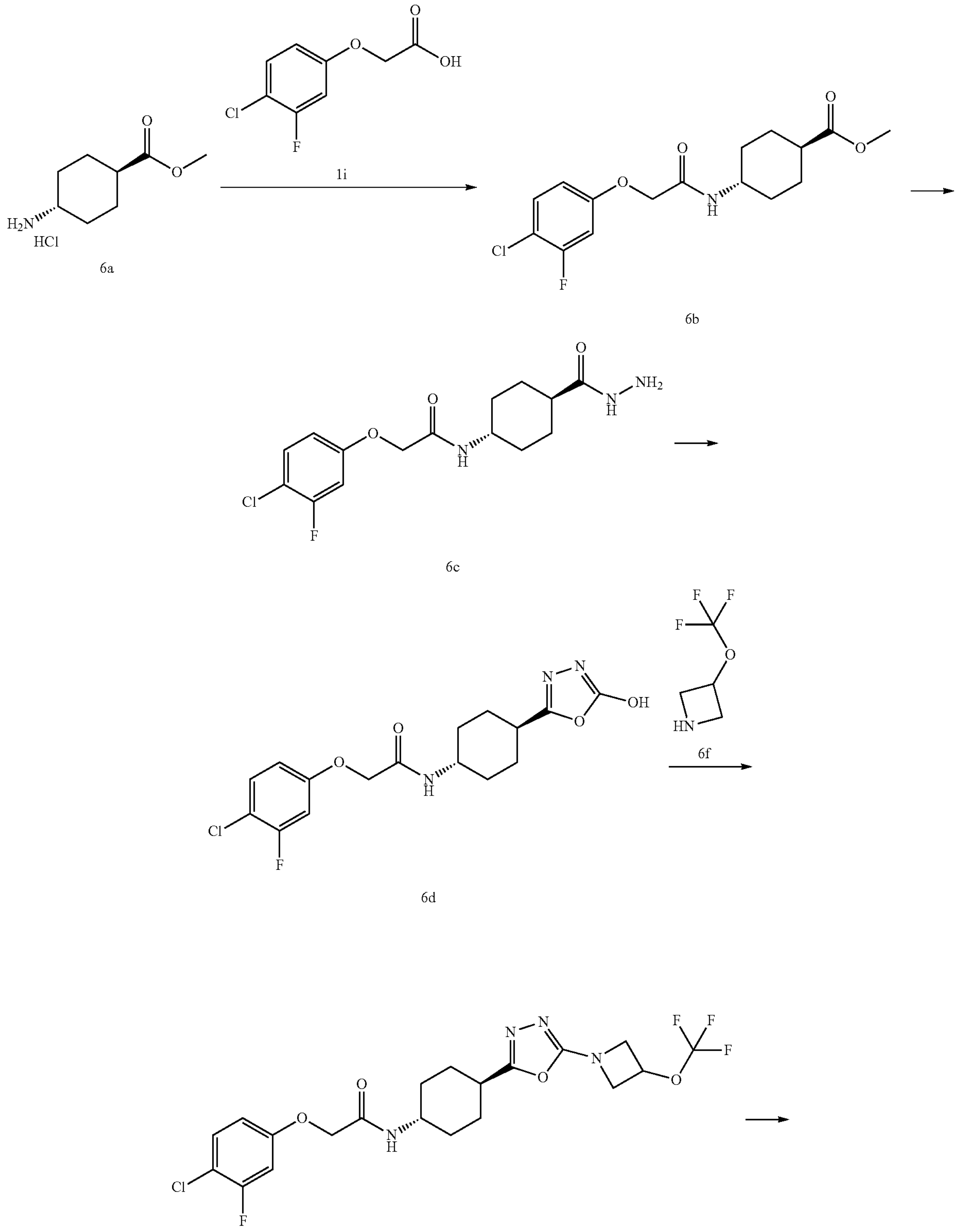
6a
6b
6c
6d
6

-continued

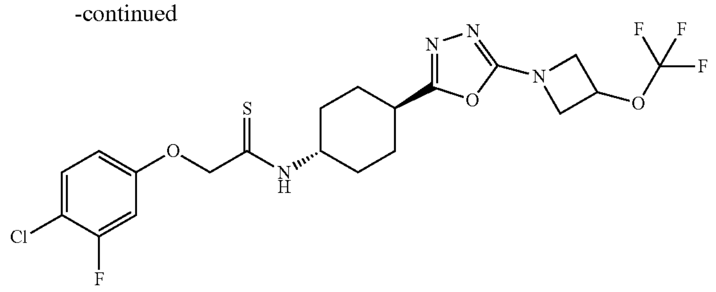

12

Step 1: Synthesis of Intermediate 6b

At 25° C., to a 50 mL single-necked flask were added compound 6a (Bidepharm, Cat. No. BD00841787, 1.50 g, 7.75 mmol) and dimethylformamide (30 mL). Under stirring, compound 1i (1.58 g, 7.75 mmol), diisopropylethylamine (5.13 mL, 30.98 mmol) and 2-(7-azobenzotriazole)-N,N,N',N'-tetramethyluronium hexafluorophosphate (4.42 g, 11.62 mmol) were sequentially added. The mixture was reacted at 25° C. for 18 hours, and then the reaction was completed. The resulting reaction solution was poured into 200 mL of water and then extracted with ethyl acetate (300 ml×2). The resulting organic phase was washed with 100 ml of a saturated sodium chloride aqueous solution, dried over anhydrous sodium sulfate overnight and filtered, and the filtrate was concentrated under reduced pressure to obtain a crude. The crude was separated and purified by column chromatography (petroleum ether:ethyl acetate=10:1-1:2) to obtain intermediate 6b. LC-MS: m/z: 344.0 (M+H)+.

Step 2: Synthesis of Intermediate 6c

At 25° C., to a 50 mL single-necked flask were added compound 6b (2.2 g, 6.40 mmol) and ethanol (20 mL). Under stirring, hydrazine hydrate (20 mL) was dropwise added. The mixture was reacted at 85° C. for 16 hours, and then the reaction was completed. The resulting reaction solution was cooled to room temperature and then concentrated under reduced pressure to obtain a crude. The crude was suspended in acetonitrile (50 mL), and the suspension was stirred at 25° C. for 2 hours, filtered and washed to obtain intermediate 6c. $^1$H NMR (400 MHZ, DMSO-$d_6$) δ8.93 (s, 1H), 7.99 (d, J=8.1 Hz, 1H), 7.50 (t, J=8.9 Hz, 1H), 7.07 (dd, J=11.4, 2.8 Hz, 1H), 6.88-6.77 (m, 1H), 4.49 (s, 2H), 3.56 (tt, J=8.0, 4.0 Hz, 1H), 3.18 (d, J=6.9 Hz, 1H), 2.00 (s, 1H), 1.79-1.62 (m, 4H), 1.46-1.22 (m, 4H). LC-MS: m/z: 344.0 $(M+H)^+$.

Step 3: Synthesis of Intermediate 6d

At 25° C., to a 50 mL single-necked flask were added intermediate 6c (1 g, 2.91 mmol) and dichloromethane (30 mL). Under stirring, N,N'-carbonyldiimidazole (0.71 g, 4.37 mmol) was added. The mixture was reacted at 25° C. for 16 hours, and then the reaction was completed. The mixture was concentrated under reduced pressure to obtain a crude. The crude was separated and purified by column chromatography (dichloromethane:methanol=10:1-5:1) to obtain intermediate 6d. LC-MS: m/z: 370.0 $(M+H)^+$.

Step 4: Synthesis of Compound 6

At 25° C., to a 50 mL single-necked flask were added intermediate 6d (100 mg, 0.27 mmol) and dimethylformamide (4 mL). Under stirring, diisopropylethylamine (0.18 mL, 1.08 mmol), 1H-benzotriazol-1-yloxytripyrrolidinyl hexafluorophosphate (179.41 mg, 0.41 mmol) and compound 6f (71.50 mg, 0.40 mmol) were sequentially added. The mixture was reacted at 25° C. for 18 hours, and then the reaction was completed. The reaction solution was poured into 20 ml of water and then extracted with ethyl acetate (30 mL×2). The resulting organic phase was washed with 10 ml of a saturated sodium chloride aqueous solution, dried over sodium sulfate and filtered, and the filtrate was concentrated under reduced pressure to obtain a crude. The crude was separated and purified by high performance liquid chromatography (trifluoroacetic acid/acetonitrile/water system) to obtain compound 6. $^1$H NMR (400 MHZ, DMSO-d6) δ8.05 (d, J=8.0 Hz, 1H), 7.50 (t, J=8.9 Hz, 1H), 7.07 (dd, J=11.4, 2.9 Hz, 1H), 6.85 (dd, J=8.7, 2.9 Hz, 1H), 5.37-5.24 (m, 1H), 4.56-4.37 (m, 4H), 4.19 (dd, J=9.7, 4.0 Hz, 2H), 3.66 (t, J=3.8 Hz, 1H), 2.73 (td, J=11.9, 10.1, 6.1 Hz, 1H), 2.09-1.97 (m, 2H), 1.90-1.79 (m, 2H), 1.55-1.35 (m, 4H). LC-MS: m/z: 493.1 $(M+H)^+$.

Step 5: Synthesis of Compound 12

At 25° C., to a 50 mL single-necked flask were added compound 6 (40 mg, 0.08 mmol) and toluene (3 mL). Under stirring, Lawson's reagent (32.82 mg, 0.08 mmol) was added. The mixture was reacted at 120° C. for 1 hour, and then the reaction was completed. The resulting reaction solution was cooled to 25° C., poured into 20 ml of water and then extracted with ethyl acetate (30 mL×2). The resulting organic phase was washed with 10 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 12. $^1$H NMR (400 MHZ, DMSO-$d_6$) δ 8.05 (d, J=8.0 Hz, 1H), 7.50 (t, J=8.9 Hz, 1H), 7.07 (dd, J=11.4, 2.9 Hz, 1H), 6.85 (dd, J=8.7, 2.9 Hz, 1H), 5.37-5.24 (m, 1H), 4.56-4.37 (m, 4H), 4.19 (dd, J=9.7, 4.0 Hz, 2H), 3.66 (t, J=3.8 Hz, 1H), 2.73 (td, J=11.9, 10.1, 6.1 Hz, 1H), 2.09-1.97 (m, 2H), 1.90-1.79 (m, 2H), 1.55-1.35 (m, 4H). LC-MS: m/z: 509.0 $(M+H)^+$.

Example 36: Synthesis of Compound 13

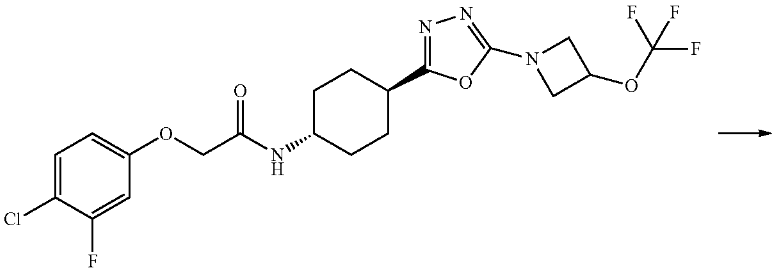

12

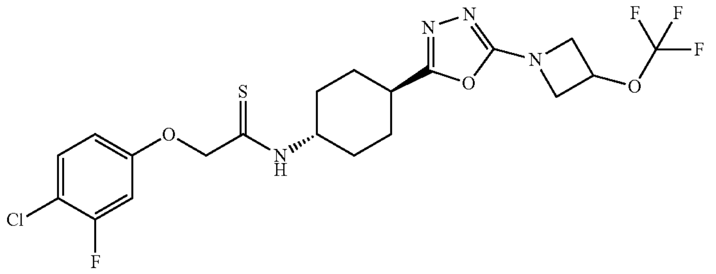

13

At 25° C., to a 50 mL single-necked flask were added compound 12 (80 mg, 0.16 mmol) and toluene (5 mL). Under stirring, Lawson's reagent (64.71 mg, 0.16 mmol) was added. The mixture was reacted at 120° C. for 18 hour, and then the reaction was completed. The resulting reaction solution was cooled to 25° C., poured into 20 ml of water and then extracted with ethyl acetate (30 mL×2). The resulting organic phase was washed with 10 ml of a saturated sodium chloride aqueous solution, dried over sodium sulfate and filtered, and then the filtrate was concentrated under reduced pressure to obtain a crude. The crude was separated by high performance liquid chromatography (trifluoroacetic acid/acetonitrile/water system) to obtain compound 13. $^1$H NMR (400 MHZ, DMSO-$d_6$) δ8.05 (d, J=8.0 Hz, 1H), 7.50 (t, J=8.9 Hz, 1H), 7.07 (dd, J=11.4, 2.9 Hz, 1H), 6.85 (dd, J=8.7, 2.9 Hz, 1H), 5.37-5.24 (m, 1H), 4.56-4.37 (m, 4H), 4.19 (dd, J=9.7, 4.0 Hz, 2H), 3.66 (t, J=3.8 Hz, 1H), 2.73 (td, J=11.9, 10.1, 6.1 Hz, 1H), 2.09-1.97 (m, 2H), 1.90-1.79 (m, 2H), 1.55-1.35 (m, 4H). LC-MS: m/z: 525.0 $(M+H)^+$.

Example 37: Synthesis of Compound 11

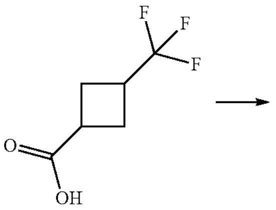

11a

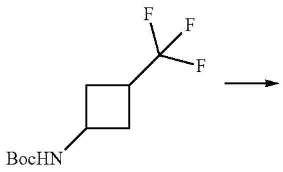

11b

-continued

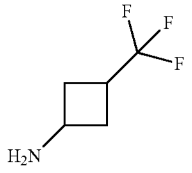

11c

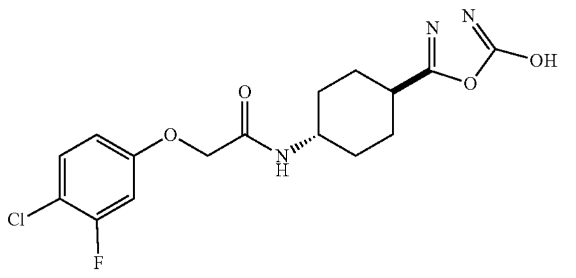

6d

-continued

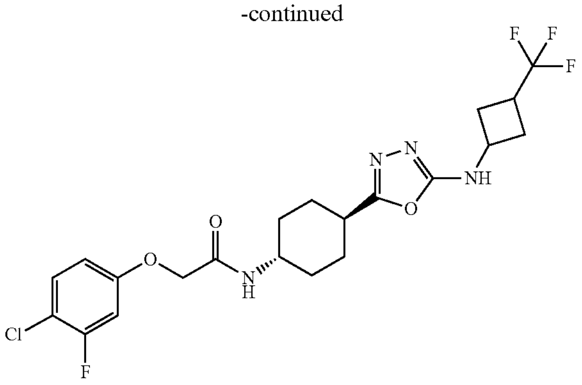

11

Step 1: Synthesis of Intermediate 11b

At 25° C., to a 50 mL single-necked flask were added compound 11a (Bidepharm, Cat. No. BD254006, 150 mg, 0.89 mmol), tert-butanol (0.5 mL) and toluene (3 mL). Under stirring, the compounds diphenylphosphoryl azide (0.25 mL, 1.16 mmol) and triethylamine (0.27 mL, 1.96 mmol) were sequentially added. The mixture was reacted at 85° C. for 8 hour, and then the reaction was completed. The resulting reaction solution was concentrated under reduced pressure to obtain a crude. The crude was separated and purified by column chromatography (petroleum ether:ethyl acetate=100:1-10:1) to obtain intermediate 11b. LC-MS: m/z: 240.1 $(M+H)^+$.

Step 2: Synthesis of Intermediate 11c

At 25° C., to a 50 mL single-necked flask were added intermediate 11b (200 mg, 0.42 mmol) and hydrogen chloride in dioxane (5 mL). The mixture was reacted at 25° C. for 3 hours, and then the reaction was completed. The resulting reaction solution was concentrated under reduced pressure to obtain intermediate 11c. LC-MS: m/z: 140.0 $(M+H)^+$.

Step 3: Synthesis of Compound 11

At 25° C., to a 50 mL single-necked flask were added intermediate 6d (50 mg, 0.14 mmol) and dimethylformamide (2 mL). Under stirring, diisopropylethylamine (0.09 mL, 0.54 mmol), 1H-benzotriazol-1-yloxytripyrrolidinyl hexafluorophosphate (89.71 mg, 0.20 mmol) and intermediate 11c (28.22 mg, 0.20 mmol) were sequentially added. The mixture was reacted at 25° C. for 18 hours, and then the reaction was completed. The resulting reaction solution was poured into 20 ml of water and then extracted with ethyl acetate (30 ml×2). The resulting organic phase was washed with 10 ml of a saturated sodium chloride aqueous solution, dried over sodium sulfate and filtered, and then the filtrate was concentrated under reduced pressure to obtain a crude. The crude was separated by high performance liquid chromatography (trifluoroacetic acid/acetonitrile/water system) to obtain compound 11. $^1H$ NMR (400 MHZ, DMSO-$d_6$) δ7.97 (d, J=67.1 Hz, 1H), 7.50 (s, 1H), 7.08 (s, 1H), 6.85 (d, J=9.0 Hz, 1H), 4.50 (s, 2H), 3.97 (s, 2H), 3.72-3.59 (m, 1H), 3.11 (s, 1H), 2.92 (s, 1H), 2.68 (s, 1H), 2.36 (s, 1H), 1.91 (d, J=64.6 Hz, 6H), 1.43 (d, J=30.2 Hz, 4H). LC-MS: m/z: 491.0 $(M+H)^+$.

Example 38: Synthesis of Compound 14

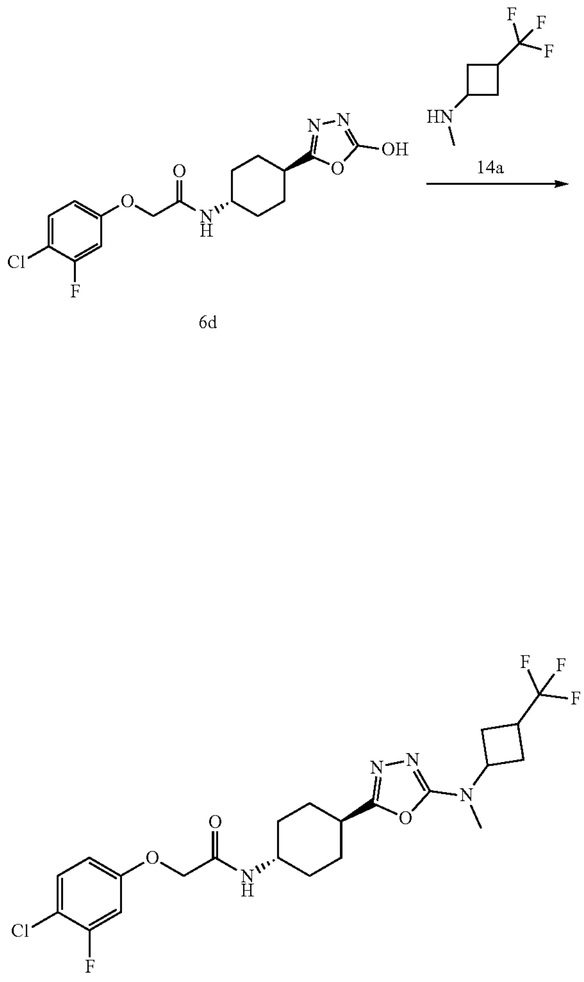

6d

14a

14

At 25° C., to a 50 mL single-necked flask were added intermediate 6d (50 mg, 0.14 mmol) and dimethylformamide (2 mL). Under stirring, diisopropylethylamine (0.09 mL, 0.54 mmol), 1H-benzotriazol-1-yloxytripyrrolidinyl hexafluorophosphate (89.71 mg, 0.20 mmol) and compound 14a (Bidepharm, Cat. No. BD00841787, 71.61 mg, 0.41 mmol) were sequentially added. The mixture was reacted at 25° C. for 18 hours, and then the reaction was completed. The resulting reaction solution was poured into 20 ml of water and then extracted with ethyl acetate (30 ml×2). The resulting organic phase was washed with 10 mL of a saturated sodium chloride aqueous solution, dried over sodium sulfate and filtered, and then the filtrate was concentrated under reduced pressure to obtain a crude. The crude was separated by high performance liquid chromatography (trifluoroacetic acid/acetonitrile/water system) to obtain compound 14. $^1H$ NMR (400 MHZ, DMSO-$d_6$) δ7.88 (d, J=8.1 Hz, 1H), 7.36 (s, 1H), 6.94 (dd, J=11.1, 2.9 Hz, 1H), 6.83-6.74 (m, 1H), 4.46 (s, 2H), 4.02 (d, J=7.1 Hz, 1H), 3.78-3.62 (m, 1H), 2.95 (d, J=14.9 Hz, 3H), 2.81 (q, J=8.7 Hz, 1H), 2.13-2.03 (m, 2H), 1.90 (dd, J=13.2, 3.8 Hz, 2H), 1.61-1.13 (m, 9H). LC-MS: m/z: 505.2 $(M+H)^+$.

Example 39: Synthesis of Compound 4
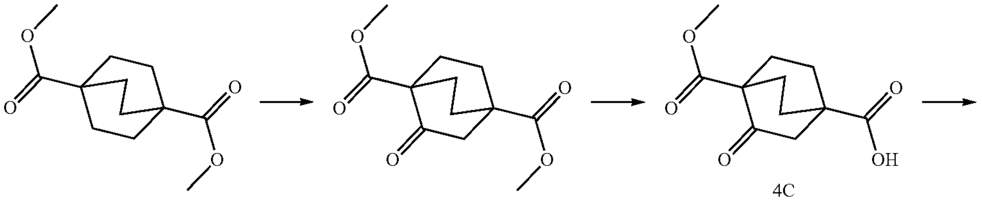
4a 4b 4C
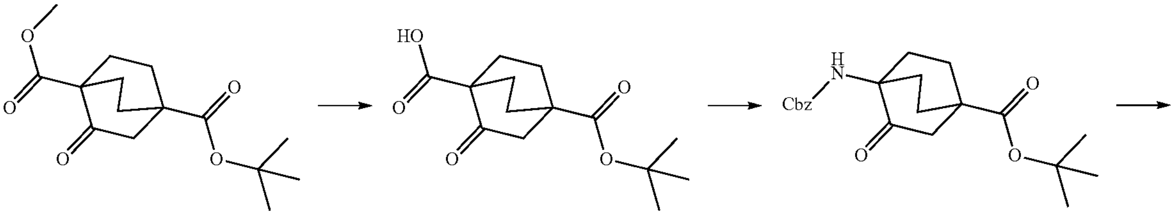
4d 4e 4f
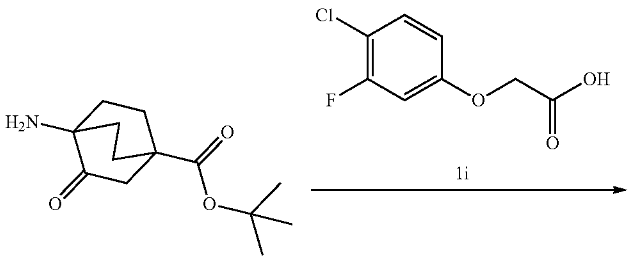
4g
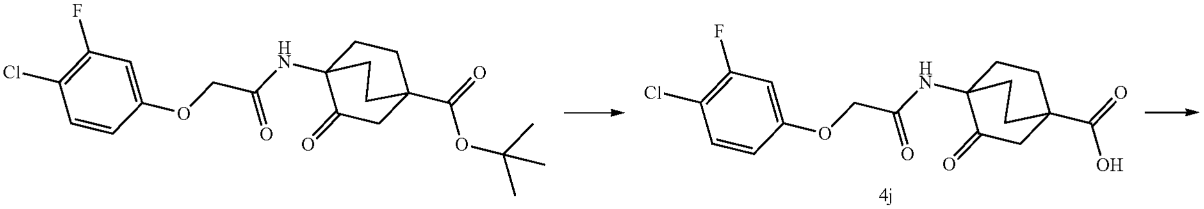
4i 4j
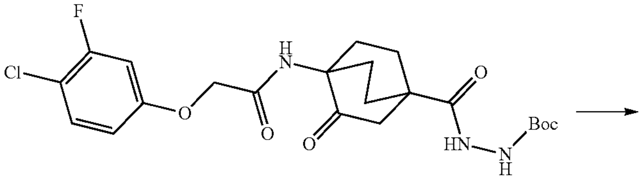
4k
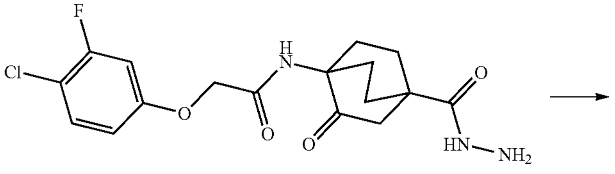
4l -continued

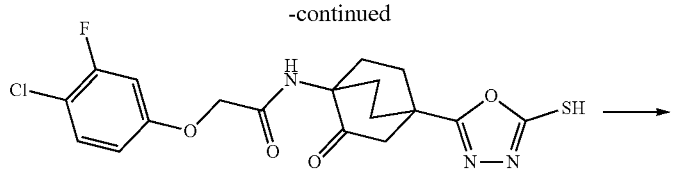

4m

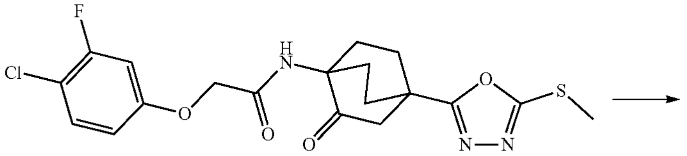

4n

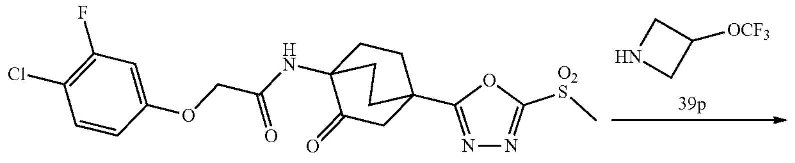

4o

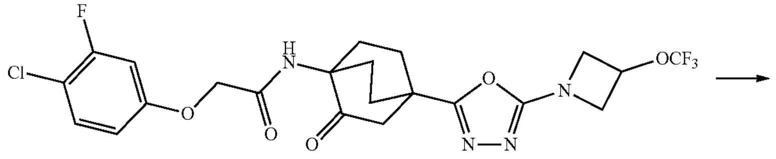

4q

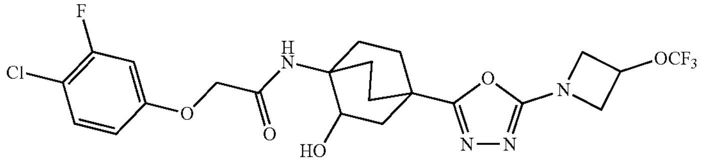

4

Step 1: Synthesis of Intermediate 4b

At 25° C., to a 500 mL single-necked flask were added compound 4a (Bidepharm, Cat. No. BD163186, 15.5 g, 68.5 mmol) and glacial acetic acid (125 mL). Under stirring, the compound chromium trioxide (13.70 g, 137 mmol) was added. The mixture was stirred at 90° C. for 16 hours, and then the reaction was completed. Ethyl acetate (100 mL) was added to the reaction mixture, and the mixture was poured into $H_2O$ (200 mL). The resulting mixture was adjusted to pH 9 by adding solid $NaHCO_3$ and then extracted. The organic layers were combined, washed with a sodium chloride aqueous solution (200 mL), dried over $Na_2SO_4$, filtered, and concentrated. The crude was purified by silica gel column chromatography (petroleum ether:ethyl acetate=10:1) to obtain intermediate 4b. LC-MS: m/z: 241.0 $(M+H)^+$.

Step 2: Synthesis of Intermediate 4c

At 25° C., to a 250 ml single-necked flask were added intermediate 4b (5.023 g, 20.91 mmol), tetrahydrofuran (60 mL) and methanol (15 mL), and then an aqueous solution (15 mL) of LiOH (400 mg, 16.73 mmol) was added. The mixture was stirred at 25° C. for 16 hours, and then the reaction was completed. The reaction mixture was concentrated under reduced pressure to remove tetrahydrofuran, and adjusted to pH 2-3 by adding 2 mol/L HCl, with solids precipitated. The mixture was filtered, and the filter cake was collected to obtain intermediate 4c. LC-MS: m/z: 225.0 $(M-H)^-$.

Step 3: Synthesis of Intermediate 4d

At 25° C., to a 100 mL single-necked flask were added intermediate 4c (2.15 g, 9.5 mmol) and tert-butyl alcohol (30 mL). Pyridine (5.37 mL, 66.53 mmol), DMAP (1.16 g, 9.5 mmol) and $(Boc)_2O$ (4.07 mL, 19.01 mmol) were added. The mixture was stirred at 35° C. for 16 hours, and then the reaction was completed. The reaction mixture was concentrated under reduced pressure, poured into water (50 mL) and extracted with ethyl acetate (50 ml×3). The organic layers were combined, washed with a sodium chloride aqueous solution (50 mL), dried over $Na_2SO_4$, filtered and concentrated. The crude was purified by silica gel column chromatography (petroleum ether:ethyl acetate=10:1) to obtain intermediate 4d. LC-MS: m/z: 283.10 $(M+H)^+$.

Step 4: Synthesis of Intermediate 4e

At 25° C., to a 100 mL single-necked flask were added intermediate 4d (1.204 g, 4.26 mmol), tetrahydrofuran (20 mL) and methanol (5 mL), and then an aqueous solution (4 mL) of lithium hydrate (100 mg, 4.26 mmol) was added. The mixture was stirred at 25° C. for 16 hours, and then the reaction was completed. The reaction mixture was concentrated under reduced pressure to remove tetrahydrofuran, and adjusted to pH 2-3 by adding 2 M HCl, with solids precipitated. The mixture was filtered, and the filter cake was collected to obtain intermediate 4e. LC-MS: m/z: 269.10 $(M+H)^+$.

Step 5: Synthesis of Intermediate 4f

At 25° C., to a 100 mL single-necked flask were added intermediate 4e (800 mg, 2.98 mmol) and toluene (50 mL). Under stirring, triethylamine (1.24 mL, 8.94 mmol) and diphenylphosphoryl azide (1641.09 mg, 5.96 mmol) were added, and the mixture was stirred at 120° C. for 2 hours. Then, benzyl alcohol (0.93 mL, 8.94 mmol) was added. The mixture was stirred at 120° C. for 12 hours, and then the reaction was completed. Water (50 mL) was added to the reaction mixture, and the mixture was extracted with ethyl acetate (60 mL×3). The organic layers were combined, washed with a sodium chloride aqueous solution (50 mL), dried over $Na_2SO_4$, filtered and concentrated. The crude was purified by silica gel column chromatography (petroleum ether:ethyl acetate=10:1) to obtain intermediate 4f. LC-MS: m/z: 374.2 $(M+H)^+$ Step 6: Synthesis of Intermediate 4g At 25° C., to a 100 mL single-necked flask were added intermediate 4f (890 mg, 2.38 mmol) and tetrahydrofuran (20 mL). Under stirring, palladium hydroxide (297.79 mg, 2.12 mmol) was added. The mixture was subjected to hydrogen replacement three times and stirred at 25° C. for 16 hours, and then the reaction was completed. The mixture was filtered, and the filtrate was concentrated under reduced pressure to obtain intermediate 4 g. LC-MS: m/z: 240.1 $(M+H)^+$.

Step 7: Synthesis of Intermediate 4i

At 25° C., to a 25 mL single-necked flask were added intermediate 4 g obtained in the previous step and dichloromethane (6 mL). Under stirring, intermediate 1i (300.39 mg, 1.26 mmol), diisopropylethylamine (0.83 mL, 5.02 mmol) and 1-propylphosphonic anhydride (1597.59 mg, 2.51 mmol) were added. The mixture was stirred at 25° C. for 16 hours, and then the reaction was completed. Water (10 mL) was added to the reaction mixture, and the mixture was extracted with ethyl acetate (15 ml×3). The organic layers were combined, washed with a sodium chloride aqueous solution (10 mL), dried over anhydrous sodium sulfate, filtered and concentrated. The crude was purified by silica gel column chromatography (petroleum ether:ethyl acetate=4:1) to obtain intermediate 4i. LC-MS: m/z: 426.2 $(M+H)^+$.

Step 8: Synthesis of Intermediate 4j

At 0° C., to a 25 mL single-necked flask were added intermediate 4i (260 mg, 0.61 mmol) and dichloromethane (5 mL). Under stirring, trifluoroacetic acid (5 mL) was added. The mixture was stirred at 50° C. for 1 hour, and then the reaction was completed. The solvent was removed by concentration under reduced pressure to obtain intermediate 4j. LC-MS: m/z: 370.1 $(M+H)^+$.

Step 9: Synthesis of Intermediate 4k

At 25° C., to a 25 mL single-necked flask were added intermediate 4j (225.7 mg, 0.61 mmol) and dimethylformamide (5 mL). Under stirring, tert-butyl carbazate (0.09 mL, 0.73 mmol), 1-ethyl-(3-dimethylaminopropyl) carbodiimide hydrochloride (234.02 mg, 1.22 mmol), 1-hydroxybenzotriazole (315.54 mg, 2.44 mmol) and N,N-diisopropylethylamine (0.21 mL, 1.22 mmol) were added. The mixture was stirred at 25° C. for 16 hours, and then the reaction was completed. Water (10 mL) was added to the reaction mixture, and the mixture was extracted with ethyl acetate (15 ml×3). The organic layers were combined, washed with a sodium chloride aqueous solution (10 mL), dried over sodium sulfate, filtered and concentrated. The crude was purified by silica gel column chromatography (petroleum ether:ethyl acetate=1:1) to obtain intermediate 4k. LC-MS: m/z: 484.2 $(M+H)^+$.

Step 10: Synthesis of Intermediate 41

At 0° C., to a 25 mL single-necked flask were added intermediate 4k (296 mg, 0.61 mmol) and dichloromethane (3 mL). Under stirring, 4 M hydrogen chloride in dioxane (3 mL) was added. The mixture was stirred at 25° C. for 1 hour, and then the reaction was completed. The solvent was removed by concentration under reduced pressure to obtain intermediate 41. LC-MS: m/z: 385.8 (M+H).

Step 11: Synthesis of Intermediate 4m

At 25° C., to a 10 mL single-necked flask were added intermediate 41 obtained in the previous step and tetrahydrofuran (2 mL). Under stirring, N,N-diisopropylethylamine (0.09 mL, 0.57 mmol) and thiocarbonyldiimidazole (61.29 mg, 0.34 mmol) were added. The mixture was stirred at 25° C. for 16 hours and then stirred at 70° C. for 3 hours, and then the reaction was completed. Water (3 mL) was added to the reaction mixture, and the mixture was extracted with ethyl acetate (5 ml×3). The organic layers were combined, washed with a sodium chloride aqueous solution (3 mL), dried over sodium sulfate, filtered and concentrated. The crude was purified by silica gel column chromatography (pure ethyl acetate) to obtain intermediate 4m. LC-MS: m/z: 426.1 (M+H).

Step 12: Synthesis of Intermediate 4n

At 25° C., to a 10 mL single-necked flask were added intermediate 4m (122 mg, 0.29 mmol) and dimethylformamide (1.5 mL). Under stirring, potassium carbonate (79.18 mg, 0.57 mmol) and iodomethane (35.68 μL, 0.57 mmol) were added. The mixture was stirred at 25° C. for 3 hours, and then the reaction was completed. Water (5 mL) was added to the reaction mixture, and the mixture was extracted with ethyl acetate (6 mL×3). The organic layers were combined, washed with a sodium chloride aqueous solution (5 mL), dried over sodium sulfate, filtered and concentrated. The crude was purified by silica gel column chromatography (petroleum ether:ethyl acetate=1:1) to obtain intermediate 4n. LC-MS: m/z: 440.1 $(M+H)^+$.

Step 13: Synthesis of Intermediate 4o

At 0° C., to a 10 mL single-necked flask were added intermediate 4n (65 mg, 0.15 mmol) and dichloromethane (1 mL). Under stirring, m-chloroperoxybenzoic acid (105.00 mg, 0.52 mmol) was added. The mixture was stirred at 25° C. for 16 hours, and then the reaction was completed. To the reaction mixture were added a saturated sodium thiosulfate solution and then water (3 mL). The mixture was extracted with ethyl acetate (5 mL×3). The organic layers were combined, washed with a sodium chloride aqueous solution (3 mL), dried over sodium sulfate, filtered and concentrated. The crude was purified by silica gel column chromatography (petroleum ether:ethyl acetate=1:1) to obtain intermediate 40. LC-MS: m/z: 472.1 $(M+H)^+$.

Step 14: Synthesis of Intermediate 4q

At 25° C., to a 10 mL single-necked flask were added intermediate 40 (44 mg, 0.09 mmol) and dimethylformamide (1 mL). Under stirring, compound 4p (65.78 mg, 0.47 mmol) and potassium carbonate (90.20 mg, 0.65 mmol) were added. The mixture was stirred at 25° C. for 4 hours, and then the reaction was completed. Water (2 mL) was added to the reaction mixture, and the mixture was extracted with ethyl acetate (5 ml×3). The organic layers were combined, washed with a sodium chloride aqueous solution (3 mL), dried over sodium sulfate, filtered and concentrated. The crude was purified by silica gel column chromatography (petroleum ether:ethyl acetate=2:1) to obtain intermediate 4q. LC-MS: m/z: 533.2 $(M+H)^+$.

Step 15: Synthesis of Compound 4

At 0° C., to a 10 mL single-necked flask were added intermediate 4q (35 mg, 0.07 mmol) and methanol (1 mL). Under stirring, sodium borohydride (4.97 mg, 0.13 mmol) was added. The mixture was stirred at 25° C. for 1 hour, and then the reaction was completed. The reaction mixture was adjusted to pH=7 by adding a 2 M hydrogen chloride solution, and then water (2 mL) was added. The mixture was extracted with ethyl acetate (3 mL×3). The organic layers were combined, washed with a sodium chloride aqueous solution (3 mL), dried over sodium sulfate, filtered and concentrated. The crude was purified by preparative thin layer chromatography (petroleum ether:ethyl acetate=3:1) to obtain compound 4. LC-MS: m/z: 535.2 $(M+H)^+$. $^1H$ NMR (DMSO-$d_6$) δ: 7.55 (t, J=8.9 Hz, 1H), 7.42 (s, 1H), 7.13 (dd, J=11.4, 2.8 Hz, 1H), 6.90 (dd, J=8.9, 2.7 Hz, 1H), 5.33-5.41 (m, 1H), 5.12-5.32 (m, 1H), 4.55 (s, 2H), 4.51 (dd, J=9.4, 6.9 Hz, 2H), 4.25 (dd, J=9.6, 3.9 Hz, 2H), 4.17 (br d, J=7.1 Hz, 1H), 2.23-2.37 (m, 1H), 2.13 (br d, J=5.0 Hz, 1H), 1.80-2.05 (m, 7H), 1.74 (dd, J=13.6, 2.5 Hz, 1H).

Example 40: Synthesis of Compound 3

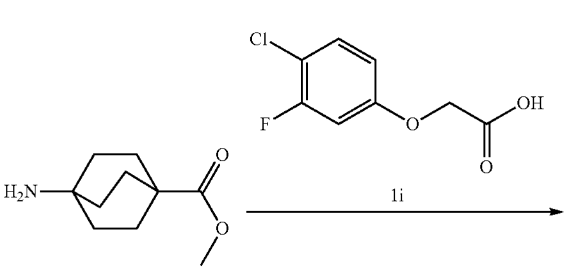

3a

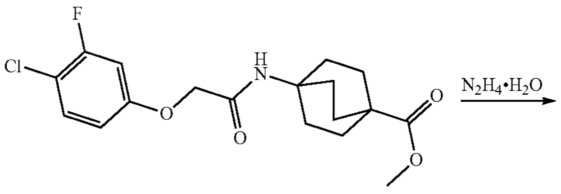

3b

-continued

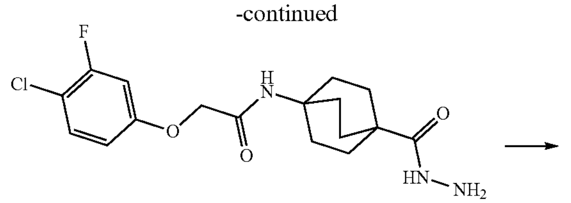

3c

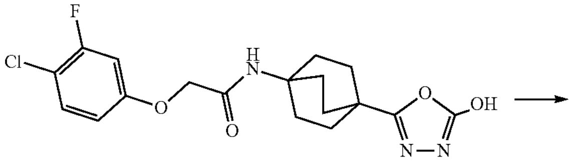

3d

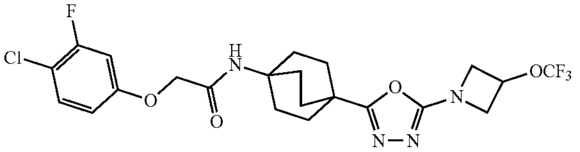

3

Step 1: Synthesis of Intermediate 3b

To a solution of 3a (Bidepharm, Cat. No. BD234253, 1 g, 5.46 mmol) and 1i (1 g, 4.96 mmol) in DCM (20 mL) were added DIEA (3.28 mL, 19.84 mmol) and T3P (3.16 g, 9.92 mmol), and the mixture was stirred at room temperature for 16 hours. The reaction mixture was poured into water (20 mL), and extracted with DCM (20 mL×3). The resulting organic layers were combined, washed with a sodium chloride aqueous solution (20 mL), dried over $Na_2SO_4$, filtered and concentrated. The crude was purified by silica gel column chromatography (petroleum ether:ethyl acetate=1:1) to obtain intermediate 3b. m/z $ES^+$ $[M+H]^+$=370.1.

Step 2: Synthesis of Intermediate 3c

To a solution of intermediate 3b (1.13 g, 3.06 mmol) in EtOH (8 mL) was added $N_2H_4 \cdot H_2O$ (9 mL), and the mixture was stirred at 100° C. overnight. The reaction mixture was poured into water (30 mL), and extracted with dichloromethane (30 mL×3). The resulting organic layers were combined, washed with a sodium chloride aqueous solution (30 mL), dried over $Na_2SO_4$, filtered and concentrated. The crude was purified by silica gel column chromatography (dichloromethane:methanol=10:1) to obtain intermediate 3c. m/z $ES^+$ $[M+H]^+$=370.1.

Step 3: Synthesis of Intermediate 3d

To a solution of intermediate 3c (100 mg, 0.27 mmol) and DIEA (90 μL, 0.54 mmol) in THF (1.5 mL) was added CDI (48 mg, 0.30 mmol), and the resulting mixture was stirred at room temperature for 1 hour. The resulting reaction mixture was poured into water (5 ml), and extracted with dichloromethane (5 mL×3). The organic layers were combined, washed with a sodium chloride aqueous solution (5 mL), dried over sodium sulfate, filtered and concentrated. The crude was purified by silica gel column chromatography (pure ethyl acetate) to obtain intermediate 3d. m/z $ES^+$ $[M+H]^+$=396.1.

Step 4: Synthesis of Compound 3

To a solution of intermediate 3d (75 mg, 0.19 mmol) and 3-(trifluoromethoxy)-azetidine (67 mg, 0.38 mmol) in dimethylformamide (1.5 mL) was added DIEA (94 μL, 0.57 mmol), and the resulting mixture was stirred at room temperature for 10 minutes. Then, Castro's reagent (92 mg, 0.21 mmol) was added, and the mixture was stirred overnight at room temperature. The resulting reaction mixture was poured into water (5 mL), and extracted with dichloromethane (5 mL×3). The organic layers were combined, washed with a sodium chloride aqueous solution (5 mL), dried over sodium sulfate, filtered and concentrated. The crude was purified by silica gel column chromatography (petroleum ether:ethyl acetate=1:1) to obtain compound 3. m/z $ES^+$ $[M+H]^+$=519.1. $^1H$ NMR (DMSO-$d_6$) δ: 7.58 (s, 1H), 7.48 (t, J=8.8 Hz, 1H), 7.03 (dd, J=11.4, 2.6 Hz, 1H), 6.82 (d, J=9.1 Hz, 1H), 5.26-5.35 (m, 1H), 4.46 (s, 2H), 4.40-4.45 (m, 2H), 4.18 (br dd, J=9.5, 3.6 Hz, 2H), 1.90 (br d, J=5.1 Hz, 12H).

Example 41: Synthesis of Compound 10

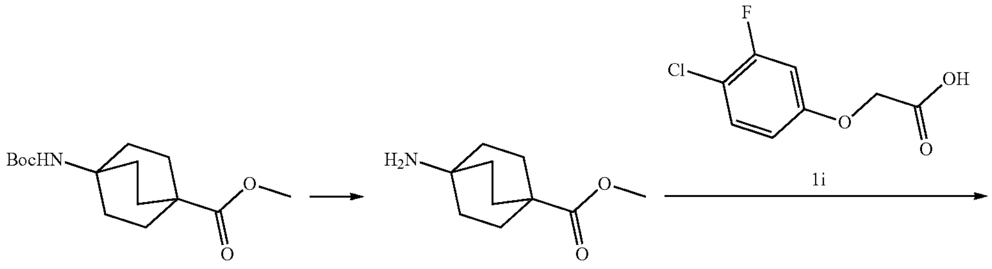

10a

10b

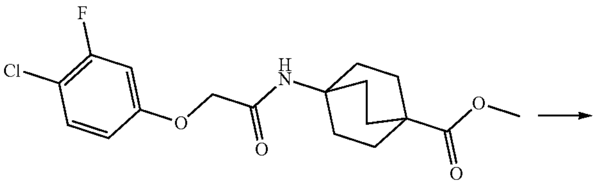

10c

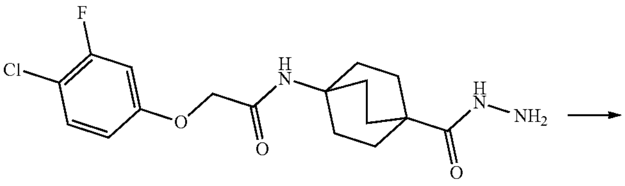

10d

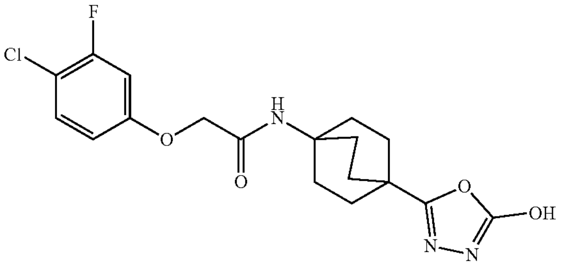

10e

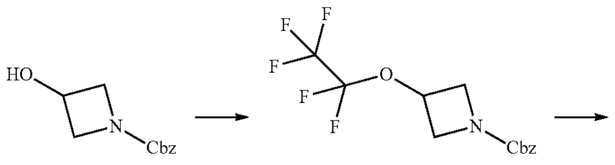

10g

-continued

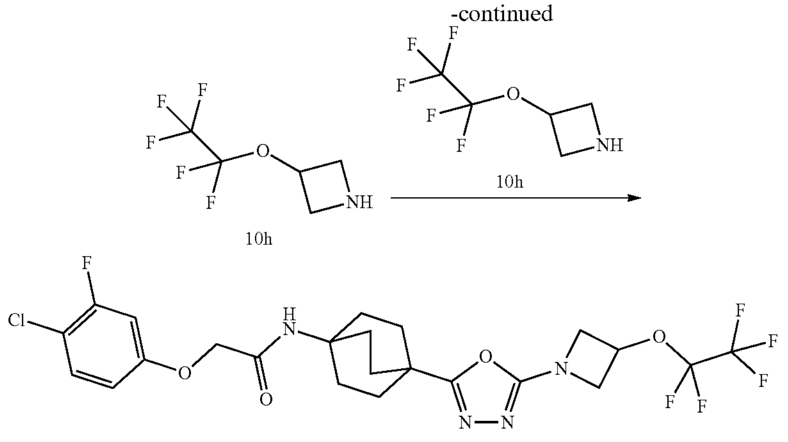

10

Step 1: Preparation of Intermediate 10b

At 25° C., to a 100 mL single-necked flask were added compound 10a (Bidepharm, Cat. No. BD234295, 2 g, 7.06 mmol) and dichloromethane (15 mL). Under stirring, trifluoroacetic acid (5.0 mL) was added. The mixture was reacted at 25° C. for 3 hours, and then the reaction was completed. The reaction mixture was concentrated under reduced pressure to obtain intermediate 10b.

Step 2: Preparation of Intermediate 10c

Under ice bath, to a 100 mL single-necked flask were added compound 1i (1.74 g, 8.51 mmol) and dimethylformamide (15 mL). Under stirring, 2-(7-azobenzotriazole)-N,N,N',N'-tetramethyluronium hexafluorophosphate (4.04 g, 10.64 mmol) and diisopropylethylamine (3.69 g, 28.83 mmol) were sequentially added. The mixture was reacted at 25° C. for half an hour, and then intermediate 10b (1.3 g, 7.09 mmol) was added to the resulting reaction solution. At 25° C., the mixture was reacted overnight. To the resulting reaction solution was added 150 ml of water, and the mixture was extracted with 150 ml of ethyl acetate. The organic phase was washed with 150 ml of a saturated sodium chloride aqueous solution, dried over sodium sulfate and filtered, and then the filtrate was concentrated under reduced pressure to obtain a crude. The crude was purified by high performance liquid chromatography (ammonium bicarbonate/acetonitrile/water system) to obtain intermediate 10c. LC-MS: m/z: 393.0 $(M+Na)^+$.

Step 3: Preparation of Intermediate 10d

At 25° C., to a 100 mL single-necked flask were added intermediate 10c (1.6 g, 4.33 mmol) and ethanol (15 mL). Under stirring, 50% hydrazine hydrate (3.61 g, 43.3 mmol) was added. The mixture was reacted overnight at 80° C., and then the reaction was completed. The reaction mixture was concentrated under reduced pressure to obtain a crude. The crude was purified by recrystallization using an acetonitrile solvent, so as to obtain intermediate 10d. LC-MS: m/z: 370.2 $(M+H)^+$.

Step 4: Preparation of Intermediate 10e

At 25° C., to a 100 mL single-necked flask were added intermediate 10d (616 mg, 1.67 mmol) and 1,2-dichloroethane (5 mL). Under stirring, the compound N,N'-carbonyldiimidazole (350 mg, 2.16 mmol) was sequentially added. The mixture was reacted at 25° C. for 18 hours. To the reaction solution was added 50 ml of water, and the mixture was extracted with 50 ml of ethyl acetate. The resulting organic phase was washed with 100 ml of a saturated sodium chloride aqueous solution, dried over sodium sulfate and filtered, and then the filtrate was concentrated under reduced pressure to obtain a crude. The crude was purified by column chromatography to obtain intermediate 10e. LC-MS: m/z: 396.0 $(M+H)^+$.

Step 5: Preparation of Intermediate 10g

Under ice bath, to a 100 mL three-necked flask were added compound 10f (1.0 g, 4.83 mmol) and ethyl acetate (20 mL). After the three-necked flask was wrapped with tin foil to block light, silver trifluoromethanesulfonate (3.72 g, 14.48 mmol), 1-chloromethyl-4-fluoro-1,4-diazoniabicyclo[2.2.2]octane bis(tetrafluoroborate) (2.56 g, 7.24 mmol), potassium fluoride (1.12 g, 19.32 mmol), 2-fluoropyridine (1.34 g, 14.48 mmol), and (pentafluoroethyl)trimethylsilane (2.78 mg, 11.48 mmol) were added under stirring. The mixture was reacted at 25° C. for 16 hours, and then the reaction was completed as detected by TLC. The resulting reaction solution was filtered, and then the filtrate was concentrated under reduced pressure to obtain a crude. The crude was purified by column chromatography to obtain intermediate 10g. $^1H$ NMR (400 MHZ, DMSO-d6) δ 7.32-7.18 (m, 5H), 5.13-5.10 (s, 2H), 4.97-4.98 (m, 1H), 4.28-4.26 (m, 2H), 4.04-4.02 (m, 2H).

Step 6: Preparation of Intermediate 10h

At 25° C., to a 50 mL single-necked flask were added intermediate 10 g (110 mg, 0.34 mmol) and anhydrous methanol (5.0 mL). Under stirring, palladium on carbon (22 mg) and a few drops of concentrated hydrochloric acid were sequentially added. The mixture was subjected to hydrogen replacement three times. Under a hydrogen atmosphere, the mixture was reacted at 25° C. for 16 hours, and then the reaction was completed. The mixture was filtered, and then the filtrate was concentrated under reduced pressure to obtain intermediate 10h.

Step 7: Preparation of Compound 10

Under ice bath, to a 50 mL single-necked flask were added intermediate 10h (51 mg, 0.13 mmol) and dimethylformamide (5.0 mL). Under stirring, 2-(7-azobenzotriazole)-N,N,N',N'-tetramethyluronium hexafluorophosphate (86 mg, 0.19 mmol), diisopropylethylamine (68 mg, 0.78 mmol) and intermediate 10e (22 mg, 0.12 mmol) were sequentially added. The mixture was reacted overnight at 25° C. To the reaction solution was added 25 ml of water, and the mixture was extracted with 25 ml of ethyl acetate. The resulting organic phase was washed with 50 ml of a saturated sodium chloride aqueous solution, dried over sodium sulfate and filtered, and then the filtrate was concentrated under reduced pressure to obtain a crude. The crude was purified by high performance liquid chromatography (ammonium bicarbonate/acetonitrile/water system) to obtain compound 10. $^{1}H$ NMR (400 MHZ, DMSO-d6) δ 7.60 (s, 1H), 7.53-7.48 (m, 1H), 7.06-7.02 (m, 1H), 6.87-6.84 (m, 1H), 5.48-5.45 (m, 1H), 4.49-4.45 (m, 4H), 4.20-4.16 (m, 2H), 1.93-1.86 (m, 12H), LC-MS: m/z: 569.0 $(M+H)^+$.

Example 42: Synthesis of Compound 8 mmol) was added. The mixture was reacted for 16 hours, and then the reaction was completed. The mixture was spun to dryness to remove the solvent, so as to obtain intermediate 8c. $^{1}H$ NMR (400 MHZ, $CDCl_3$) δ=4.57-3.89 (m, 4H), 3.13-2.57 (m, 4H).

Step 3: Synthesis of Compound 8

At 25° C., to a 50 mL single-necked flask were added intermediate 10e (30 mg, 0.08 mmol) and dimethylformamide (1 mL). Under stirring, intermediate 8c (20.18 mg, 0.15 mmol), Castro's reagent (67.0 mg, 0.15 mmol) and diisopropylethylamine (0.08 mL, 0.45 mmol) were sequentially added. The mixture was reacted at 25° C. for 16 hours, and then the reaction was completed. The reaction solution was filtered for further preparation. The crude was purified

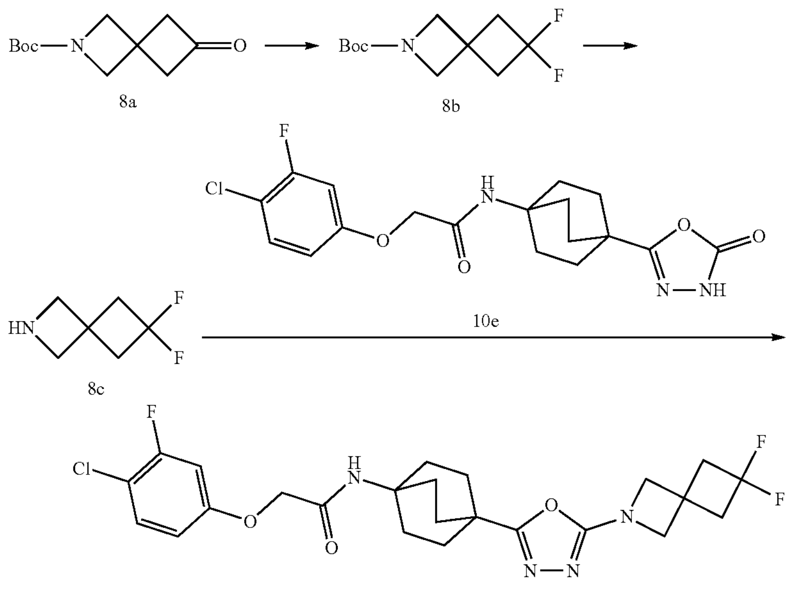

8a 8b 10e 8c 8

Step 1: Synthesis of Intermediate 8b

Under ice bath, to a 250 ml single-necked flask were added compound 8a (Bidepharm, Cat. No. BD159912, 1000 mg, 4.73 mmol) and dichloromethane (50 mL). Under stirring, diethylaminosulfur trifluoride (2.5 mL, 18.93 mmol) was slowly added dropwise. The mixture was reacted at 25° C. for 16 hours, and then the reaction was completed. The reaction was quenched by slowly dropwise adding the resulting reaction solution to 20 ml of ice water and extracted with 20 ml of dichloromethane, and the organic phase was dried over anhydrous sodium sulfate and concentrated to obtain intermediate 8b. $^{1}H$ NMR (400 MHZ, MeOD) δ=3.99 (s, 4H), 2.75 (t, J=12.1 Hz, 4H), 1.43 (s, 9H).

Step 2: Synthesis of Intermediate 8c

At 25° C., to a 50 mL single-necked flask were added intermediate 8b (100 mg, 0.43 mmol) and dichloromethane (1 mL). Under stirring, trifluoroacetic acid (0.3 mL, 4.03 by high performance liquid chromatography (formic acid/acetonitrile/water system) to obtain compound 8. LC-MS: m/z: 511.0 $(M+H)^+$. $^{1}H$ NMR (400 MHZ, MeOD) δ=7.37 (t, J=8.7 Hz, 1H), 6.91 (dd, J=2.8, 11.0 Hz, 1H), 6.80 (ddd, J=1.3, 2.9, 8.9 Hz, 1H), 4.43 (s, 2H), 4.21 (s, 4H), 2.84 (t, J=12.1 Hz, 4H), 2.09-1.98 (m, 12H).

Example 43: Synthesis of Compound 9

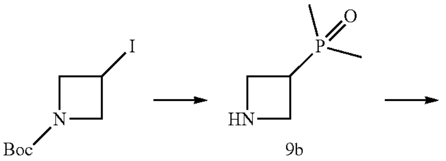

9b 9a

-continued

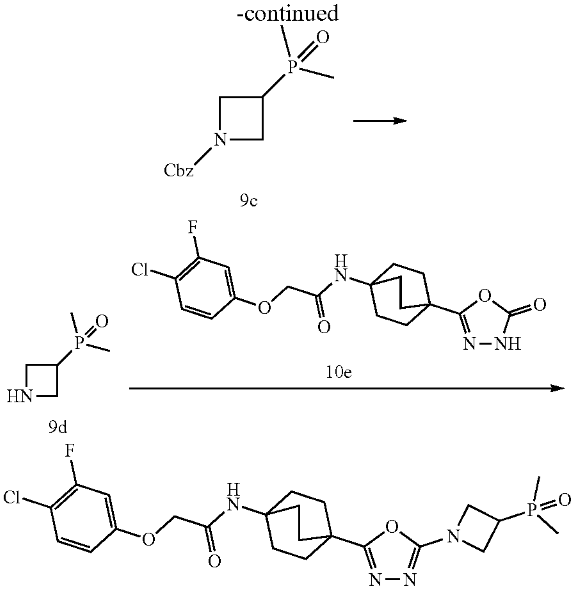

9c

10e

9d

9

Step 1: Preparation of Intermediate 9b

At 25° C., to a 50 mL single-necked flask were added the compounds dimethylphosphine oxide (0.55 g, 7.06 mmol) and tetrahydrofuran (30 mL). Under ice bath and stirring, the compound sodium bis(trimethylsilyl)amide (3.53 mL, 7.06 mmol) was added. The mixture was reacted at 25° C. for 1 hour, and then compound 9a (Bidepharm, Cat. No. BD32891, 1 g, 3.53 mmol) was added. The mixture was reacted at 25° C. for 16 hours, and then the reaction was completed. To the resulting reaction solution was added 100 ml of water, and the mixture was extracted with ethyl acetate (200 mL×2). The resulting organic phase was washed with 100 ml of a saturated sodium chloride aqueous solution, dried over anhydrous sodium sulfate and filtered, and then the filtrate was concentrated under reduced pressure to obtain intermediate 9b. LC-MS: m/z: 134.0 $(M+H)^+$.

Step 2: Preparation of Compound 9c

At 25° C., to a 50 mL single-necked flask were added intermediate 9b (200 mg, 1.50 mmol), sodium bicarbonate (378.62 mg, 4.51 mmol), tetrahydrofuran (20 mL) and water (10 mL). Under stirring, benzyl chloroformate (0.32 mL, 2.25 mmol) was added dropwise. The mixture was reacted at 25° C. for 16 hours, and then the reaction was completed. To the resulting reaction solution was added 100 ml of water, and the mixture was extracted with ethyl acetate (200 mL×2). The resulting organic phase was washed with 100 ml of a saturated sodium chloride aqueous solution, dried over sodium sulfate and filtered, and then the filtrate was concentrated under reduced pressure to obtain intermediate 9c. LC-MS: m/z: 268.0 $(M+H)^+$.

Step 3: Preparation of Intermediate 9d

At 25° C., to a 50 mL single-necked flask were added intermediate 9c (100 mg, 0.37 mmol), 1 mol/L hydrochloric acid (2 mL), methanol (10 mL) and 10% palladium on carbon (39.82 mg, 0.37 mmol). After the addition, the mixture was subjected to hydrogen replacement three times and then reacted at 25° C. for 16 hours under hydrogen. After the reaction was completed, the mixture was filtered and concentrated under reduced pressure to obtain intermediate 9d. LC-MS: m/z: 134.0 $(M+H)^+$.

Step 4: Preparation of Compound 9

At 25° C., to a 50 mL single-necked flask were added intermediate 9d (15.98 mg, 0.12 mmol), intermediate 10e (30 mg, 0.08 mmol) and dimethylformamide (4 mL). Under stirring, diisopropylethylamine (0.05 mL, 0.30 mmol) and Castro's reagent (50.28 mg, 0.11 mmol) were sequentially added. The mixture was reacted at 25° C. for 18 hours, and then the reaction was completed. 20 ml of water was added to the resulting reaction solution, and the mixture was extracted with ethyl acetate (30 mL×2). The resulting organic phase was washed with 10 ml of a saturated sodium chloride aqueous solution, dried over sodium sulfate and filtered, and then the filtrate was concentrated under reduced pressure to obtain a crude. The crude was separated by high performance liquid chromatography (trifluoroacetic acid/acetonitrile/water system) to obtain compound 9. $^1H$ NMR (400 MHZ, DMSO-d6) δ 8.36 (s, 1H), 7.60 (s, 1H), 7.49 (t, J=8.9 Hz, 1H), 7.04 (dd, J=11.4, 2.9 Hz, 1H), 6.85-6.80 (m, 1H), 4.46 (s, 2H), 4.30-4.03 (m, 4H), 3.12 (d, J=9.3 Hz, 1H), 1.90 (d, J=5.9 Hz, 11H), 1.41 (d, J=13.1 Hz, 6H). LC-MS: m/z: 511.2 $(M+H)^+$.

Example 44: Synthesis of Compound 15

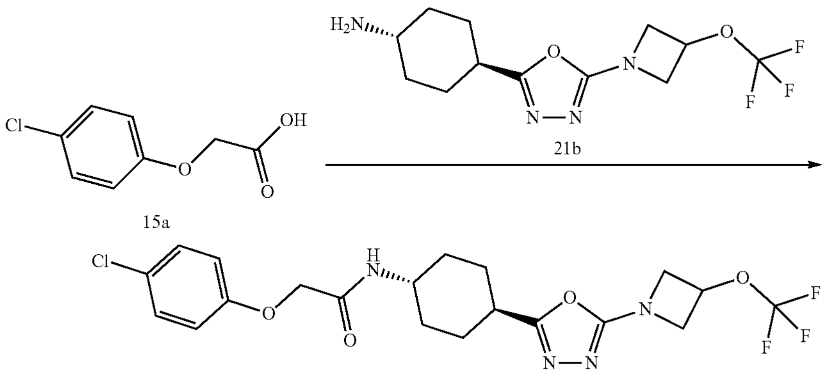

21b

15a

15

At 25° C., in an 8 mL reaction flask, compound 15a (Bidepharm, Cat. No. BD17826, 28 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 15. $^{1}H$ NMR (400 MHZ, DMSO-d6) δ=8.00 (d, J=8.0 Hz, 1H), 7.39-7.28 (m, 2H), 7.04-6.90 (m, 2H), 5.35-5.24 (m, 1H), 4.48-4.41 (m, 4H), 4.19 (dd, J=3.9, 9.5 Hz, 2H), 3.70-3.59 (m, 1H), 2.71 (tt, J=3.4, 11.7 Hz, 1H), 2.02 (br d, J=11.9 Hz, 2H), 1.84 (br dd, J=2.9, 12.5 Hz, 2H), 1.56-1.32 (m, 4H). LC-MS: m/z: 475.2 (M+H)+.

Example 45: Synthesis of Compound 16

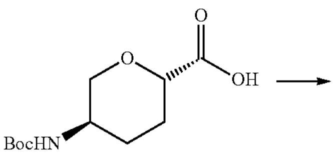
16a

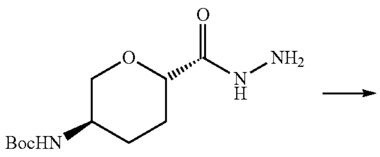
16b

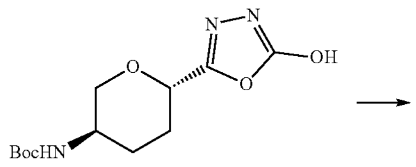
16c

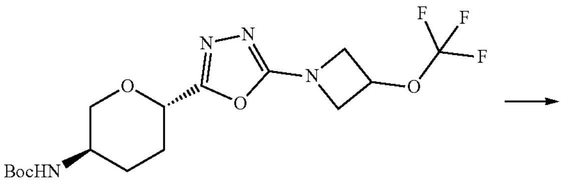
16d

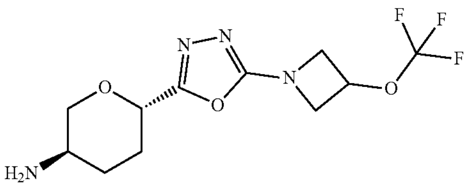
16e

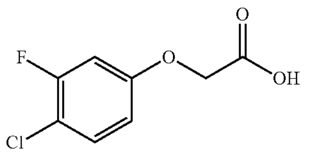
1i

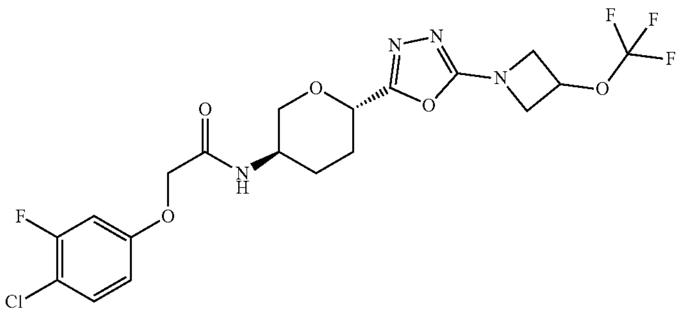
16

Step 1: Preparation of Intermediate 16b

At 25° C., to a 100 mL single-necked flask were added 16a (Bidepharm, Cat. No. BD263092, 800 mg, 3.26 mmol) and anhydrous tetrahydrofuran (8 mL). Under stirring, the compound N,N'-thiocarbonyldiimidazole (821 mg, 4.89 mmol) was added. The mixture was stirred at 25° C. for 16 hours. Hydrazine hydrate (1.92 g, 32.6 mmol) was added, and the mixture was reacted for half an hour. The reaction mixture was concentrated under reduced pressure to obtain a crude. The crude was subjected to recrystallization with acetonitrile to obtain intermediate 16b. LC-MS: m/z: 260.0 $(M+H)^+$.

Step 2: Preparation of Intermediate 16c

At 25° C., to a 100 mL single-necked flask were added intermediate 16b (710 mg, 2.46 mmol) and 1,2-dichloroethane (10.0 mL). Under stirring, the compound N,N'-carbonyldiimidazole (887 mg, 5.46 mmol) was sequentially added. The mixture was reacted at 25° C. for 18 hours, and then the reaction was completed. To the resulting reaction solution was added 25 ml of water. The organic phase was washed with 100 ml of a saturated sodium chloride aqueous solution, dried over sodium sulfate and filtered, and then the filtrate was concentrated under reduced pressure to obtain a crude. The crude was purified by column chromatography to obtain intermediate 16c. LC-MS: m/z: 230.0 $(M+H-56)^+$.

Step 3: Preparation of Intermediate 16d

At 25° C., to a 100 mL single-necked flask were added intermediate 16c (680 mg, 2.03 mmol) and dimethylformamide (10 mL). Under stirring, the compounds 3-(trifluoromethoxy)-azetidine (336 mg, 2.38 mmol), diisopropylethylamine (1.2 g, 9.53 mmol) and Castro's reagent (1.6 g, 3.6 mmol) were sequentially added. The mixture was reacted for 16 hours, and then the reaction was completed. To the resulting reaction solution was added 100 ml of water, and the mixture was extracted with 100 mL of ethyl acetate. The resulting organic phase was washed with 100 ml of a saturated sodium chloride aqueous solution, dried over sodium sulfate and filtered, and then the filtrate was concentrated under reduced pressure to obtain a crude. The crude was purified by high performance liquid chromatography (ammonium bicarbonate/acetonitrile/water system) to obtain intermediate 16d. LC-MS: m/z: 409.0 (M+H)+.

Step 4: Preparation of Intermediate 16e

At 25° C., to a 100 mL single-necked flask were added intermediate 16d (70 mg, 0.17 mmol) and dichloromethane (5.0 mL). Under stirring, trifluoroacetic acid (2.0 mL, 4.5 mmol) was added. The mixture was reacted for 2 hours, and then the reaction was completed. The reaction mixture was concentrated under reduced pressure to obtain intermediate 16e. LC-MS: m/z: 309.1 $(M+H)^+$.

Step 5: Preparation of Compound 16

Under ice bath, to a 50 mL single-necked flask were added compound 1i (47 mg, 0.23 mmol) and dimethylformamide (5.0 mL). Under stirring, 2-(7-azobenzotriazole)-N,N,N',N'-tetramethyluronium hexafluorophosphate (110 mg, 0.29 mmol), diisopropylethylamine (101 mg, 0.78 mmol) and 16e (65 mg, 0.21 mmol) were sequentially added. The mixture was reacted overnight at room temperature. To the resulting reaction solution was added 25 ml of water, and the mixture was extracted with 25 ml of ethyl acetate. The resulting organic phase was washed with 50 ml of a saturated sodium chloride aqueous solution, dried over sodium sulfate and filtered, and then the filtrate was concentrated under reduced pressure to obtain a crude. The crude was purified by high performance liquid chromatography (ammonium bicarbonate/acetonitrile/water system) to obtain compound 16. $^1H$ NMR (400 MHZ, DMSO-d6) δ 8.08-8.01 (m, 1H), 7.53-7.48 (m, 1H), 7.10-7.06 (m, 1H), 6.87-6.84 (m, 1H), 5.35-5.31 (m, 1H), 4.55-4.49 (m, 5H), 4.26-4.21 (m, 2H), 3.88-3.80 (m, 2H), 3.29-3.26 (m, 1H), 2.04-2.0 (m, 2H), 1.90-1.86 (m, 1H), 1.69-1.65 (m, 1H), LC-MS: m/z: 495.0 $(M+H)^+$.

Example 46: Synthesis of Compound 17

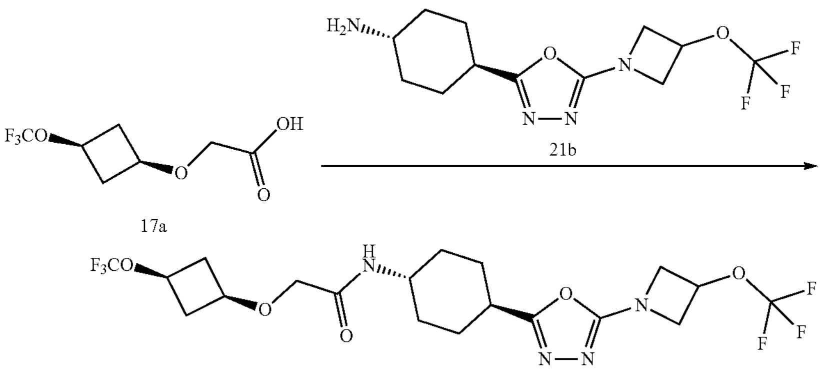

21b

17a

17

At 25° C., in an 8 mL reaction flask, compound 17a (Bidepharm, Cat. No. BD01523901, 76 mg, 0.35 mmol) and intermediate 21b (90 mg, 0.22 mmol) were dissolved in dimethylformamide (5.0 mL). Under stirring, triethylamine (101.0 mg, 0.95 mmol) and 2-(7-azobenzotriazole)-N,N,N',N'-tetramethyluronium hexafluorophosphate (167 mg, 0.47 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over sodium sulfate and filtered, and then the filtrate was concentrated under reduced pressure to obtain a crude. The crude was separated and purified by high performance liquid chromatography (trifluoroacetic acid/acetonitrile/water system) to obtain compound 17. $^1$H NMR (400 MHZ, DMSO-d6) δ 7.65-7.63 (m, 1H), 5.33-5.30 (m, 1H), 4.50-4.43 (m, 3H), 4.20-4.17 (m, 2H), 3.76 (s, 2H), 3.73-3.69 (m, 1H), 3.64-3.62 (m, 1H), 2.78-2.72 (m, 3H), 2.17-2.14 (m, 2H), 1.84-1.80 (m, 2H), 1.52-1.48 (m, 2H), 1.46-1.38 (m, 4H). LC-MS: m/z: 503.02 (M+H)$^+$.

Example 47: Synthesis of Compound 18

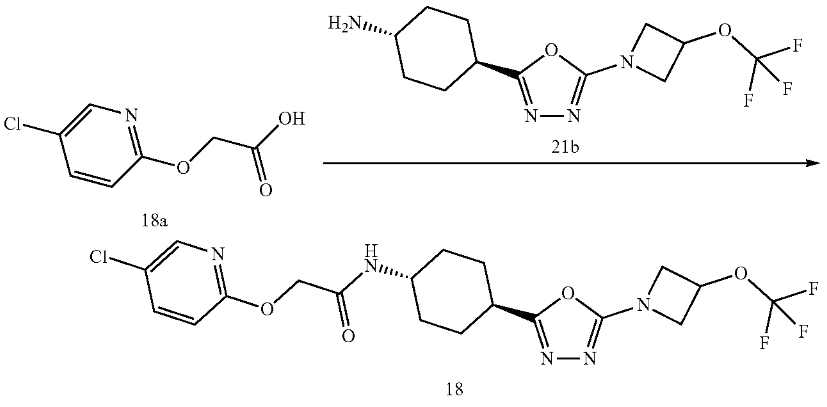

At 25° C., in an 8 mL reaction flask, compound 18a (Bidepharm, Cat. No. BD00971063, 28 mg, 0.15 mmol) and intermediate 21b (30 mg, 0.1 mmol) were dissolved in dimethylformamide (1.5 mL). Under stirring, triethylamine (40.48 mg, 0.4 mmol) and 2-(7-azobenzotriazole)-N,N,N',N'-tetramethyluronium hexafluorophosphate (57.03 mg, 0.15 mmol) were sequentially added. The mixture was stirred at 25° C. for 10 hours until the reaction was completed. To the resulting reaction solution was added 20 ml of water, and the mixture was extracted with 20 ml of ethyl acetate. The resulting organic phase was washed with 20 ml of a saturated sodium chloride aqueous solution, dried over anhydrous sodium sulfate and filtered, and then the filtrate was concentrated under reduced pressure to obtain a crude. The crude was separated and purified by high performance liquid chromatography (trifluoroacetic acid/acetonitrile/water system) to obtain compound 18. $^1$H NMR (400 MHZ, Methanol-d4) δ 8.09 (d, J=2.7 Hz, 1H), 7.72 (dd, J=8.8, 2.7 Hz, 1H), 6.94 (d, J=8.9 Hz, 1H), 5.44-5.21 (m, 2H), 4.75 (s, 2H), 4.50 (dd, J=9.7, 6.7 Hz, 2H), 4.25 (dd, J=9.6, 4.2 Hz, 2H), 3.77 (t, J=4.0 Hz, 1H), 2.92-2.64 (m, 1H), 2.20-2.09 (m, 2H), 2.00 (ddd, J=13.6, 8.9, 4.7 Hz, 2H), 1.63 (qd, J=13.1, 3.3 Hz, 2H), 1.43 (td, J=12.4, 12.0, 3.5 Hz, 2H). LC-MS: m/z: 476.1 (M+H)$^+$.

Example 48: Synthesis of Compound 7

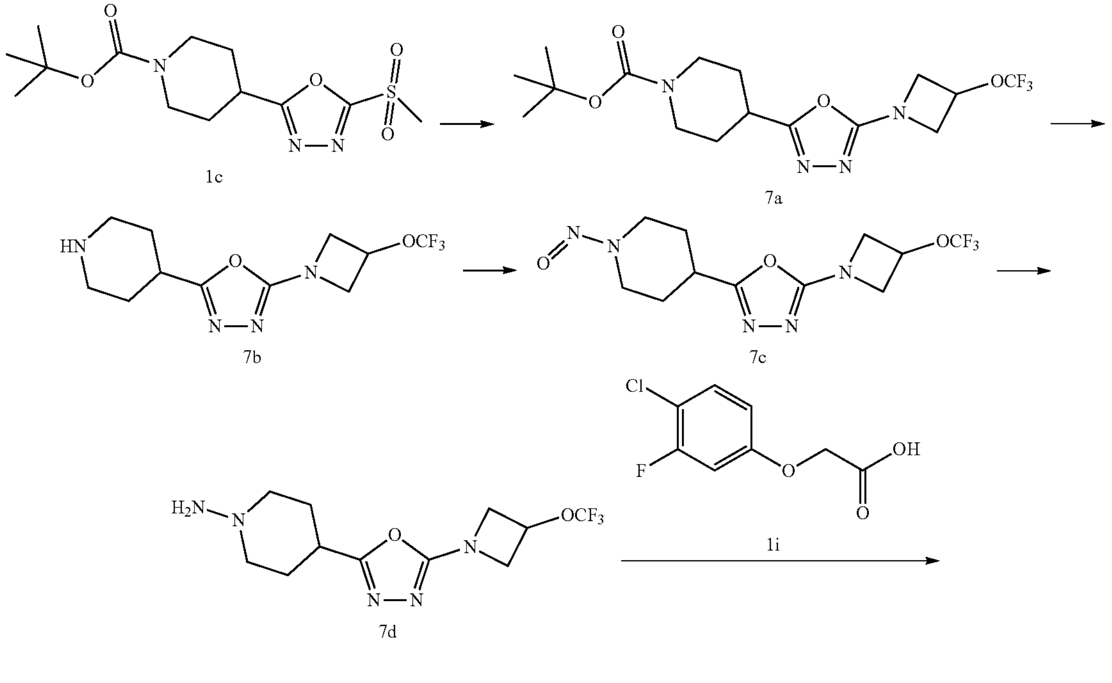

-continued

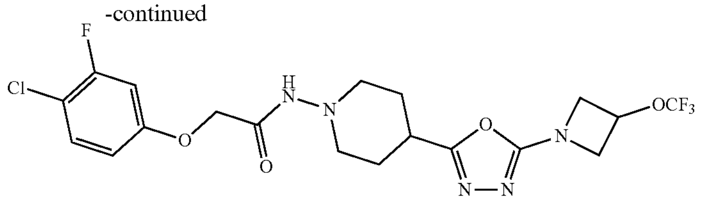

7

Step 1: Preparation of Intermediate 7a

At room temperature, to a single-necked flask were added intermediate 1c (1000 mg, 3.02 mmol), 3-(trifluoromethoxy)-azetidine (1277.25 mg, 9.06 mmol), potassium carbonate (2085.15 mg, 15.1 mmol) and N,N-dimethylformamide (20 mL), and the mixture was stirred at room temperature for 12 hours. To the reaction solution was added 50 ml of water, and the mixture was extracted with ethyl acetate (50 mL×3). The combined organic layer was washed with 50 ml of a saturated sodium chloride aqueous solution, dried over sodium sulfate, filtered and concentrated. The crude was purified by silica gel column chromatography (petroleum ether:ethyl acetate=100:1-1:1) to obtain intermediate 7a. LC-MS: m/z: 393.2 (M+H)+.

Step 2: Preparation of Intermediate 7b

At room temperature, to a single-necked flask were added intermediate 7a (1100 mg, 2.80 mmol) and dichloromethane (3 mL). Under ice bath, a hydrogen chloride dioxane solution (4 M, 3 mL) was added, and the mixture was stirred at room temperature for 2 hours. The reaction solution was directly concentrated to obtain intermediate 7b. LC-MS: m/z: 293.2 (M+H)+.

Step 3: Preparation of Intermediate 7c

At room temperature, to a single-necked flask were added 7b (230 mg, 0.79 mmol) and water (1 mL). Under ice bath, acetic acid (3 mL) and sodium nitrite (162.88 mg, 2.36 mmol) were added. The mixture was stirred under ice bath for 1 hour, and then the reaction was completed. The reaction solution was directly concentrated under reduced pressure to obtain intermediate 7c. LC-MS: m/z: 322.1 (M+H)+.

Step 4: Preparation of Intermediate 7d

At room temperature, to a single-necked flask were added 7c (890 mg, 2.77 mmol), acetic acid (2 mL) and methanol (6 mL). Under ice bath, zinc powder (905.62 mg, 13.85 mmol) was added, and the mixture was stirred at room temperature for 2 hours. The reaction solution was directly filtered, and the filtrate was concentrated under reduced pressure to obtain intermediate 7d. LC-MS: m/z: 308.1 (M+H)+.

Step 5: Preparation of Compound 7

At room temperature, to a single-necked flask were added intermediate 7d (100 mg, 0.33 mmol), 1i (66.58 mg, 0.33 mmol) and N,N-dimethylformamide (1 mL). Under stirring, 1-propylphosphonic anhydride (414.19 mg, 0.65 mmol) and N,N-diisopropylethylamine (126.19 mg, 0.98 mmol) were sequentially added, and the mixture was stirred at room temperature for 12 hours. The reaction solution was directly concentrated under reduced pressure to obtain a crude. The crude was purified by high performance liquid chromatography (ammonium bicarbonate/acetonitrile/water system) to obtain compound 7 (6 mg). LC-MS: m/z: 494.5 (M+H)+. $^1$H NMR (DMSO-d6) δ: 8.77-9.19 (m, 1H), 7.32-7.48 (m, 1H), 6.90-7.03 (m, 1H), 6.68-6.80 (m, 1H), 5.22-5.29 (m, 1H), 4.84 (s, 1H), 4.35-4.44 (m, 3H), 4.13 (m, 2H), 2.87 (d, J=11.1 Hz, 1H), 2.56-2.81 (m, 3H), 1.83-2.00 (m, 3H), 1.60-1.78 (m, 2H).

Example 49: Synthesis of Compounds 51-1 and 51-2

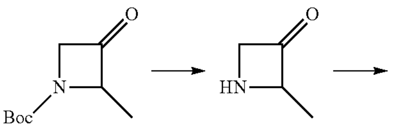

51a 51b

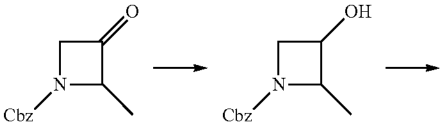

51c 51d

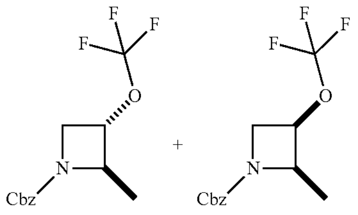

51ea 51eb

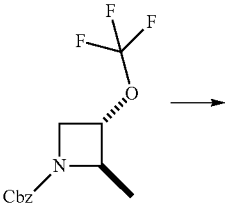

51ea

-continued

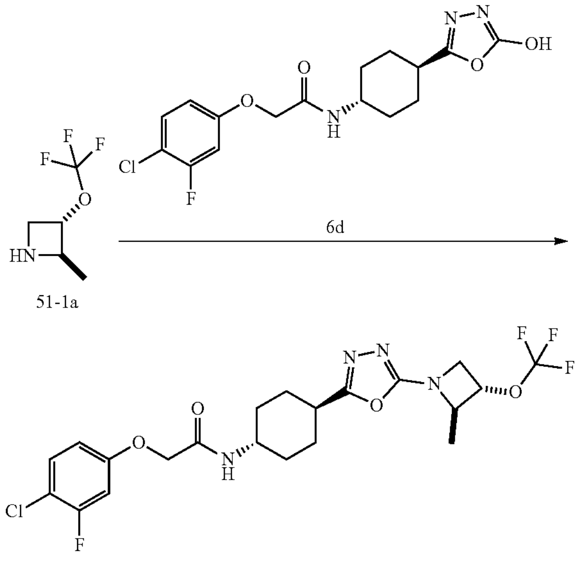

51-1a 51-1

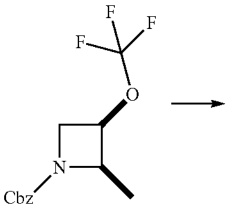

51eb

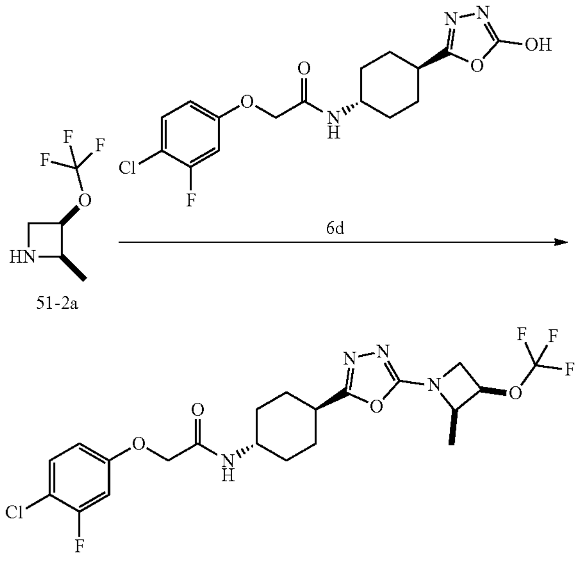

51-2a 51-2

Step 1: Preparation of Intermediate 51b

At room temperature, 51a (Accela ChemBio Co., Ltd., 800 mg, 4.32 mmol) and 1,4-dioxane (2.0 mL). Under stirring, a hydrogen chloride/dioxane solution (4 M, 6.0 mL) was added, and the mixture was reacted at room temperature for 18 hours. The reaction solution was concentrated under reduced pressure to obtain intermediate 51b.

Step 2: Preparation of Intermediate 51c

At room temperature, to a single-necked flask were added intermediate 51b (350 mg, 4.11 mmol) and dimethylformamide (8.0 mL). Under stirring, the compounds benzyl chloroformate (1.08 g, 6.34 mmol) and potassium carbonate (2.34 g, 16.92 mmol) were sequentially added, and the mixture was stirred at room temperature for 18 hours. To the reaction solution was added 50 mL of water, and the mixture was extracted with ethyl acetate (50 mL×1). The organic phase was washed with 100 ml of a saturated sodium chloride aqueous solution, dried over sodium sulfate and filtered, and then the filtrate was concentrated under reduced pressure to obtain a crude. The crude was purified by flash column chromatography (petroleum ether:ethyl acetate=100:1-5:1) to obtain intermediate 51c.

Step 3: Preparation of Intermediate 51d

At room temperature, to a single-necked flask were added 51c (620 mg, 2.83 mmol) and anhydrous methanol (10.0 mL). Under stirring, sodium borohydride (214 mg, 5.63 mmol) was added. The mixture was reacted at 50° C. for 3 hours. The reaction solution was quenched with 50 ml of aqueous ammonium chloride solution and extracted with 30 mL of ethyl acetate each time. The combined organic phase was washed with 50 ml of a saturated sodium chloride aqueous solution, dried over anhydrous sodium sulfate and filtered, and then the filtrate was concentrated under reduced pressure to obtain intermediate 51d.

Step 4: Preparation of Intermediates 51ea and 51eb

Under ice bath, to a three-necked flask were added intermediate 51d (300 mg, 1.36 mmol) and ethyl acetate (20 mL). After the three-necked flask was wrapped with tin foil to block light, silver trifluoromethanesulfonate (1.05 g, 4.07 mmol), 1-chloromethyl-4-fluoro-1,4-diazoniabicyclo[2.2.2] octane bis(tetrafluoroborate) (0.72 g, 2.03 mmol), potassium fluoride (0.32 g, 5.42 mmol), 2-fluoropyridine (0.38 g, 4.07 mmol), and (trifluoromethyl)trimethylsilane (0.58 mg, 4.07 mmol) were added under stirring. The mixture was reacted at room temperature for 16 hours. The reaction solution was filtered, and then the filtrate was concentrated under reduced pressure to obtain a crude. The crude was purified by flash column chromatography (petroleum ether:ethyl acetate=100:1-8:1) to obtain intermediates 51ea (60 mg) and intermediates 51eb (110 mg) (confirmed by 1H-1H NOESY (two-dimensional NMR)).

51ea: $^{1}H$ NMR (400 MHZ, DMSO) δ 7.40-7.30 (m, 5H), 5.06 (s, 2H), 4.79-4.75 (m, 1H), 4.38-4.35 (m, 1H), 4.21-4.17 (m, 1H), 3.92-3.90 (m, 1H), 1.37 (d, J=6.6 Hz, 3H).

51eb: $^{1}H$ NMR (400 MHZ, DMSO) δ 7.46-7.21 (m, 5H), 5.19-5.15 (m, 1H), 5.05 (s, 2H), 4.65-4.62 (m, 1H), 4.28-4.25 (m, 1H), 3.92-3.90 (m, 1H), 1.30 (d, J=6.6 Hz, 3H).

Step 5: Preparation of Intermediate 51-1a

At room temperature, to a single-necked flask were added intermediate 51ea (60 mg, 0.21 mmol) and anhydrous methanol (5.0 mL). Under stirring, palladium on carbon (12 mg) and 2 drops of concentrated hydrochloric acid were sequentially added. The mixture was subjected to hydrogen replacement three times. Under a hydrogen atmosphere, the mixture was reacted at room temperature for 16 hours. The reaction solution was filtered, and then the filtrate was concentrated under reduced pressure to obtain intermediate 51-1a.

Step 6: Preparation of Compound 51-1

Under ice bath, to a single-necked flask were added intermediate 51-1a (30 mg, 0.18 mmol) and dimethylformamide (5.0 mL). Under stirring, Castro's reagent (125 mg, 0.27 mmol), diisopropylethylamine (70 mg, 0.54 mmol) and intermediate 6d (70 mg, 0.18 mmol) were sequentially added. The mixture was reacted overnight at room temperature. To the reaction solution was added 25 ml of water, and the mixture was extracted with 30 ml of ethyl acetate each time. The organic phase was washed with 50 ml of a saturated sodium chloride aqueous solution, dried over sodium sulfate and filtered, and then the filtrate was concentrated under reduced pressure to obtain a crude. The crude was purified by high performance liquid chromatography (ammonium bicarbonate/acetonitrile/water system) to obtain compound 51-1 (7.34 mg). $^1$H NMR (400 MHZ, DMSO) δ 8.02 (d, J=8.0 Hz, 1H), 7.50 (t, J=8.9 Hz, 1H), 7.07 (dd, J=11.4, 2.9 Hz, 1H), 6.87-6.85 (m, 1H), 4.98-4.94 (m, 1H), 4.51 (s, 2H), 4.48-4.45 (m, 1H), 4.30-4.26 (m, 1H), 4.03-4.00 (m, 1H), 3.67-3.63 (m, 1H), 2.86-2.61 (m, 1H), 2.06-2.01 (m, 2H), 1.87-1.83 (m, 2H), 1.56-1.47 (m, 2H), 1.44 (t, J=5.8 Hz, 3H), 1.41-1.29 (m, 2H), LC-MS: m/z: 507.0 (M+H)+.

Step 7: Preparation of Intermediate 51-2a

At room temperature, to a single-necked flask were added intermediate 51eb (70 mg, 0.24 mmol) and anhydrous methanol (5.0 mL). Under stirring, palladium on carbon (12 mg) and 2 drops of concentrated hydrochloric acid were sequentially added. The mixture was subjected to hydrogen replacement three times. Under a hydrogen atmosphere, the mixture was reacted at room temperature for 16 hours. The reaction solution was filtered, and then the filtrate was concentrated under reduced pressure to obtain intermediate 51-2a.

Step 8: Preparation of Compound 51-2

Under ice bath, to a 50 mL single-necked flask were added intermediate 51-2a (32 mg, 0.20 mmol) and dimethylformamide (5.0 mL). Under stirring, Castro's reagent (149 mg, 0.34 mmol), diisopropylethylamine (88 mg, 0.68 mmol) and intermediate 6d (83 mg, 0.22 mmol) were sequentially added. The mixture was reacted overnight at room temperature. To the reaction solution was added 25 ml of water, and the mixture was extracted with ethyl acetate (30 mL×3). The combined organic phase was washed with 50 ml of a saturated sodium chloride aqueous solution, dried over sodium sulfate and filtered, and then the filtrate was concentrated under reduced pressure to obtain a crude. The crude was purified by high performance liquid chromatography (ammonium bicarbonate/acetonitrile/water system) to obtain compound 51-2 (4.54 mg). $^1$H NMR (400 MHZ, DMSO) δ 8.02 (d, J=8.0 Hz, 1H), 7.50 (t, J=8.9 Hz, 1H), 7.08-7.06 (m, 1H), 7.05-6.86 (m, 1H), 5.26-5.22 (m, 1H), 4.75-4.73 (m, 1H), 4.40 (s, 2H), 4.39-4.36 (m, 1H), 4.03-4.02 (m, 1H), 3.65-3.63 (m, 1H), 2.74-2.70 (m, 1H), 2.04-2.01 (m, 2H), 1.86-1.83 (m, 2H), 1.55-1.49 (m, 2H), 1.48-1.42 (m, 2H), 1.37 (t, J=5.8 Hz, 3H), LC-MS: m/z: 507.1 (M+H)+.

Example 50: Synthesis of Compound 90

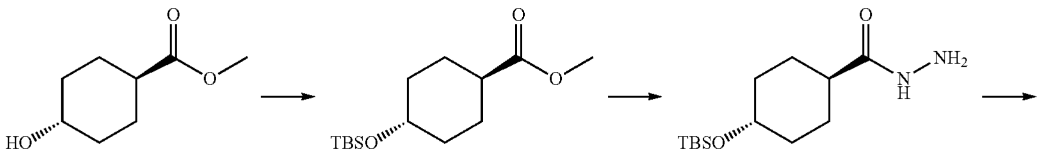

90a 90b 90c

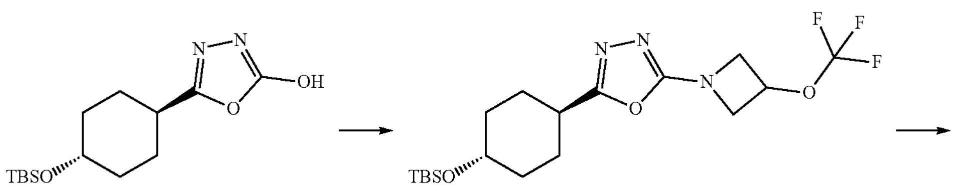

90d 90e

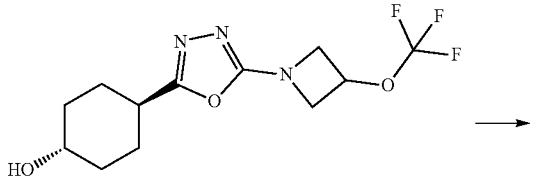

90f

-continued

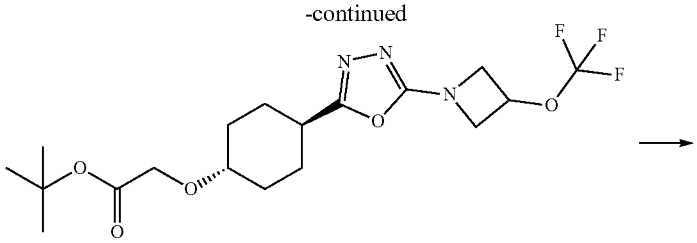

90g

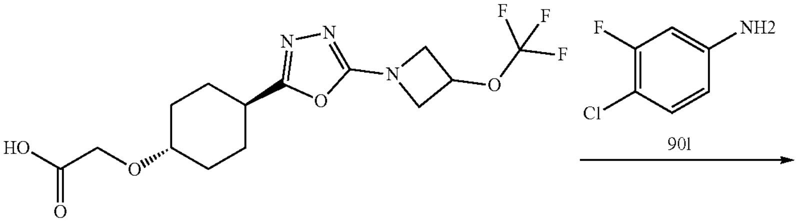

90h

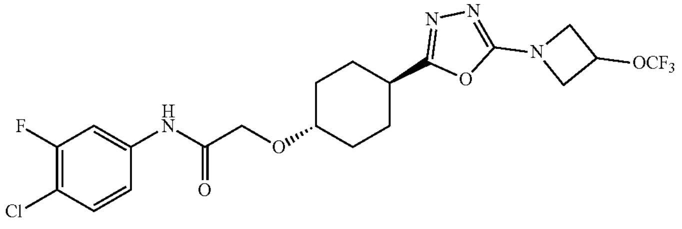

90

Step 1: Preparation of Intermediate 90b

At room temperature, to a single-necked flask were added 90a (Bidepharm, Cat. No. BD253909, 5.0 g, 31.61 mmol) and N,N-dimethylformamide (40.0 mL). Under stirring, imidazole (4.30 g, 63.22 mmol) and tert-butyldimethylsilyl chloride (5.24 g, 34.77 mmol) were added, and the mixture was reacted at room temperature for 3 hours. To the reaction solution was added 200 ml of water, and the mixture was extracted with ethyl acetate (100 mlx3). The combined organic phase was washed with 100 ml of a saturated sodium chloride aqueous solution, dried over anhydrous sodium sulfate and filtered, and then the filtrate was concentrated under reduced pressure to obtain a crude. The crude was purified by flash column chromatography (petroleum ether: ethyl acetate=100:1-10:1) to obtain intermediate 90b. $^1$H NMR (400 MHZ, CDCl3) δ 3.65 (s, 3H), 3.59-3.51 (m, 1H), 2.30-2.15 (m, 1H), 2.00-1.84 (m, 4H), 1.54-1.40 (m, 2H), 1.36-1.23 (m, 2H), 0.87 (s, 9H), 0.04 (s, 6H).

Step 2: Preparation of Intermediate 90c

At room temperature, to a single-necked flask were added intermediate 90b (4.50 g, 16.52 mmol) and ethanol (40.0 mL). Hydrazine hydrate (9.73 g, 165.16 mmol) was added at room temperature, and the mixture was reacted at 85° C. for 18 hours. The reaction solution was concentrated under reduced pressure to obtain intermediate 90c. LC-MS: m/z: 273.3 (M+H)+.

Step 3: Preparation of Intermediate 90d

At room temperature, to a single-necked flask were added intermediate 90c (1.80 g, 6.61 mmol) and 1,2-dichloroethane (20.0 mL). Under stirring, triethylamine (2.75 mL, 19.82 mmol) and N,N'-carbonyldiimidazole (1.50 g, 9.25 mmol) were added, and the mixture was reacted at room temperature for 18 hours. The reaction solution was poured into 80 ml of water, and the mixture was extracted with ethyl acetate (50 mlx3). The organic phase was dried over anhydrous sodium sulfate and filtered. The filtrate was concentrated under reduced pressure to obtain a crude. The crude was purified by flash column chromatography (petroleum ether: ethyl acetate=100:1-1:1) to obtain intermediate 90d. LC-MS: m/z: 299.3 (M+H)+, $^1$H NMR (400 MHZ, DMSO-d6) δ 12.05 (s, 1H), 3.69-3.57 (m, 1H), 2.63-2.52 (m, 1H), 2.00-1.88 (m, 2H), 1.87-1.78 (m, 2H), 1.51-1.38 (m, 2H), 1.37-1.25 (m, 2H), 0.86 (s, 9H), 0.04 (d, J=3.0 Hz, 6H).

Step 4: Preparation of Intermediate 90e

At room temperature, to a single-necked flask 90d were added (900 mg, 3.02 mmol) and N,N-dimethylformamide (10.0 mL). Under stirring, N,N-diisopropylethylamine (2.00 mL, 12.06 mmol), 3-(trifluoromethoxy)-azetidine (425 mg, 3.02 mmol) and Castro's reagent (1.60 g, 3.62 mmol) were added, and the mixture was reacted at room temperature for 18 hours. The reaction solution was poured into 60 ml of water, and the mixture was extracted with ethyl acetate (50 mlx3), dried over anhydrous sodium sulfate and filtered. The filtrate was concentrated under reduced pressure to obtain a crude. The crude was purified by flash column chromatography (petroleum ether:ethyl acetate=100:1-2:1) to obtain intermediate 90e. LC-MS: m/z: 422.4 (M+H)+, $^1$H NMR (400 MHZ, DMSO-d6) δ 5.38-5.26 (m, 1H), 4.50-4.40 (m, 2H), 4.24-4.14 (m, 2H), 3.73-3.58 (m, 1H), 2.83-2.64 (m, 1H), 2.01-1.93 (m, 2H), 1.90-1.80 (m, 2H), 1.57-1.28 (m, 4H), 0.87 (s, 9H), 0.06 (s, 6H).

Step 5: Preparation of Intermediate 90f

At room temperature, to a 50 mL single-necked flask were added intermediate 90e (850 mg, 2.02 mmol) and tetrahydrofuran (10.0 mL). Under stirring, tetrabutylammonium fluoride (6.05 mL, 6.05 mmol, 1 M) was added, and the mixture was reacted at room temperature for 5 hours. The reaction solution was poured into 60 ml of water, and the mixture was extracted with ethyl acetate (50 ml×3). The organic phase was dried over anhydrous sodium sulfate and filtered. The filtrate was concentrated under reduced pressure to obtain a crude. The crude was purified by flash column chromatography (petroleum ether:ethyl acetate=100:1-1:1) to obtain intermediate 90f. LC-MS: m/z: 308.2 (M+H)+.

Step 6: Preparation of Intermediate 90g

At room temperature, to a single-necked flask were added intermediate 90f (480 mg, 1.56 mmol) and N,N-dimethylformamide (6.0 mL). Under stirring, sodium hydride (125 mg, 3.12 mmol) and tert-butyl bromoacetate (456 mg, 2.34 mmol) were added, and the mixture was reacted at 60° C. for 18 hours. The reaction solution was poured into 40 ml of ice water, and the mixture was extracted with ethyl acetate (30 ml×3). The organic phase was dried over anhydrous sodium sulfate and filtered. The filtrate was concentrated under reduced pressure to obtain a crude. The crude was purified by flash column chromatography (petroleum ether:ethyl acetate=100:1-3:1) to obtain intermediate 90g. LC-MS: m/z: 422.3 (M+H)+.

Step 7: Preparation of Intermediate 90h

At room temperature, to a single-necked flask were added intermediate 90g (70 mg, 0.17 mmol) and dichloromethane (2.0 mL). Under stirring, trifluoroacetic acid (0.5 mL) was added, and the mixture was reacted at room temperature for 2 hours. The filtrate of the reaction solution was concentrated under reduced pressure to obtain intermediate 90h. LC-MS: m/z: 366.2 (M+H)+.

Step 8: Preparation of Compound 90

At room temperature, to a single-necked flask were added intermediate 90h (50 mg, 0.14 mmol) and N,N-dimethylformamide (1.0 mL). Under stirring, N,N-diisopropylethylamine (53 mg, 0.41 mmol), compound 90i (20 mg, 0.14 mmol) and (7-azabenzotriazol-1-yloxy)tripyrrolidinophosphonium hexafluorophosphate (86 mg, 0.16 mmol) were added. The mixture was reacted at room temperature for 3 hours. The reaction solution was concentrated under reduced pressure to obtain a crude. The crude was purified by preparative high performance liquid chromatography (formic acid/acetonitrile/water system) to obtain compound 90. LC-MS: m/z: 493.3 (M+H)+, $^{1}$H NMR (400 MHZ, DMSO-d6) δ 9.96 (s, 1H), 7.84 (dd, J=12.0, 2.0 Hz, 1H), 7.59-7.40 (m, 2H), 5.37-5.23 (m, 1H), 4.52-4.40 (m, 2H), 4.23-4.15 (m, 2H), 4.11 (s, 2H), 3.47-3.37 (m, 1H), 2.82-2.70 (m, 1H), 2.17-1.94 (m, 4H), 1.60-1.30 (m, 4H).

Example 51: Synthesis of Compound 19

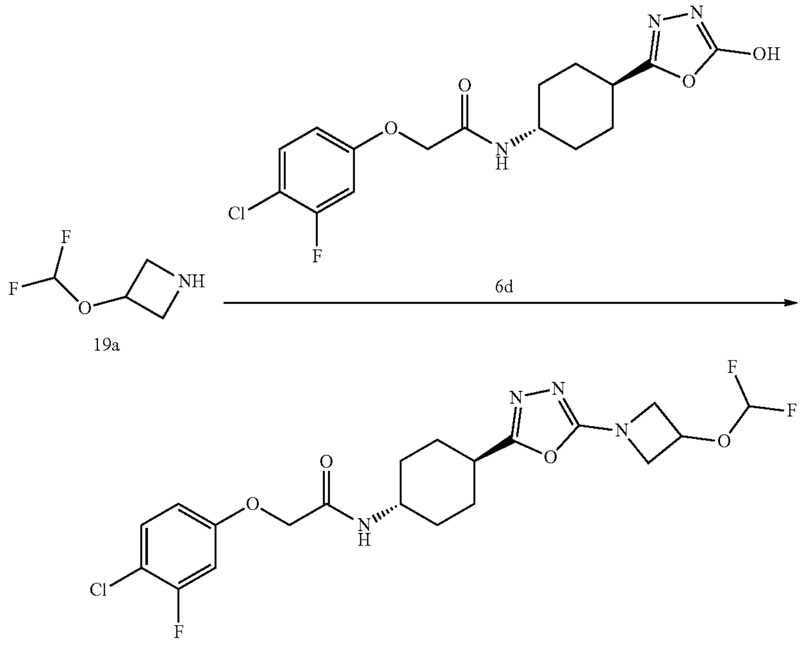

19a

19

At room temperature, to a single-necked flask were added 19a (Bidepharm, Cat. No. BD00755909, 16 mg, 0.13 mmol) and dimethylformamide (3 mL). Under stirring, diisopropylethylamine (52 mg, 0.40 mmol), 1H-benzotriazol-1-yloxytripyrrolidinyl hexafluorophosphate (90 mg, 0.20 mmol) and compound 6d (50 mg, 0.14 mmol) were sequentially added, and the mixture was reacted at room temperature for 18 hours. The reaction solution was poured into 30 ml of water and then extracted with ethyl acetate (30 ml×2). The organic phase was washed with 30 ml of a saturated sodium chloride aqueous solution, dried over sodium sulfate and filtered, and then the filtrate was concentrated under reduced pressure to obtain a crude. The crude was separated by high performance liquid chromatography (formic acid/acetonitrile/water system) to obtain compound 19. LC-MS: m/z: 475.0 $(M+H)^+$, 1H NMR (400 MHZ, DMSO) δ 8.02 (d, J=8.0 Hz, 1H), 7.50 (t, J=8.9 Hz, 1H), 7.07 (dd, J=11.4, 2.9 Hz, 1H), 6.97-6.57 (m, 2H), 5.15-5.04 (m, 1H), 4.51 (s, 2H), 4.40-4.36 (m, 2H), 4.07-4.04 (m, 2H), 3.73-3.57 (m, 1H), 2.83-2.63 (m, 1H), 2.05-2.01 (m, 2H), 1.87-1.85 (m, 2H), 1.61-1.43 (m, 2H), 1.43-1.28 (m, 2H).

Example 52: Synthesis of Compound 86

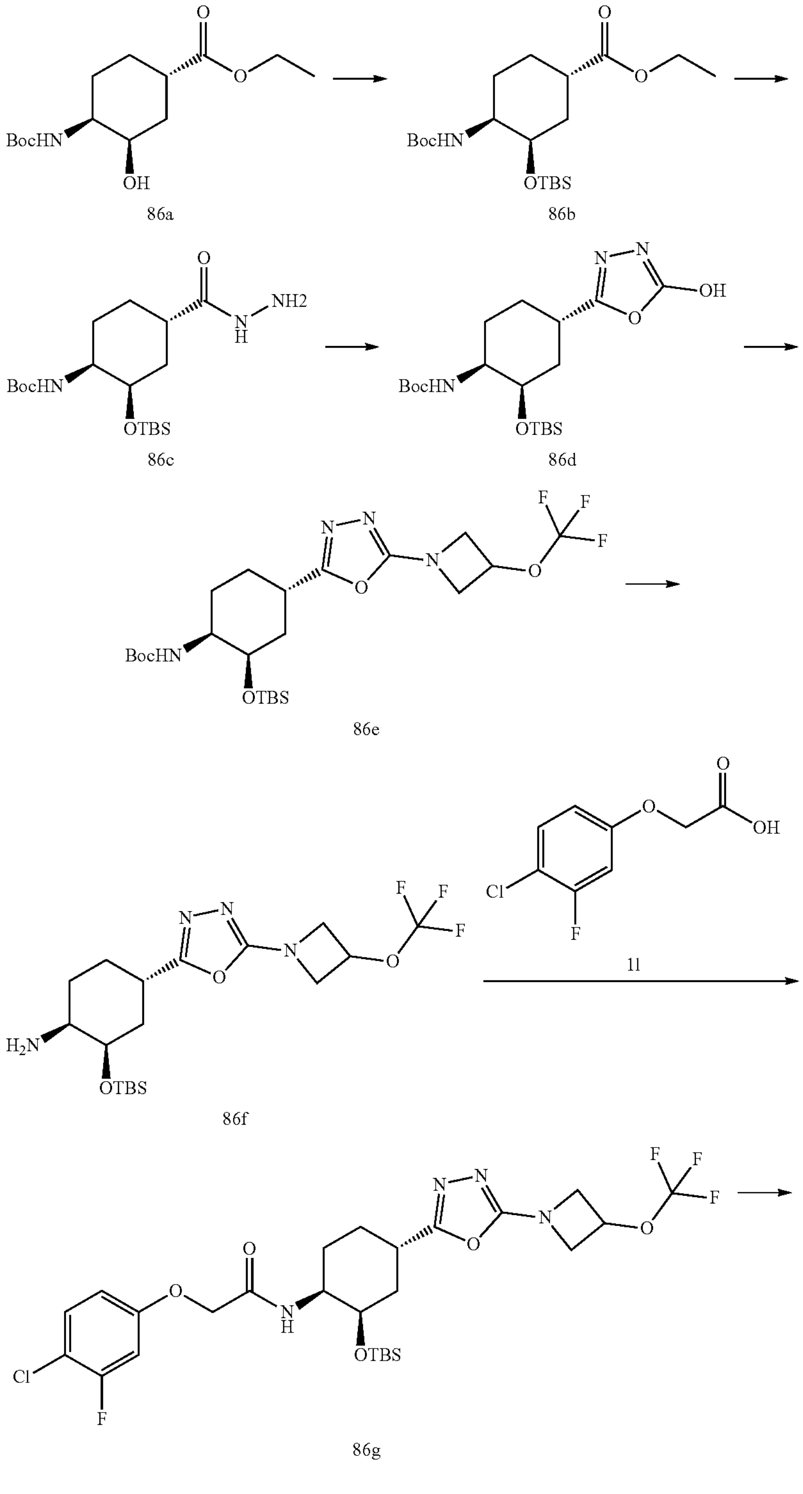

86a

86b

86c

86d

86e

11

86f

86g

-continued

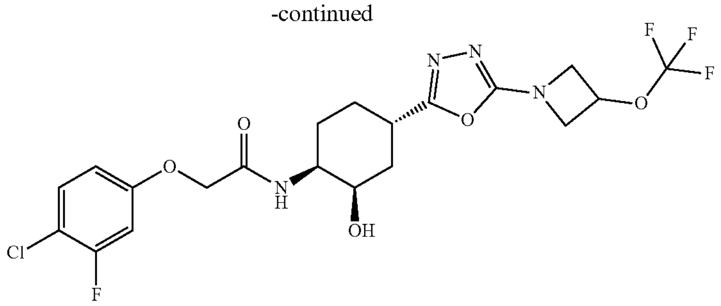

86

Step 1: Preparation of Intermediate 86b

At room temperature, to a single-necked flask were added compound 86a (PharmaBlock, 470 mg, 1.72 mmol) and N,N-dimethylformamide (10.0 mL). Under stirring, imidazole (334 mg, 4.91 mmol) and tert-butyldimethylsilyl chloride (370 mg, 2.45 mmol) were added, and the mixture was reacted at room temperature for 18 hours. To the reaction solution was added 50 ml of water, and the mixture was extracted with ethyl acetate (50 ml×2). The combined organic phase was washed with 50 mL of a saturated sodium chloride aqueous solution, dried over anhydrous sodium sulfate and filtered, and then the filtrate was concentrated under reduced pressure to obtain a crude. The crude was purified by flash column chromatography (petroleum ether: ethyl acetate=100:1-10:1) to obtain intermediate 86b. LC-MS: m/z: 424.2 $(M+Na)^+$.

Step 2: Preparation of Intermediate 86c

At room temperature, to a single-necked flask were added intermediate 86b (570 mg, 1.47 mmol) and ethanol (10.0 mL). Hydrazine hydrate (836 mg, 14.19 mmol) was added at room temperature, and the mixture was reacted at 80° C. for 18 hours. The reaction solution was concentrated under reduced pressure to obtain intermediate 86c as a white solid. LC-MS: m/z: 410.2 (M+Na)+.

Step 3: Preparation of Intermediate 86d

At room temperature, to a single-necked flask were added intermediate 86c (520 mg, 1.34 mmol) and 1,2-dichloroethane (10.0 mL). Under stirring, triethylamine (0.56 mL, 4.02 mmol) and N,N'-carbonyldiimidazole (326 mg, 2.01 mmol) were added, and the mixture was reacted at room temperature for 18 hours. The reaction solution was concentrated under reduced pressure to obtain a crude. The crude was purified by flash column chromatography (petroleum ether: ethyl acetate=100:1-1:1) to obtain intermediate 86d. LC-MS: m/z: 436.2 (M+Na)+.

Step 4: Preparation of Intermediate 86e

At room temperature, to a single-necked flask were added intermediate 86d (470 mg, 1.14 mmol) and N,N-dimethylformamide (10.0 mL). Under stirring, N,N-diisopropylethylamine (589 mg, 4.56 mmol), 3-(trifluoromethoxy)-azetidine (176 mg, 1.25 mmol) and Castro's reagent (603 mg, 1.36 mmol) were added, and the mixture was reacted at room temperature for 18 hours. The reaction solution was poured into 50 ml of water, and the mixture was extracted with ethyl acetate (50 mL×3). The combined organic phase was dried over anhydrous sodium sulfate and filtered. The filtrate was concentrated under reduced pressure to obtain a crude. The crude was purified by flash column chromatography (petroleum ether:ethyl acetate=100:1-2:1) to obtain intermediate 86e. LC-MS: m/z: 537.4 (M+H)+.

Step 5: Preparation of Intermediate 86f

At room temperature, to a single-necked flask were added intermediate 86e (100 mg, 0.19 mmol) and dichloromethane (2.0 mL). Trifluoroacetic acid (0.5 mL) was added, and the mixture was reacted at room temperature for 2 hours. The filtrate of the reaction solution was concentrated under reduced pressure to obtain intermediate 86f. LC-MS: m/z: 437.4 (M+H)+.

Step 6: Preparation of Intermediate 86g

At room temperature, to a single-necked flask were added intermediate 86f (82 mg, 0.19 mmol) and N,N-dimethylformamide (2.0 mL). Under stirring, N,N-diisopropylethylamine (98 mg, 0.76 mmol), compound 1i (42 mg, 0.14 mmol) and (7-azabenzotriazol-1-yloxy)tripyrrolidinophosphonium hexafluorophosphate (119 mg, 0.23 mmol) were added, and the mixture was reacted at room temperature for 18 hours. The reaction solution was poured into 30 ml of water, and the mixture was extracted with ethyl acetate (30 ml×3). The combined organic phase was dried over anhydrous sodium sulfate and filtered. The filtrate was concentrated under reduced pressure to obtain a crude. The crude was purified by flash column chromatography (petroleum ether:ethyl acetate=100:1-3:1) to obtain intermediate 86g. LC-MS: m/z: 623.4 (M+H)+.

Step 7: Preparation of Compound 86

At room temperature, to a single-necked flask were added intermediate 86g (117 mg, 0.19 mmol) and tetrahydrofuran (2.0 mL). Under stirring, tetrabutylammonium fluoride (0.38 mL, 0.38 mmol, 1 M) was added, and the mixture was reacted at room temperature for 3 hours. The reaction solution was concentrated under reduced pressure to obtain a crude, which was then purified by preparative high performance liquid chromatography (formic acid/acetonitrile/water system) to obtain compound 86. LC-MS: m/z: 509.2 $(M+H)^+$, $^1H$ NMR (400 MHz, DMSO-d6) δ 7.90 (d, J=7.7 Hz, 1H), 7.49 (t, J=8.9 Hz, 1H), 7.08 (dd, J=11.4, 2.8 Hz, 1H), 6.87 (dd, J=8.9, 1.9 Hz, 1H), 5.36-5.27 (m, 1H), 4.83 (d, J=5.0 Hz, 1H), 4.52 (s, 2H), 4.49-4.42 (m, 2H), 4.23-4.16

(m, 2H), 3.58-3.41 (m, 2H), 2.91-2.80 (m, 1H), 2.24-2.16 (m, 1H), 1.99-1.90 (m, 1H), 1.88-1.80 (m, 1H), 1.50-1.30 (m, 3H).

Other compounds of the present invention can be prepared by methods similar to those described in the above examples (with appropriate modifications, if necessary).

Biological Test

1. Cell Activity Test

The ATF4 luciferase reporter plasmid consists of two parts, i.e., the 5' untranslated region sequence of the ATF4 gene and the luciferase coding sequence. Specifically, the ATF4 5' untranslated region sequence (NCBI database number BC022088.2) containing two upstream open reading frames (uORFs), and the firefly luciferase encoding gene were cloned into the pLVX-Puro vector (YouBio, VT1465). The lentivirus packaging plasmids were psPAX2 (YouBio, VT1444) and pMD2.G (YouBio, VT1443). HEK293T/17 cells were transfected with the above three plasmids simultaneously using X-tremeGENE 9 DNA transfection reagent, and after 48 hours, a culture medium containing lentivirus was collected. HEK293T/17 cells transduced with the virus were screened with 1 μg/mL puromycin, and then monoclonal cells were obtained by limiting dilution.

By using this cell line and the cold fluorescence readings, the translational regulation of ATF4 can be detected, and the activity of the eIF2B activator can be tested. The specific experimental process is as follows: 6000 HEK293T/17-ATF4 uORF-Luc-Puro monoclonal cells were plated in a 384-well plate and allowed to adhere overnight. The test compounds were dissolved in DMSO and added together with 50 nM thapsigargin to the cell culture medium and incubated for 6 hours, wherein the thapsigargin was used to cause cellular stress and upregulate the protein translation of ATF4. Six hours after the addition, the cells were lysed using the One-Glo Luciferase Assay Kit (Promega #E6120), and then the cold fluorescence values were read using the LUM program of the EnVision 2104 plate reader.

The ATF4 reporter expression % was calculated as follows:

$$ATF4\text{ reporter expression }\% = (\text{ave\_samples} - \text{ave\_vc})/(\text{ave\_pc} - \text{ave\_vc}) * 100\%.$$

ave_vc: average signal value of negative control ave_pc: average signal value of positive control ave_sample: average signal value of sample The dose-response curves were fitted, and the $EC_{50}$ values were calculated.

The nonlinear regression log (inhibitor) vs. response—variable slope (four parameters) method of GraphPad 9 software was used to fit the corresponding relationship between the ATF4 reporter expression % and the compound concentration.

X-axis: log value of compound concentration; Y-axis: ATF4 reporter expression %; Top: evaluation of upper asymptote of curve; Bottom: evaluation of lower asymptote of curve; Hillslope: slope of the fitted curve.

$$Y = \text{Bottom} + (\text{Top} - \text{Bottom})/(1 + 10\hat{}((\text{Log}EC_{50} - X) \times HillSlope)), \text{ that is, } \quad \text{Formula}$$

$$\text{Log}EC_{50} = X + (1/HillSlope) \times \log((\text{Top} - Y)/(Y - \text{Bottom}))$$

In Table 1, "+" indicates an $EC_{50}$ of >100 nM, "++" indicates an $EC_{50}$ of 10 nM to 100 nM, "+++" indicates an $EC_{50}$ of 1 nM to 10 nM, and "++++" indicates an $EC_{50}$ of less than 1 nM.

TABLE 1

Structures of exemplary compounds and activity in HEK293T/17-ATF4 uORF-Luc-Puro monoclonal cells

| Compound No. | $EC_{50}$ (nM) |
|---|---|
| 1 | ++ |
| 2 | ++ |
| 3 | +++ |
| 4 | ++++ |
| 6 | ++++ |
| 7 | ++++ |
| 8 | ++ |
| 9 | + |
| 10 | +++ |
| 11 | ++ |
| 12 | +++ |
| 13 | + |
| 14 | ++ |
| 15 | ++++ |
| 16 | +++ |
| 17 | ++ |
| 18 | ++ |
| 21 | ++ |
| 22 | + |
| 23 | ++ |
| 24 | ++ |
| 25 | +++ |
| 26 | ++++ |
| 27 | ++ |
| 28 | ++++ |
| 29 | + |
| 30 | + |
| 31 | + |
| 32 | + |
| 33 | +++ |
| 34 | +++ |
| 35 | + |
| 36 | +++ |
| 37 | +++ |
| 38 | ++ |
| 40 | ++ |
| 41 | + |
| 42 | + |
| 43 | ++ |
| 44 | +++ |
| 45 | + |
| 46 | + |
| 47 | +++ |
| 48 | +++ |
| 49 | + |
| 50 | +++ |
| 51-1 | ++ |
| 51-2 | + |
| 52 | + |
| 53 | + |
| 90 | +++ |
| 19 | +++ |
| 86 | +++ |

The experimental results (partially not shown) show that the compounds of the present application can enhance/activate the activity of eIF2B and reduce the expression of ATF4, thereby weakening the fluorescence intensity. It is indicated that the compounds of the present application can significantly alleviate the cellular stress caused by thapsigargin and weaken the integrated stress response of cells, so that proteins in the cells tend to be synthesized normally, and the compounds are eIF2B activators. Most of the compounds in the present application have an $EC_{50}$ value for HEK293T/17 cells of <100 nM, many of the compounds have an $EC_{50}$ value for HEK293T/17 cells of 10 nM to 100 nM, quite a few of the compounds have an $EC_{50}$ value for HEK293T/17 cells of less than 10 nM, some preferred compounds have an $EC_{50}$ value for HEK293T/17 cells of <1 nM, and the most preferred compounds have an $EC_{50}$ value for HEK293T/17 cells of less than 10 pM.

2. Kinetic Solubility Evaluation

The test compounds were dissolved in DMSO to prepare 10 mM stock solutions. 8.71 g of $K_2HPO_4$ was added to 500 mL of deionized water to prepare a 100 mM $K_2HPO_4$ solution. 2.05 g of potassium dihydrogen phosphate was added to 150 ml of deionized water to prepare a 100 mM potassium dihydrogen phosphate solution. 405 mL of 100 mM $K_2HPO_4$ and 95 mL of 100 mM $KH_2PO_4$ were mixed, and the mixed solution was adjusted to pH 7.4 by a 100 mM $K_2HPO_4/KH_2PO_4$ solution. 10.41 g of FaSSIF buffer concentrate was added to 240.3 g of deionized water to prepare a buffer solution (fasted-state simulated intestinal fluid, pH=6.5). 4.071 g of FeSSIF buffer concentrate was added to 45.97 g of deionized water to prepare a buffer solution (fed-state simulated intestinal fluid, pH=5.0).

16 μL of the 10 mM stock solution of the compound was added to 784 μL of different buffer solutions (n=3) in a 96-well plate, and the plate was sealed and shaken at 1000 rpm for 1.5 h at 25° C. (for PBS) or 37° C. (for others). After the incubation, the solution was transferred to a filter plate. All samples were filtered. 5 μL of the filtrate was added to 5 μL of DMSO, and 490 μl of an aqueous acetonitrile solution containing the internal standard (1:1), and the mixture was mixed evenly. Based on the properties of the compound and its response in mass spectrometry, dilution with an aqueous acetonitrile solution containing the internal standard (1:1) was performed. The dilution factor was varied according to the solubility value and UPLC-MS/MS signal response.

The experiments show that at least some of the compounds of the present application have good solubility in the above-mentioned different simulated environments. For example, compound 6 exhibits a solubility of >10 μg/mL in the fasted-state simulated intestinal fluid (pH=6.5) environment, and a solubility of >80 μg/mL in the fed-state simulated intestinal fluid (pH=5.0) environment.

3. Evaluation of In Vitro Liver Microsome Stability

A 5 mM $MgCl_2$ 100 mM K-Mg buffer solution was pre-heated. 5 μL of a 10 mM compound and a reference stock solution were added to 95 μL of acetonitrile (ACN) to prepare a spiked solution. 1.5 μL of a 500 UM spiked solution and 18.75 μL of 20 mg/mL liver microsomes were added to 479.8 μL of the K-Mg buffer solution. NADPH was dissolved in the K-Mg-buffer solution to prepare an NADPH stock solution (3 mM). At different time points (0, 5, 15, 30 and 45 minutes), 30 μL of a 1.5 μM spiked solution containing the microsomes was evenly dropped into an assay plate. The plate was preincubated at 37° C. for 5 minutes. At 0 min, 200 μL of ACN containing IS (internal standard, tolbutamid/terfenadine) was added to the wells, and then 15 μl of the NADPH stock solution (6 mM) was added. For other time points, 15 μL of the NADPH stock solution (6 mM) was added to the wells to initiate the reaction and start the timing. At 5, 15, 30 and 45 min, the reaction was stopped by adding 200 μL of ACN containing IS to the corresponding wells of the plate. After quenching, the plate was shaken at 600 rpm for 10 minutes and then centrifuged at 4000 rpm for 50 minutes. 80 μL of the supernatant from each well was transferred to a 96-well sample plate containing 160 μL of pure water for UPLC/MS/MS analysis.

TABLE 2

In vitro liver microsome stability of exemplary compounds

| Compound No. | $T_{1/2}$ (minute) |
|---|---|
| 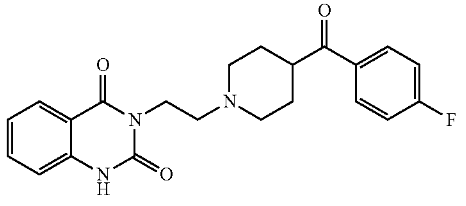 [SMILES: O=C(c1ccc(F)cc1)C1CCN(CCn2c(=O)[nH]c3ccccc3c2=O)CC1] Ketanserin | 36.83 |
| 6 | >90 |

Experiments show that at least some of the compounds of the present application have good in vitro liver microsome stability.

4. Evaluation of Cell Membrane Permeability

The test compounds were diluted from 10 mM stock solutions to a concentration of 10 μM using the transport buffer (HBSS+BSA) and applied to the apical or basolateral side of the cell monolayer. After the incubation at 37° C., 5% $CO_2$ and 95% relative humidity for 120 minutes, the permeability of the test compounds in the A to B direction or the B to A direction was tested in duplicate. In addition, the efflux ratio of each compound was determined. The test substances and reference substances were quantitatively analyzed by the LC-MS/MS method based on the analyte/IS peak area ratio.

TABLE 3

Cell membrane permeability of exemplary compounds

| Compound No. | Papp ($10^{-6}$ cm/s) A to B | Papp ($10^{-6}$ cm/s) B to A | Efflux ratio |
|---|---|---|---|
| Atenolol | 0.41 | 0.61 | |
| Propranolol | 32.43 | 20.14 | |
| Digoxin | 0.25 | 11.17 | 44.07 |
| 6 | 25.75 | 18.35 | 0.71 |

The experimental results show that at least some of the compounds of the present application have good cell membrane permeability and are not P-glycoprotein substrates.

5. P450 Enzyme Inhibition Evaluation

A phosphate buffer solution of liver microsomes was prepared. 169 μL of the phosphate buffer solution of liver microsomes and 1 μL of working solutions of various concentrations of test compounds or positive control compounds were added to a 96-well plate. The culture plate was placed in a water bath and pre-heated at 37° C. for 15 minutes. After the incubation, 10 μL of substrates were added to the culture plate (1 μL of substrates and 9 μL of the K-Mg buffer solution were added to the plate for CYP3A4-T). The incubation mixture was mixed on a rotating mixer for 10 seconds, and then 20 μL of a 10 mM NADPH solution was added to start the reaction at a final concentration of 1 mM. The experiment was repeated twice. At the predetermined time points listed in Table 4, the reaction was quenched by adding 400 μL of the quenching solution (cold ACN containing 500 nM mephetedrine and 10 nM terfenadine). Centrifugation was performed at 3220 g for 50 minutes at 4° C. 100 μl of the supernatant was transferred to a new plate. The supernatant was diluted with 100 μL of pure water. The mixture was mixed evenly, and the sample was analyzed by UPLC-MS/MS.

TABLE 4

| Preparation of substrate stock solution | | | | | |
|---|---|---|---|---|---|
| CYP subtype | Substrate | Working concentration (μM) | Final concentration (μM) | Incubation time | Human liver microsome (mg/mL) |
| 1A2 | Phenacetin | 400 | 20 | 20 | 0.05 |
| 2C9 | Diclofenac sodium | 80 | 4 | 10 | 0.05 |
| 2C19 | Mephenytoin | 200 | 10 | 40 | 0.2 |
| 2D6 | Dextromethorphan | 200 | 10 | 10 | 0.05 |
| CYP3A4 | Testosterone | 8000 | 40 | 10 | 0.05 |

The experimental results show that at least some of the compounds of the present application have weak inhibitory effects on five major P450 enzymes (CYP1A2, CYP2C9, CYP2D6, CYP2C19 and CYP3A4), suggesting a low risk of drug-drug interactions. For example, the $IC_{50}$ values of compound 6 for these five major P450 enzymes are generally >10 μM, and particularly, the $IC_{50}$ values for CYP2D6 and CYP3A4 are both >30 μM.

6. Pharmacokinetic Evaluation in Mice

The test compounds were dissolved in vehicles to prepare clear solutions or homogeneous suspensions. Three mice were placed in each group and received an intravenous administration via the tail vein at 1 mg/kg and an oral (PO) administration at 10 mg/kg. Blood samples were collected at 0.083 h, 0.25 h, 0.5 h, 1 h, 2 h, 4 h, 8 h, and 24 h after the intravenous administration, and at 0.25 h, 0.5 h, 1 h, 2 h, 4 h, 6 h, 8 h, and 24 h after the oral administration. Plasma samples were centrifuged, and the supernatant was collected to prepare samples, which were then quantitatively analyzed by LC/MS/MS.

TABLE 5

| PK properties of compound 6 in mice | | |
|---|---|---|
| mouse IV (1 mg/kg) | $C_0$ (ng/mL) | 1239 |
| | $T_{1/2}$ (h) | 6.35 |
| | Cl (mL/h/kg) | 87.57 |
| | $V_{ss}$ (L/kg) | 706.99 |
| | $AUC_{(0\text{-}inf)}$ (ng*h/ml) | 11423 |
| mouse PO (30 mg/kg) | $C_{max}$ (ng/mL) | 47979 |
| | $T_{1/2}$ (h) | 3.11 |
| | $T_{max}$(h) | 3.33 |
| | $AUC_{(0\text{-}inf)}$ (ng*h/ml) | 516193 |
| | F % | 161.14 |

The experimental results show that at least some of the compounds of the present application (such as compound 6) have excellent pharmacokinetic properties in mice (including but not limited to Cl (clearance), $T_{1/2}$ (half-life), $C_{max}$ (peak concentration), AUC (area under the plasma drug concentration-time curve) and F (bioavailability)).

Although the present application has been described with reference to preferred examples, various improvements can be made thereto and components therein can be replaced with equivalents without departing from the scope of the present application. In particular, as long as there is no structural conflict, the technical features mentioned in each of the examples can be combined in any manner. The present application is not limited to the specific examples disclosed herein but includes all the technical solutions that fall within the scope of the claims.

The invention claimed is:

1. A compound represented by the following formula:

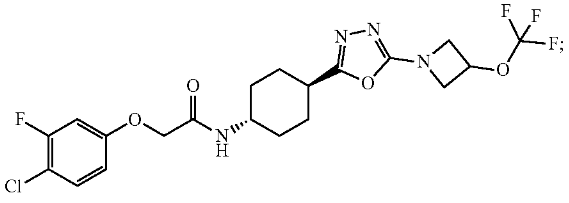 [SMILES: O=C(COc1ccc(Cl)c(F)c1)N[C@H]1CC[C@H](c2nnc(N3CC(OC(F)(F)F)C3)o2)CC1]

or a pharmaceutically acceptable salt thereof.

2. A pharmaceutical composition comprising a compound of claim 1 or a pharmaceutically acceptable salt thereof, and a pharmaceutically acceptable carrier.

3. A compound represented by the following formula:

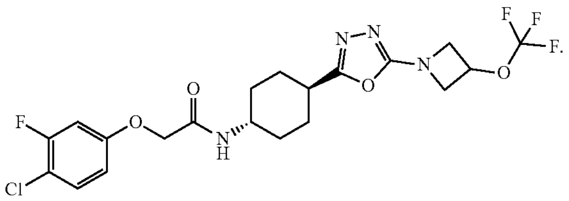 [SMILES: O=C(COc1ccc(Cl)c(F)c1)N[C@H]1CC[C@H](c2nnc(N3CC(OC(F)(F)F)C3)o2)CC1]

4. A pharmaceutical composition comprising a compound of claim 3 and a pharmaceutically acceptable carrier.

* * * * *